US012203104B2

(12) United States Patent
Li et al.

(10) Patent No.: US 12,203,104 B2
(45) Date of Patent: Jan. 21, 2025

(54) FLAVONOID AND ANTHOCYANIN BIOPRODUCTION USING MICROORGANISM HOSTS

(71) Applicant: DEBUT BIOTECHNOLOGY, INC., San Diego, CA (US)

(72) Inventors: Jingyi Li, San Diego, CA (US); Nicholas Brideau, San Diego, CA (US); Joshua Britton, San Diego, CA (US); Erik Holtzapple, San Diego, CA (US)

(73) Assignee: DEBUT BIOTECHNOLOGY, INC., San Diego, CA (US)

( * ) Notice: Subject to any disclaimer, the term of this patent is extended or adjusted under 35 U.S.C. 154(b) by 0 days.

(21) Appl. No.: 17/720,027

(22) Filed: Apr. 13, 2022

(65) Prior Publication Data

US 2022/0333122 A1 Oct. 20, 2022

Related U.S. Application Data

(60) Provisional application No. 63/174,403, filed on Apr. 13, 2021.

(51) Int. Cl.

| | |
|---|---|
| ***C12N 9/02*** | (2006.01) |
| ***C12N 1/20*** | (2006.01) |
| ***C12N 9/00*** | (2006.01) |
| ***C12N 9/10*** | (2006.01) |
| ***C12N 9/88*** | (2006.01) |
| ***C12N 9/90*** | (2006.01) |
| ***C12N 15/04*** | (2006.01) |
| ***C12N 15/52*** | (2006.01) |
| ***C12N 15/70*** | (2006.01) |
| ***C12N 15/82*** | (2006.01) |
| ***C12P 7/42*** | (2006.01) |
| ***C12P 17/06*** | (2006.01) |
| ***C12P 19/44*** | (2006.01) |

(52) U.S. Cl.

CPC ............. *C12N 9/0073* (2013.01); *C12N 1/20* (2013.01); *C12N 9/0042* (2013.01); *C12N 9/0071* (2013.01); *C12N 9/1029* (2013.01); *C12N 9/1085* (2013.01); *C12N 9/88* (2013.01); *C12N 9/90* (2013.01); *C12N 9/93* (2013.01); *C12N 15/04* (2013.01); *C12N 15/52* (2013.01); *C12N 15/70* (2013.01); *C12N 15/8243* (2013.01); *C12N 15/825* (2013.01); *C12P 7/42* (2013.01); *C12P 17/06* (2013.01); *C12P 19/44* (2013.01); *C12Y 106/02004* (2013.01); *C12Y 114/11009* (2013.01); *C12Y 114/13021* (2013.01)

(58) Field of Classification Search

CPC ...... C12N 1/20; C12N 9/1029; C12N 9/1085; C12N 9/93; C12N 15/04; C12N 15/52; C12N 15/70; C12N 15/8243; C12P 7/42

See application file for complete search history.

(56) References Cited

U.S. PATENT DOCUMENTS

| | | | | |
|---|---|---|---|---|
| 6,524,842 | B1 | 2/2003 | Vainberg et al. | |
| 10,287,566 | B2 | 5/2019 | Kelly et al. | |
| 2005/0277179 | A1 | 12/2005 | Takai et al. | |
| 2009/0239272 | A1 | 9/2009 | Koffas et al. | |
| 2010/0081182 | A1 | 4/2010 | Paul et al. | |
| 2010/0129886 | A1 | 5/2010 | Anthony et al. | |
| 2012/0034661 | A1 | 2/2012 | Stephanopoulos et al. | |
| 2014/0273144 | A1 | 9/2014 | Hawkins et al. | |
| 2015/0044734 | A1 | 2/2015 | Juminaga et al. | |
| 2017/0121748 | A1 | 5/2017 | Koffas et al. | |
| 2017/0218405 | A1 | 8/2017 | Maggio-Hall et al. | |
| 2017/0226497 | A1 | 8/2017 | Kelly et al. | |
| 2017/0240932 | A1* | 8/2017 | Park | C12N 9/0008 |
| 2018/0252713 | A1 | 9/2018 | Weiss et al. | |
| 2019/0062768 | A1 | 2/2019 | Ibdah | |
| 2020/0080115 | A1 | 3/2020 | Clark et al. | |
| 2020/0165558 | A1 | 5/2020 | Shevitz | |
| 2020/0255881 | A1 | 8/2020 | Watkins et al. | |

FOREIGN PATENT DOCUMENTS

| | | | |
|---|---|---|---|
| EP | 3901256 | A1 | 10/2021 |
| WO | 2017/050853 | A1 | 3/2017 |
| WO | WO 2021108617 | A1 * | 7/2021 |

OTHER PUBLICATIONS

Whisstock et al. Quaterly Reviews of Biophysics, 2003, "Prediction of protein function from protein sequence and structure", 36(3): 307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Weatherly et al. (Expression and characterization of recombinant fungal acetyl-CoA carboxylase and isolation of a soraphen-binding domain. Biochem. J. (2004) 380: 105-110). (Year: 2004).*

Davis et al. (Overproduction of Acetyl-CoA Carboxylase Activity Increases the Rate of Fatty Acid Biosynthesis in *Escherichia coli.* JBC (2000), 275(37): 28593-28598. (Year: 2000).*

Cheng, 2014, Unraveling the mechanism underlying thhe Glycosylation and Methylation of Anthocyanins in Peach, Plant Physiology, 166:1044-1058.

(Continued)

*Primary Examiner* — Iqbal H Chowdhury

(74) *Attorney, Agent, or Firm* — Brown Rudnick LLP; Adam M. Schoen

(57) ABSTRACT

The invention is directed to methods involved in the production of flavonoids, anthocyanins and other organic compounds. The invention provides cells engineered for the production of flavonoids, anthocyanins and other organic compounds, where the engineered cells include one or more genetic modifications that increase flavonoid production by increasing metabolic flux to flavonoid precursors and/or reducing carbon losses resulting from the production of byproducts.

10 Claims, 5 Drawing Sheets

Specification includes a Sequence Listing.

(56) References Cited

OTHER PUBLICATIONS

Chuck, 2014, Liquid transport fuels from microbial yeasts—current and future perspectives, Biofuels, 5(3):293-311.
Clomburg, 2019, The isoprenoid alcohol pathway, a synthetic route for isoprenoid biosynthesis, PNAS, 116 (26):12810-12815.
Degenhardt, 2018, Evaluation of C-prenylating enzymes for the heterologous biosynthesis of cannabigerolic acid, Technical University Dortmund, 180 pages.
Dudley, 2017, Cell-free Biosynthess of Isoprenoids using *Escherichia coli* Crude Lysates, Nothwestern University, 280 pages.
Gao, 2015, An artificial enzymatic reaction cascade for a cell-free bio-system based on glycerol, Green Chemistry, 2 (17):804-807.
International Search Report and Written Opinion issued in International Application No. PCT/US2021/063992, date of mailing: Mar. 18, 2022, 9 pages.
International Search Report and Written Opinion issued in International Application No. PCT/US2021/064034, date of mailing: Mar. 10, 2022, 11 pages.
International Search Report and Written Opinion issued in International Application No. PCT/US2021/064049, date of mailing: Mar. 9, 2022, 8 pages.
International Search Report and Written Opinion issued in International Application No. PCT/US2022/023497, date of mailing: Aug. 17, 2022, 17 pages.
International Search Report and Written Opinion issued in International Application No. PCT/US2022/24591, date of mailing: Sep. 23, 2022, 26 pages.
Sutiono, 2020, Enabling the Direct Enzymatic Dehydration of D-Glycerate to Pyruvate as the Key Step in Synthetic Enzyme Cascades Used in the Cell-Free Production of Fine Chemicals, ACS Catal, 10(5):3110-3118.
Valliere, 2019, A cell-free platform for the prenylation of natural products and application to cannabinoid production. Nature Communications, 10(565), 9 pages.
Yan, 2005, Metabolic Engineering of Anthocyanin Biosynthesis in *Escherichia coli*, Applied and Environmental Microbiology, 71(7):3617-3623.
Amor, 2010, Biotransformation of Naringenin to Eriodictyol by *Saccharomyces cerevisiea* Functionally Expressing Flavonoid 3' Hydroxylase, Natural Product Communications, 5(12)1893-1898.
Banerjee, 2010, Improving enzymes for biomass conversion: A basic research perspective., Bioenerg. Res., 3:82-92.
Broun, 1998, Caralytic plasticity of fatty acid modification enzymes underlying chemical diversity of plant lipids, Science, 282:1315-1317.
Chica, 2005, Semi-rational approaches to engineering enzyme activity: combining the benefits of directed evolution and rational design, Curr. Opi. Biotechnol., 16:378-384.
Davis, 2000, Overproduction of Acetyl-CoA Carboxylase Activity Increases the Rate of Fatty Acid Biosynthesis in *Escherichia coli,* JBC, 275(37):28593-28598.
Devos, 2000, Practical limits of function pediction, Proteins: Structure, Function, and Genetics, 41:98-107.
Franceus, 2017, Correlated positions in protein evolution and engineering, J Ind Microbiol Biotechnol, 44:687-695.
Gosset, 2009, Production of aromatic compounds in bacteria, Curr Opin Biotechnol 20:651-658.
Gowrishankar, 1982, Regulation of Phenylalanine Biosynthesis in *Escherichia col.* K-12, J. Bacteriol, 150:1130-1137.
Guo, 2017, Mini-review: In vitro Metabolic Engineering for Biomanufacturing of High-value Products, Computational and Structural Biotechnology Journal, 15:161-167.
Kisselev, 2002, Polypeptide release factors in prokaryotes and eukaryotes: same function, different structure, Structure, 10:8-9.
Koma, 2020, Chromosome Engineering to Generate Plasmid-Free Phenylalanine- and Tyrosine-Overproducing *Escherichia coli* Strains, Appl Environ Microbiol, 86:e00525-20.
Leonard, 2006, Functional expression of a P450 flavonoid hydroxylase for the biosynthesis of plant-specific hydroxylated flavonols in *Escherichia coli,* Metabolic Engineering, 8:172-181.
Lutke-Eversloh, 2007, L-Tyrosine production by deregulated strains of *Escherichia coli,* Appl Microbiol Biotechnol., 75:103-110.
Pittard, 1991, TyrR protein of *Escherichia coli* and its role as repressor and activator, Mol Microbiol, 5:1585-1592.
Pittard, 2005, The TyrR regulon, Mol. Microbiol., 55(1):16-26.
Sanavia, 2020, Limitations and challenges in protein stability prediction upon genome variations: towards future applications in precision medicine, Computational and Structural Biotechnology Journal, 18:1968-1979.
Seffernick, 2001, Melamine deaminase and Atrazine chlorohydrolase: 98 percent identical but functionally different, J. Bacteriol., 183(8):2405-2410.
Seitz, 2006, Cloning, functional identification and sequence analysisof flavonoid 3'-hydroxylase and flavonoid 3',5'-hydroxylase cDNAs reveals independent evolution of flavonoid 3',5'-hydroxylase in the Asteraceae family, Plant Molecular Biology, 61:365-381.
Sen, 2007, Developments in directed evolution for enzyme functions, Appl. Biochem. Biotechnol., 143:212-223.
Uniprot, Accession No. A0A2X1IY66, 2020, www.unitprot.org, (Year: 2020).
Uniprot, Accession No. A0A377C6J5, 2020, www. uniprot. org (Year:2020).
Uniprot, Accession No. P0AB91, 2018, www.uniprot. org (Year: 2018).
Uniprot, Accession No. P39912, 2018, www.uniprot.org (Year: 2018).
Weatherly, 2004, Expression and characterization of recombinant fungal acetyl-CoA caboxylase and isolation of a soraphen-binding domain, Biochem J 380:105-110.
Whisstock, 2003, Prediction of protein function from protein sequence, Q. Rev. Biophysics., 36(3):307-340.
Witkowski, 1999, Conversion of a β-Ketoacyl Synthase to a Malonyl Decarboxylase by Replacement of the Active-Site Cysteine with Glutamine, Biochemistry, 38:11643-11650.
Xu, 2007, Cloning and molecular characterization of a funcational flavonoid 3'-hydroxylase gene from *Brassica napus,* Journal of Plant Physiology, 164:350-363.
Zhu, 2014, Efficient Synthese of Eriodictyol from L-Tyrosine in *Escherichia coli,* Applied and Evironmental Microbiology, 80(1):3072-3080.

* cited by examiner

The metabolic pathway of flavonoid and anthocyanin bioproduction

Structures of the flavonoid and anthocyanin molecules produced

HPLC spectra showing produced molecules

FLAVONOID AND ANTHOCYANIN BIOPRODUCTION USING MICROORGANISM HOSTS

I. RELATED APPLICATIONS

This application claims priority to U.S. Provisional Application No. 63/174,403, filed on Apr. 13, 2021. The content of U.S. Provisional Application No. 63/174,403 is hereby incorporated by reference in its entirety.

II. SEQUENCE LISTING

This application contains a sequence listing filed in electronic form as an ASCII.txt file entitled DEBU-009-02-US-Sequence-Listing.txt, created on Mar. 21, 2022, last modified Apr. 13, 2022, and having a size of 448 KB. The content of the sequence listing is incorporated herein its entirety.

III. FIELD OF THE INVENTION

The invention related to materials (including engineered cells and cell lines) and methods involved in the production of flavonoids, anthocyanins and other organic compounds.

IV. BACKGROUND OF THE INVENTION

Flavonoids and anthocyanins are natural products produced in plants that find a variety of roles such as antioxidants, ultraviolet (UV) defense mechanisms, and colors. Over the past several years, the health benefits of flavonoids and anthocyanins have been widely demonstrated. These compounds are capable of scavenging radicals and can act as enzyme inhibitors and anti-inflammatory agents. With these recognized health and color benefits, much research has gone into understanding how these compounds are made in nature. Flavonoids and anthocyanins are synthesized from phenylpropanoid starter units and malonyl-Cofactor-A (malonyl-CoA) extender units that then undergo modifications to create many polyphenol compounds such as taxifolin, naringenin, and (+)-catechin. However, in most cases, these compounds are extracted or chemically manufactured.

V. SUMMARY OF THE INVENTION

To move away from agriculture and chemically derived products, we have created engineered cells for the bioproduction of flavonoids and anthocyanins. This approach provides a feasible route for the rapid, safe, economical, and sustainable production of a wide variety of important flavonoids.

Herein, a range of flavonoids and anthocyanins including naringenin, eriodictyol, taxifolin, dihydrokaempferol, (+)-catechin, cyanidin, and cyaninidin-3-glucoside are biomanufactured using a modified microbial host. Herein, the engineered cells include one or more genetic modifications that increase(s) flavonoid and anthocyanin bioproduction by increasing metabolic flux to flavonoid precursors and/or reducing carbon losses resulting from the production of byproducts.

Provided herein are cells engineered for the production of flavonoids, anthocyanins and other organic compounds, where the engineered cells include one or more genetic modifications that increase flavonoid production by increasing metabolic flux to flavonoid precursors and/or reducing carbon losses resulting from the production of byproducts. As nonlimiting examples, a genetic modification can be a modification for over-expressing or under-expressing one or more endogenous genes in the engineered host cell or can be a modification for expressing one or more non-native genes in the engineered host cell. Engineered cells as provided herein can include multiple genetic modifications.

Also provided are cell cultures for producing one or more flavonoids or anthocyanins. The cell cultures include engineered cells as disclosed herein in a culture medium that includes a carbon source that can also be an energy source, such as glycerol, sugar, or an organic acid. In various embodiments, the culture medium can include at least one feed molecule such as but not limited to one or more organic acids or amino acids that can be converted into a flavonoid precursor (such as tyrosine, p-coumaroyl-CoA or malonyl-CoA). Examples of feed molecules include, but are not limited to, acetate, malonate, tyrosine, phenylalanine, pantothenate, coumarate, etc. In some embodiments, the feed molecules may be of reduced or low purity. For example, glycerol as a feed molecule may be crude glycerol, including a biomass comprising glycerol, for example, glycerol obtained as a byproduct of biodiesel processing. Alternatively, or in addition, the culture medium can include a supplemental compound that can be a cofactor or a precursor of a cofactor used by an enzyme that functions in a flavonoid pathway, such as, for examples, bicarbonate, biotin, thiamine, pantothenate, alpha-ketoglutarate, ascorbate, or 5-aminolevulinic acid.

Further provided are methods for producing flavonoids and anthocyanins that include culturing a cell engineered for the production of flavonoids or anthocyanins as provided herein under conditions in which the cell produces flavonoids or anthocyanins. In some examples, the methods include culturing the engineered cells in a culture medium that includes at least one feed molecule or supplement such as but not limited to: tyrosine, phenylalanine, malonate, p-coumarate, bicarbonate, acetate, pantothenate, biotin, thiamine, alpha-ketoglutarate, ascorbate, and 5-aminolevulinic acid. The methods can further include recovering at least one of the flavonoids from culture medium, whole culture, or the cells.

In a first aspect, provided herein are cells engineered to produce one or more flavonoids or anthocyanins, wherein the cells include, in addition to nucleic acid sequences encoding either tyrosine ammonia lyase activity and/or phenylalanine ammonia lyase activity and cinnamate-4-hydroxylase activity, 4-coumarate-CoA ligase activity, chalcone synthase activity, chalcone isomerase activity, flavanone-3-hydroxylase activity, flavonoid 3'-hydroxylase activity or flavonoid 3'5'-hydroxylase activity, cytochrome P450 reductase activity, leucoanthocyanidin reductase activity, and dihydroflavonol-4-reductase activity, one or more genetic modifications for improving production of the flavonoids or anthocyanins. As set forth herein, a cell that is engineered to produce one or more of the flavonoids is engineered to include an exogenous nucleic acid sequence encoding tyrosine ammonia lyase activity that can form 4-coumaric acid using tyrosine as substrate (e.g., tyrosine ammonia lyase TAL, EC: 4.3.1.25) or, alternatively or in addition, an exogenous nucleic acid sequence encoding phenylalanine ammonia lyase activity that can convert phenylalanine to trans-cinnamic acid and an exogenous nucleic acid sequence encoding cinnamate-4-hydroxylase activity that forms 4-coumaric acid from trans-cinnamic acid, an exogenous nucleic acid sequence encoding CoA ligase activity that forms p-coumaroyl-CoA from coumaric acid (e.g., 4-coumarate-CoA ligase, 4CL, EC:6.2.1.12), an exogenous nucleic acid sequence encoding polyketide synthase activity that forms naringenin chalcone using malonyl-CoA and p-coumaroyl-CoA as substrates (e.g., chalcone synthase, CHS, EC:2.3.1.74), an exogenous nucleic acid sequence encoding chalcone isomerase activity that forms naringenin from naringenin chalcone via its cyclase activity (e.g., chalcone-flavonone isomerase, CHI, EC:5.5.1.6), an exogenous nucleic acid sequence encoding flavanone-3-hydroxylase activity that forms dihydrokaempferol from naringenin or forms taxifolin from eriodictyol (e.g., naringenin 3-dioxygenase, F3H, EC: 1.14.11.9), an exogenous nucleic acid sequence encoding flavonoid 3'-hydroxylase or flavonoid 3'5'-hydroxylase activity coupled with an exogenous nucleic acid sequence encoding cytochrome P450 reductase activity to form taxifolin or dihydromyricetin from dihydrokaempferol or to form eriodictyol or pentahydroxyflavone from naringenin (e.g., flavonoid 3'-monooxygenase, F3'H, EC: 1.14.13.21, EC: 1.14.14.82; cytochrome P450/NADPH-P450 reductase, EC:1.14.14.1; F3'5'H, EC:1.14.14.81), an exogenous nucleic acid sequence encoding dihydroflavonol-4-reductase activity that forms leucocyanidin from taxifolin, leucodelphinidin from dihydromyricetin, or leucopelargonidin from dihydrokaempferol (e.g., dihydroflavonol 4-reductase, EC:1.1.1), and an exogenous nucleic acid sequence encoding leucoanthocyanidin reductase activity that forms catechin from leucocyanidin (e.g., leucoanthocyanidin reductase, LAR, EC:1.17.1.3). Optionally, a cell that is engineered to produce anthocyanins is further engineered to include an exogenous nucleic acid sequence encoding anthocyanin synthase activity that forms cyanidin from catechin or leucocyanidin, forms delphinidin from leucodelphinidin, or forms pelargonidin from leucopelargonidin (e.g., anthocyanin synthase, ANS, EC:1.14.20.4) and to include an exogenous nucleic acid sequence encoding glucosyltransferase activity that forms cyanidin-3-O-beta-D-glucoside from cyanidin, delphinidin-3-O-beta-D-glucoside from delphinidin, or pelagonidin-3-O-beta-D-glucoside from pelagonidin (e.g., anthocyanidin 3-O-glucosyltransferase, 3GT, EC:2.4.1.115). The cells provided herein that are engineered to produce flavonoids or anthocyanins are further engineered to increase the production of flavonoids or anthocyanins product, for example by increasing metabolic flux to a flavonoid or anthocyanin pathway, or by decreasing byproduct formation.

A cell engineered to produce a flavonoid is further engineered to increase the supply of precursor malonyl-CoA. One strategy for increasing malonyl-CoA includes increasing acetyl-CoA carboxylase (ACC) activity. In various embodiments, the ACC enzyme, which in most eukaryotes, including fungi, is a large single chain polypeptide, and in plant and bacteria such as *E. coli* is a multi-subunit enzyme, is overexpressed in the host strain. Examples of acetyl-CoA carboxylase that can be expressed in a host cell engineered to produce a flavonoid or anthocyanin include, without limitation, the ACC genes of *Mucor circinelloides, Rhodotorula toruloides, Lipomyces starkeyi, Ustilago maydis*, and orthologs of these ACCs in other species having at least 50% amino acid identity to these ACCs.

Additional strategies for increasing malonyl-CoA include increasing acetyl-CoA, which is converted to malonyl-CoA by acetyl-CoA carboxylase (ACC). In some embodiments, acetyl-CoA synthase (ACS) that converts acetate and CoA to acetyl-CoA is over-expressed in the host cells. Cultures of engineered host cells that include overexpressed nucleic acid sequence encoding ACS can optionally include acetate in the culture medium. Examples of acetyl-CoA synthase that can be expressed in a host cell engineered to produce a flavonoid or anthocyanin include, without limitation, the ACS gene of *E. coli*, the ACS of *Salmonella typhimurium*, orthologs of these ACSs in other species having at least 50% amino acid identity to these ACSs.

Also considered, in further embodiments, is an engineered host cell that overexpresses a gene encoding pyruvate dehydrogenase (PDH), which converts pyruvate to acetyl-CoA. Further, in *E. coli*, a variant of the Lpd subunit of PDH can be expressed that includes a mutation (E354K) that reduces inhibition of PDH by NADH.

Alternatively, or in addition to strategies for increasing ACC activity and strategies for increasing acetyl-CoA, strategies for increasing malonyl-CoA by mechanisms that do not rely on the activity of an ACC can be employed. In some embodiments, a cell engineered to produce a flavonoid, or an anthocyanin, is further engineered to increase the cell's supply of malonyl-CoA includes an exogenous nucleic acid sequence encoding a malonyl-CoA synthetase that generates malonyl-CoA from malonate. Examples of malonyl-CoA synthetases include the malonyl-CoA synthetases of *Streptomyces coelicolor, Rhodopseudomonas palustris*, or a malonyl-CoA synthetase having at least 50% identity to any of these or other naturally occurring malonyl-CoA synthetases. Malonate can optionally be added to the culture medium of a culture that includes a cell engineered to express a malonyl-CoA synthetase. An engineered cell that includes an exogenous gene encoding a malonyl-CoA synthetase can also include an exogenous nucleic acid sequence encoding a malonate transporter, such as a malonate transporter encoded by a matC gene, for example, of *Streptomyces coelicolor*, or a malonate transporter encoded by DctPQM of *Sinorhizobium medicae*.

In additional embodiments, a cell engineered to produce a flavonoid or an anthocyanin is further engineered to include an exogenous nucleic acid sequence encoding malonate CoA-transferase that makes malonyl-CoA by direct transfer of the CoA from acetyl-CoA. Examples of malonate CoA-transferase that can be expressed in an engineered cell as provided herein include, without limitation, the alpha subunit (mdcA) of malonate decarboxylase from *Acinetobacter calcoaceticus, Geobacillus* sp, or a transferase having at least 50% identity to any of these or other naturally occurring malonate CoA-transferases.

In some embodiments, a cell engineered to produce flavonoids or anthocyanins is further engineered to increase the supply of coenzyme A (CoA) to increase its availability for producing acetyl-CoA, malonyl-CoA, and/or p-coumaroyl-CoA. Strategies for increasing CoA supply include upregulating endogenous pantothenate kinase (PanK) (EC: 2.7.1.33) that produces CoA from pantothenate. Alternatively, or in addition, a host cell can be engineered to include a nucleic acid sequence encoding type III pantothenate kinase that is not feedback inhibited by coenzyme A, such as CoaX gene of *Pseudomonas aeruginosa* (EC:2.7.1.33). Cultures of cells engineered for the production of flavonoids or anthocyanins can in some embodiments include a medium that includes pantothenate, a precursor of CoA biosynthesis, and can optionally also include cysteine, used in the CoA biosynthesis.

Additional strategies to increase malonyl-CoA flux to the flavonoid pathway include mutation or downregulation of one or more genes that function in fatty acid biosynthesis. Without limiting the embodiments to any particular mechanism, limiting fatty acid biosynthesis can increase the malonyl-CoA supply available for flavonoid biosynthesis. In some embodiments, the gene beta-ketoacyl-ACP synthase II (*E. coli* fabF) can be disrupted to reduce fatty acid biosynthesis. Another example of a fatty acid biosynthesis gene of a host cell that may be mutated or downregulated is a gene encoding malonyl-CoA-ACP transacylase (*E. coli* fabD). Other fatty acid biosynthesis genes of the engineered host cell that can be downregulated include a beta-ketoacyl-ACP synthase I enzyme (*E. coli* fabB) and acyl carrier protein (*E. coli* acpP).

Additional genetic modifications that may be present in a host cell engineered to produce flavonoids or anthocyanins include downregulation, disruption, or deletion of genes encoding alcohol dehydrogenase, lactate dehydrogenase, pyruvate oxidase, acetyl phosphate transferase and acetate kinase. In an *E. coli* host cell, genes that are downregulated, disrupted, or deleted can include aldehyde-alcohol dehydrogenase (adhE), lactate dehydrogenase (ldhA), pyruvate oxidase (poxB), and enzyme acetate kinase phosphate acetyltransferase (ackA-pta).

Further, a cell engineered for the production of flavonoids or anthocyanins can have one or more genes encoding thioesterases downregulated, disrupted, or deleted to prevent hydrolysis of precursors malonyl-CoA, actetyl-CoA, and/or p-coumaryol-CoA. For example, in an *E. coli* host one or more of the thioesterase genes tesA, tesB, yciA, and ybgC can be downregulated, disrupted, or deleted.

Alternatively, or in addition, genes encoding enzymes of the tricarboxylic acid cycle (TCA), such as succinate dehydrogenase, can be disrupted or downregulated to increase alpha-ketoglutarate supply which serves as a cofactor for one or more of the flavonoid and anthocyanin pathway enzymes. Other TCA enzymes that can be downregulated include citrate synthase that converts acetyl-CoA to citrate.

Also considered, in further embodiments, is an engineered host cell for the production of flavonoids or anthocyanins to upregulate the endogenous biosynthesis of amino acid tyrosine. Tyrosine is one of the precursors for the flavonoid biosynthesis and its conversion to coumaric acid is the first committed step of the pathway. L-tyrosine is one of the three aromatic amino acids derived from the shikimate pathway. The initial step of the shikimate pathway is catalyzed by DAHP synthase isozymes and regulated through feedback-inhibition. Strategies to increase tyrosine production can include, without limitation, transcriptional deregulation, removing feedback inhibition, overexpression of rate-limiting enzymes, and/or deletion of the L-phenylalanine branch of the aromatic acid biosynthetic pathway. For example, in an *E. coli* host the tyrR gene can be disrupted, feedback-inhibition-resistant versions of the DAHP synthase (aroG) and chorismate mutase (tyrA) can be introduced, and/or rate-limiting enzymes, shikimate kinase (aroK or aroL) and quinate (QUIN)/shikimate dehydrogenase (ydiB) can be overexpressed. Further, the Phosphoenolpyruvate synthase (ppsA) and transketolase (tktA) can be exogenously introduced to enhance tyrosine production.

Also considered, in further embodiments, is an engineered host cell for the production of flavonoids or anthocyanins further engineered to upregulate the endogenous biosynthesis of cofactor heme. Cytochrome P450 (CYPs), one of the exogenous genes in the engineered cells provided herein, contain heme as a cofactor. Improving heme supply can be an effective strategy to increase flavonoid biosynthesis. 5-aminolevulinic acid (ALA) is the first committed precursor to the heme pathway. Strategies to increase heme supply include overexpression of the genes that synthesize the precursor ALA. In an *E. coli* host, ALA is formed from the 5-carbon skeleton of glutamate (the C5 pathway). The three enzymes involved in ALA biosynthesis are glutamyl-tRNA synthetase (gltX), glutamyl-tRNA reductase (hemA), and glutamate-1-semialdehyde aminotransferase (hemL). In an *E. coli* host, the engineered cells provided herein can be further engineered to express or overexpress hemA or its variants, and/or hemL to increase the heme precursor ALA production. The nonlimiting examples of hemA gene that can be overexpressed include a mutated hemA (inserting two lysine residuals between Thr-2 and Leu-3 at N terminus of hemA gene from *Salmonella typhimurium* (EC:1.1.1.70). Alternatively, or in addition, a heterologous ALAS gene can be introduced to produce ALA via the C4 pathway (ALS is synthesized by the condensation of glycine and succinyl-CoA). Nonlimiting examples of heterologous ALAS that can be expressed in *E. coli* include ALAS of *Bradyrhizobium japonicum* (EC: 2.3.1.37), ALAS of *Rhodobacter capsulatus*, or an ALAS having at least 50% sequence identity to a naturally occurring ALAS. Further, one or more of the downstream genes (e.g., in *E. coli* hemB, hemC, hemD, hemE, hemF, hemG, hemL, or hemH) that catalyze the synthesis of heme from ALA can be overexpressed to drive the flux from ALA to heme production. Cultures of cells engineered for the production of flavonoids or anthocyanins can in some embodiments include a medium that includes succinate and/or glycine, precursors of heme biosynthesis via the C4 pathway.

In another aspect, provided herein are cell cultures that include engineered cells as provided herein in a culture medium, where the culture medium includes a carbon source that is also an energy source for the cells, where the carbon source can be, for example, glycerol, a sugar, or an organic acid, as nonlimiting examples. The culture medium can further include a feed molecule that is used to produce flavonoids or anthocyanins. A feed molecule can be, for example, acetate, malonate, tyrosine, pantothenate, coumarate, biotin, alpha-ketoglutarate, ascorbate, 5-aminolevulinic acid, succinate, or glycine. In some embodiments, the culture comprises a culture medium that includes a carbon source and at least one supplement that is a cofactor of an enzyme or is a precursor of an enzyme cofactor.

In yet another aspect, methods for producing flavonoids and anthocyanins that include incubating a culture of engineered host cell as provided herein to produce flavonoids or anthocyanins. The methods can further include recovering at least one of the flavonoids from the cells, the culture medium, or the whole culture.

In yet another aspect, the invention provides an engineered host cell that comprises one or more genetic modifications resulting in production of flavonoid or anthocyanin from a carbon source that can also be an energy source, through multiple chemical intermediates, by the engineered host cell. In certain embodiments, the production of flavonoid or anthocyanin from glycerol occurs through enzymatic transformation. In certain embodiments, the production of flavonoid or anthocyanin from a carbon source that can also be an energy source occurs through enzymatic transformation. In certain embodiments, the carbon source is selected from a group consisting of: (i) glycerol, (ii) a sugar, (iii) an organic acid, (iv) an amino acid, (v) a biomass comprising glycerol; and (vi) any combination thereof. In certain embodiments, the engineered host cell is cultured in a medium comprising molecules selected from a group consisting of: (i) glycerol, (ii) a sugar, (iii) an organic acid, (iv) an amino acid, (v) a biomass comprising glycerol; and (vi) any combination thereof. In certain embodiments, one or more genetic modifications lead to increase metabolic flux to flavonoid precursors or cofactors. In certain embodiments, one or more genetic modifications cause reduction of formation of byproducts. In certain embodiments, one or more genetic modifications are selected from: (i) one or more modifications for over-expressing one or more endogenous genes in the engineered host cells; (ii) one or more modifications for under-expressing one or more endogenous genes in the engineered host cells; (iii) one or more genetic modification is expressing one or more non-native genes in the engineered host cells; and (iv) a combination thereof. In certain embodiments, the engineered host cell is cultured in a medium comprising molecules selected from: tyrosine, phenylalanine, malonate, p-coumarate, bicarbonate, acetate, pantothenate, biotin, thiamine, alpha-ketoglutarate, ascorbate, and 5-aminolevulinic acid, wherein one or more of the selected molecules are the chemical intermediates, including molecules in the biosynthesis pathway or cofactors. In certain embodiments, the engineered host cell comprises at least one or more nucleic acid sequences selected from: (i) nucleic acid sequences encoding tyrosine ammonia lyase activity; (ii) nucleic acid sequences encoding phenylalanine ammonia lyase activity; (iii) nucleic acid sequences encoding cinnamate 4-hydroxylase activity; (iv) nucleic acid sequences encoding 4-courmarate-CoA ligase (4CL) activity; and (v) any combination thereof. In certain embodiments, the engineered host cell comprises at least one or more peptides selected from: (i) chalcone isomerase; (ii) chalcone synthase; (iii) a fusion protein comprises a chalcone synthase and a chalcone isomerase; and (iv) any combination thereof. In certain embodiments, the engineered cell is *E. coli*. In certain embodiments, one or more genetic modifications decreases fatty acid biosynthesis. In certain embodiments, the engineered host cell comprises an exogenous nucleic acid sequence selected from: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding flavanone-3-hydroxylase, wherein flavanone-3-hydroxylase forms dihydrokaempferol from naringenin; and (v) any combinations thereof. In certain embodiments, the engineered host cell comprises an exogenous nucleic acid sequence selected from the group consisting of: (i) nucleic acid sequences encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding 4-courmarate-CoA ligase activity, wherein 4-courmarate-CoA ligase forms p-coumaroyl-CoA from coumaric acid (v) nucleic acid sequence encoding chalcone synthase activity, wherein chalcone synthase forms naringenin chalcone from malonyl-CoA and p-coumaroyl-CoA; (vi) nucleic acid sequence encoding chalcone isomerase activity, wherein chalcone isomerase forms naringenin from naringenin chalcone; (vii) nucleic acid sequence encoding flavanone-3-hydroxylase, wherein flavanone-3-hydroxylase forms dihydrokaempferol from naringenin; and (viii) any combinations thereof. In certain embodiments, the flavonoid is catechin.

In yet another aspect, the invention provides a method of increasing the production of flavonoids or anthocyanins, the method comprising: providing an engineered host cell that comprises one or more genetic modifications resulting in production of flavonoid or anthocyanin from a carbon source that can also be an energy source, through multiple chemical intermediates, by the engineered host cell. In certain embodiments, the production of flavonoid or anthocyanin from a carbon source that can also be an energy source occurs through enzymatic transformation. In certain embodiments, the carbon source is selected from a group consisting of: (i) glycerol, (ii) a sugar, (iii) an organic acid, (iv) an amino acid, (v) a biomass comprising glycerol; and (vi) any combination thereof. In certain embodiments, the engineered host cell is cultured in a medium comprising molecules selected from a group consisting of: (i) glycerol, (ii) a sugar, (iii) an organic acid, (iv) an amino acid, (v) a biomass comprising glycerol; and (vi) any combination thereof. In certain embodiments, one or more genetic modifications lead to increase metabolic flux to flavonoid precursors or cofactors. In certain embodiments, one or more genetic modifications cause increased metabolic flux to flavonoid precursors. In certain embodiments, one or more genetic modifications cause reduction in the formation of byproducts. In certain embodiments, one or more genetic modifications are selected from: (i) one or more modifications for over-expressing one or more endogenous genes in the engineered host cells; (ii) one or more modifications for under-expressing one or more endogenous genes in the engineered host cells; (iii) one or more genetic modification is expressing one or more non-native genes in the engineered host cells; and (iv) a combination thereof. In certain embodiments, the engineered host cell is cultured in a medium comprising molecules selected from: tyrosine, phenylalanine, malonate, p-coumarate, bicarbonate, acetate, pantothenate, biotin, thiamine, alpha-ketoglutarate, ascorbate, and 5-aminolevulinic acid, wherein one or more of the selected molecules are the chemical intermediates, including molecules in the biosynthesis pathway or cofactors. In certain embodiments, the engineered host cell comprises at least one or more nucleic acid sequences selected from: (i) a nucleic acid sequences encoding tyrosine ammonia lyase activity; (ii) a nucleic acid sequences encoding phenylalanine ammonia lyase activity; (iii) cinnamate 4-hydroxylase; and (iv) any combination thereof. In certain embodiments, the engineered host cell comprises at least one or more peptides selected from: (i) chalcone isomerase; (ii) chalcone synthase; (iii) a fusion protein comprises a chalcone synthase and a chalcone isomerase; and (iv) any combination thereof. In certain embodiments, the engineered cell is *E. coli*. In certain embodiments, one or more genetic modifications decreases fatty acid biosynthesis. In certain embodiments, the engineered host cell comprises an exogenous nucleic acid sequence selected from: (i) nucleic acid sequences encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding flavanone-3-hydroxylase, wherein flavanone-3-hydroxylase forms dihydrokaempferol from naringenin; and (v) any combinations thereof. In certain embodiments, the engineered host cell comprises an exogenous nucleic acid sequence selected from the group consisting of: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding 4-courmarate-CoA ligase activity, wherein 4-courmarate-CoA ligase forms p-coumaroyl-CoA from coumaric acid (v) nucleic acid sequence encoding chalcone synthase activity, wherein chalcone synthase forms naringenin chalcone from malonyl-CoA and p-coumaroyl-CoA; (vi) nucleic acid sequence encoding chalcone isomerase activity, wherein chalcone isomerase forms naringenin from naringenin chalcone; (vii) nucleic acid sequence encoding flavanone-3-hydroxylase, wherein flavanone-3-hydroxylase forms dihydrokaempferol from naringenin; and (viii) any combinations thereof. In certain embodiments, the flavonoid is catechin.

In yet another aspect, the invention provides a plurality of engineered host cells, wherein each of the plurality of the engineered host cells comprises one or more genetic modifications resulting in production of flavonoid or anthocyanin from a carbon source that can also be an energy source, through multiple chemical intermediates. In certain embodiments, the production of flavonoid or anthocyanin from a carbon source that can also be an energy source occurs through enzymatic transformation. In certain embodiments, the carbon source is selected from a group consisting of: (i) glycerol, (ii) a sugar, (iii) an organic acid, (iv) an amino acid, (v) a biomass comprising glycerol; and (vi) any combination thereof. In certain embodiments, the engineered host cell is cultured in a medium comprising molecules selected from a group consisting of: (i) glycerol, (ii) a sugar, (iii) an organic acid, (iv) an amino acid, (v) a biomass comprising glycerol; and (vi) any combination thereof. In certain embodiments, one or more genetic modifications lead to increase metabolic flux to flavonoid precursors or cofactors. In certain embodiments, one or more genetic modifications lead to increase metabolic flux to flavonoid precursors or cofactors. In certain embodiments, one or more genetic modifications cause reduction of formation of byproducts. In certain embodiments, one or more genetic modifications are selected from: (i) one or more modifications for over-expressing one or more endogenous genes in the engineered host cells; (ii) one or more modifications for under-expressing one or more endogenous genes in the engineered host cells; (iii) one or more genetic modification is expressing one or more non-native genes in the engineered host cells; and (iv) a combination thereof. In certain embodiments, at least one of the engineered cells from the plurality of the engineered host cells is cultured in a medium comprising molecules selected from: tyrosine, phenylalanine, malonate, p-coumarate, bicarbonate, acetate, pantothenate, biotin, thiamine, alpha-ketoglutarate, ascorbate, and 5-aminolevulinic acid, wherein one or more of the selected molecules are the chemical intermediates, including molecules in biosynthesis pathway or cofactors. In certain embodiments, at least one of the engineered cells from the plurality of the engineered host cells comprise at least one or more nucleic acid sequences selected from: (i) nucleic acid sequences encoding tyrosine ammonia lyase activity; (ii) nucleic acid sequences encoding phenylalanine ammonia lyase activity; (iii) nucleic acid sequences encoding cinnamate 4-hydroxylase activity; (iv) nucleic acid sequences encoding 4-courmarate-CoA ligase (4CL) activity; and (v) any combination thereof. In certain embodiments, at least one of the engineered host cell from the plurality of engineered host cells comprise at least one or more peptides selected from: (i) chalcone isomerase; (ii) chalcone synthase; (iii) a fusion protein comprises a chalcone synthase and a chalcone isomerase; and (iv) any combination thereof. In certain embodiments, at least one the engineered host cell is *E. coli*. In certain embodiments, one or more genetic modifications decreases fatty acid biosynthesis. In certain embodiments, at least one of the engineered host cell from the plurality of the engineered host cells comprises an exogenous nucleic acid sequence selected from: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding flavanone-3-hydroxylase, wherein flavanone-3-hydroxylase forms dihydrokaempferol from naringenin; and (v) any combinations thereof. In certain embodiments, the engineered host cell comprises an exogenous nucleic acid sequence selected from the group consisting of: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding 4-courmarate-CoA ligase activity, wherein 4-courmarate-CoA ligase forms p-coumaroyl-CoA from coumaric acid (v) nucleic acid sequence encoding chalcone synthase activity, wherein chalcone synthase forms naringenin chalcone from malonyl-CoA and p-coumaroyl-CoA; (vi) nucleic acid sequence encoding chalcone isomerase activity, wherein chalcone isomerase forms naringenin from naringenin chalcone; (vii) nucleic acid sequence encoding flavanone-3-hydroxylase, wherein flavanone-3-hydroxylase forms dihydrokaempferol from naringenin; and (viii) any combinations thereof. In certain embodiments, the flavonoid is catechin.

In yet another aspect, the invention provides a method of increasing the production of flavonoids or anthocyanins, the method comprising: providing a plurality of engineered host cells, wherein each of the plurality of the engineered host cell comprises one or more genetic modifications resulting production of flavonoid or anthocyanin from a carbon source that can also be an energy source, through multiple chemical intermediates, by the engineered host cell. In certain embodiments, the production of flavonoid or anthocyanin from a carbon source that can also be an energy source occurs through enzymatic transformation. In certain embodiments, the carbon source is selected from a group consisting of: (i) glycerol, (ii) a sugar, (iii) an organic acid, (iv) an amino acid, (v) a biomass comprising glycerol; and (vi) any combination thereof. In certain embodiments, the engineered host cell is cultured in a medium comprising molecules selected from a group consisting of: (i) glycerol, (ii) a sugar, (iii) an organic acid, (iv) an amino acid, (v) a biomass comprising glycerol; and (vi) any combination thereof. In certain embodiments, one or more genetic modifications lead to increase metabolic flux to flavonoid precursors or cofactors. In certain embodiments, one or more genetic modifications lead to increase metabolic flux to flavonoid precursors or cofactors. In certain embodiments, one or more genetic modifications cause reduction of formation of byproducts. In certain embodiments, one or more genetic modifications are selected from: (i) one or more modifications for over-expressing one or more endogenous genes in the engineered host cells; (ii) one or more modifications for under-expressing one or more endogenous genes in the engineered host cells; (iii) one or more genetic modification is expressing one or more non-native genes in the engineered host cells; and (iv) a combination thereof. In certain embodiments, at least one of the engineered cells from the plurality of the engineered host cells is cultured in a medium comprising molecules selected from: tyrosine, phenylalanine, malonate, p-coumarate, bicarbonate, acetate, pantothenate, biotin, thiamine, alpha-ketoglutarate, ascorbate, and 5-aminolevulinic acid, wherein one or more of the selected molecules are the chemical intermediates, including molecules in biosynthesis pathway or cofactors. In certain embodiments, at least one of the engineered cells from the plurality of the engineered host cells comprise at least one or more nucleic acid sequences selected from: (i) nucleic acid sequences encoding tyrosine ammonia lyase activity; (ii) nucleic acid sequences encoding phenylalanine ammonia lyase activity; (iii) nucleic acid sequences encoding cinnamate 4-hydroxylase activity; (iv) nucleic acid sequences encoding 4-courmarate-CoA ligase (4CL) activity; and (v) any combination thereof. In certain embodiments, at least one of the engineered host cell from the plurality of engineered host cells comprise at least one or more peptides selected from: (i) chalcone isomerase; (ii) chalcone synthase; (iii) a fusion protein comprises a chalcone synthase and a chalcone isomerase; and (iv) any combination thereof. In certain embodiments, at least one the engineered host cell is *E. coli*. In certain embodiments, one or more genetic modifications decreases fatty acid biosynthesis. In certain embodiments, at least one of the engineered host cell from the plurality of the engineered host cells comprises an exogenous nucleic acid sequence selected from: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding flavanone-3-hydroxylase, wherein flavanone-3-hydroxylase forms dihydrokaempferol from naringenin; and (v) any combinations thereof. In certain embodiments, the engineered host cell comprises an exogenous nucleic acid sequence selected from the group consisting of: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding 4-courmarate-CoA ligase activity, wherein 4-courmarate-CoA ligase forms p-coumaroyl-CoA from coumaric acid (v) nucleic acid sequence encoding chalcone synthase activity, wherein chalcone synthase forms naringenin chalcone from malonyl-CoA and p-coumaroyl-CoA; (vi) nucleic acid sequence encoding chalcone isomerase activity, wherein chalcone isomerase forms naringenin from naringenin chalcone; (vii) nucleic acid sequence encoding flavanone-3-hydroxylase, wherein flavanone-3-hydroxylase forms dihydrokaempferol from naringenin; and (viii) any combinations thereof. In certain embodiments, the flavonoid is catechin.

In yet another aspect, the engineered host cell comprises one or more genetic modifications to increase the production and/or availability of malonyl-CoA. In certain embodiments, the production and/or availability of malonyl-CoA is increased by transformation of acetyl-CoA to malonyl-CoA. In certain embodiments, the engineered host cell comprises one or more genetic modifications selected from: (i) expression of acetyl-CoA carboxylase (ACC); and (ii) overexpression of acetyl-CoA carboxylase. In another embodiment, the engineered host cell is an *E. coli*. In certain embodiments, the *E. coli* cell further comprises genes from fungi. In certain embodiments, the acetyl-CoA carboxylase is from: *Mucor circinelloides, Rhodotorula toruloides, Lipomyces starkeyi*, and *Ustilago maydis*, and orthologs of acetyl-CoA carboxylase having at least 50% amino acid identity to the acetyl-CoA carboxylase of these aforementioned species. In certain embodiments, one or more genetic modification is deletion or attenuation of one or more fatty biosynthetic genes resulting in decrease in fatty acid biosynthesis. In certain embodiments, one or more genetic modification is overexpression of acetyl-CoA synthase (ACS). In certain embodiments, the acetyl-CoA synthase is selected from: acetyl-CoA synthase gene of *E. coli*, acetyl-CoA synthase gene of *Salmonella typhimurium*, and orthologs of acetyl-CoA synthase gene in any other species having at least 50% amino acid identity to the acetyl-CoA synthase gene of *E. coli* and *Salmonella typhimurium*. In certain embodiments, one or more genetic modification is selected from a group consisting of: (i) overexpression a gene encoding pyruvate dehydrogenase (PDH), wherein the PDH may include E354K mutation; (ii) exogenous nucleic acid sequence encoding a malonyl-CoA synthetase; (iii) upregulation of endogenous pantothenate kinase (PanK), wherein PanK is not feedback inhibited by coenzyme A; (iv) exogenous nucleic acid sequence encoding a malonate transporter; and (v) any combinations thereof. In certain embodiments, the malonyl-CoA synthetase is selected from of malonyl-CoA synthetases of *Streptomyces coelicolor, Rhodopseudomonas palustris*, or a malonyl-CoA synthetase having at least 50% identity to any of these or other naturally occurring malonyl-CoA synthetases. In certain embodiments, one or more genetic modifications to decrease fatty acid biosynthesis is selected from: (i) mutation or downregulation of a gene encoding malonyl-CoA-ACP transacylase (*E. coli* fabD); (ii) modifications to the gene beta-ketoacyl-ACP synthase II (*E. coli* fabF); (iii) downregulation of beta-ketoacyl-ACP synthase I enzyme (*E. coli* fabB); (iv) downregulation of acyl carrier protein (*E. coli* acpP); and (v) any combinations thereof. In certain embodiments, the engineered host cell comprises peptides selected from: (i) acetyl-CoA carboxylase (ACC) having an amino acid sequence at least 80% identical to the polypeptide set forth in SEQ ID NO: 15 or SEQ ID NO: 16; (ii) malonate CoA-transferase having an amino acid sequence at least 80% identical to the polypeptide set forth in SEQ ID NO: 19; (iii) acetyl-CoA synthase (ACS) having an amino acid sequence at least 80% identical to the polypeptide set forth in SEQ ID NO: 16; (iv) malonyl-CoA synthase having an amino acid sequence at least 80% identical SEQ ID NO: 77, SEQ ID NO: 78, or SEQ ID NO: 79; (v) malonate transporter having an amino acid sequence at least 80% identical to SEQ ID NO: 80, SEQ ID NO: 81, SEQ ID NO: 82, SEQ ID NO: 83, SEQ ID NO: 84, SEQ ID NO: 85, SEQ ID NO: 86, or SEQ ID NO: 87; (vi) pantothenate kinase having an amino acid sequence at least 80% identical to SEQ ID NO: 88, SEQ ID NO: 89, or SEQ ID NO: 90; and (vii) any combinations thereof.

In another aspect, the invention provides a method of increasing the production of flavonoids comprising an engineered host cell, wherein the one or more engineered host cells comprise one or more genetic modifications to increase the production and/or availability of malonyl-CoA. In certain embodiments, the production and/or availability of malonyl-CoA is increased by transformation of acetyl-CoA to malonyl-CoA. In certain embodiments, the engineered host cell comprises one or more genetic modifications selected from: (i) expression of acetyl-CoA carboxylase (ACC); and (ii) overexpression of acetyl-CoA carboxylase. In another embodiment, the engineered host cell is an *E. coli*. In certain embodiments, the *E. coli* cell further comprises genes from fungi. In certain embodiments, the acetyl-CoA carboxylase is from: *Mucor circinelloides, Rhodotorula toruloides, Lipomyces starkeyi*, and *Ustilago maydis*, and orthologs of acetyl-CoA carboxylase having at least 50% amino acid identity to the acetyl-CoA carboxylase of these aforementioned species. In certain embodiments, one or more genetic modification is deletion or attenuation of one or more fatty biosynthetic genes resulting in decrease in fatty acid biosynthesis. In certain embodiments, one or more genetic modification is overexpression of acetyl-CoA synthase (ACS). In certain embodiments, the acetyl-CoA synthase is selected from: acetyl-CoA synthase gene of *E. coli*, acetyl-CoA synthase gene of *Salmonella typhimurium*, and orthologs of acetyl-CoA synthase gene in any other species having at least 50% amino acid identity to the acetyl-CoA synthase gene of *E. coli* and *Salmonella typhimurium*. In certain embodiments, one or more genetic modification is selected from a group consisting of: (i) overexpression a gene encoding pyruvate dehydrogenase (PDH), wherein the PDH may include E354K mutation; (ii) exogenous nucleic acid sequence encoding a malonyl-CoA synthetase; (iii) upregulation of endogenous pantothenate kinase (PanK), wherein PanK is not feedback inhibited by coenzyme A; (iv) exogenous nucleic acid sequence encoding a malonate transporter; and (v) any combinations thereof. In certain embodiments, the malonyl-CoA synthetase is selected from of malonyl-CoA synthetases of *Streptomyces coelicolor, Rhodopseudomonas palustris*, or a malonyl-CoA synthetase having at least 50% identity to any of these or other naturally occurring malonyl-CoA synthetases. In certain embodiments, one or more genetic modifications to decrease fatty acid biosynthesis is selected from: (i) mutation or downregulation of a gene encoding malonyl-CoA-ACP transacylase (*E. coli* fabD); (ii) modifications to the gene beta-ketoacyl-ACP synthase II (*E. coli* fabF); (iii) downregulation of beta-ketoacyl-ACP synthase I enzyme (*E. coli* fabB); (iv) downregulation of acyl carrier protein (*E. coli* acpP); and (v) any combinations thereof. In certain embodiments, the engineered host cell comprises peptides selected from: (i) acetyl-CoA carboxylase (ACC) having an amino acid sequence at least 80% identical to the polypeptide set forth in SEQ ID NO: 15 or SEQ ID NO: 16; (ii) malonate CoA-transferase having an amino acid sequence at least 80% identical to the polypeptide set forth in SEQ ID NO: 19; (iii) acetyl-CoA synthase (ACS) having an amino acid sequence at least 80% identical to the polypeptide set forth in SEQ ID NO: 16; (iv) malonyl-CoA synthase having an amino acid sequence at least 80% identical SEQ ID NO: 77, SEQ ID NO: 78, or SEQ ID NO: 79; (v) malonate transporter having an amino acid sequence at least 80% identical to SEQ ID NO: 80, SEQ ID NO: 81, SEQ ID NO: 82, SEQ ID NO: 83, SEQ ID NO: 84, SEQ ID NO: 85, SEQ ID NO: 86, or SEQ ID NO: 87; (vi) pantothenate kinase having an amino acid sequence at least 80% identical to SEQ ID NO: 88, SEQ ID NO: 89, or SEQ ID NO: 90; and (vii) any combinations thereof.

In another aspect, the invention provides an engineered host cell, wherein the engineered host cell comprises one or more genetic modifications to increase endogenous biosynthesis of tyrosine. In certain embodiments, one or more genetic modifications comprises upregulation of 3-deoxy-D-arabino-heptulosonate synthase. In certain embodiments, one or more genetic modifications are selected from: (i) upregulation of chorismate mutase; (ii) upregulation of prephenate dehydrogenase; (iii) overexpression of shikimate kinase; (iv) overexpression of shikimate dehydrogenase; and (v) any combinations thereof. In certain embodiments, one or more genetic modifications comprises downregulation of L-phenylalanine biosynthetic pathway. In certain embodiments, one or more genetic modifications comprises expression of exogenous phosphoenolpyruvate synthase (ppsA). In certain embodiments, one or more genetic modifications comprises expression of exogenous transketolase (tktA). In certain embodiments, wherein the one or more genetic modifications comprises disruption of tyrR gene. In certain embodiments, one or more genetic modifications are selected from a group consisting of: (i) expression or overexpression of (D146N) variant of phospho-2-dehydro-3-deoxyheptonate aldolase; (ii) expression or overexpression of variant of 3-dehydroquinate synthase (aroB); (iii) overexpression of transketolase tktA; (iv) deletion of shikimate kinase (aroK); (v) deletion of tyrR; (vi) expression or overexpression of A354V variant of chorismate mutase (tyrA); (vi) and any combination thereof.

In another aspect, the invention provides a method of increasing endogenous biosynthesis of tyrosine comprising an engineered cell, wherein the engineered host cell comprises one or more genetic modifications to increase endogenous biosynthesis of tyrosine. In certain embodiments, one or more genetic modifications comprises upregulation of 3-deoxy-D-arabino-heptulosonate synthase. In certain embodiments, one or more genetic modifications are selected from: (i) upregulation of chorismate mutase; (ii) upregulation of prephenate dehydrogenase; (iii) overexpression of shikimate kinase; (iv) overexpression of shikimate dehydrogenase; and (v) any combinations thereof. In certain embodiments, one or more genetic modifications comprises downregulation of L-phenylalanine biosynthetic pathway. In certain embodiments, one or more genetic modifications comprises expression of exogenous phosphoenolpyruvate synthase (ppsA). In certain embodiments, one or more genetic modifications comprises expression of exogenous transketolase (tktA). In certain embodiments, wherein the one or more genetic modifications comprises disruption of tyrR gene. In certain embodiments, one or more genetic modifications are selected from a group consisting of: (i) expression or overexpression of (D146N) variant of phospho-2-dehydro-3-deoxyheptonate aldolase; (ii) expression or overexpression of variant of 3-dehydroquinate synthase (aroB); (iii) overexpression of transketolase tktA; (iv) deletion of shikimate kinase (aroK); (v) deletion of tyrR; (vi) expression or overexpression of A354V variant of chorismate mutase (tyrA); (vi) and any combination thereof.

In another aspect, the invention provides an engineered host cell, wherein the engineered host cell comprises one or more genetic modifications to increase transformation of leucocyanidin or catechin to cyanidin-3-glucoside (Cy3G). In certain embodiments, one or more genetic modifications comprises overexpression of anthocyanin synthase. In certain embodiments, the anthocyanin synthase is selected from: (i) anthocyanin synthase of *Carica papaya* (SEQ. ID NO:13); (ii) the anthocyanin synthase has an amino acid sequence at least 80% identical to SEQ. ID NO: 66, SEQ. ID NO: 67, SEQ. ID NO: 68, or SEQ. ID NO: 69; (iii) the anthocyanin synthase has an amino acid sequence at least 80% identical to SEQ. ID NO: 13; and (iv) any combinations thereof. In certain embodiments, one or more engineered host cells comprises flavonoid-3-glucosyl transferase (3GT). In certain embodiments, flavonoid-3-glucosyl transferase is selected from: (i) flavonoid-3-glucosyl transferase in *Vitis labrusca* (SEQ. ID NO:14); (ii) the flavonoid-3-glucosyl transferase has an amino acid sequence at least 80% identical to SEQ. ID NO: 70, SEQ. ID NO: 71, SEQ. ID NO: 72, or SEQ. ID NO: 73; and (iii) any combinations thereof. In certain embodiments, one or more genetic modifications comprises overexpression of anthocyanin synthase and flavonoid-3-glucosyl transferase (3GT). In certain embodiments, the one or more genetic modifications comprises overexpression of anthocyanin synthase and flavonoid-3-glucosyl transferase (3GT). In certain embodiments, the one or more genetic modifications are selected from a group consisting of: (i) anthocyanin synthase, (ii) flavonoid-3-glucosyl transferase (3GT), and (iii) a combination thereof.

In another aspect, the invention provides a method for increasing the production of flavonoids comprising an engineered host cell, wherein the engineered host cell comprises one or more genetic modifications to increase transformation of leucocyanidin or catechin to cyanidin-3-glucoside (Cy3G). In certain embodiments, one or more genetic modifications comprises overexpression of anthocyanin synthase. In certain embodiments, the anthocyanin synthase is selected from: (i) anthocyanin synthase of *Carica papaya* (SEQ. ID NO:13); (ii) the anthocyanin synthase has an amino acid sequence at least 80% identical to SEQ. ID NO: 66, SEQ. ID NO: 67, SEQ. ID NO: 68, or SEQ. ID NO: 69; (iii) the anthocyanin synthase has an amino acid sequence at least 80% identical to SEQ. ID NO: 13; and (iv) any combinations thereof. In certain embodiments, one or more engineered host cells comprises flavonoid-3-glucosyl transferase (3GT). In certain embodiments, flavonoid-3-glucosyl transferase is selected from: (i) flavonoid-3-glucosyl transferase in *Vitis labrusca* (SEQ. ID NO:14); (ii) the flavonoid-3-glucosyl transferase has an amino acid sequence at least 80% identical to SEQ. ID NO: 70, SEQ. ID NO: 71, SEQ. ID NO: 72, or SEQ. ID NO: 73; and (iii) any combinations thereof. In certain embodiments, one or more genetic modifications comprises overexpression of anthocyanin synthase and flavonoid-3-glucosyl transferase (3GT). In certain embodiments, the one or more genetic modifications comprises overexpression of anthocyanin synthase and flavonoid-3-glucosyl transferase (3GT). In certain embodiments, the one or more genetic modifications are selected from a group consisting of: (i) anthocyanin synthase, (ii) flavonoid-3-glucosyl transferase (3GT), and (iii) a combination thereof.

In another aspect, the invention provides a method of increasing the transformation of leucocyanidin or catechin to cyanidin-3-glucoside (Cy3G), delphinidin or gallocatechin to delphindin-3-glucoside (De3G), or afzelechin or pelargonidin to pelargonidin-3-glucoside (Pe3G) comprising anthocyanin synthase, wherein the anthocyanin synthase is selected from: (i) anthocyanin synthase of *Carica papaya* (SEQ. ID NO:13); (ii) the anthocyanin synthase has an amino acid sequence at least 80% identical to SEQ. ID NO: 66, SEQ. ID NO: 67, SEQ. ID NO: 68, or SEQ. ID NO: 69; (iii) the anthocyanin synthase has an amino acid sequence at least 80% identical to SEQ. ID NO: 13; and (iv) any combinations thereof. In certain embodiments, one or more genetic modifications comprises overexpression of anthocyanin synthase and flavonoid-3-glucosyl transferase (3GT). In certain embodiments, the one or more genetic modifications are selected from a group consisting of: (i) anthocyanin synthase, (ii) flavonoid-3-glucosyl transferase (3GT), and (iii) a combination thereof.

In another aspect, the invention provides a method of increasing the transformation of cyanidin to cyanidin-3-glucoside (Cy3G), delphindin to delphindin-3-glucoside (De3G), or pelargonidin to pelagonidin-3-glucoside (Pe3G), comprising flavonoid-3-glucosyl transferase (3GT), wherein the flavonoid-3-glucosyl transferase is selected from: (i) flavonoid-3-glucosyl transferase in *Vitis labrusca* (SEQ. ID NO:14); (ii) the flavonoid-3-glucosyl transferase has an amino acid sequence at least 80% identical to SEQ. ID NO: 70, SEQ. ID NO: 71, SEQ. ID NO: 72, or SEQ. ID NO: 73; and (iii) any combinations thereof.

In another aspect, the invention provides an engineered host cell comprises one or more genetic modifications to increase the production of dihydroquercetin (DHQ), dihydromyricein (DHM), eriodictoyl (EDL), and/or pentahydroxyflayaone (PHF), wherein the engineered host cell comprises cytochrome P450 reductase (CPR) and at least one of flavanone-3-hydroxylase (F3H), flavanone-3'-hydroxylase (F3'H), or flavonoid 3',5'-hydroxylase (F3'5'H). In certain embodiments, the precursor for increase in production of dihydroquercetin (DHQ), dihydromyricein (DHM), eriodictoyl (EDL), and/or pentahydroxyflayanone (PHF) is naringenin and/or dihydrokaempferol (DHK). In certain embodiments, the engineered host cell further comprises peptides selected from a group consisting of: (i) flavonoid 3'-hydroxylase (F3'H); (ii) cytochrome P450 reductase (CPR); and (iii) any combination thereof. In certain embodiments, the engineered host cell produces eriodictyol or taxifolin. In certain embodiments, the engineered host cell further comprises flavonoid 3',5'-hydroxylase (F3'5'H). In certain embodiments, the engineered host cell produces pentahydroxyflavone or dihydromyricetin. In certain embodiments, flavonoid 3'-hydroxylase (F3'H) is truncated to remove the N-terminal leader sequence. In certain embodiments, cytochrome P450 reductase (CPR) is truncated to remove the N-terminal leader sequence. In certain embodiments, flavonoid 3'-hydroxylase (F3'H) is fused with cytochrome P450 reductase (CPR). In certain embodiments, flavonoid 3',5'-hydroxylase (F3'5'H) is fused with cytochrome P450 reductase (CPR). In certain embodiments, flavanone-3-hydroxylase (F3H) has an amino acid sequence at least 80% identical to the polypeptide set forth in SEQ ID NO. 7. In certain embodiments, flavanone-3'-hydroxylase (F3'H) has an amino acid sequence at least 80% identical to the polypeptide set forth in SEQ ID NO. 8. In certain embodiments, cytochrome P450 reductase (CPR) has an amino acid sequence at least 80% identical to the polypeptide set forth in SEQ ID NO. 9. In certain embodiments, flavonoid 3',5'-hydroxylase (F3'5'H) has an amino acid sequence at least 80% identical to the polypeptides selected from a group consisting of: (i) SEQ ID NO. 10, (ii) SEQ ID NO. 56, and (iii) SEQ ID NO. 57. In certain embodiments, the engineered host cell further comprises cytochrome b5. In certain embodiments, cytochrome b5 has an amino acid sequence at least 80% identical to the polypeptide set forth in SEQ ID NO. 98. In certain embodiments, wherein the flavanone-3-hydroxylase (F3H) has an amino acid sequence at least 80% identical to the polypeptides selected from a group consisting of: (i) SEQ ID NO. 7, (ii) SEQ ID NO. 45, (iii) SEQ ID NO. 46, (iv) SEQ ID NO. 47, and (v) SEQ ID NO. 48.

In another aspect, the invention provides method of increasing the production of dihydroquercetin (DHQ), dihydromyricein (DHM), eriodictoyl (EDL), and/or pentahydroxyflayaone (PHF) comprising an engineered host cell, wherein the engineered host cell comprises cytochrome P450 reductase (CPR) and at least one of flavanone-3-hydroxylase (F3H), flavanone-3'-hydroxylase (F3'H), or flavonoid 3',5'-hydroxylase (F3'5'H). In certain embodiments, the precursor for increase in production of dihydroquercetin (DHQ), dihydromyricein (DHM), eriodictoyl (EDL), and/or pentahydroxyflayanone (PHF) is naringenin and/or dihydrokaempferol (DHK). In certain embodiments, the engineered host cell further comprises peptides selected from a group consisting of: (i) flavonoid 3'-hydroxylase (F3'H); (ii) cytochrome P450 reductase (CPR); and (iii) any combination thereof. In certain embodiments, the engineered host cell produces eriodictyol or taxifolin. In certain embodiments, the engineered host cell further comprises flavonoid 3',5'-hydroxylase (F3'5'H). In certain embodiments, the engineered host cell produces pentahydroxyflavone or dihydromyricetin. In certain embodiments, flavonoid 3'-hydroxylase (F3'H) is truncated to remove the N-terminal leader sequence. In certain embodiments, cytochrome P450 reductase (CPR) is truncated to remove the N-terminal leader sequence. In certain embodiments, flavonoid 3'-hydroxylase (F3'H) is fused with cytochrome P450 reductase (CPR). In certain embodiments, flavonoid 3',5'-hydroxylase (F3'5'H) is fused with cytochrome P450 reductase (CPR). In certain embodiments, flavanone-3-hydroxylase (F3H) has an amino acid sequence at least 80% identical to the polypeptide set forth in SEQ ID NO. 7. In certain embodiments, flavanone-3'-hydroxylase (F3'H) has an amino acid sequence at least 80% identical to the polypeptide set forth in SEQ ID NO. 8. In certain embodiments, cytochrome P450 reductase (CPR) has an amino acid sequence at least 80% identical to the polypeptide set forth in SEQ ID NO. 9. In certain embodiments, flavonoid 3',5'-hydroxylase (F3'5'H) has an amino acid sequence at least 80% identical to the polypeptides selected from a group consisting of: (i) SEQ ID NO. 10, (ii) SEQ ID NO. 56, and (iii) SEQ ID NO. 57. In certain embodiments, the engineered host cell further comprises cytochrome b5. In certain embodiments, cytochrome b5 has an amino acid sequence at least 80% identical to the polypeptide set forth in SEQ ID NO. 98. In certain embodiments, wherein the flavanone-3-hydroxylase (F3H) has an amino acid sequence at least 80% identical to the polypeptides selected from a group consisting of: (i) SEQ ID NO. 7, (ii) SEQ ID NO. 45, (iii) SEQ ID NO. 46, (iv) SEQ ID NO. 47, and (v) SEQ ID NO. 48.

VI. BRIEF DESCRIPTION OF THE SEVERAL VIEWS OF THE DRAWING(S)

VII. DETAILED DESCRIPTION OF THE INVENTION

Figure 1:
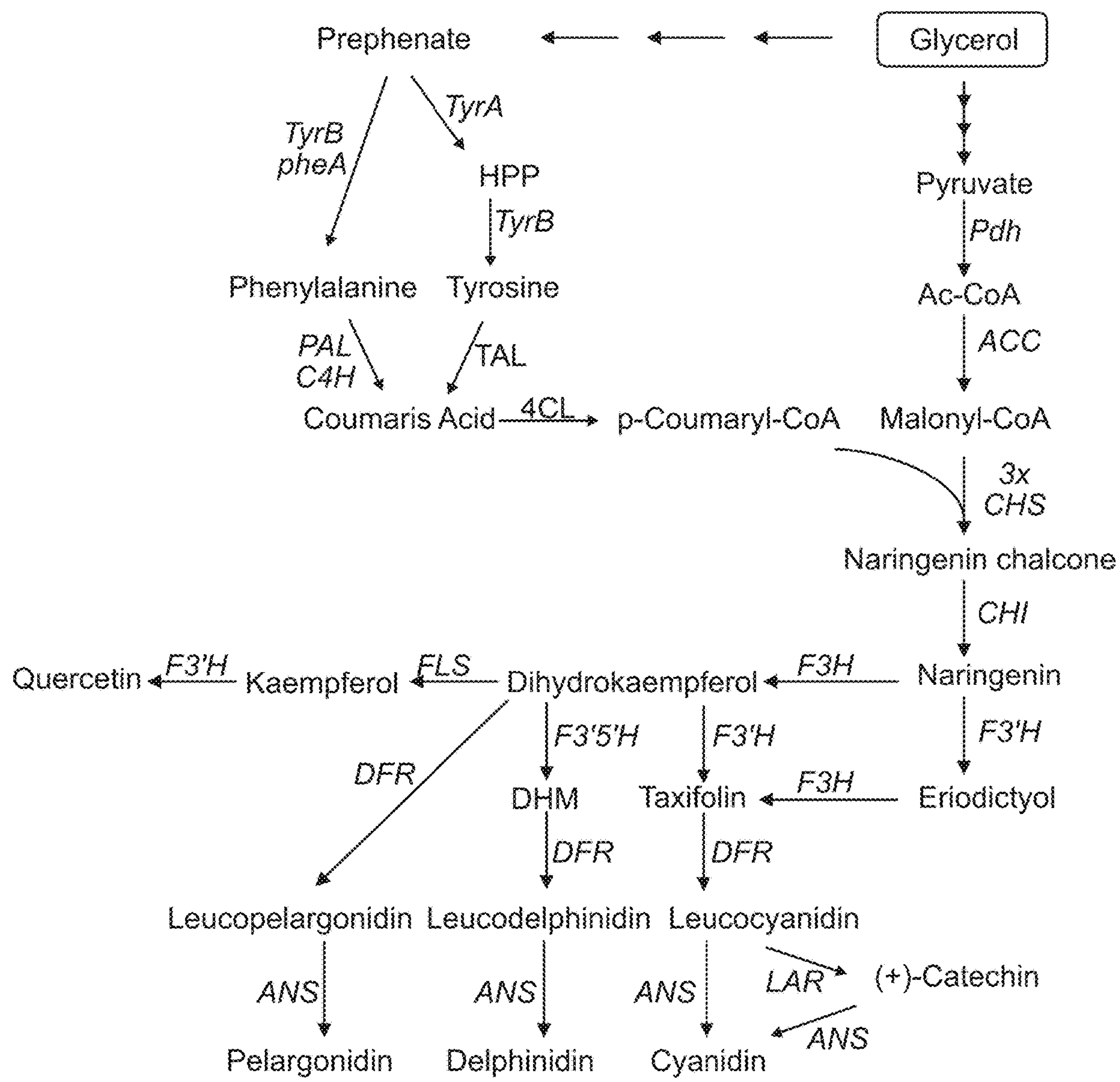
FIG. 1 shows the metabolic pathway of flavonoid and anthocyanin bioproduction in engineered cells and methods of preparing anthocyanins described herein.
Figure 2:
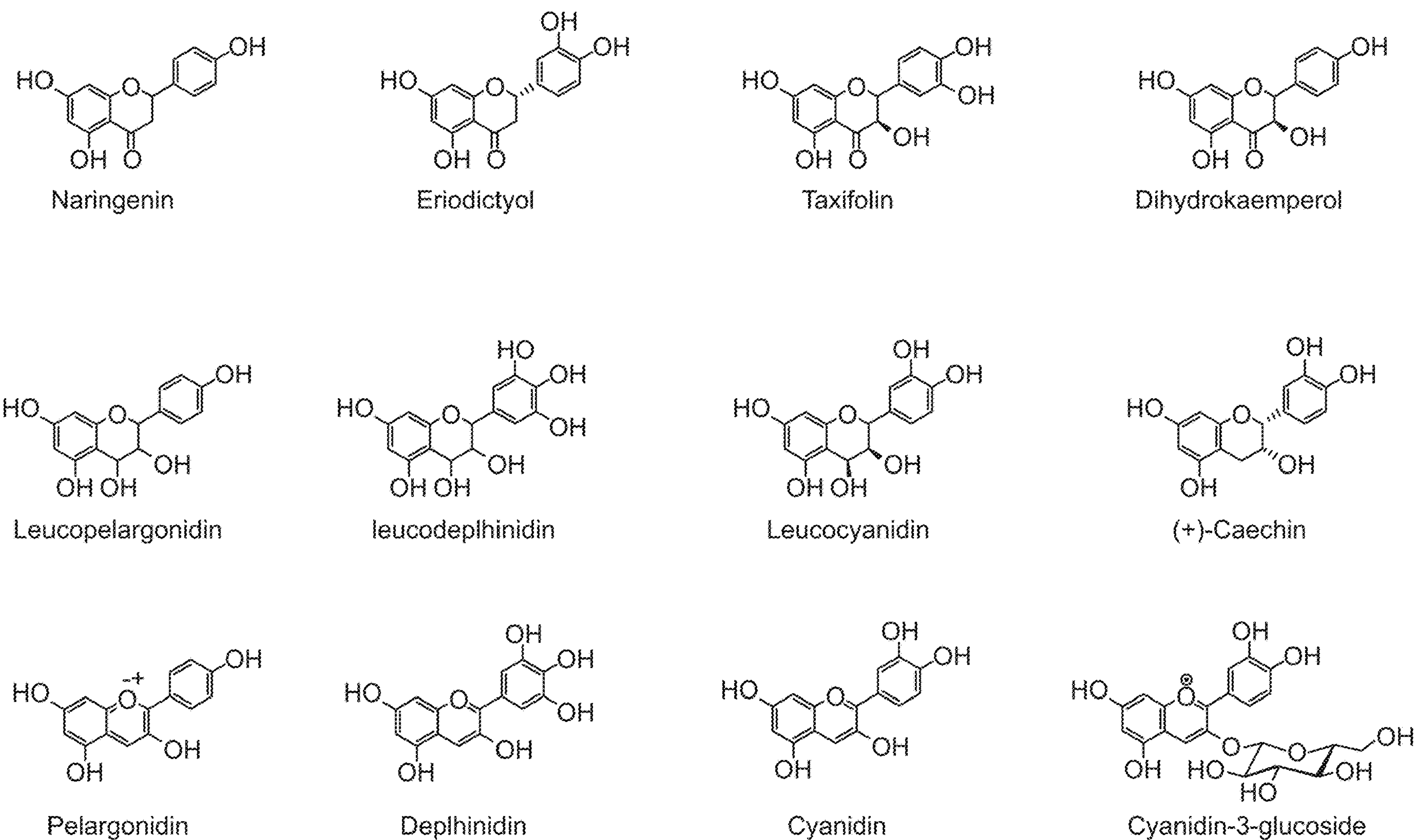
FIG. 2 shows structures of the flavonoid and anthocyanin molecules that may be produced using engineered cells and methods of preparing anthocyanins described herein.
Figure 3:
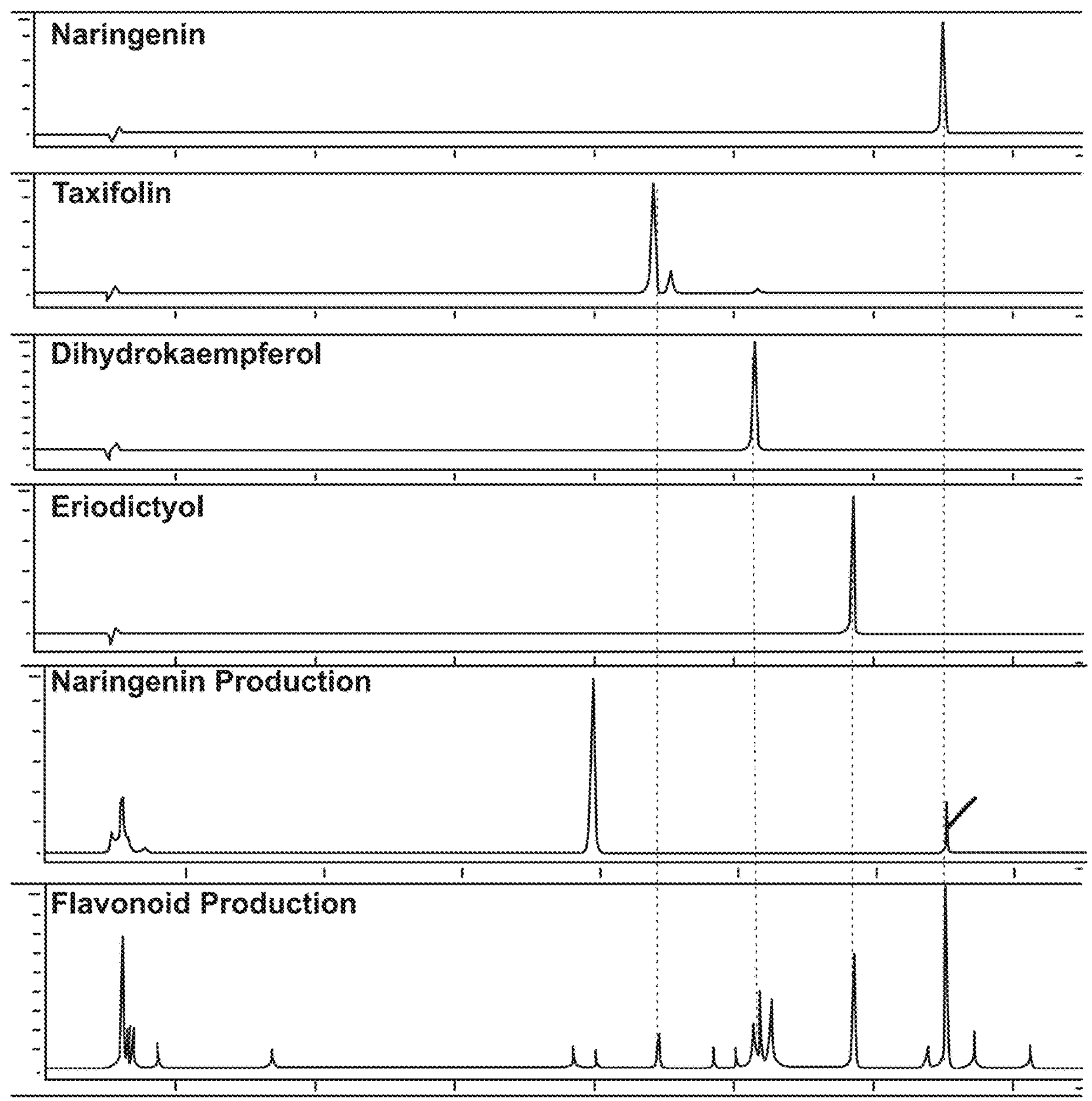
FIG. 3 shows HPLC spectra showing peaks corresponding to the molecules prepared using engineered cells and methods of preparing anthocyanins described herein.

The present application provides engineered cells for producing one or more flavonoids, cultures that include the engineered cells, and methods of producing one or more flavonoids, or at least one anthocyanin. The terms "flavonoid", "flavonoid product", or "flavonoid compound" are used herein to refer to a member of a diverse group of phytonutrients found in almost all fruits and vegetables. As used herein, the terms "flavonoid", "flavonoid product", or "flavonoid compound" are used interchangeably to refer a molecule containing the general structure of a 15-carbon skeleton, which consists of two phenyl rings (A and B) and a heterocyclic ring. Flavonoids may include, but are not limited to, isoflavone type (e.g., genistein), flavone type (e.g., apigenin), flavonol type (e.g., kaempferol), flavanone type (e.g., naringenin), chalcone type (e.g., phloretin), anthocyanidin type (e.g., cyanidin), catechins, flavanones, and flavanonols. Flavonoid compounds of interest include, without limitation, naringenin, naringenin chalcone, eriodictyol, taxifolin, dihydrokaempferol, dihydroquercetin, dihydromyricetin, leucocyanidin, leucopelargonidin, leucodelphindin, pentahydroxyflavone, cyanidin, catechin, delphinidin, pelargonidin, and kaempferol. Anthocyanins are in the forms of anthocyanidin glycosides and acylated anthocyanins. Anthocyanin compounds of interest include, without limitation, cyanidin glycoside, delphinidin glycoside, pelargonidin glycoside, peonidin glycoside, and petunidin glycoside.

The terms 'precursor' or 'flavonoid precursor' as used herein may refer to any intermediate present in the biosynthetic pathway that leads to the production of catechins or anthocyanins. flavonoid precursors may include, but are not limited to tyrosine, phenylalanine, coumaric acid, p-coumaroyl-CoA, malonyl-CoA, pyruvate, acetyl-CoA, and naringenin.

Cells engineered for the production of a flavonoid or an anthocyanin can have one or multiple modifications, including, without limitation, the downregulation, disruption, or deletion of endogenous genes, the upregulation of an endogenous gene, and the introduction of exogenous genes.

The term "non-naturally occurring", when used in reference to an enzyme is intended to mean that nucleic acids or polypeptides include at least one genetic alteration not normally found in a naturally occurring polypeptide or nucleic acid sequence. Naturally occurring nucleic acids, and polypeptides can be referred to as "wild-type" or "original". A host cell, organism, or microorganism that includes at least one genetic modification generated by human intervention can also be referred to as "non-naturally occurring", "engineered", "genetically engineered," or "recombinant".

A host cell, organism, or microorganism engineered to express or overexpress a gene or nucleic acid sequence, or to overexpress an enzyme or polypeptide has been genetically engineered through recombinant DNA technology to include a gene or nucleic acid sequence that does not naturally encode the enzyme or polypeptide or to express an endogenous gene at a level that exceeds its level of expression in a non-altered cell. As nonlimiting examples, a host cell, organism, or microorganism engineered to express or overexpress a gene or a nucleic acid sequence, or to overexpress an enzyme or polypeptide can have any modifications that affect a coding sequence of a gene, the position of a gene on a chromosome or regulatory elements associated with a gene. Overexpression of a gene can also be by increasing the copy number of a gene in the cell or organism. Similarly, a host cell, organism, or microorganism engineered to under-express or to have reduced expression of a gene, nucleic acid sequence, or to under-express an enzyme or polypeptide can have any modifications that affect a coding sequence of a gene, the position of a gene on a chromosome or regulatory elements associated with a gene. Specifically included are gene disruptions, which include any insertions, deletions, or sequence mutations into or of the gene or a portion of the gene that affect its expression or the activity of the encoded polypeptide. Gene disruptions include "knockout" mutations that eliminate expression of the gene. Modifications to under-express a gene also include modifications to regulatory regions of the gene that can reduce its expression.

The term "exogenous" or "heterologous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material that may be introduced on a vehicle such as a plasmid. Therefore, the term "endogenous" refers to a referenced molecule or activity that is naturally present in the host.

Genes or nucleic acid sequences can be introduced stably or transiently into a host cell using techniques well known in the art including, but not limited to, conjugation, electroporation, chemical transformation, transduction, and transfection. Optionally, for exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. Furthermore, genes can be subjected to codon optimization with techniques well known in the art to achieve optimized expression of the proteins.

The percent identity (% identity) between two sequences is determined when sequences are aligned for maximum homology. Algorithms well known to those skilled in the art, such as Align, BLAST, Clustal Omega, and others compare and determine a raw sequence similarity or identity, and also determine the presence or significance of gaps in the sequence which can be assigned a weight or score. Such algorithms also are known in the art and are similarly applicable for determining nucleotide or amino acid sequence similarity or identity and can be useful in identifying orthologs of genes of interest. Additional sequences added to a polypeptide sequence, such as but not limited to immunodetection tags, purification tags, localization sequences (presence or absence), etc., do not affect the % identity.

A homolog is a gene or genes that have the same or identical functions in different organisms. Genes that are orthologous can encode proteins with sequence similarity of about 45% to 100% amino acid sequence identity, and more preferably about 60% to 100% amino acid sequence identity. Genes can also be considered orthologs if they share three-dimensional structure but not necessarily sequence similarity, of a sufficient amount to indicate that they have evolved from a common ancestor to the extent that the primary sequence similarity is not identifiable. Paralogs are genes related by duplication within a genome, and can evolve new functions, even if these are related to the original one.

An engineered cell for producing flavonoids include an exogenous nucleic acid sequence encoding tyrosine ammonia lyase (TAL) activity (alternatively or in addition, an exogenous nucleic acid encoding phenylalanine ammonia-lyase (PAL) activity and an exogenous nucleic acid encoding cinnamate-4-hydroxylase (C4H) activity), an exogenous nucleic acid sequence encoding 4-coumarate-CoA ligase (4CL) activity, an exogenous nucleic acid sequence encoding chalcone synthase (CHS) activity, and an exogenous nucleic acid sequence encoding chalcone isomerase (CHI) activity. Optionally, the engineered cell can further include an exogenous nucleic acid sequence encoding an exogenous nucleic acid sequence encoding flavanone-3-hydroxylase (F3H) activity, an exogenous nucleic acid sequence encoding flavonoid 3'-hydroxlase (F3'H) activity or flavonoid 3',5'-hydroxylase (F3'5'H), an exogenous nucleic acid sequence encoding cytochrome P450 reductase (CPR) activity, an exogenous nucleic acid sequence encoding dihydroflavonol-4-reductase (DFR) activity, and/or an exogenous nucleic acid sequence encoding leucoanthocyanidin reductase (LAR) activity.

Tyrosine ammonia-lyase (TAL) can be, for example, a member of the aromatic amino acid deaminase family that catalyzes the elimination of ammonia from L-tyrosine to yield p-coumaric acid. An exemplary tyrosine ammonia lyase is the *Saccharothrix espanaensis* tyrosine ammonia lyase (TAL; SEQ ID NO: 1). Also considered for use in the engineered cells provided herein are TALs with SEQ ID NOS. 23-26, TALs listed in Table 1, TAL homologs and variants having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID:1 that have the activity of a tyrosine ammonia lyase that produces p-coumaric acid from tyrosine.

TABLE 1

Tyrosine ammonia-lyase

| Organism | GenBank Accession Number |
|---|---|
| *Rhodotorula glutini* | AGZ04575.1 |
| *Flavobacterium johnsoniae* | WP_012023194.1 |
| *Herpetosiphon aurantiacus* | ABX02653.1 |
| *Rhodobacter capsulatus* | ADE83766.1 |
| *Saccharothrix espanaensis* | AKE50820.1 |
| *Trichosporon cutaneum* | AKE50834.1 |

Similar to tyrosine ammonia-lyase, phenylalanine ammonia-lyase (PAL) can be a member of the aromatic amino acid deaminase family that catalyzes the non-oxidative deamination of L-phenylalanine to form trans-cinnamic acid. An exemplary phenylalanine ammonia-lyase is the *Brevibacillus laterosporus* phenylalanine ammonia-lyase (PAL; SEQ ID NO:2). Also considered for use in the engineered cells provided herein are PALs with SEQ ID NOS: 27-29, PAL homologs and variants having at least 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO: 2 that have the activity of a phenylalanine ammonia lyase that produces trans-cinnamic acid from phenylalanine.

Cinnamate-4-hydroxylase (C4H) belongs to the cytochrome P450-dependent monooxygenase family and catalyzes the formation of p-coumaric acid from trans-cinnamic acid. Considered for use in the engineered cells provided herein are C4H of *Helianthus annuus* L. (C4H; SEQ ID NO: 3), C4Hs with SEQ ID NOS: 30-32, and C4H homologs of other species, as well as variants of naturally occurring C4Hs having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to the SEQ ID NO: 3 (C4H, *Helianthus annuus* L.) that have the activity of a C4H.

4-coumarate-CoA ligase (4CL) catalyzes the activation of 4-coumarate to its CoA ester. Considered for use in the engineered cells provided herein are 4CLs of Petroselinum crispum (SEQ ID NO: 4), 4CLs in Table 2, 4CLs with SEQ ID NOS: 33-36, and 4CL homologs of other species, as well as variants of naturally occurring 4CLs having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID No: 4 (4CL, Petroselinum crispum) that have the activity of a 4CL.

TABLE 2

| 4-coumarate-CoA ligases | |
|---|---|
| Organism | GenBank Accession Number |
| *Petroselinum crispum* | CAA31697.1 |
| *Camellia sinensis* | ASU87409.1 |
| *Capsicum annuum* | KAF3620173.1 |
| *Castanea mollissima* | KAF3954751.1 |
| *Daucus carota* | AIT52344.1 |
| *Gynura bicolor* | BAJ17664.1 |
| *Ipomoea purpurea* | AHJ60263.1 |
| *Lonicera japonica* | AGE10594.1 |
| *Lycium chinense* | QDL52638.1 |
| *Nelumbo nucifera* | XP_010265453.1 |
| *Nyssa sinensis* | KAA8540582.1 |
| *Solanum lycopersicum* | NP_001333770.1 |
| *Striga asiatica* | GER48539.1 |

The chalcone synthase (CHS) can be, for example, a type III polyketide synthase that sequentially condenses three molecules of malonyl-CoA with one molecule of p-coumaryol-CoA to produce the naringenin precursor naringenin chalcone or naringenin. An exemplary chalcone synthase is the chalcone synthase of *Petunia* x *hybrida* (CHS, SEQ TD NO: 5). Also considered for use in the engineered cells provided herein are the genes listed in Table 3, CHSs with SEQ ID: 37-40, and CHS homologs and variants having at least 50%, at least 55%, at least 60%, at least 65%, at least 70%, at least 75% at least 80%, at least 85%, at least 90%, at least 95% at least 96%, at least 97% at least 98%, or at least 99% amino acid identity to SEQ ID NO: 5 (CHS, *Petunia* x *hybrida*) that have the activity of a chalcone synthase.

TABLE 3

| Chalcone synthases | |
|---|---|
| Organism | GenBank Accession Number |
| *Petunia hybrida* | AAF60297.1 |
| *Acer palmatum* | AWN08245.1 |
| *Callistephus chinensis* | CAA91930.1 |
| *Camellia japonica* | BAI66465.1 |
| *Capsicum annuum* | XP_016566084.1 |
| *Coffea arabica* | XP_027118978.1 |
| *Curcuma alismatifolia* | ADP08987.1 |

TABLE 3-continued

| Chalcone synthases | |
|---|---|
| Organism | GenBank Accession Number |
| *Dendrobium catenatum* | ALE71934.1 |
| *Garcinia mangostana* | ACM62742.1 |
| *Iochroma calycinum* | AIY22758.1 |
| *Iris germanica* | BAE53636.1 |
| *Lilium speciosum* | BAE79201.1 |
| *Lonicera caerulea* | ALU09326.1 |
| *Lycium ruthenicum* | ATB56297.1 |
| *Magnolia liliiflora* | AHJ60259.1 |
| *Matthiola incana* | BBM96372.1 |
| *Morus alba* var. *multicaulis* | AHL83549.1 |
| *Nelumbo nucifera* | NP_001305084.1 |
| *Nyssa sinensis* | KAA8548459.1 |
| *Paeonia lactiflora* | AEK70334.1 |
| *Panax notoginseng* | QKV26463.1 |
| *Ranunculus asiaticus* | AYV99476.1 |
| *Rosa chinensis* | AEC13058.1 |
| *Theobroma cacao* | XP_007032052.2 |

Chalcone isomerase (CHI, also referred to as chalcone flavonone isomerase) catalyzes the stereospecific and intramolecular isomerization of naringenin chalcone into its corresponding (2S)-flavanones. Considered for use in the engineered cells provided herein are CHI of *Medicago sativa* (SEQ TD NO: 6), CHI of Table 4, CHIs with SEQ TD NOS: 41-44, and CHI homologs of other species, as well as variants of naturally occurring CHI having at least 50%, at least 55% at least 60%, at least 65%, at least 70%, at least 75%, at least 80%, at least 85%, at least 90%, at least 95% at least 96%, at least 97% at least 98%, or at least 99% amino acid identity to SEQ ID NO: 6 (CHI, *Medicago sativa*) that have the activity of a chalcone isomerase.

TABLE 4

| Chalcone Isomerases | |
|---|---|
| Organism | GenBank Accession Number |
| *Medicago sativa* | AGZ04578.1 |
| Dendrobium hybrid cultivar | AGY46120.1 |
| *Abrus precatorius* | XP_027366189.1 |
| *Antirrhinum majus* | BA032070.1 |
| *Arachis duranensis* | XP_015942246.1 |
| *Astragalus membranaceus* | ATY39974.1 |
| *Camellia sinensis* | XP_028119616.1 |
| *Castanea mollissima* | KAF3958409.1 |
| *Cephalotus follicularis* | GAV77263.1 |
| *Clarkia gracilis* subsp. *sonomensis* | QPF47150.1 |
| *Dianthus caryophyllus* | CAA91931.1 |
| *Glycyrrhiza uralensis* | AXO59749.1 |
| *Handroanthus impetiginosus* | PIN05040.1 |
| *Lotus japonicus* | CAD69022.1 |
| *Morus alba* | AFM29131.1 |
| *Phaseolus vulgaris* | XP_007142690.1 |
| *Punica granatum* | ANB66204.1 |
| *Rhodamnia argentea* | XP_030524476.1 |
| *Spatholobus suberectus* | TKY50621.1 |
| *Trifolium subterraneum* | GAU12132.1 |

A nucleic acid sequence encoding a CHI can in some embodiments be fused to a nucleic acid sequence encoding a CHS in an engineered cell as provided herein, such that the CHI activity is fused to the chalcone synthase activity, i.e., a fusion protein is produced in the engineered cell that has both condensing and cyclization activities.

Flavanone 3-hydroxylase (F3H) catalyzes the stereospecific hydroxylation of (2S)-naringenin to form (2R,3R)-dihydrokaempferol. Other substrates include (2S)-eriodictyol, (2S)-dihydrotricetin and (2S)-pinocembrin. Some F3H enzymes are bifunctional and also catalyzes as flavonol synthase (EC: 1.14.20.6). Considered for use in the engineered cells provided herein are F3H of *Rubus occidentalis* (SEQ ID NO: 7), F3Hs with SEQ ID NOS: 45-48, F3Hs listed in Table 5, and other F3H homologs and variants having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID NO:7 (F3H, *Rubus occidentalis*) that have the activity of a F3H.

TABLE 5

| Flavanone 3-hydroxylases | |
|---|---|
| Organism | GenBank Accession Number |
| *Rubus occidentalis* | ACM17897.1 |
| *Abrus precatorius* | XP_027347564.1 |
| *Nyssa sinensis* | KAA8547483.1 |
| *Camellia sinensis* | AAT68774.1 |
| *Morelia rubra* | KAB1219056.1 |
| *Rosa chinensis* | PRQ47414.1 |
| *Malus domestica* | AAD26206.1 |
| *Vitis amurensis* | ALB75302.1 |
| *Iochroma ellipticum* | AMQ48669.1 |
| *Hibiscus sabdariffa* | ALB35017 |
| *Cephalotus follicularis* | GAV71832 |

Flavonoid 3'-hydroxylases (F3'H) belongs to the cytochrome P450 family with systematic name of flavonoid, NADPH:oxygen oxidoreductase (3'-hydroxylating). In the flavonoid biosynthetic pathway, F3'H converts dihydrokaempferol to dihydroquercetin (taxifolin) or naringenin to eriodictyol. Considered for use in the engineered cells provided herein are F3'H of *Brassica napus* (F3'H; SEQ ID NO: 8), F3'H with SEQ ID NOS: 49-52, those listed in Table 6, and homologs and variants having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to these F3'H. F3'H is a cytochrome P450 enzyme that requires a cytochrome P450 reductase (CPR) to function. Cytochrome P450 reductases are diflavin oxidoreductases that supply electrons to F3'Hs. The P450 reductase can be from the same species as F3'H or different species from F3'H. Considered for use in the engineered cells provided herein are CPR of *Catharanthus roseus* (SEQ ID NO: 9), additional CPRs listed in Table 7, CPRs with SEQ ID NOS: 53-55, CPR homologs of other species, and variants of naturally occurring CPRs having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to these CPRs that have the activity of a CPR. In various embodiments, the N-terminal nucleic acid sequences in the genes of F3'H and/or CPR originated from eukaryotic cells can encode targeting leader peptides, which can be removed before introduction into prokaryotic host cells, if desired. In some embodiments, the hydroxylase complex HpaBC from *E. coli* was used to hydroxylate naringenin to eriodictyol or dihydrokaempferol to dihydroquercetin (taxifolin).

TABLE 6

| Flavonoid 3'-hydroxylases | |
|---|---|
| Organism | GenBank Accession Number |
| *Brassica napus* | ABC58722.1 |
| Gerbera hybrid cultivar D1 | ABA64468.1 |
| *Cephalotus follicularis* | GAV84063.1 |
| *Theobroma cacao* | XP_007037548.1 |
| *Phoenix dactylifera* | XP_008791304.2 |

TABLE 7

| Cytochrome P450 reductases | |
|---|---|
| Organism | GenBank Accession Number |
| *Catharanthus roseus* | CAA49446.1 |
| *Brassica napus* | XP_013706600.1 |
| *Cephalotus follicularis* | GAV59576.1 |
| *Camellia sinensis* | XP_028084858.1 |

A nucleic acid sequence encoding a F3'H can in some embodiments be fused to a nucleic acid sequence encoding a CPR in an engineered cell as provided herein, such that the F3'H activity is fused to the CPR activity.

In the cells engineered to produce dihydomyricetin, flavonoid 3', 5'-hydroxylase (F3'5'H) can be used to convert dihydrokaempferol to dihydromyricetin or naringenin to pentahydroxyflavone, which is further converted to dihydromyricetin by a F3H. F3'5'H has the systematic name flavanone, NADPH: oxygen oxidoreductase and catalyzes the formation of 3',5'-dihydroxyflavanone from flavanone. An exemplary F3'5'H is the *Delphinium grandiflorum* F3'5'H (SEQ ID NO: 10), Also considered for use in the engineered cells provided herein include F3'5'H with SEQ ID NOS:56-57, F3'5'H homologs of other species, and variants of naturally occurring F3'5'H having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID NOS:10 that have the activity of a F3'5'H.

Dihydroflavonol 4-reductase (DFR) acts on (+)-dihydrokaempferol (DHK), (+)-dihydroquercetin (Taxifolin, DHQ), or dihydromyricein (DHM) to reduce those compounds to the corresponding cis-flavan-3,4-diol (DHK to leucopelargonidin; Taxifolin to leucocyanidin; DHM to leucodelphinidin). An exemplary DFR is the *Anthurium andraeanum* DFR (SEQ ID NO: 11). Also considered for use in the engineered cells provided herein include DFRs in Table 8, DFRs with SEQ ID NOS: 58-61, and DFR homologs of other species, as well as variants of naturally occurring DFR having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID NO: 11. Table 8. Dihydroflavonol 4-reductases

TABLE 8

| Dihydroflavonol 4-reductases | |
|---|---|
| Organism | GenBank Accession Number |
| *Eustoma grandiflorum* | BAD34461.1 |
| *Anthurium andraeanum* | AAP20866.1 |
| *Camellia sinensis* | AAT66505.1 |

TABLE 8-continued

| Dihydroflavonol 4-reductases | |
|---|---|
| Organism | GenBank Accession Number |
| *Morelia rubra* | KAB1203810.1 |
| *Dendrobium moniliforme* | AEB96144.1 |
| *Fragaria × ananassa* | AHL46451.1 |
| *Rosa chinensis* | XP_024167119.1 |
| *Acer palmatum* | AWN08247.1 |
| *Nyssa sinensis* | KAA8531902.1 |
| *Vitis amurensis* | I82380.1 |
| *Abrus precatorius* | XP_027329642.1 |
| *Angelonia angustifolia* | AHM27144.1 |
| *Pyrus pyrifolia* | Q84KP0.1 |
| *Theobroma cacao* | XP_017985307 |
| *Theobroma cacao* | XP_007051597.2 |
| *Brassica oleracea* var. *capitata* | QKO29328.1 |
| *Rubus idaeus* | AXK92786.1 |
| *Citrus sinensis* | AAY87035.1 |
| *Gerbera hybrida* | P51105.1 |
| *Cephalotus follicularis* | GAV76940.1 |
| *Ginkgo biloba* | AGR34043.1 |
| *Dryopteris erythrosora* | QFQ61498.1 |
| *Dryopteris erythrosora* | QFQ61499.1 |
| *Cephalotus follicularis* | GAV76942.1 |

Leucoanthocyanidin reductase (LAR) catalyzes the synthesis of catechin from 3,4-cis-leucocyanidin. LAR also synthesizes afzelechin and gallocatechin. Considered for use in the engineered cells provided herein are LAR of *Desmodium uncinatum* (SEQ ID NO: 12), LARs with SEQ ID NOS: 62-65, and LAR homologs of other species, as well as variants of naturally occurring LAR having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID NO: 12 (LAR, *Desmodium uncinatum*) that have the activity of a LAR.

Optionally, the cells are further engineered to include an anthocyanin synthase (ANS) which catalyzes the conversion of leucoanthocyanidin or catechin to anthocyanidin, leucopelargonidin to pelargonidin, or leucodelphinidin to delphinidin. Considered for use in the engineered cells provided herein are ANS of *Carica papaya* (SEQ ID NO: 13), ANS with SEQ ID NOS: 66-69, and ANS homologs of other species, as well as variants of naturally occurring ANS having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID NO:13 (ANS, *Carica papaya*) that have the activity of a ANS.

Optionally, the cells are further engineered to include a flavonoid-3-glucosyl transferase (3GT) to generate anthocyanins by transfer of a sugar moiety such as, without limitation, UDP-α-D-glucose to anthocyanidins to form glycosylated anthocyanins. Considered for use in the engineered cells provided herein are 3GT of *Vitis labrusca* (SEQ ID NO:14), 3GT with SEQ ID NOS: 70-73, and 3GT homologs of other species, as well as variants of naturally occurring 3GT having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to SEQ ID NO: 14 (3GT, *Vitis labrusca*) that have the activity of a 3GT.

In various aspects, host cells may be engineered for enhanced production of flavonoids or anthocyanins by introducing additional exogenous pathways and/or modifying endogenous metabolic pathways to remove or downregulate competitive pathways to reduce carbon loss, increase precursor supply, improve cofactor availability, reduce byproduct formation, or improve cell fitness. Enhancing or improving production of flavonoids or anthocyanins can be increasing yield, titer, or rate of production.

Thus, a host cell engineered for the production of a flavonoid or anthocyanin can be engineered to include any or any combination of: overexpression of an acetyl-CoA carboxylase (ACC) or an ACC variant; expression or overexpression of at least one enzyme for increasing cell's malonyl-CoA supply that does not rely on the ACC step; expression or overexpression of at least one enzyme to increase tyrosine supply; expression or overexpression of at least one enzyme to increase CoA availability for synthesizing precursors malonyl-CoA or p-coumaryol-CoA; expression or overexpression at least one enzyme to increase heme biosynthesis; deletion or downregulation of at least one fatty acid synthesis enzyme; at least one alcohol dehydrogenase, lactate dehydrogenase, pyruvate oxidase, phosphate acetyl transferase, or acetate kinase; at least one enzyme of a fatty acid degradation pathway, at least one thioesterase, or at least one TCA gene. The foregoing list of modifications is nonlimiting.

Malonyl-CoA is the direct precursor for chalcone synthase to perform sequential condensations with p-coumaryol-CoA. Malonyl-CoA supply can be increased by one or more modifications. Malonyl-CoA is synthesized by acetyl-CoA carboxylase (ACC) via the ATP-dependent carboxylation of acetyl-CoA in a multistep reaction. First, the biotin carboxylase domain catalyzes the ATP-dependent carboxylation of biotin using bicarbonate as a $CO_2$ donor. In the second reaction, the carboxyl-group is transferred from biotin to acetyl-CoA to form malonyl-CoA. In most eukaryotes, including fungi, both reactions are catalyzed by a large single chain protein, but in *E. coli* and other bacteria, the activity is catalyzed by a multi-subunit enzyme. Host cells can be engineered for example to express an exogenous acetyl-CoA carboxylase or a variant ACC to increase malonyl-CoA synthesis from acetyl-CoA. For example, *Mucor circinelloides* (SEQ ID NO: 15) acetyl-CoA carboxylase can be introduced into the host cells. Additional examples of ACC genes that may be used in the engineered cells provided herein include, without limitation, the genes listed in Table 9, genes with SEQ ID NOS: 74-76, naturally occurring orthologs of these ACCs, or variants having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to referenced genes. Further, naturally occurring acetyl-CoA carboxylase genes can be further engineered to introduce single or multiple amino acid mutations to increase catalytic activity and/or remove feedback inhibition.

TABLE 9

| Acetyl-CoA carboxylases | |
|---|---|
| Organism | GenBank Accession Number |
| *Lipomyces starkeyi* | AJT60321.1 |
| *Rhodotorula toruloides* | GEM08739.1 |
| *Ustilago maydis* | XP_011390921.1 |
| *Mucor circinelloides* | EPB82652.1 |
| *Kalaharituber pfeilii* | KAF8466702.1 |
| *Aspergillus fumigatus* | KEY77072.1 |
| *Rhodotorula diobovata* | TNY18634.1 |
| *Leucosporidium creatinivorum* | ORY74050.1 |

TABLE 9-continued

| Acetyl-CoA carboxylases | |
|---|---|
| Organism | GenBank Accession Number |
| *Microbotryum intermedium* | SCV70467.1 |
| *Mixia osmundae* | GAA98306.1 |
| *Puccinia graminis* | KAA1079218.1 |
| *Suillus occidentalis* | KAG1764021.1 |
| *Gymnopilus junonius* | KAF8909366.1 |

Additional strategies for increasing malonyl-CoA include increasing acetyl-CoA, which is converted to malonyl-CoA by acetyl-CoA carboxylase (ACC). Acetyl-CoA can be synthesized from acetate by an acyl-CoA ligase in an ATP-dependent reaction. Acetyl-CoA synthetase (ACS) or acetate-CoA ligase (EC 6.2.1.1.) catalyzes the formation of a new chemical bond between acetate and CoA coenzyme A (CoA). ACSs with native activity on acetate will provide the function of increasing acetyl-CoA supply when cells are either supplied with acetate as a co-feed, or where acetate is produced as a by-product. Other acyl-CoA ligases, having their main activity on other acid substrates, may also have substantial activity on acetate, and are viable candidates for providing acetate-CoA ligase activity in the engineered cells provided herein. The ACSs expressed in the host cells can be prokaryotic or eukaryotic. Cultures of engineered host cells that overexpress a nucleic acid sequence encoding ACS can optionally include acetate in the culture medium. Examples of acetyl-CoA synthase that can be expressed in a host cell engineered to produce a flavonoid or anthocyanin include, without limitation, the ACS gene of *E. coli*, the ACS of *Salmonella typhimurium* (SEQ ID NO:16), and orthologs of these ACSs in other species having at least 50%, at least 55%, at least 60%, at least 65%, at least 70%, at least 75%, at least 80%, at least 85%, at least 90%, at least 95%, at least 96%, at least 97%, at least 98%, or at least 99% amino acid identity to these ACSs.

Alternatively, or in addition, an engineered host cell can overexpress a gene encoding pyruvate dehydrogenase (PDH), which converts pyruvate to acetyl-CoA, to increase acetyl-CoA supply. PDH catalyzes an irreversible metabolic step, and the control of its activity is complex and involves control by its substrates and products. Nicotinamide adenine dinucleotide hydrogen (NADH), a product of the PDH reaction, is a competitive inhibitor of the PDH complex. The NADH sensitivity of the PDH complex has been demonstrated to reside in LPD, the enzyme that interacts with NAD+ as a substrate. Thus, a variant of the Lpd subunit of PDH can be expressed that includes one or more mutations that reduces inhibition of PDH by NADH. Such an example is a LPD variant in *E. coli* that contains E354K mutation, and the mutated enzyme was less sensitive to NADH inhibition than the native LPD.

Alternatively, or in addition to strategies for increasing ACC activity and strategies for increasing acetyl-CoA, strategies for increasing malonyl-CoA by mechanisms that do not rely on the activity of an ACC can be employed. For example, a cell engineered to produce a flavonoid or an anthocyanin as provided herein can include an exogenous nucleic acid sequence encoding a malonyl-CoA synthetase (EC 6.2.1.14) that generates malonyl-CoA from malonate. Acyl-CoA synthetase catalyzes the conversion of a carboxylic acid to its acyl-CoA thioester through an ATP-dependent two-step reaction. In the first step, the free fatty acid is converted to an acyl-AMP intermediate with the release of pyrophosphate. In the second step, the activated acyl group is coupled to the thiol group of CoA, releasing AMP and the acyl-CoA product. Nonlimiting examples of malonyl-CoA synthetases include the malonyl-CoA synthetases of *Streptomyces coelicolor* (SEQ ID NO:17), matB of *Rhodopseudomonas palustris* (SEQ ID NO: 77), matB of *Rhizobium* sp, BUS003 (SEQ ID NO: 78), matB of *Ochrobacrum* sp. (SEQ ID NO: 79), or other homologs having at least 50%, at least 55%, at least 60%, at least 65%, at least 70%, at least 75%, at least 80%, at least 85%, at least 90%, at least 95%, at least 96%, at least 97%, at least 98%, or at least 99% identity to the referenced sequences. Malonate can optionally be added to the culture medium of a culture that includes a cell engineered to express a malonyl-CoA synthetase. In *Rhizobium trifolii*, the matB gene is part of the matABC operon, with matA encoding a malonyl-CoA decarboxylase and matC encoding a putative dicarboxylate carrier protein or malonate transporter. An engineered cell that includes an exogenous gene encoding a malonyl-CoA synthetase can also include an exogenous nucleic acid sequence encoding a malonate transporter, such as a malonate transporter encoded by a matC gene, for example of *Streptomyces coelicolor* (SEQ ID NO:18), of *Rhizobiales bacterium* (SEQ ID NO:80), of *Rhizobium leguminosarum* (SEQ ID NO:81), of *Agrobacterium vitis* (SEQ ID NO: 82), of *Neorhizobium* sp. (SEQ ID NO: 83), or a malonate transporter encoded by DctPQM of *Sinorhizobium medicae*, or encoding a malonyl-CoA transporter having at least 50%, at least 55%, at least 60%, at least 65%, at least 70%, at least 75%, at least 80%, at least 85%, at least 90%, at least 95%, at least 96%, at least 97%, at least 98%, or at least 99% identity to a naturally-occurring malonate transporter. Cell cultures of a host cell engineered to express a malonyl-CoA synthetase and a malonate transporter can include a culture medium that includes malonate.

In additional embodiments, a cell engineered to produce a flavonoid or an anthocyanin is further engineered to include an exogenous nucleic acid sequence encoding malonate CoA-transferase (EC:2.8.3.3; also referred to as the alpha subunit of malonate decarboxylase) that makes malonyl-CoA by direct transfer of the CoA from acetyl-CoA. For example, the alpha subunit of malonate decarboxylase from the mdcACDE gene cluster in *Acinetobacter calcoaceticus* has the malonate CoA-transferase activity. The mdcA gene product, the a subunit, is malonate CoA-transferase, and mdcD gene product, the β subunit, is a malonyl-CoA decarboxylase. The mdcE gene product, the γ subunit, may play a role in subunit interaction to form a stable complex or as a codecarboxylase. The mdcC gene product, the δ subunit, was an acyl-carrier protein, which has a unique CoA-like prosthetic group. When the α subunit is removed from the complex and incubated with malonate and acetyl-CoA, the acetyl-CoA moiety of the prosthetic group binds on an α subunit to exchange the acetyl group for a malonyl group. As the thioester transfer should be thermodynamically favorable, the engineered cells can include a nucleic acid encoding a malonate CoA-transferase to increase malonyl-CoA supply. Examples of mdcAs that can be expressed in an engineered cell as provided herein include, without limitation, mdcA of *Acinetobacter calcoaceticus* (SEQ ID NO: 19), mdcAs of Table 10, mdcAs with SEQ ID NOS: 84-87, or a transferase having at least 50%, at least 55%, at least 60%, at least 65%, at least 70%, at least 75%, at least 80%, at least 85%, at least 90%, at least 95%, at least 96%, at least 97%, at least 98%, or at least 99% identity to any of these or other naturally occurring malonate CoA-transferases.

TABLE 10

Malonate CoA-transferases (malonate decarboxylase subunit alpha)

| Organism | GenBank Accession Number |
|---|---|
| *Acinetobacter calcoaceticus* | AAB97627.1 |
| *Geobacillus* sp. | QNU36929.1 |
| *Acinetobacter johnsonii* | WP_087014029.1 |
| *Acinetobacter marinus* | WP_092618543.1 |
| *Acinetobacter rudis* | WP_016655668.1 |
| *Psychrobacter* sp. G | WP_020444454.1 |
| *Moraxella catarrhalis* | WP_064617969.1 |
| *Zoogloea* sp. | MBL0283742.1 |
| *Dechloromonas* sp. | KAB2923906.1 |
| *Stenotrophomonas rhizophila* | WP_123729366.1 |
| *Xanthomonas cucurbitae* | WP_159407614.1 |

In some embodiments, a cell engineered to produce flavonoids or anthocyanins is further engineered to increase the supply of coenzyme A (CoA) to increase its availability for producing acetyl-CoA, malonyl-CoA, and/or p-coumaroyl-CoA. Strategies for increasing CoA supply include expressing or overexpressing at least one enzyme of a CoA biosynthesis pathway. Pantothenate kinase (EC 2.7.1.33, PanK; CoaA) is the first enzyme in the coenzyme CoA biosynthetic pathway. It phosphorylates pantothenate (vitamin B5) to form 4'-phosphopantothenate at the expense of a molecule of adenosine triphosphate (ATP). It is the rate-limiting step in the biosynthesis of CoA. Three distinct types of PanK have been identified—PanK-I (found in bacteria), PanK-II (mainly found in eukaryotes, but also in the Staphylococci) and PanK-III, also known as CoaX (found in bacteria). In *E. coli*, pantothenate kinase is competitively inhibited by CoA itself, as well as by some CoA esters. The type III enzymes CoaX are not subject to feedback inhibition by CoA. In some embodiments, a host cell can be engineered to include a nucleic acid sequence encoding type III pantothenate kinase that is not feedback inhibited by coenzyme A, such as, without limitation, CoaX gene of *Pseudomonas aeruginosa* (EC:2.7.1.33, SEQ ID NO: 20), CoaX of *Streptomyces* sp. CLI2509 (SEQ ID NO: 88), CoaX of *Streptomyces cinereus* (SEQ ID:89), or CoaX of *Kitasatospora kifunensis* (SEQ ID NO: 90) Cultures of cells engineered for the production of flavonoids or anthocyanins can in some embodiments include a medium that includes pantothenate, a precursor of CoA biosynthesis, and can optionally also include cysteine, used in the CoA biosynthesis.

Additional strategies to increase malonyl-CoA flux to the flavonoid pathway include mutation or downregulation of one or more genes that function in fatty acid biosynthesis. Fatty acid biosynthesis directly competes with flavonoid biosynthesis for the precursor malonyl-CoA and thus limits flavonoid formation. Without limiting the embodiments to any particular mechanism, limiting fatty acid biosynthesis can increase the malonyl-CoA supply available for flavonoid biosynthesis. In some embodiments, the gene beta-ketoacyl-ACP synthase II (*E. coli* fabF) can be disrupted, attenuated or deleted to reduce fatty acid biosynthesis. Another example of a fatty acid biosynthesis gene of a host cell that may be mutated or downregulated is a gene encoding malonyl-CoA-ACP transacylase (*E. coli* fabD). Other fatty acid biosynthesis genes of the engineered host cell that can be downregulated include a beta-ketoacyl-ACP synthase I enzyme (*E. coli* fabB) and/or acyl carrier protein (*E. coli* acpP).

Additional genetic modifications that may be present in a host cell engineered to produce flavonoids or anthocyanins include downregulation, disruption, or deletion of the gene targets that divert carbon flux to form byproducts such as ethanol, acetate, and lactate. They include genes encoding alcohol dehydrogenase, lactate dehydrogenase, pyruvate oxidase, acetyl phosphate transferase and acetate kinase. In an *E. coli* host cell, genes that are downregulated, disrupted, or deleted can include adhE, ldhA, poxB, and ackA-pta.

Further, a cell engineered for the production of flavonoids or anthocyanins can have one or more genes encoding thioesterases downregulated, disrupted, or deleted to prevent hydrolysis of precursors malonyl-CoA, acetyl-CoA, and/or p-coumaryol-CoA. Acyl-CoA thioesterase enzymes (ACOTs) catalyze the hydrolysis of acyl-CoAs (short-, medium-, long- and very long-chain), bile acid-CoAs, and methyl branched-CoAs, to the free fatty acid and coenzyme A. For example, in an *E. coli* host one or more of the thioesterase genes tesA, tesB, yciA, and/or ybgC can be downregulated, disrupted, or deleted.

In further embodiments, a cell engineered for the production of flavonoids or anthocyanins can have one or more of fatty acid degradation genes downregulated, disrupted, or deleted to improve precursor supply to the flavonoid pathway. In *E. coli*, for example, the acyl-coenzyme A dehydrogenase (fade) gene encoding acyl-CoA dehydrogenase, adhesion A (fadA) gene encoding 3-ketoacyl-CoA thiolase, and/or gene encoding fatty acid oxidation complex subunit alpha (fadB) can be downregulated, disrupted, or deleted.

Alternatively, or in addition, genes encoding enzymes of the tricarboxylic acid cycle (TCA), such as succinate dehydrogenase, can be disrupted or downregulated to increase alpha-ketoglutarate supply which serves as a cofactor for the flavonoid and anthocyanin pathway enzymes. Other TCA enzymes that can be downregulated include citrate synthase that converts acetyl-CoA to citrate.

Also considered, in further embodiments, is an engineered host cell for the production of flavonoids or anthocyanins to upregulate the endogenous biosynthesis of amino acid tyrosine. Tyrosine is one of the precursors for the flavonoid biosynthesis and its conversion to 4-coumaric acid is the first committed step of the pathway. Efficient biosynthesis of L-tyrosine from feedstock such as glucose or glycerol is necessary to make biological production economically viable. L-tyrosine is one of the three aromatic amino acids derived from the shikimate pathway. The shikimate pathway is the central metabolic route leading to formation of tryptophan (TRP), tyrosine (TYR), and phenylalanine (PHE), this pathway exclusively exists in plants and microorganisms. It starts with the condensation of intermediates of glycolysis and pentosephosphate-pathway, phosphoenolpyruvate (PEP), and erythrose-4-phosphate (E4P), respectively, which enter the pathway through a series of condensation and redox reactions via 3-deoxy-d-arabino-heptulosonate-7-phosphate (DAHP), 3-dehydroquinate (DHQ), 3-dehydroshikimate (DHS) to shikimate. From there the central branch point metabolite chorismate is obtained via shikimate-3-phosphate under ATP hydrolysis and introduction of a second PEP. The initial step of the shikimate pathway is catalyzed by DAHP synthase isozymes and regulated through feedback-inhibition. In *E. coli* three DAHP synthase isozymes exist (aroF, aroG, aroH), which are each feedback inhibited by one of the three aromatic amino acids (TYR, PHE, TRP), in contrast the two DAHP synthases of plants are not subject to feedback-inhibition. In plants and bacteria, the subsequent five steps are catalyzed by single enzymes. From the central intermediate chorismate the pathway branches off to anthranilate and prephenate leading to aromatic amino acid, para-hydroxybenzoic acid (pHBA) and para-aminobenzoic acid (pABA) synthesis, the latter being a precursor for folate metabolism. Strategies to increase L-tyrosine production can include, without limitation, transcriptional deregulation, removing feedback inhibition, overexpression of rate-limiting enzymes, and/or deletion of the L-phenylalanine branch of the aromatic acid biosynthetic pathway. For example, in an *E. coli* host the tyrR gene can be disrupted, feedback-inhibition-resistant versions of the DAHP synthase (aroG) and chorismate mutase (tyrA) can be introduced, and/or rate-limiting enzymes, shikimate kinase (aroK or aroL) and quinate (QUIN)/shikimate dehydrogenase (ydiB) can be overexpressed. Further, the ppsA, aroG, and/or transketolase (tktA) can be overexpressed or exogenously introduced to enhance tyrosine production.

Also considered, in further embodiments, is an engineered host cell for the production of flavonoids or anthocyanins further engineered to upregulate the endogenous biosynthesis of cofactor heme. Cytochrome P450 (CYPs), one of the exogenous genes in the engineered cells provided herein, contain heme as a cofactor. Improving heme supply can be an effective strategy to increase flavonoid biosynthesis. 5-aminolevulinic acid (ALA) is the first committed precursor to the heme pathway. There exist two known alternate routes by which this committed intermediate is generated. One route is the C4 pathway (Shemin pathway), which involves the condensation of succinyl-CoA and glycine to D-aminolevulinic acid by ALA synthase (ALAS). The C4 pathway is restricted to mammals, fungi and purple nonsulfur bacteria. The second route is the C5 pathway, which involves three enzymatic reactions resulting in the biosynthesis of ALA from the five-carbon skeleton of glutamate. The C5 pathway is active in most bacteria, all archaea and plants. Seven additional reactions, including assembly of eight ALA molecules into a cyclic tetrapyrrole, modification of the side chains, and incorporation of reduced iron into the molecule, are required to convert ALA to heme. In an *E. coli* host, the three enzymes involved in ALA biosynthesis are glutamyl-tRNA synthetase (GltX), glutamyl-tRNA reductase (hemA), and glutamate-1-semialdehyde aminotransferase (hemL). In an *E. coli* host, the engineered cells provided herein can be further engineered to express or overexpress hemA or its variants, and/or hemL to increase the heme precursor ALA production. The nonlimiting examples of hemA gene that can be overexpressed include, without limitation, a mutated hemA gene from *Salmonella typhimurium* (EC:1.1.1.70, SEQ ID NO: 21) and hemA with SEQ ID NOS: 91-93. Alternatively, or in addition, a heterologous ALAS gene can be introduced to produce ALA via the C4 pathway. Nonlimiting examples of heterologous ALAS that can be expressed in *E. coli* include ALAS of *Rhodobacter capsulatus* (SEQ ID:22), ALAS with SEQ ID NOS: 94-97, or an ALAS having at least 50%, at least 55%, at least 60%, at least 65%, at least 70%, at least 75%, at least 80%, at least 85%, at least 90%, at least 95%, at least 96%, at least 97%, at least 98%, or at least 99% identity to any of these or other naturally-occurring ALAS. Further, one or more of the downstream genes (*E. coli* hemB, hemC, hemD, hemE, hemF, hemG, hemI, or hemH) that catalyze the synthesis of heme from ALA can be overexpressed to drive the flux from ALA to heme production. Cultures of cells engineered for the production of flavonoids or anthocyanins can in some embodiments include a medium that includes succinate and/or glycine, precursors of heme biosynthesis via the C4 pathway.

Engineered cells that produce a flavonoid can be engineered to include multiple pathways to enhance flavonoid production. Those skilled in the art will recognize that the embodiments described herein can be combined in multiple ways. Examples of engineered cells having multiple genetic modifications are exemplary only and do not limit the scope of the invention.

Enzymes to be expressed or overexpressed in engineered cells according to the invention are set forth in Table 11.

Host Cells

A host cell as provided herein can be a prokaryotic cell or a eukaryotic cell. Eukaryotic cells may be microbial eukaryotic cells, such as, for example, fungal cells or yeast cells. Prokaryotic cells that can be engineered as provided herein include bacterial cells and cyanobacterial cells.

Host can be selected based on their ability to take up and utilize particular carbon sources, nitrogen sources, or precursor molecules or may be engineered to take up and utilize molecules that may be added to the culture medium.

Nonlimiting examples of suitable microbial hosts for the bio-production of a flavonoid include, but are not limited to, any gram-negative organisms, more particularly a member of the family Enterobacteriaceae, such as *E. coli*, any gram-positive microorganism, for example *Bacillus subtilis, Lactobacillus* sp. or *Lactococcus* sp.; a yeast, for example *Saccharomyces cerevisiae, Pichia pastoris* or *Pichia stipitis*; and other groups or microbial species. More particularly, suitable microbial hosts for the bio-production of a flavonoid generally include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula*, and *Saccharomyces.*

Culture Medium

In yet another aspect, methods for producing a flavonoid or an anthocyanin that include incubating a culture of an engineered host cell as provided herein to produce a flavonoid or an anthocyanin. The methods can further include recovering the flavonoid or anthocyanin from the culture medium, whole culture, or cells.

The culture comprises cells engineered for the production of flavonoids or anthocyanins in a culture medium. In various embodiments the engineered cells can be prokaryotic or eukaryotic cells. The culture medium includes at least one carbon source that is also an energy source. Exemplary carbon sources include glucose, glycerol, sucrose, fructose, and xylose. Such carbon sources may be purified or crude, including a biomass comprising glycerol, for example, crude glycerol produced as a byproduct of biodiesel production from corn waste. In addition, the culture medium can include one or more other carbon sources or compounds to increase precursor generation or cofactor supply such as, without limitation, tyrosine, phenylalanine, coumaric acid, acetate, malonate, succinate, glycine, bicarbonate, biotin, naringenin, 5-aminolevulinic acid, thiamine, pantothenate, alpha-ketoglutarate, and ascorbate. In some embodiments, tyrosine and coumaric acid are provided in the culture medium. In some embodiments, tyrosine, alpha-ketoglutarate, 5-aminolevulinic acid, and ascorbate are provided in the culture medium.

Culture conditions can include aerobic, microaerobic or any combination alternating aerobic/microaerobic growth conditions. Further, culture conditions can include shake flasks, fermentation, and other large scale culture procedures. An exemplary growth condition for achieving a flavonoid product include aerobic or microaerobic fermentation conditions. The culture conditions can be scaled up and grown continuously for manufacturing flavonoid product. Exemplary growth procedures include, for example, fed-batch fermentation and batch separation. In an exemplary batch fermentation protocol, the cells are grown in a bioreactor that is well controlled for growth temperature, oxygen, pH, carbon sources, and other compounds. The desired temperature can be from, for example, 20-37° C., depending on the growth characteristics of the production cells and desired conditions for the fermented products. The pH of the bioreactor can be controlled to range from 5-8 or left uncontrolled in some cases. The batch fermentation period can last in the range of several hours to several days, for examples, 8 to 96 hours. Upon completion of the cultivation period, the fermenter contents can be passed through a cell separation unit to remove cells and cell debris. The cells can be lysed or disrupted enzymatically or chemically prior to or after separation of cells from the fermentation broth, as desired, in order to release additional product. To purify the flavonoids and/or anthocyanins to homogeneity the solution containing the flavonoids and/or anthocyanins was concentrated and the product purified via ion exchange or silica-based chromatography. The resulting solution was either lyophilized to yield the products in a solid form or was concentrated into a liquid solution.

In some embodiments, a method of producing a flavonoid or an anthocyanin comprises culturing an engineered cell disclosed herein in a culture medium to produce a flavonoid or an anthocyanin. In some embodiments, glycerol is used as a carbon feedstock. In some embodiments, the glycerol is crude glycerol. In some embodiments, the method comprises isolating naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside. In some embodiments the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of greater than 50%, greater than 55%, greater than 60%, greater than 65%, greater than 70%, greater than 75%, greater than 80%, greater than 85%, greater than 90%, or greater than 95%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 50% to about 99%, e.g., from about 50% to about 95% (for example from: about 50%, 55%, 60%, 65%, 70%, 75%, 80% to about: 85%, 90%, 95%, 97.5%, 99% or 99.9%). In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 50% to: about 55%, about 60%, about 65%, about 70%, about 75%, about 80%, about 85%, about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 55% to: about 60%, about 65%, about 70%, about 75%, about 80%, about 85%, about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 60% to: about 65%, about 70%, about 75%, about 80%, about 85%, about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 65% to: about 70%, about 75%, about 80%, about 85%, about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 70% to: about 75%, about 80%, about 85%, about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 75% to: about 80%, about 85%, about 90%, about 95%, or about 99%, from about 80% to about 85%, about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 85% to: about 90%, about 95%, or about 99%. In some embodiments, the naringenin, dihydrokaempferol, taxifolin, eriodictyol, leucocyanidin, leucodelphinidin, leucopelargonidin, (+)-catechin, cyanidin, delphinidin, pelargonidin, cyanidin glucoside, delphinidin glucoside or pelargonidin glucoside may be isolated at a purity of from about 90% to about 95%, or about 99%, or from about 95% to about 99% or greater.

VIII. EXAMPLES

Using the Modified Cell to Create Products

Example 1—Production of Naringenin in *E. coli*

An *E. coli* cell derived from MG1655 was engineered to overexpress ACC (SEQ ID NO: 15), TAL (SEQ ID NO: 1), 4CL (SEQ ID NO: 4), CHS (SEQ ID NO: 5), and CHI (SEQ ID NO: 6) to produce naringenin when substrates tyrosine and coumaric acid were supplied in culture medium. ACC was expressed on a medium-copy plasmid (15-20 copies) while TAL, 4CL, CHS, and CHI were expressed on the chromosome. Cells of an OD 2.5 were cultured in a 48-well plate at 30 degree for 24 hours with a shaking speed of 600 RPM in minimal medium supplied with trace element, vitamins, 1 mM tyrosine, 1 mM coumaric acid, and 2% glycerol. Cell cultures were extracted with DMSO at 1:1 ratio and centrifuged for 15 mins. The supernatant was analyzed for naringenin with HPLC. The cells produced 232 μM naringenin.

Variants of the foregoing host cell may be prepared using one or more of ACC (SEQ ID NO: 15), TAL (SEQ ID NO: 1), 4CL (SEQ ID NO: 4), CHS (SEQ ID NO: 5), and CHI (SEQ ID NO: 6) with one or more homologs of ACC (SEQ ID NO: 15), TAL (SEQ ID NO: 1), 4CL (SEQ ID NO: 4), CHS (SEQ ID NO: 5), or CHI (SEQ ID NO: 6), or combinations of two or more thereof, wherein the homologous enzymes have at least 50%, at least 55%, at least 60%, at least 65%, at least 70%, at least 75%, at least 80%, at least 85%, at least 90%, at least 95%, at least 96%, at least 97%, at least 98%, or at least 99% identity to the referenced enzymes.

Example 2—Production of Dihydrokaempferol in *E. coli*

An *E. coli* cell derived from MG1655 was engineered to overexpress F3H (SEQ ID NO: 7) on the chromosome to produce dihydrokaempferol when substrate naringenin was supplied in culture medium. Cells of an OD 0.5-0.7 were cultured in a 24-well plate at 30 degree for 18 hours with a shaking speed of 200 RPM in minimal medium supplied with 2% glycerol, trace elements, 0.8 mM naringenin, 65 mg/L 5-aminoleuvinic acid, 0.1 mM ferrous sulfate, 0.1 mM 2-oxoglutarate, and 2.5 mM ascorbic acid. Cell cultures were extracted with DMSO and centrifuged for 15 minutes. The supernatant was analyzed for dihydrokaempferol with HPLC. The cells produced 315 μM dihydrokaempferol.

Variants of the foregoing host cell may be prepared using a homolog of F3H (SEQ ID NO: 7), wherein the homologous enzyme has at least 50%, at least 55%, at least 60%, at least 65%, at least 70%, at least 75%, at least 80%, at least 85%, at least 90%, at least 95%, at least 96%, at least 97%, at least 98%, or at least 99% identity to the referenced enzyme.

Example 3—Production of Taxifolin in *E. coli*

An *E. coli* strain derived from MG1655 was engineered to overexpress F3H (SEQ ID NO: 7), F3'H (SEQ ID NO: 8), and CPR (SEQ ID NO: 9) to produce taxifolin when the substrate naringenin was supplied in culture medium. F3H was overexpressed on the chromosome while F3'H and CPR were overexpressed on a medium-copy plasmid. Cells of an OD 0.5-0.7 were cultured in a 24-well plate at 30 degree for 18 hours with a shaking speed of 200 RPM in minimal medium supplied with 2% glucose, 0.8 mM naringenin, 65 mg/L 5-aminoleuvinic acid, 0.1 mM ferrous sulfate, 0.1 mM 2-oxoglutarate, and 2.5 mM ascorbic acid. Cell cultures were extracted with 50% DMSO and centrifuged for 15 minutes. The supernatant was analyzed for taxifolin with HPLC. The cells produced 500 μM taxifolin.

Variants of the foregoing host cell may be prepared using one or more of F3H (SEQ ID NO: 7), F3'H (SEQ ID NO: 8), and CPR (SEQ ID NO: 9) along with one or more homologs of F3H (SEQ ID NO: 7), F3'H (SEQ ID NO: 8), and CPR (SEQ ID NO: 9), or combinations of two or more thereof, wherein the homologous enzymes have at least 50%, at least 55%, at least 60%, at least 65%, at least 70%, at least 75%, at least 80%, at least 85%, at least 90%, at least 95%, at least 96%, at least 97%, at least 98%, or at least 99% identity to the referenced enzymes.

Example 4—Production of Anthocyanidins and Anthocyanins

An *E. coli* strain derived from MG1655 was engineered to overexpress ANS (SEQ ID NO: 13) and 3GT (SEQ ID NO: 14) to produce cyanidin-3-O-glucoside when the substrate (+)-catechin was supplied in culture medium. ANS and 3GT were overexpressed on the chromosome. Cells of an OD 0.5-0.7 were cultured in a 24-well plate at 30 degree for 18 hours with a shaking speed of 200 RPM in minimal medium supplied with 1.0% glucose, 2.0 mM (+)-catechin, 0.1 mM 2-oxoglutarate, and 2.5 mM ascorbic acid. Cell cultures were acidified with 2M HCL and extracted with 100% Ethanol. The supernatant was analyzed for cyanidin-3-O-glucoside by HPLC. The cells produced 50 mg/L cyanidin-3-O-glucoside.

Variants of the foregoing host cell may be prepared using one or both of ANS (SEQ ID NO: 13) and 3GT (SEQ ID NO: 14) along with a homolog of ANS (SEQ ID NO: 13), 3GT (SEQ ID NO: 14), or both, wherein the homologous enzymes have at least 50%, at least 55%, at least 60%, at least 65%, at least 70%, at least 75%, at least 80%, at least 85%, at least 90%, at least 95%, at least 96%, at least 97%, at least 98%, or at least 99% identity to the referenced enzymes.

Analytical Methods

Example 5—Flavonoid Precursors and Flavonoids

For sampling naringenin, eriodictyol, dihydrokaempferol and taxifolin, extraction of total flavonoids from *E. coli* were performed on whole cell broth. 500 μL of whole cell broth was vortexed for 30 seconds with 500 μL of DMSO (dimethyl sulfoxide) and centrifuged for 15 minutes. For HPLC analysis, 50 μL of supernatant was transferred to an HPLC vial.

The HPLC method was as follows: An Agilent 1200 HPLC was fitted with an Ascentis C18 Column 150 mm×4.6 mm, 3 μm, equipped with a R-18 (3 μm) guard column. The column was heated to 30° C. with the sample block being maintained at 25° C. For each sample, 5 μL was injected and the product was eluted at a flow rate of 1.5 mL/min using 0.1% phosphoric acid in water (solvent A), acetonitrile (solvent B), and methanol (solvent C) with the following gradient:

| Time | A (%) | B (%) | C (%) |
|---|---|---|---|
| 0 | 85 | 10 | 5 |
| 2.5 | 85 | 10 | 5 |
| 7.5 | 70 | 25 | 5 |
| 12.5 | 50 | 45 | 5 |
| 15 | 85 | 10 | 5 |

The run time was a total of 15 minutes with naringenin, eriodictyol, dihydrokaempferol and taxifolin eluting at 12.50, 11.56, 10.20, and 8.85 minutes respectively. A diode array detector (DAD) was used for the detection of the molecule of interest at 288 nm.

Example 6—Anthocyanidins and Anthocyanins

For sampling (+)-catechin, cyanidin, and cyanidin-3-glucoside the reaction fluid was acidified with 13 M HCl (1:40 v/v), and extracted with 100% ethanol followed by mixing, centrifugation and filtration through a 0.45 μm filter. The HPLC method was as follows: An Agilent 1200 HPLC was fitted with a LiChrospher RP-8 Column 250 mm×4.6 mm, 5 μm, equipped with a LiChrospher 100 RP-8 (5 μm) LiChroCART 4-4 guard column. The column was heated to 25° C. with the sample block being maintained at 25° C. For each sample, 10 μL was injected and the product was eluted at a flow rate of 1.0 ml/min using 0.1% phosphoric acid in water (solvent A) and acetonitrile (solvent B) with the following gradient: 90% A to 10% A for 12 min, 90% A for 0.5 min, and 90% A for 3.5 min for column equilibration. The run time was a total of 16 minutes with cyanidin-3-glycoside eluting at 6.95 mins and cyanidin eluting at 8.9 minutes. A diode array detector (DAD) was used for the detection of the molecule of interest at either 280 nm or 530 nm.

Example 7—Flavonoid Production

Figure 4:
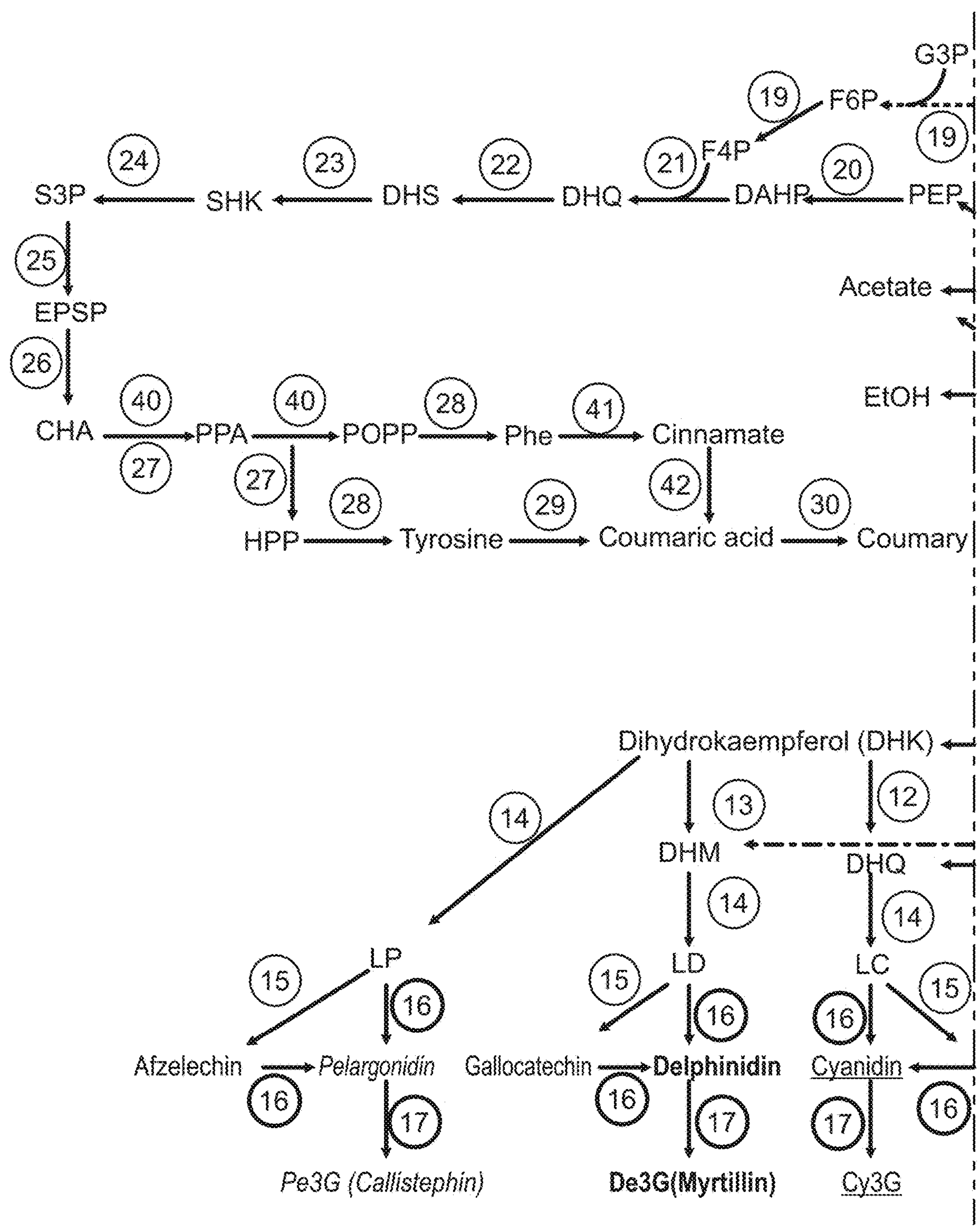
FIG. 4 shows the pathway of flavonoid and anthocyanin bioproduction in engineered cells and methods of preparing anthocyanins described herein.
Figure 4:
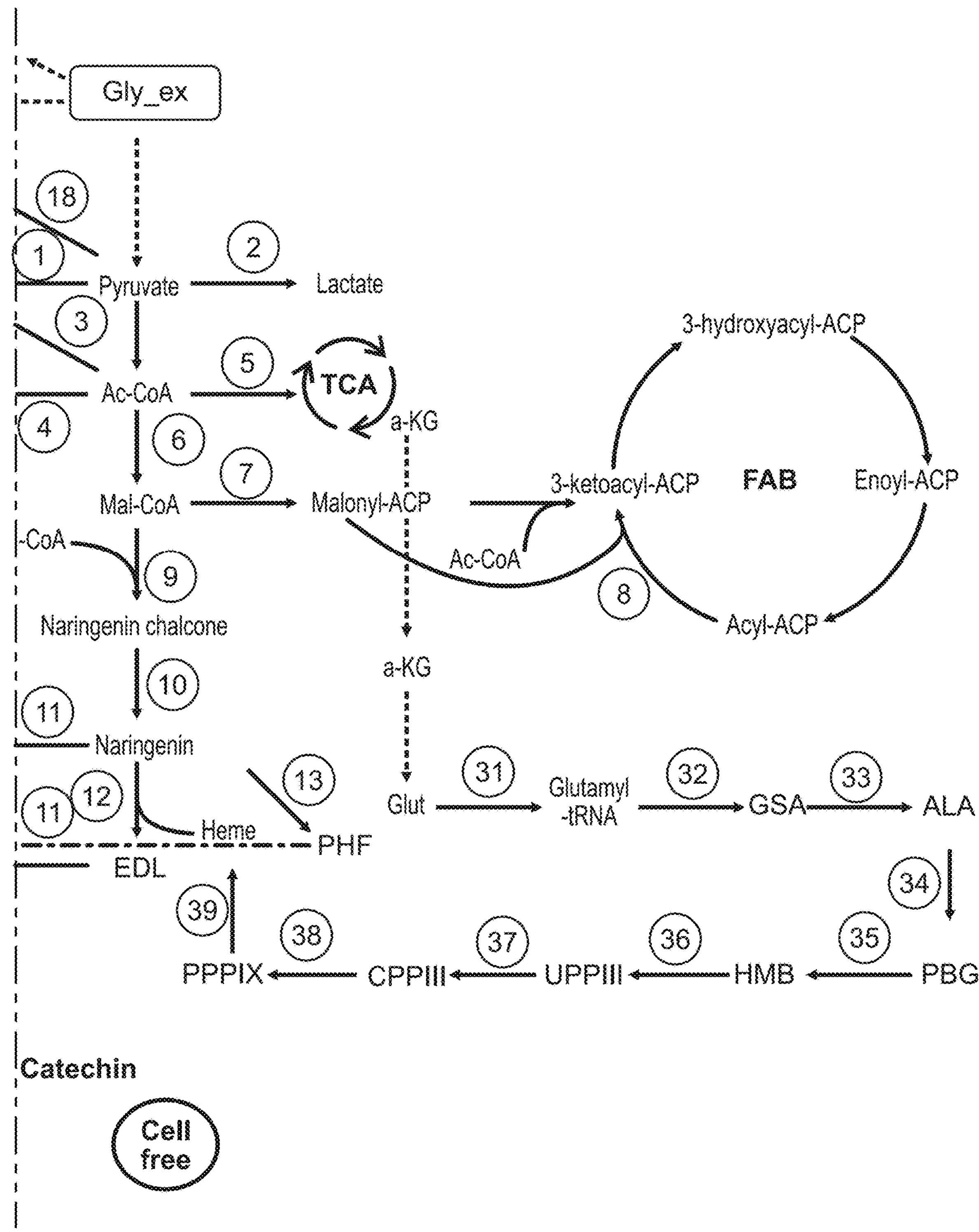

The example provides a combination of modifications to the *E. coli* host genome including deletions and overexpression of enzymes from other organisms to recapitulate the bioproduction pathway described in FIG. 4. Accordingly, the invention provides an engineered host cell that comprises one or more genetic modifications (as shown in FIG. 4 and described in this Example 7 and herein above in this application) that result in production of flavonoid or anthocyanin from a carbon source that can also be an energy source, through multiple chemical intermediates, by the engineered host cell. In certain embodiments, the production of flavonoid or anthocyanin from a carbon source that can also be an energy source occurs through enzymatic transformation. In certain embodiments, the carbon source is selected from a group consisting of: (i) glycerol, (ii) a sugar, (iii) an organic acid, (iv) an amino acid, and (v) any combination thereof. In certain embodiments, the engineered host cell is cultured in a medium comprising molecules selected from a group consisting of: (i) glycerol, (ii) a sugar, (iii) an organic acid, (iv) an amino acid, and (v) any combination thereof. As shown in FIG. 4, in certain embodiments, one or more genetic modifications lead to increase in metabolic flux to flavonoid precursors or cofactors. As shown in FIG. 4, in certain embodiments, one or more of the genetic modifications cause reduction of formation of byproducts. As shown in FIG. 4, in certain embodiments, one or more genetic modifications are selected from: (i) one or more modifications for over-expressing one or more endogenous genes in the engineered host cells; (ii) one or more modifications for under-expressing one or more endogenous genes in the engineered host cells; (iii) one or more genetic modification is expressing one or more non-native genes in the engineered host cells; and (iv) a combination thereof.

As shown in FIG. 4, in certain embodiments, the engineered host cell is cultured in a medium comprising molecules selected from: tyrosine, phenylalanine, malonate, p-coumarate, bicarbonate, acetate, pantothenate, biotin, thiamine, alpha-ketoglutarate, ascorbate, and 5-aminolevulinic acid.

As shown in FIG. 4, in certain embodiments, the engineered host cell comprises at least one or more nucleic acid sequences selected from: (i) a nucleic acid sequences encoding tyrosine ammonia lyase activity; (ii) a nucleic acid sequences encoding phenylalanine ammonia lyase activity; (iii) cinnamate 4-hydroxylase; and (iv) any combination thereof. As shown in FIG. 4, in certain embodiments, the engineered host cell comprises at least one or more peptides selected from: (i) chalcone isomerase; (ii) chalcone synthase; (iii) a fusion protein comprises a chalcone synthase and a chalcone isomerase; and (iv) any combination thereof.

As shown in FIG. 4, in certain embodiments, one or more genetic modifications decreases fatty acid biosynthesis. As shown in FIG. 4, in certain embodiments, the engineered host cell comprises an exogenous nucleic acid sequence selected from: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding flavanone-3-hydroxylase, wherein flavanone-3-hydroxylase forms dihydrokaempferol from naringenin; and (v) any combinations thereof.

As shown in FIG. 4, in certain embodiments, the engineered host cell comprises at least one or more nucleic acid sequences selected from: (i) nucleic acid sequences encoding tyrosine ammonia lyase activity; (ii) nucleic acid sequences encoding phenylalanine ammonia lyase activity; (iii) nucleic acid sequences encoding cinnamate 4-hydroxylase activity; (iv) nucleic acid sequences encoding 4-courmarate-CoA ligase (4CL) activity; and (v) any combination thereof.

As shown in FIG. 4, in certain embodiments, the engineered host cell comprises an exogenous nucleic acid sequence selected from the group consisting of: (i) nucleic acid sequence encoding tyrosine ammonia lyase, wherein the encoded tyrosine ammonia lyase forms 4-coumaric acid using tyrosine as a substrate; (ii) nucleic acid sequence encoding phenylalanine ammonia lyase, wherein the encoded phenylalanine ammonia lyase converts phenylalanine to trans-cinnamic acid; (iii) nucleic acid sequence encoding cinnamate-4-hydroxylase, wherein the cinnamate-4-hydroxylase produces 4-coumaric acid from trans-cinnamic acid; (iv) nucleic acid sequence encoding 4-courmarate-CoA ligase activity, wherein 4-courmarate-CoA ligase forms p-coumaroyl-CoA from coumaric acid (v) nucleic acid sequence encoding chalcone synthase activity, wherein chalcone synthase forms naringenin chalcone from malonyl-CoA and p-coumaroyl-CoA; (vi) nucleic acid sequence encoding chalcone isomerase activity, wherein chalcone isomerase forms naringenin from naringenin chalcone; (vii) nucleic acid sequence encoding flavanone-3-hydroxylase, wherein flavanone-3-hydroxylase forms dihydrokaempferol from naringenin; and (viii) any combinations thereof.

The compositions as described above, can be used in methods described herein for increasing the production of flavonoids or anthocyanins. Such methods involve providing any of the compositions described above to result in enzymatic transformation by the engineered host cell of glycerol through multiple chemical intermediates into a flavonoid or anthocyanin (such as shown in part or in whole in FIG. 4).

In yet another aspect, it is envisioned that the pathway illustrated in FIG. 4 can be carried out using a plurality of engineered host cells, as opposed to a single host cell as described above. In such embodiments, the plurality of the engineered host cells have one or more genetic modifications that result in enzymatic transformation by the engineered host cell of glycerol through multiple chemical intermediates into a flavonoid or anthocyanin (as shown in FIG. 4).

Aspects of the invention are now described with reference herein to FIG. 4.

Step 1: conversion of pyruvate to acetate. poxB is deleted to reduce carbon loss and eliminate the byproducts.

Step 2: conversion of pyruvate to lactate. ldhA is deleted to reduce carbon loss and eliminate the byproducts.

Step 3: conversion of Acetyl-CoA to acetate. ackA-pta is deleted to reduce carbon loss and eliminate the byproducts.

Step 4: conversion of Acetyl-CoA to ethanol (EtOH). adhE is deleted to reduce carbon loss and eliminate the byproducts.

Step 5: conversion of acetyl-CoA to a substrate for the tricarboxylic acid cycle (TCA).

Step 6: conversion of acetyl-CoA to mal-CoA. Heterologous ACC is expressed to increase the concentration of available mal-CoA. Heterologous ACC may be obtained from fungal species. Accordingly, embodiments of the invention provide an engineered host cell that comprises one or more genetic modifications to increase the production and/or availability of malonyl-CoA. In certain embodiments, the engineered host cell comprises one or more genetic modifications selected from: (i) expression of acetyl-CoA carboxylase (ACC); and (ii) overexpression of acetyl-CoA carboxylase. In another embodiment, the engineered host cell is an *E. coli*. In certain embodiments, the acetyl-CoA carboxylase is from: *Mucor circinelloides, Rhodotorula toruloides, Lipomyces starkeyi*, and *Ustilago maydis*, and orthologs of acetyl-CoA carboxylase having at least 50% amino acid identity to the acetyl-CoA carboxylase of these aforementioned species. In certain embodiments, one or more genetic modification is deletion or attenuation of one or more fatty biosynthetic genes resulting in decrease in fatty acid biosynthesis. In certain embodiments, one or more genetic modification is overexpression of acetyl-CoA synthase (ACS). In certain embodiments, the acetyl-CoA synthase is selected from: acetyl-CoA synthase gene of *E. coli*, acetyl-CoA synthase gene of *Salmonella typhimurium*, and orthologs of acetyl-CoA synthase gene in any other species having at least 50% amino acid identity to the acetyl-CoA synthase gene of *E. coli* and *Salmonella typhimurium*. In certain embodiments, one or more genetic modification is selected from a group consisting of: (i) overexpression a gene encoding pyruvate dehydrogenase (PDH), wherein the PDH may include E354K mutation; (ii) exogenous nucleic acid sequence encoding a malonyl-CoA synthetase; (iii) upregulation of endogenous pantothenate kinase (PanK), wherein PanK is not feedback inhibited by coenzyme A; (iv) exogenous nucleic acid sequence encoding a malonate transporter; and (v) any combinations thereof. In certain embodiments, the malonyl-CoA synthetase is selected from of malonyl-CoA synthetases of *Streptomyces coelicolor, Rhodopseudomonas palustris*, or a malonyl-CoA synthetase having at least 50% identity to any of these or other naturally occurring malonyl-CoA synthetases. In certain embodiments, one or more genetic modifications to decrease fatty acid biosynthesis is selected from: (i) mutation or downregulation of a gene encoding malonyl-CoA-ACP transacylase (*E. coli* fabD); (ii) modifications to the gene beta-ketoacyl-ACP synthase II (*E. coli* fabF); (iii) downregulation of beta-ketoacyl-ACP synthase I enzyme (*E. coli* fabB); (iv) downregulation of acyl carrier protein (*E. coli* acpP); and (v) any combinations thereof. In certain embodiments, the engineered host cell comprises peptides selected from: (i) acetyl-CoA carboxylase (ACC) having an amino acid sequence at least 80% identical to the polypeptide set forth in SEQ ID NO: 15 or SEQ ID NO: 16; (ii) malonate CoA-transferase having an amino acid sequence at least 80% identical to the polypeptide set forth in SEQ ID NO: 19; (iii) acetyl-CoA synthase (ACS) having an amino acid sequence at least 80% identical to the polypeptide set forth in SEQ ID NO: 16; (iv) malonyl-CoA synthase having an amino acid sequence at least 80% identical SEQ ID NO: 77, SEQ ID NO: 78, or SEQ ID NO: 79; (v) malonate transporter having an amino acid sequence at least 80% identical to SEQ ID NO: 80, SEQ ID NO: 81, SEQ ID NO: 82, SEQ ID NO: 83, SEQ ID NO: 84, SEQ ID NO: 85, SEQ ID NO: 86, or SEQ ID NO: 87; (vi) pantothenate kinase having an amino acid sequence at least 80% identical to SEQ ID NO: 88, SEQ ID NO: 89, or SEQ ID NO: 90; and (vii) any combinations thereof.

In another aspect, the invention provides a method of increasing the production of flavonoids comprising an engineered host cell, wherein the one or more engineered host cells comprise one or more genetic modifications to increase production and/or availability of malonyl-CoA. In certain embodiments, the engineered host cell comprises one or more genetic modifications selected from: (i) expression of acetyl-CoA carboxylase (ACC); and (ii) overexpression of acetyl-CoA carboxylase. In another embodiment, the engineered host cell is an *E. coli*. In certain embodiments, the acetyl-CoA carboxylase is from: *Mucor circinelloides, Rhodotorula toruloides, Lipomyces starkeyi*, and *Ustilago maydis*, and orthologs of acetyl-CoA carboxylase having at least 50% amino acid identity to the acetyl-CoA carboxylase of these aforementioned species. In certain embodiments, one or more genetic modification is deletion or attenuation of one or more fatty biosynthetic genes resulting in decrease in fatty acid biosynthesis. In certain embodiments, one or more genetic modification is overexpression of acetyl-CoA synthase (ACS). In certain embodiments, the acetyl-CoA synthase is selected from: acetyl-CoA synthase gene of *E. coli*, acetyl-CoA synthase gene of *Salmonella typhimurium*, and orthologs of acetyl-CoA synthase gene in any other species having at least 50% amino acid identity to the acetyl-CoA synthase gene of *E. coli* and *Salmonella typhimurium*. In certain embodiments, one or more genetic modification is selected from a group consisting of: (i) overexpression a gene encoding pyruvate dehydrogenase (PDH), wherein the PDH may include E354K mutation; (ii) exogenous nucleic acid sequence encoding a malonyl-CoA synthetase; (iii) upregulation of endogenous pantothenate kinase (PanK), wherein PanK is not feedback inhibited by coenzyme A; (iv) exogenous nucleic acid sequence encoding a malonate transporter; and (v) any combinations thereof. In certain embodiments, the malonyl-CoA synthetase is selected from of malonyl-CoA synthetases of *Streptomyces coelicolor, Rhodopseudomonas palustris*, or a malonyl-CoA synthetase having at least 50% identity to any of these or other naturally occurring malonyl-CoA synthetases. In certain embodiments, one or more genetic modifications to decrease fatty acid biosynthesis is selected from: (i) mutation or downregulation of a gene encoding malonyl-CoA-ACP transacylase (*E. coli* fabD); (ii) modifications to the gene beta-ketoacyl-ACP synthase II (*E. coli* fabF); (iii) downregulation of beta-ketoacyl-ACP synthase I enzyme (*E. coli* fabB); (iv) downregulation of acyl carrier protein (*E. coli* acpP); and (v) any combinations thereof. In certain embodiments, the engineered host cell comprises peptides selected from: (i) acetyl-CoA carboxylase (ACC) having an amino acid sequence at least 80% identical to the polypeptide set forth in SEQ ID NO: 15 or SEQ ID NO: 16; (ii) malonate CoA-transferase having an amino acid sequence at least 80% identical to the polypeptide set forth in SEQ ID NO: 19; (iii) acetyl-CoA synthase (ACS) having an amino acid sequence at least 80% identical to the polypeptide set forth in SEQ ID NO: 16; (iv) malonyl-CoA synthase having an amino acid sequence at least 80% identical SEQ ID NO: 77, SEQ ID NO: 78, or SEQ ID NO: 79; (v) malonate transporter having an amino acid sequence at least 80% identical to SEQ ID NO: 80, SEQ ID NO: 81, SEQ ID NO:

82, SEQ ID NO: 83, SEQ ID NO: 84, SEQ ID NO: 85, SEQ ID NO: 86, or SEQ ID NO: 87; (vi) pantothenate kinase having an amino acid sequence at least 80% identical to SEQ ID NO: 88, SEQ ID NO: 89, or SEQ ID NO: 90; and (vii) any combinations thereof.

Step 7: conversion of mal-CoA to malonyl-ACP (acyl carrier protein). malonyl-coA-ACP transacylase (fabD) is downregulated to increase carbon flux.

Step 8: conversion of malonyl-ACP to 3-ketyoacyl-ACP. beta-ketoacyl-ACP synthase II (fabF) is downregulated to increase carbon flux.

Step 9: conversion to mal-CoA to naringenin chalcone; conversion of coumaryl-CoA to naringenin chalcone. A heterologous CHS is overexpressed.

Step 10: conversion to naringenin chalcone to naringenin. A heterologous CHI is overexpressed.

Steps 11, 12, and 13: conversion of naringenin to dihydrokaempferol (DHK); conversion of naringenin to eriodictyol (EDL); conversion of eriodictyol (EDL) to dihydroquercetin (DHQ); conversion of (DHK) to dihydroquercetin (DHQ); conversion of dihydrokaempferol (DHK) to dihydromyricetin (DHM); conversion of pentahydroxyflayaone (PHF) to dihydromyricein (DHM). Heterologous F3'5'H, F3H, F3H, and/or CPR are overexpressed. Accordingly, as shown in FIG. 4, in another aspect, the invention provides method of increasing the production of dihydroquercetin (DHQ), dihydromyricein (DHM), eriodictyol (EDL), and/or pentahydroxyflayaone (PHF) comprising an engineered host cell, wherein the engineered host cell comprises cytochrome P450 reductase (CPR) and at least one of flavanone-3'-hydroxylase (F3'H) or flavonoid 3',5'-hydroxylase (F3'5'H). In certain embodiments, the precursor for increase in production of dihydroquercetin (DHQ), dihydromyricein (DHM), eriodictyol (EDL), and/or pentahydroxyflavone (PHF) is naringenin and/or dihydrokaempferol (DHK). In certain embodiments, the engineered host cell further comprises peptides selected from a group consisting of: (i) flavonoid 3'-hydroxylase (F3'H); (ii) cytochrome P450 reductase (CPR); and (iii) any combination thereof. In certain embodiments, the engineered host cell produces eriodictyol or taxifolin. In certain embodiments, the engineered host cell further comprises flavonoid 3',5'-hydroxylase (F3'5'H). In certain embodiments, the engineered host cell produces pentahydroxyflavone or dihydromyricetin. In certain embodiments, flavonoid 3'-hydroxylase (F3'H) is truncated to remove the N-terminal leader sequence. In certain embodiments, cytochrome P450 reductase (CPR) is truncated to remove the N-terminal leader sequence. In certain embodiments, flavonoid 3'-hydroxylase (F3'H) is fused with cytochrome P450 reductase (CPR). In certain embodiments, flavonoid 3',5'-hydroxylase (F3'5'H) is fused with cytochrome P450 reductase (CPR). In certain embodiments, flavanone-3-hydroxylase (F3H) has an amino acid sequence at least 80% identical to the polypeptide set forth in SEQ ID NO. 7. In certain embodiments, flavanone-3'-hydroxylase (F3'H) has an amino acid sequence at least 80% identical to the polypeptide set forth in SEQ ID NO. 8. In certain embodiments, cytochrome P450 reductase (CPR) has an amino acid sequence at least 80% identical to the polypeptide set forth in SEQ ID NO. 9. In certain embodiments, flavonoid 3',5'-hydroxylase (F3'5'H) has an amino acid sequence at least 80% identical to the polypeptides selected from a group consisting of: (i) SEQ ID NO. 10, (ii) SEQ ID NO. 56, and (iii) SEQ ID NO. 57. In certain embodiments, the engineered host cell further comprises cytochrome b5. In certain embodiments, cytochrome b5 has an amino acid sequence at least 80% identical to the polypeptide set forth in SEQ ID NO. 98.

As shown in FIG. 4, in another aspect, the invention provides method of increasing the production of dihydroquercetin (DHQ), dihydromyricein (DHM), eriodictyol (EDL), and/or pentahydroxyflayaone (PIF) comprising an engineered host cell, wherein the engineered host cell comprises cytochrome P450 reductase (CPR) and at least one of flavanone-3'-hydroxylase (F3'H) or flavonoid 3',5'-hydroxylase (F3'5'H). In certain embodiments, the precursor for increase in production of dihydroquercetin (DHQ), dihydromyricetin (DHM), eriodictyol (EDL), and/or pentahydroxyflavone (PIF) is naringenin and/or dihydrokaempferol (DHK). In certain embodiments, the engineered host cell further comprises peptides selected from a group consisting of: (i) flavonoid 3'-hydroxylase (F3'H); (ii) cytochrome P450 reductase (CPR); and (iii) any combination thereof. In certain embodiments, the engineered host cell produces eriodictyol or taxifolin. In certain embodiments, the engineered host cell further comprises flavonoid 3',5'-hydroxylase (F3'5'H). In certain embodiments, the engineered host cell produces pentahydroxyflavone or dihydromyricetin. In certain embodiments, flavonoid 3'-hydroxylase (F3'H) is truncated to remove the N-terminal leader sequence. In certain embodiments, cytochrome P450 reductase (CPR) is truncated to remove the N-terminal leader sequence. In certain embodiments, flavonoid 3'-hydroxylase (F3'H) is fused with cytochrome P450 reductase (CPR). In certain embodiments, flavonoid 3',5'-hydroxylase (F3'5'H) is fused with cytochrome P450 reductase (CPR). In certain embodiments, flavanone-3-hydroxylase (F3H) has an amino acid sequence at least 80% identical to the polypeptide set forth in SEQ ID NO. 7. In certain embodiments, flavanone-3'-hydroxylase (F3'H) has an amino acid sequence at least 80% identical to the polypeptide set forth in SEQ ID NO. 8. In certain embodiments, cytochrome P450 reductase (CPR) has an amino acid sequence at least 80% identical to the polypeptide set forth in SEQ ID NO. 9. In certain embodiments, flavonoid 3',5'-hydroxylase (F3'5'H) has an amino acid sequence at least 80% identical to the polypeptides selected from a group consisting of: (i) SEQ ID NO. 10, (ii) SEQ ID NO. 56, and (iii) SEQ ID NO. 57. In certain embodiments, the engineered host cell further comprises cytochrome b5. In certain embodiments, cytochrome b5 has an amino acid sequence at least 80% identical to the polypeptide set forth in SEQ ID NO. 98.

Step 14: conversion of dihydroquercetin (DHQ) to leucocyanidin (LC); conversion of dihydrokaempferol (DHK) to leucopelargonidin (LP); and conversion of dihydromyricetin (DHM) to leucodelphinidin (LD). Heterologous DFR is overexpressed.

Step 15: conversion of leucocyanidin (LC) to catechin; conversion of leucodelphinidin (LD) to gallocatechin; and conversion of leucopelargonidin (LP) to afzelechin. Heterologous LAR is overexpressed.

Step 16: conversion of catechin to cyanidin; conversion of leucocyanidin (LC) to catechin; conversion to leucodelphinidin (LD) to delphinidin; conversion of gallocatechin to delphinidin; conversion of leucopelargonidin (LP) to pelargonidin; or conversion of afzelechin to pelargonidin. Heterologous ANS is overexpressed. Step 16 could be carried in vivo or in a cell-free medium. Accordingly, as shown in FIG. 4, in another aspect, the invention provides an engineered host cell, wherein the engineered host cell comprises one or more genetic modifications to increase transformation of leucocyanidin or catechin to cyanidin-3-glucoside (Cy3G). In certain embodiments, one or more genetic modifications comprises overexpression of anthocyanin synthase. In certain embodiments, the anthocyanin synthase is selected from: (i) anthocyanin synthase of *Carica papaya* (SEQ. ID NO:13); (ii) the anthocyanin synthase has an amino acid sequence at least 80% identical to SEQ. ID NO: 66, SEQ. ID NO: 67, SEQ. ID NO: 68, or SEQ. ID NO: 69; (iii) the anthocyanin synthase has an amino acid sequence at least 80% identical to SEQ. ID NO: 13; and (iv) any combinations thereof. In certain embodiments, one or more engineered host cells comprises flavonoid-3-glucosyl transferase (3GT). In certain embodiments, flavonoid-3-glucosyl transferase is selected from: (i) flavonoid-3-glucosyl transferase in *Vitis labrusca* (SEQ. ID NO:14); (ii) the flavonoid-3-glucosyl transferase has an amino acid sequence at least 80% identical to SEQ. ID NO: 70, SEQ. ID NO: 71, SEQ. ID NO: 72, or SEQ. ID NO: 73; and (iii) any combinations thereof. In certain embodiments, one or more genetic modifications comprises overexpression of anthocyanin synthase and flavonoid-3-glucosyl transferase (3GT). In certain embodiments, one or more genetic modifications comprises overexpression of anthocyanin synthase and flavonoid-3-glucosyl transferase (3GT). In certain embodiments, the one or more genetic modifications comprises overexpression of anthocyanin synthase and flavonoid-3-glucosyl transferase (3GT). In certain embodiments, the one or more genetic modifications are selected from a group consisting of: (i) anthocyanin synthase, (ii) flavonoid-3-glucosyl transferase (3GT), and (iii) a combination thereof.

In another aspect, the invention provides a method for increasing the production of flavonoids comprising an engineered host cell, wherein the engineered host cell comprises one or more genetic modifications to increase transformation of leucocyanidin or catechin to cyanidin-3-glucoside (Cy3G). In certain embodiments, one or more genetic modifications comprises overexpression of anthocyanin synthase. In certain embodiments, the anthocyanin synthase is selected from: (i) anthocyanin synthase of *Carica papaya* (SEQ. ID NO:13); (ii) the anthocyanin synthase has an amino acid sequence at least 80% identical to SEQ. ID NO: 66, SEQ. ID NO: 67, SEQ. ID NO: 68, or SEQ. ID NO: 69; (iii) the anthocyanin synthase has an amino acid sequence at least 80% identical to SEQ. ID NO: 13; and (iv) any combinations thereof. In certain embodiments, one or more engineered host cells comprises flavonoid-3-glucosyl transferase (3GT). In certain embodiments, flavonoid-3-glucosyl transferase is selected from: (i) flavonoid-3-glucosyl transferase in *Vitis labrusca* (SEQ. ID NO:14); (ii) the flavonoid-3-glucosyl transferase has an amino acid sequence at least 80% identical to SEQ. ID NO: 70, SEQ. ID NO: 71, SEQ. ID NO: 72, or SEQ. ID NO: 73; and (iii) any combinations thereof. In certain embodiments, one or more genetic modifications comprises overexpression of anthocyanin synthase and flavonoid-3-glucosyl transferase (3GT). In certain embodiments, one or more genetic modifications comprises overexpression of anthocyanin synthase and flavonoid-3-glucosyl transferase (3GT). In certain embodiments, the one or more genetic modifications comprises overexpression of anthocyanin synthase and flavonoid-3-glucosyl transferase (3GT). In certain embodiments, the one or more genetic modifications are selected from a group consisting of: (i) anthocyanin synthase, (ii) flavonoid-3-glucosyl transferase (3GT), and (iii) a combination thereof.

In another aspect, the invention provides a method of increasing the transformation of leucocyanidin or catechin to cyanidin-3-glucoside (Cy3G) comprising anthocyanin synthase, wherein the anthocyanin synthase is selected from: (i) anthocyanin synthase of *Carica papaya* (SEQ. ID NO:13); (ii) the anthocyanin synthase has an amino acid sequence at least 80% identical to SEQ. ID NO: 66, SEQ. ID NO: 67, SEQ. ID NO: 68, or SEQ. ID NO: 69; (iii) the anthocyanin synthase has an amino acid sequence at least 80% identical to SEQ. ID NO: 13; and (iv) any combinations thereof.

In another aspect, the invention provides a method of increasing the transformation of leucocyanidin or catechin to cyanidin-3-glucoside (Cy3G) comprising flavonoid-3-glucosyl transferase (3GT), wherein the flavonoid-3-glucosyl transferase is selected from: (i) flavonoid-3-glucosyl transferase in *Vitis labrusca* (SEQ. ID NO:14); (ii) the flavonoid-3-glucosyl transferase has an amino acid sequence at least 80% identical to SEQ. ID NO: 70, SEQ. ID NO: 71, SEQ. ID NO: 72, or SEQ. ID NO: 73; and (iii) any combinations thereof.

Step 17: conversion of pelargonidin to callistephin; conversion of delphinidin to myrtillin (De3G); conversion of cyanidin to Cy3G. Heterologous 3GT was overexpressed in *E. coli*. Step 17 could be carried in vivo or as a cell-free reaction.

Step 18: conversion of pyruvate to phosphoenolpyruvate (PEP). ppsA is overexpressed to upregulate tyrosine.

Step 19: conversion of fructose-6-phosphate (F6P) to erythrose-4-phosphate (E4P). tktA is overexpressed to upregulate tyrosine.

Step 20: conversion of phosphoenolpyruvate (PEP) to deoxy-d-arabino-heptulosonate-7-phosphate (DAHP). aroG variant is overexpressed to upregulate tyrosine.

Step 21: conversion of deoxy-d-arabino-heptulosonate-7-phosphate (DAHP) to dehydroquinate (DHQ); conversion of erythrose-4-phosphate (E4P) to dehydroquinate (DHQ).

Step 22: conversion of dehydroquinate (DHQ) to 3-dehydroshikimate (DHS).

Step 23: conversion of 3-dehydroshikimate (DHS) to shikimic acid (SHK). aroE is overexpressed to upregulate tyrosine.

Step 24: conversion of shikimic acid (SHK) to shikimate-3-phosphate (S3P).

Step 25: conversion of shikimate-3-phosphate (S3P) to 5-enolpyruvylshikimate-3-phosphate (EPSP).

Step 26: conversion of 5-enolpyruvylshikimate-3-phosphate (EPSP) to chorismic acid (CHA).

Step 27: conversion of chorismic acid (CHA) to prephenate (PPA); conversion of prephenate (PPA) to 4-hydroxy-phenylpyruvate (HPP). tryA variant is overexpressed.

Step 28: conversion of 4-hydroxy-phenylpyruvate (HPP) to tyrosine; conversion of phenylpyruvate (POPP) to phenylalanine (Phe). Accordingly, as shown in FIG. 4, embodiments of the invention provide an engineered host cell, wherein the engineered host cell comprises one or more genetic modifications to increase endogenous biosynthesis of tyrosine. In certain embodiments, one or more genetic modifications comprises upregulation of 3-deoxy-D-arabino-heptulosonate synthase. In certain embodiments, one or more genetic modifications are selected from: (i) upregulation of chorismate mutase; (ii) upregulation of prephenate dehydrogenase; (iii) overexpression of shikimate kinase; (iv) overexpression of shikimate dehydrogenase; and (v) any combinations thereof. In certain embodiments, one or more genetic modifications comprises downregulation of L-phenylalanine biosynthetic pathway. In certain embodiments, one or more genetic modifications comprises expression of exogenous phosphoenolpyruvate synthase (ppsA). In certain embodiments, one or more genetic modifications comprises expression of exogenous transketolase (tktA). In certain embodiments, wherein the one or more genetic modifications comprises disruption of tyrR gene.

As shown in FIG. 4, in another aspect, the invention provides a method of increasing endogenous biosynthesis of tyrosine comprising an engineered cell, wherein the engineered host cell comprises one or more genetic modifications to increase endogenous biosynthesis of tyrosine. In certain embodiments, one or more genetic modifications comprises upregulation of 3-deoxy-D-arabino-heptulosonate synthase. In certain embodiments, one or more genetic modifications are selected from: (i) upregulation of chorismate mutase; (ii) upregulation of prephenate dehydrogenase; (iii) overexpression of shikimate kinase; (iv) overexpression of shikimate dehydrogenase; and (v) any combinations thereof. In certain embodiments, one or more genetic modifications comprises downregulation of L-phenylalanine biosynthetic pathway. In certain embodiments, one or more genetic modifications comprises expression of exogenous phosphoenolpyruvate synthase (ppsA). In certain embodiments, one or more genetic modifications comprises expression of exogenous transketolase (tktA). In certain embodiments, wherein the one or more genetic modifications comprises disruption of tyrR gene.

Step 29: conversion of tyrosine to coumaric acid. A heterologous TAL is overexpressed.

Step 30: conversion of coumaric acid to coumaryl-CoA. A heterologous 4CL is overexpressed.

Step 31: conversion of glutamate (Glut) to glutamyl-tRNA.

Step 32: conversion of glutamyl-tRNA to glutamate semialdehyde (GSA). hemA is overexpressed to upregulate ALA.

Step 33: conversion of glutamate semialdehyde (GSA) to 6 amino levulinic acid (ALA). hemL is overexpressed to upregulate ALA.

Step 34: conversion of 6 amino levulinic acid (ALA) to porphobilinogen (PBG).

Step 35: conversion of porphobilinogen (PBG) to hydroxymethylbilane (HMB).

Step 36: conversion of hydroxymethylbilane (HMB) to uroporphyrinogen III (UPPIII).

Step 37: conversion of uroporphyrinogen III (UPPIII) to coproporphyrinogen III (CPPIII).

Step 38: conversion of coproporphyrinogen III (CPPIII) to protoporphyrinogen IX (PPPIX).

Step 39: conversion of protoporphyrinogen IX (PPPIX) to protoporphyrin IX, which is subsequently covered to heme.

Step 40: conversion of prephenate (PPA) to phenylpyruvate (POPP).

Step 41: conversion of phenylalanine (Phe) to cinnamate. Heterologous PAL and/or TAL are overexpressed.

Step 42: conversion of cinnamate to coumaric acid. Heterologous C4H/CPR are overexpressed.

TABLE 11

| Enzyme Sequences: | | |
|---|---|---|
| Enzyme: | Sequence: | SEQ ID: |
| Tyrosine ammonia-lyase (TAL) *Saccharothrix espanaensis* Accession: ABC88669.1 | MTQVVERQADRLSSREYLARVVRSAGWDAGLTSCTD EEIVRMGASARTIEEYLKSDKPIYGLTQGFGPLVLFDA DSELEQGGSLISHLGTGQGAPLAPEVSRLILWLRIQNM RKGYSAVSPVFWQKLADLWNKGFTPAIPRHGTVSAS GDLQPLAHAALAFTGVGEAWTRDADGRWSTVPAVD ALAALGAEPFDWPVREALAFVNGTGASLAVAVLNHR SALRLVRACAVLSARLATLLGANPEHYDVGHGVARG QVGQLTAAEWIRQGLPRGMVRDGSRPLQEPYSLRCA PQVLGAVLDQLDGAGDVLAREVDGCQDNPITYEGEL LHGGNFHAMPVGFASDQIGLAMHMAAYLAERQLGL LVSPVTNGDLPPMLTPRAGRGAGLAGVQISATSFVSRI RQLVFPASLTTLPTNGWNQDHVPMALNGANSVFEAL ELGWLTVGSLAVGVAQLAAMTGHAAEGVWAELAGI CPPLDADRPLGAEVRAARDLLSAHADQLLVDEADGK DFG | 1 |
| Phenylalanine ammonia-lyase (PAL) *Brevibacillus laterosporus* LMG 15441 Accession: WP_003337219.1 | MSQVALFEQELMLHGKHTLLLNGNDLTITDVAQMAK GTFEAFTFHISEEANKRIEECNELKHEIMNQHNPIYGV TTGFGDSVHRQISGEKAWDLQRNLIRFLSCGVGPVAD EAVARATMLIRTNCLVKGNSAVRLEVIHQLIAYMERG ITPIIPERGSVGASGDLVPLSYLASILVGEGKVLYKGEE REVAEALGAEGLEPLTLEAKEGLALVNGTSFMSAFAC LAYADAEEIAFIADICTAMASEALLGNRGHFYSFIHEQ KPHLGQMASAKNIYTLLEGSQLSKEYSQIVGNNEKLD SKAYLELTQSIQDRYSIRCAPHVTGVLYDTLDWVKK WLEVEINSTNDNPIFDVETRDVYNGGNFYGGHVVQA MDSLKVAVANIADLLDRQLQLVVDEKFNKDLTPNLIP RFNNDNYEIGLHHGFKGMQIASSALTAEALKMSGPVS VFSRSTEAHNQDKVSMGTISSRDARTIVELTQHVAAIH LIALCQALDLRDSKKMSPQTTKIYNMIRKQVPFVERD RALDGDIEKVVQLIRSGNLKKEIHDQNVND | 2 |

TABLE 11-continued

| Enzyme Sequences: | | |
|---|---|---|
| Enzyme: | Sequence: | SEQ ID: |
| Cinnamate-4-<br>hydroxylase (C4H)<br>*Helianthus annuus*<br>*L.*<br>Accession:<br>QJC72299.1 | MDLLLIEKTLLALFAAIIGAIVISKLRGKRFKLPPGPLP<br>VPIFGNWLQVGDDLNHRNLTDLAKKFGEIFLLRMGQ<br>RNLVVVSSPDLAKEVLHTQGVEFGSRTRNVVFDIFTG<br>KGQDMVFTVYGEHWRKMRRIMTVPFFTNKVVQQYR<br>YGWEAEAAAVVEDVKKNPAAATEGVVIRRRLQLMM<br>YNNMFRIMFDRRFESEDDPLFVKLKALNGERSRLAQS<br>FEYNYGDFIPILRP<br>FLKGYLKLCKEVKEKRFQLFKDYFVDERKKLESTKSV<br>DNNQLKCAIDHILDAKEKGEINEDNVLYIVENINVAAI<br>ETTLWSIEWGIAELVNHPEIQAKLRNELDTKLGPGVQ<br>VTEPDLHKLPYLQAVIKETLRLRMAIPLLVPHMNLHD<br>AKLGGYDIPAESKILVNAWWLANNPEQWKKPEEFRP<br>ERFFEEESKVEANGNDFRYLPFGVGRRSCPGIILALPIL<br>GITIGRLVQNFELLPPPGQSKVDTTEKGGQFSLHILKHS<br>TIVAKPRAL | 3 |
| 4-coumarate-CoA<br>ligase (4CL)<br>*Petroselinum*<br>*crispum*<br>Accession:<br>P14912.1 | MGDCVAPKEDLIFRSKLPDIYIPKHLPLHTYCFENISKV<br>GDKSCLINGATGETFTYSQVELLSRKVASGLNKLGIQ<br>QGDTIMLLLPNSPEYFFAFLGASYRGAISTMANPFFTS<br>AEVIKQLKASQAKLIITQACYVDKVKDYAAEKNIQIIC<br>IDDAPQDCLHFSKLMEADESEMPEVVINSDDVVALPY<br>SSGTTGLPKGVMLTHKGLVTSVAQQVDGDNPNLYM<br>HSEDVMICILPLFHIYSLNAVLCCGLRAGVTILIMQKF<br>DIVPFLELIQKYKVTIGPFVPPIVLAIAKSPVVDKYDLS<br>SVRTVMSGAAPLGKELEDAVRAKFPNAKLGQGYGM<br>TEAGPVLAMCLAFAKEPYEIKSGACGTVVRNAEMKIV<br>DPETNASLPRNQRGEICIRGDQIMKGYLNDPESTRTTI<br>DEEGWLHTGDIGFIDDDDELFIVDRLKEIIKYKGFQVA<br>PAELEALLLTHPTISDAAVVPMIDEKAGEVPVAFVVRT<br>NGFTTTEEEIKQFVSKQVVFYKRIFRVFFVDAIPKSPSG<br>KILRKDLRARIASGDLPK | 4 |
| Chalcone synthase<br>(CHS)<br>Petunia x hybrida<br>Accession:<br>AAF60297.1 | MVTVEEYRKAQRAEGPATVMAIGTATPTNCVDQSTY<br>PDYYFRITNSEHKTDLKEKFKRMCEKSMIKKRYMHLT<br>EEILKENPSMCEYMAPSLDARQDIVVVEVPKLGKEAA<br>QKAIKEWGQPKSKITHLVFCTTSGVDMPGCDYQLTKL<br>LGLRPSVKRLMMYQQGCFAGGTVLRLAKDLAENNK<br>GARVLVVCSEITAVTFRGPNDTHLDSLVGQALFGDGA<br>GAIIIGSDPIPGVERPLFELVSAAQTLLPDSHGAIDGHL<br>REVGLTFHLLKDVPGLISKNIEKSLEEAFRPLSISDWNS<br>LFWIAHPGGPAILDQVEIKLGLKPEKLKATRNVLSNY<br>GNMSSACVLFILDEMRKASAKEGLGTTGEGLEWGVL<br>FGFGPGLTVETVVLHSVAT | 5 |
| Chalcone isomerase<br>(CHI)<br>*Medicago sativa*<br>Accession:<br>P28012.1 | MAASITAITVENLEYPAVVTSPVTGKSYFLGGAGERG<br>LTIEGNFIKFTAIGVYLEDIAVASLAAKWKGKSSEELL<br>ETLDFYRDIISGPFEKLIRGSKIRELSGPEYSRKVMENC<br>VAHLKSVGTYGDAEAEAMQKFAEAFKPVNFPPGASV<br>FYRQSPDGILGLSFSPDTSIPEKEAALIENKAVSSAVLE<br>TMIGEHAVSPDLKRCLAARLPALLNEGAFKIGN | 6 |
| Flavanone 3-<br>hydroxylase (F3H)<br>*Rubus occidentalis*<br>Accession:<br>ACM17897.1 | MAPTPTTLTAIAGEKTLQQSFVRDEDERPKVAYNQFS<br>NEIPIISLSGIDEVEGRRAEICNKIVEACEDWGVFQIVD<br>HGVDAKLISEMTRLARDFFALPPEEKLRFDMSGGKKG<br>GFIVSSHLQGEAVQDWREIVTYFSYPVRHRDYSRWPD<br>KPEGWRAVTQQYSDELMGLACKLLEVLSEAMGLEKE<br>ALTKACVDMDQKVVVNFYPKCPQPDLTLGLKRHTDP<br>GTITLLLQDQVGGLQATRDGGKTWITVQPVEGAFVV<br>NLGDHGHFLSNGRFKNADHQAVVNSNHSRLSIATFQ<br>NPAQEAIVYPLKVREGEKPILEEPITYTEMYKKKMSK<br>DLELARLKKLAKEQQPEDSEKAKLEVKQVDDIFA | 7 |
| Flavonoid 3'<br>hydroxylase (F3'H)<br>*Brassica napus*<br>Accession:<br>ABC58723.1 | MTNLYLTILLPTFIFLIVLVLSRRRNNRLPPGPNPWPIIG<br>NLPHMGPKPHQTLAAMVTTYGPILHLRLGFADVVVA<br>ASKSVAEQFLKVHDANFASRPPNSGAKHMAYNYQDL<br>VFAPYGQRWRMLRKISSVHLFSAKALEDFKHVRQEE<br>VGTLMRELARANTKPVNLGQLVNMCVLNALGREMI<br>GRRLFGADADHKAEEFRSMVTEMMALAGVFNIGDFV<br>PALDCLDLQGVAGKMKRLHKRFDAFLSSILEEHEAM<br>KNGQDQKHTDMLSTLISLKGTDFDGEGGTLTDTEIKA<br>LLLNMFTAGTDTSASTVDWAIAELIRHPEIMRKAQEE<br>LDSVVGRGRPINESDLSQLPYLQAVIKENFRLHPPTPLS<br>LPHIASESCEINGYHIPKGSTLLTNIWAIARDPDQWSDP<br>LTFRPERFLPGGEKAGVDVKGNDFELIPFGAGRRICAG<br>LSLGLRTIQLLTATLVHGFEWELAGGVTPEKLNMEET<br>YGITLQRAVPLVVHPKLRLDMSAYGLGSA | 8 |

TABLE 11-continued

| Enzyme Sequences: | | |
|---|---|---|
| Enzyme: | Sequence: | SEQ ID: |
| Cytochrome P450 reductase (CPR) *Catharanthus roseus* Accession: Q05001 | MDSSSEKLSPFELMSAILKGAKLDGSNSSDSGVAVSPA VMAMLLENKELVMILTTSVAVLIGCVVVLIWRRSSGS GKKVVEPPKLIVPKSVVEPEEIDEGKKKFTIFFGTQTGT AEGFAKALAEEAKARYEKAVIKVIDIDDYAADDEEYE EKFRKETLAFFILATYGDGEPTDNAARFYKWFVEGND RGDWLKNLQYGVFGLGNRQYEHFNKIAKVVDEKVA EQGGKRIVPLVLGDDDQCIEDDFAAWRENVWPELDN LLRDEDDTTVSTTYTAAIPEYRVVFPDKSDSLISEANG HANGYANGNTVYDAQHPCRSNVAVRKELHTPASDRS CTHLDFDIAGTGLSYGTGDHVGVYCDNLSETVEEAER LLNLPPETYFSLHADKEDGTPLAGSSLPPPFPPCTLRTA LTRYADLLNTPKKSALLALAAYASDPNEADRLKYLAS PAGKDEYAQSLVANQRSLLEVMAEFPSAKPPLGVFFA AIAPRLQPRFYSISSSPRMAPSRIHVTCALVYEKTPGGR IHKGVCSTWMKNAIPLEESRDCSWAPIFVRQSNFKLP ADPKVPVIMIGPGTGLAPFRGFLQERLALKEEGAELGT AVFFFGCRNRKMDYIYEDELNHFLEIGALSELLVAFSR EGPTKQYVQHKMAEKASDIWRMISDGAYVYVCGDA KGMARDVHRTLHTIAQEQGSMDSTQAEGFVKNLQM TGRYLRDVW | 9 |
| Flavonoid 3', 5'-hydroxylase (F3'5'H) *Delphinium* grandiflorum Accession: BAO66642 | MSTSLLLAAAAILFFITHLFLRFLLSPRRTRKLPPGPKG WPVVGALPMLGNMPHAALADLSRRYGPIVYLKLGSR GMVVASTPDSARAFLKTQDLNFSNRPTDAGATHIAYN SQDMVFADYGPRWKLLRKLSSLHMLGGKAVEDWAV VRRDEVGYMVKAIYESSCAGEAVHVPDMLVFAMAN MLGQVILSRRVFVTKGVESNEFKEMVIELMTSAGLFN VGDFIPSIAWMDLQGIVRGMKRLHKKFDALLDKILRE HTATRRERKEKPDLVDVLMDNRDNKSEQERLTDTNI KALLLNLFSAGTDTSSSTIEWALTEMIKNPSIFGRAHA EMDQVIGRNRRLEESDIPKLPYLQAICKETFRKHPSTP LNLPRVAIEPCEVEGYHIPKGTRLSVNIWAIGRDPNVW ENPLEFNPDRFLTGKMAKIDPRGNNFELIPFGAGRRIC AGTRMGIVLVEYILGSLVHAFEWKLRDGETLNMEETF GIALQKAVPLAAVVTPRLPPSAYVV | 10 |
| Dihydroflavonol 4-reductase (DFR) *Anthurium andraeanum* Accession: AAP20866.1 | MMHKGTVCVTGAAGFVGSWLIMRLLEQGYSVKATV RDPSNMKKVKHLLDLPGAANRLTLWKADLVDEGSFD EPIQGCTGVFHVATPMDFESKDPESEMIKPTIEGMLNV LRSCARASSTVRRVVFTSSAGTVSIHEGRRHLYDETS WSDVDFCRAKKMTGWMYFVSKTLAEKAAWDFAEK NNIDFISIIPTLVNGPFVMPTMPPSMLSALALITRNEPH YSILNPVQFVHLDDLCNAHIFLFECPDAKGRYICSSHD VTIAGLAQILRQRYPEFDVPTEFGEMEVFDIISYSSKKL TDLGFEFKYSLEDMFDGAIQSCREKGLLPPATKEPSYA TEQLIATGQDNGH | 11 |
| Leucoanthocyanidin reductase (LAR) *Desmodium uncinatum* Accession: Q84V83.1 | MTVSGAIPSMTKNRTLVVGGTGFIGQFITKASLGFGYP TFLLVRPGPVSPSKAVIIKTFQDKGAKVIYGVINDKEC MEKILKEYEIDVVISLVGGARLLDQLTLLEAIKSVKTIK RFLPSEFGHDVDRTDPVEPGLTMYKEKRLVRRAVEEY GIPFTNICCNSIASWPYYDNCHPSQVPPPMDQFQIYGD GNTKAYFIDGNDIGKFTMKTIDDIRTLNKNVHFRPSSN CYSINELASLWEKKIGRTLPRFTVTADKLLAHAAENII PESIVSSFTHDIFINGCQVNFSIDEHSDVEIDTLYPDEKF RSLDDCYEDFVPMVHDKIHAGKSGEIKIKDGKPLVQT GTIEEINKDIKTLVETQPNEEIKKDMKALVEAVPISAM G | 12 |
| Anthocyanin dioxygenase (ANS) *Carica papaya* Accession: XP_021901846.1 | MFSSVAVPRVEILASSGIESIPKEYVRPQEELTTIGNIFD EEKKDEGPQVPTIDLRDIDSDDQQVRQRCRDELKKAA VDWGVMHLVNHGIPDHLIDRVKKAGQAFFELPVEVK EKYANDQASGNIQGYGSKLANNASGQLEWEDYYFHL IFPEEKRDLAIWPNNPADYIEVTSEYARQLRRLVSKIL GVLSLGLGLEEGRLEKEVGGLDELLLQMKINYYPTCP QPELALGVEAHTDISALTFILHNMVPGLQLFYEGKWV TAKCVPNSIVMHVGDTIEILSNGKYKSILHRGLVNKEK VRISWAVFCEPPKEKIILKPLPETVSENEPPLFPPRTFAQ HIQHKLFRKNQENLEAK | 13 |

TABLE 11-continued

| Enzyme Sequences: | | |
|---|---|---|
| Enzyme: | Sequence: | SEQ ID: |
| Anthocyanidin-3-O-glycotransferase (3GT) *Vitis labrusca* Accession: ABR24135 | MSQTTTNPHVAVLAFPFSTHAAPLLAVVRRLAVAAPH AVFSFFSTSESNASIFHDSMHTMQCNIKSYDVSDGVPE GYVFTGRPQEGIDLFMRAAPESFRQGMVMAVAETGR PVSCLVADAFIWFAADMAAEMGVAWLPFWTAGPNS LSTHVYIDEIREKIGVSGIQGREDELLNFIPGMSKVRFR DLQEGIVFGNLNSLFSRLLHRMGQVLPKATAVFINSFE ELDDSLTNDLKSKLKTYLNIGPFNLITPPPVVPNTTGCL QWLKERKPTSVVYISFGTVTTPPPAELVALAEALEASR VPFIWSLRDKARMHLPEGFLEKTRGHGMVVPWAPQA EVLAHEAVGAFVTHCGWNSLWESVAGGVPLICRPFF GDQRLNGRMVEDVLEIGVRIEGGVFTKSGLMSCFDQI LSQEKGKKLRENLRALRETADRAVGPKGSSTENFKTL VDLVSKPKDV | 14 |
| Acetyl-CoA carboxylase (ACC) *Mucor circinelloides* 1006PhL Accession: EPB82652.1 | MVEHRSLPGHFLGGNSLESAPQGPVKDFVQAHEGHT VISKVLIANNGMAAMKEIRSVRKWAYETFGNERAIEF TVMATPEDLKANAEYIRMADNFVEVPGGSNNNNYAN VELIVDVAERTAVHAVWAGWGHASENPRLPEMLAKS KHKCLFIGPPASAMRSLGDKISSTIVAQSAQVPTMGW SGDGITETEFDAAGHVIVPDNAYNEACVKTAEQGLKA AEKIGFPVMIKASEGGGGKGIRMVKDGSNFAQLFAQV QGEIPGSPIFIMKLAGNARHLEVQLLADQYGNAISLFG RDCSVQRRHQKIIEEAPVTIAKPDVFEQMEKAAVRLG KLVGYVSAGTVEYLYSHHDDQFYFLELNPRLQVEHPT TEMVSGVNLPAAQLQIAMGIPLHRIRDIRVLYGVQPNS ASEIDFGFEHPTSLTSHRRPTPKGHVIACRITAENPDAG FKPSSGIMQELNFRSSTNVWGYFSVVSAGGLHEYADS QFGHIFAYGENRQQARKNMVIALKELSIRADFRSTVE YIIRLLETPDFEENTINTGWLDMLISKKLTAERPDTML AVFCGAVTKAHMASLDCFQQYKQSLEKGQVPSKGSL KTVFTVDFIYEEVRYNFTVTQSAPGIYTLYLNGTKTQV GIRDLSDGGLLISIDGKSHTTYSRDEVQATRMMVDGK TCLLEKESDPTQLRSPSPGKLVNLLVENGDHLNAGDA YAEIEVMKMYMPLIATEDGHVQFIKQAGATLEAGDII GILSLDDPSRVKHALPFNGTVPAFGAPHITGDKPVQRF NATKLTLQHILQGYDNQALVQTVVKDFADILNNPDLP YSELNSVLSALSGRIPQRLEASIHKLADESKAANQEFP AAQFEKLVEDFAREHITLQSEATAYKNSVAPLSSIFAR YRNGLTEHAYSNYVELMEAYYDVEILFNQQREEEVIL SLRDQHKDDLDKVLAVTLSHAKVNIKNNVILMLLDLI NPVSTGSALDKYFTPILKRLSEIESRATQKVTLKAREL LILCQLPSYEERQAQMYQILKNSVTESVYGGGSEYRTP SYDAFKDLIDTKFNVFDVLPHFFYHADPYIALAAIEVY CRRSYHAYKILDVAYNLEHKPYVVAWKFLLQTAANG IDSNKRIASYSDLTFLLNKTEEEPIRTGAMTACNSLAD LQAELPRILTAFEEEPLPPMLQRNAAPKEERMENILNI AVRADEDMDDTAFRTKICEMITANADVFRQAHLRRL SVVVCRDNQWPDYYTFRERENYQEDETIRHIEPAMA YQLELARLSNFDIKPCFIENRQMHVYYAVAKENPSDC RFFIRALVRPGRVKSSMRTADYLISESDRLLTDILDTLE IVSHEYKNSDCNHLFINFIPTFAIEADDVEHALKDFVD RHGKRLWKLRVTGAEIRFNVQSKKPDAPIIPMRFTVD NVSGFILKVEVYQEVKTEKSGWILKSVNKIPGAMHM QPLSTPYPTKEWLQPRRYKAHLMGTTYVYDFPELFRQ SVQNQWTQAIKRNPLLKQPSHLVEAKELVLDEDDVL QEIDRAPGTNTVGMVAWIMTIRTPEYPSGRRIIAIANDI TFKIGSFGVAEDQVFYKASELARALGIPRIYLSANSGA RIGLADELISQFRAAWKDASNPTAGFKYLYLTPAEYD VLAQQGDAKSVLVEEIQDEGETRLRITDVIGHTDGLG VENLKGSGLIAGATSRAYDDIFTITLVTCRSVGIGAYL VRLGQRTIQNEGQPIILTGAPALNKVLGREVYTSNLQL GGTQIMYKNGVSHLTAENDLEGIAKIVQWLSFVPDVR NAPVSMRLGADPIDRDIEYTPPKGPSDPRFFLAGKSEN GKWLSGFFDQDSFVETLSGWARTVVVGRARLGGIPM GVVSVETRTVENIVPADPANSDSTEQVFMEAGGVWFP NSAYKTAQAINDFNKGEQLPLMIFANWRGFSGGQRD MYNEVLKYGAQIVDALSNYKQPVFVYIIPNGELRGGA WVVVDPTINKDMMEMYADNNARGGVLEPEGIVEIKY RKPALLATMERLDATYASLKKQLAEEGKTDEEKAAL KVQVEAREQELLPVYQQISIQFADLHDRAGRMKAKG VIRKALDWRRARHYFYWRVRRRLCEEYTFRKIVTATS AAPMPREQMLDLVKQWFTNDNETVNFEDADELVSE WFEKRASVIDQRISKLKSDATKEQIVSLGNADQEAVIE GFSQLIENLSEDARAEILRKLNSRF | 15 |

TABLE 11-continued

| Enzyme Sequences: | | |
|---|---|---|
| Enzyme: | Sequence: | SEQ ID: |
| Acetyl-CoA synthase (ACS) *Salmonella typhimurium* Accession: NP_463140.1 | MSQTHKHAIPANIADRCLINPEQYETKYKQSINDPDTF WGEQGKILDWITPYQKVKNTSFAPGNVSIKWYEDGT LNLAANCLDRHLQENGDRTAIIWEGDDTSQSKHISYR ELHRDVCRFANTLLDLGIKKGDVVAIYMPMVPEAAV AMLACARIGAVHSVIFGGFSPEAVAGRIIDSSSRLVITA DEGVRAGRSIPLKKNVDDALKNPNVTSVEHVIVLKRT GSDIDWQEGRDLWWRDLIEKASPEHQPEAMNAEDPL FILYTSGSTGKPKGVLHTTGGYLVYAATTFKYVFDYH PGDIYWCTADVGWVTGHSYLLYGPLACGATTLMFEG VPNWPTPARMCQVVDKHQVNILYTAPTAIRALMAEG DKAIEGTDRSSLRILGSVGEPINPEAWEWYWKKIGKE KCPVVDTWWQTETGGFMITPLPGAIELKAGSATRPFF GVQPALVDNEGHPQEGATEGNLVITDSWPGQARTLF GDHERFEQTYFSTFKNMYFSGDGARRDEDGYYWITG RVDDVLNVSGHRLGTAEIESALVAHPKIAEAAVVGIP HAIKGQAIYAYVTLNHGEEPSPELYAEVRNWVRKEIG PLATPDVLHWTDSLPKTRSGKIMRRILRKIAAGDTSNL GDTSTLADPGVVEKLLEEKQAIAMPS | 16 |
| Malonyl-CoA synthase (matB) *Streptomyces coelicolor* Accession: WP_011028356 | MSSLFPALSPAPTGAPADRPALRFGERSLTYAELAAA AGATAGRIGGAGRVAVWATPAMETGVAVVAALLAG VAAVPLNPKSGDKELAHILSDSAPSLVLAPPDAELPPA LGALERVDVDVRARGAVPEDGADDGDPALVVYTSGT TGPPKGAVIPRRALATTLDALADAWQWTGEDVLVQG LPLFHVHGLVLGILGPLRRGGSVRHLGRFSTEGAAREL NDGATMLFGVPTMYHRIAETLPADPELAKALAGARL LVSGSAALPVHDHERIAAATGRRVIERYGMTETLMNT SVRADGEPRAGTVGVPLPGVELRLVEEDGTPIAALDG ESVGEIQVRGPNLFTEYLNRPDATAAAFTEDGFFRTG DMAVRDPDGYVRIVGRKATDLIKSGGYKIGAGEIENA LLEHPEVREAAVTGEPDPDLGERIVAWIVPADPAAPP ALGTLADHVAARLAPHKRPRVVRYLDAVPRNDMGKI MKRALNRD | 17 |
| Malonate transporter (matC) *Streptomyces coelicolor* Accession: NP_626686.1 | MSPELISILVLVVVFVIATTRSVNMGALAFAAAFGVGT LVADLDADGIFAGFPGDLFVVLVGVTYLFAIARANGT TDWLVHAAVRLVRGRVALIPWVMFALTGALTAIGAV SPAAVAIVAPVALSFATRYSISPLLMGTMVVHGAQAG GFSPISIYGSIVNGIVEREKLPGSEIGLFLASLVANLLIA AVLFAVLGGRKLWARGAVTPEGDGAPGKAGTGTTGS GSDTGTGTGTGTGTSAGTGGTAPTAVAVRSDRETGG AEGTGVRLTPARVATLVALVALVVAVLGFDLDAGLT AVTLAVVLSTAWPDDSRRAVGEIAWSTVLLICGVLTY VGVLEEMGTITWAGEGVGGIGVPLLAAVLLCYIGAIV SAFASSVGIMGALIPLAVPFLAQGEIGAVGMVAALAV SATVVDVSPFSTNGALVLAAAPDVDRDRFFRQLMVY GGIVVAAVPALAWLVLVVPGFG | 18 |
| Malonate CoA-transferase (MdcA) *Acinetobacter calcoaceticus* Accession: AAB97627.1 | MVKKRLWDKQRTRRQEKLNLAQQKGFAKQVEHARA IELLETVIASGDRVCLEGNNQKQADFLSKCLSQCNPD AVNDLHIVQSVLALPSHIDVFEKGIASKVDFSFAGPQS LRLAQLVQQQKISIGSIHTYLELYGRYFIDLTPNICLITA HAADREGNLYTGPNTEDTPAIVEATAFKSGIVIAQVNE IVDKLPRVDVPADWVDFYIESPKHNYIEPLFTRDPAQI TEVQILMAMMVIKGIYAPYQVQRLNHGIGFDTAAIEL LLPTYAASLGLKGQICTNWALNPHPTLIPAIESGFVDS VHSFGSEVGMEDYIKERPDVFFTGSDGSMRSNRAFSQ TAGLYACDSFIGSTLQIELQGNSSTATVDRISGFGGAP NMGSDPHGRRHASYAYTKAGREATDGKLIKGRKLVV QTVETYREHMHPVFVEELDAWQLQDKMDSELPPIMI YGEDVTHIVTEEGIANLLLCRTDEEREQAIRGVAGYTP VGLKRDAAKVEELRQRGIIQRPEDLGIDPTQVSRDLLA AKSVKDLVKWSGGLYSPPSRFRNW | 19 |
| Pantothenate kinase (CoaX) *Pseudomonas aeruginosa* Accession: Q9HWCL1 | MILELDCGNSLIKWRVIEGAARSVAGGLAESDDALVE QLTSQQALPVRACRLVSVRSEQETSQLVARLEQLFPV SALVASSGKQLAGVRNGYLDYQRLGLDRWLALVAA HHLAKKACLVIDLGTAVTSDLVAADGVHLGGYICPG MTLMRSQLRTHTRRIRYDDAEARRALASLQPGQATA EAVERGCLLMLRGFVREQYAMACELLGPDCEIFLTGG DAELVRDELAGARIMPDLVFVGLALACPIE | 20 |

TABLE 11-continued

| Enzyme Sequences: | | |
|---|---|---|
| Enzyme: | Sequence: | SEQ ID: |
| glutamyl-tRNA reductase (hemA$^{M}$)<br>*Salmonella typhimurium*<br>Accession:<br>AAA88610.1 | MTKKLLALGINHKTAPVSLRERVTFSPDTLDQALDSL<br>LAQPMVQGGVVLSTCNRTELYLSVEEQDNLQEALIR<br>WLCDYHNLNEDDLRNSLYWHQDNDAVSHLMRVASG<br>LDSLVLGEPQILGQVKKAFADSQKGHLNASALRRMF<br>QKSFSVAKRVRTETDIGASAVSVAFAACTLARQIFESL<br>STVTVLLVGAGETIELVARHLREHKVQKMIIANRTRE<br>RAQALADEVGAEVISLSDIDARLQDADIIISSTASPLPII<br>GKGMVERALKSRRNQPMLLVDIAVPRDVEPEVGKLA<br>NAYLYSVDDLQSIISHNLAQRQAAAVEAETIVEQEASE<br>FMAWLRAQGASETIREYRSQSEQIRDELTTKALSALQ<br>QGGDAQAILQDLAWKLTNRLIHAPTKSLQQAARDGD<br>DERLNILRDSLGLE | 21 |
| 5-aminolevulinic acid synthase (ALAS)<br>*Rhodobacter capsulatus*<br>Accession:<br>CAA37857 | MDYNLALDKAIQKLHDEGRYRTFIDIEREKGAFPKAQ<br>WNRPDGGKQDITVWCGNDYLGMGQHPVVLAAMHE<br>ALEAVGAGSGGTRNISGTTAYHRRLEAEIADLHGKEA<br>ALVFSSAYIANDATLSTLRLLFPGLIIYSDSLNHASMIE<br>GIKRNAGPKRIFRHNDVAHLRELIAADDPAAPKLIAFE<br>SVYSMDGDFGPIKEICDIADEFGALTYIDEVHAVGMY<br>GPRGAGVAERDGLMHRIDIFNGTLAKAYGVFGGYIA<br>ASAKMVDAVRSYAPGFIFSTSLPPAIAAGAQASIAFLK<br>TAEGQKLRDAQQMHAKVLKMRLKALGMPIIDHGSHI<br>VPVVIGDPVHTKAVSDMLLSDYGVYVQPINFPTVPRG<br>TERLRFTPSPVHDLKQIDGLVHAMDLLWARCA | 22 |
| Tyrosine ammonia-lyase (TAL)<br>*Rhodobacter capsulatus* SB 1003<br>Accession:<br>ADE84832.1 | MTLQSQTAKDCLALDGALTLVQCEAIATHRSRISVTP<br>ALRERCARAHARLEHAIAEQRHIYGITTGFGPLANRLI<br>GADQGAELQQNLIYHLATGVGPKLSWAEARALMLAR<br>LNSILQGASGASPETIDRIVAVLNAGFAPEVPAQGTVG<br>ASGDLTPLAHMVLALQGRGRMIDPSGRVQEAGAVM<br>DRLCGGPLTLAARDGLALVNGTSAMTAIAALTGVEA<br>ARAIDAALRHSAVLMEVLSGHAEAWHPAFAELRPHP<br>GQLRATERLAQALDGAGRVCRTLTAARRLTAADLRP<br>EDHPAQDAYSLRVVPQLVGAVWDTLDWHDRVVTCE<br>LNSVTDNPIFPEGCAVPALHGGNFMGVHVALASDAL<br>NAALVTLAGLVERQIARLTDEKLNKGLPAFLHGGQA<br>GLQSGFMGAQVTATALLAEMRANATPVSVQSLSTNG<br>ANQDVVSMGTIAARRARAQLLPLSQIQAILALALAQA<br>MDLLDDPEGQAGWSLTARDLRDRIRAVSPGLRADRP<br>LAGHIEAVAQGLRHPSAAADPPA | 23 |
| Tyrosine ammonia-lyase (TAL)<br>*Trichosporon cutaneum*<br>Accession:<br>XP_018276715 | MITETNVAKPASTKVMNGDAAKAAPVEPFATYAHSQ<br>ATKTVVIDGHNMKVGDVVAVARHGAKVELAASVAG<br>PVQASVDFKESKKHTSIYGVTTGFGGSADTRTSDTEA<br>LQISLLEHQLCGYLPTDPTYEGMLLAAMPIPIVRGAM<br>AVRVNSCVRGHSGVRLEVLQSFADFINIGLVPCVPLR<br>GTISASGDLSPLSYIAGAICGHPDVKVFDTAASPPTVLT<br>APEAIAKYKLKTVRLASKEGLGLVNGTAVSAAAGAL<br>ALYDAECLAMMSQTNTALTVEALDGHVGSFAPFIQEI<br>RPHVGQIEAAKNIRHMLSNSKLAVHEEPELLADQDAG<br>ILRQDRYALRTSAQWIGPQLEMLGLARQQIETELNSTT<br>DNPLIDVEGGMFHHGGNFQAMAVTSAMDSTRIVLQN<br>LGKLSFAQVTELINCEMNHGLPSNLAGSEPSTNYHCK<br>GLDIHCGAYCAELGFLANPMSNHVQSTEMHNQSVNS<br>MAFASARKTMEANEVLSLLLGSQMYCATQALDLRV<br>MEVKFKMAIVKLLNDTLTKHFSTFLTPEQLAKLNTTA<br>AITLYKRLNQTPSWDSAPRFEDAAKHLVGCIMDALM<br>VNDDITDLTNLPKWKKEFAKDAGDLYRSILTATTADG<br>RNDLEPAEYLGQTRAVYEAIRSDLGVKVRRGDVAEG<br>KSGKSIGSNVARIVEAMRDGRLMGAVSKMFF | 24 |
| Tyrosine ammonia-lyase (TAL)<br>*Flavobacterium johnsoniae*<br>Accession:<br>WP_012023194 | MNTINEYLSLEEFEAIIFGNQKVTISDVVVNRVNESFNF<br>LKEFSGNKVIYGVNTGFGPMAQYRIKESDQIQLQYNLI<br>RSHSSGTGKPLSPVCAKAAILARLNTLSLGNSGVHPSV<br>INLMSELINKDITPLIFEHGGVGASGDLVQLSHLALVLI<br>GEGEVFYKGERRPTPEVFEIEGLKPIQVEIREGLALING<br>TSVMTGIGVVNVYHAKKLLDWSLKSSCAINELVQAY<br>DDHFSAELNQTKRHKGQQEIALKMRQNLSDSTLIRKR<br>EDHLYSGENTEEIFKEKVQEYYSLRCVPQILGPVLETI<br>NNVASILEDEFNSANDNPIIDVKNQHVYHGGNFHGDY<br>ISLEMDKLKIVITKLTMLAERQLNYLLNSKINELLPPFV<br>NLGTLGFNFGMQGVQFTATSTTAESQMLSNPMYVHSI<br>PNNNDNQDIVSMGTNSAVITSKVIENAFEVLAIEMITIV<br>QAIDYLGQKDKISSVSKKWYDEIRNIIPTFKEDQVMYP<br>FVQKVKDHLINN | 25 |

TABLE 11-continued

| Enzyme Sequences: | | |
|---|---|---|
| Enzyme: | Sequence: | SEQ ID: |
| Tyrosine ammonia-lyase (TAL)<br>*Herpetosiphon aurantiacus* DSM 785<br>Accession:<br>ABX04526.1 | MSTTLILTGEGLGIDDVVRVARHQDRVELTTDPAILA<br>QIEASCAYINQAVKEHQPVYGVTTGFGGMANVIISPEE<br>AAELQNNAIWYHKTGAGKLLPFTDVRAAMLLRANSH<br>MRGASGIRLEIIQRMVTFLNANVTPHVREFGSIGASGD<br>LVPLISITGALLGTDQAFMVDFNGETLDCISALERLGL<br>PRLRLQPKEGLAMMNGTSVMTGIAANCVHDARILLA<br>LALEAHALMIQGLQGTNQSFHPFIHRHKPHTGQVWA<br>ADHMLELLQGSQLSRNELDGSHDYRDGDLIQDRYSL<br>RCLPQFLGPIIDGMAFISHHLRVEINSANDNPLIDTASA<br>ASYHGGNFLGQYIGVGMDQLRYYMGLMAKHLDVQI<br>ALLVSPQFNNGLPASLVGNIQRKVNMGLKGLQLTANS<br>IMPILTFLGNSLADRFPTHAEQFNQNINSQGFGSANLA<br>RQTIQTLQQYIAITLMFGVQAVDLRTHKLAGHYNAAE<br>LLSPLTAKIYHAVRSIVKHPPSPERPYIWNDDEQVLEA<br>HISALAHDIANDGSLVSAVEQTLSGLRSIILFR | 26 |
| Phenylalanine ammonia-lyase (PAL)<br>*Physcomitrella patens*<br>Accession:<br>XP_001758374.1 | MHDDNTSPYCIGQLGNGAVHGADPLNWAKTAKAME<br>CSHLEEIKRMVDTYQNATQVMIEGATLTVPQVAAIAR<br>RPEVHVVLDAANARSRVDESSNWVLDRIMGGGDIYG<br>VTTGFGATSHRRTQQGVELQRELIRFLNAGVLSKGNS<br>LPSETARAAMLVRTNTLMQGYSGIRWEILHAMEKLL<br>NAHVTPKLPLRGTITASGDLVPLSYIAGLLTGRPNSKA<br>VTEDGREVSALEALRIAGVEKPFELAPKEGLALVNGT<br>AVGSALASTVCYDANIMVLLAEVLSALFCEVMQGKP<br>EFADPLTHKLKHHPGQMEAAAVMEWVLDGSSFMKA<br>AAKFNETDPLRKPKQDRYALRTSPQWLGPQVEVIRNA<br>THAIEREINSVNDNPIIDAARGIALHGGNFQGTPIGVSM<br>DNMRLSLAAIAKLMFAQFSELVNDYYNNGLPSNLSG<br>GPNPSLDYGMKGAEIAMASYLSEINYLANPVTTHVQS<br>AEQHNQDVNSLGLVSARKTEEAMEILKLMSATFLVG<br>LCQAIDLRHVEETMQSAVKQVVTQVAKKTLFMGSDG<br>SLLPSRFCEKELLMVVDRQPVFSYIDDSTSDSYPLMEK<br>LRGVLVSRALKSADKETSNAVFRQIPVFEAELKLQLSR<br>VVPAVREAYDTKGLSLVPNRIQDCRTYPLYKLVRGDL<br>KTQLLSGQRTVSPGQEIEKVFNAISAGQLVAPLLECVQ<br>GWTGTPGPFSARASC | 27 |
| Phenylalanine ammonia-lyase (PAL)<br>*Dictyostelium discoideum* AX4<br>Accession:<br>XP_644510.1 | MIETNHKDNFLIDGENKNLEINDIISISKGEKNIIFTNEL<br>LEFLQKGRDQLENKLKENVAIYGINTGFGGNGDLIIPF<br>DKLDYHQSNLLDFLTCGTGDFFNDQYVRGIQFIIIIALS<br>RGWSGVRPMVIQTLAKHLNKGIIPQVPMHGSVGASG<br>DLVPLSYIANVLCGKGMVKYNEKLMNASDALKITSIE<br>PLVLKSKEGLALVNGTRVMSSVSCISINKFETIFKAAIG<br>SIALAVEGLLASKDHYDMRIHNLKNHPGQILIAQILNK<br>YFNTSDNNTKSSNITFNQSENVQKLDKSVQEVYSLRC<br>APQILGIISENISNAKIVIKREILSVNDNPLIDPYYGDVL<br>SGGNFMGNHIARIMDGIKLDISLVANHLHSLVALMMH<br>SEFSKGLPNSLSPNPGIYQGYKGMQISQTSLVVWLRQE<br>AAPACIHSLTTEQFNQDIVSLGLHSANGAASMLIKLCD<br>IVSMTLIIAFQAISLRMKSIENFKLPNKVQKLYSSIIKIIPI<br>LENDRRTDIDVREITNAILQDKLDFFNLNL | 28 |
| Phenylalanine ammonia-lyase (PAL)<br>*Brevibacillus laterosporus* LMG 15441<br>Accession:<br>WP_003337219.1 | MSQVALFEQELMLHGKHTLLLNGNDLTITDVAQMAK<br>GTFEAFTFHISEEANKRIEECNELKHEIMNQHNPIYGV<br>TTGFGDSVHRQISGEKAWDLQRNLIRFLSCGVGPVAD<br>EAVARATMLIRTNCLVKGNSAVRLEVIHQLIAYMERG<br>ITPIIPERGSVGASGDLVPLSYLASILVGEGKVLYKGEE<br>REVAEALGAEGLEPLTLEAKEGLALVNGTSFMSAFAC<br>LAYADAEEIAFIADICTAMASEALLGNRGHFYSFIHEQ<br>KPHLGQMASAKNIYTLLEGSQLSKEYSQIVGNNEKLD<br>SKAYLELTQSIQDRYSIRCAPHVTGVLYDTLDWVKK<br>WLEVEINSTNDNPIFDVETRDVYNGGNFYGGHVVQA<br>MDSLKVAVANIADLLDRQLQLVVDEKFNKDLTPNLIP<br>RFNNDNYEIGLHHGFKGMQIASSALTAEALKMSGPVS<br>VFSRSTEAHNQDKVSMGTISSRDARTIVELTQHVAAIH<br>LIALCQALDLRDSKKMSPQTTKIYNMIRKQVPFVERD<br>RALDGDIEKVVQLIRSGNLKKEIHDQNVND | 29 |
| Cinnamate-4-hydroxylase (C4H)<br>*Rubus* sp. SSL-2007<br>Accession:<br>ABX74781.1 | MDLLLMEKTLLGLFVAVVVAITVSKLRGKKFKLPPGP<br>IPVPVFGNWLQVGDDLNHRNLTEMAKKFGEVFMLR<br>MGQRNLVWSSPDLAKEVLHTQGVEFGSRTRNVVFDI<br>FTGKGQDMVFTVYGEHWRKMRRIMTVPFFTNKVVQ<br>QYRYGWESEAAAVVEDVKKHPEAATNGMVLRRRLQ<br>LMMYNNMYRIMFDRRFESEDDPLFVKLKGLNGERSR<br>LAQSFEYNYGDFIPVLRPFLRGYLKICKEVKEKRIQLF<br>KDYFVDERKKLSSTQATTNEGLKCAIDHILDAQQKGE | 30 |

TABLE 11-continued

| Enzyme Sequences: | | |
|---|---|---|
| Enzyme: | Sequence: | SEQ ID: |
| | INEDNVLYIVENINVAAIETTLWSIEWGIAELVNHPEIQ KKLRDELDTVLGRGVQITEPEIQKLPYLQAVVKETLR LRMAIPLLVPHMNLHDAKLGGFDIPAESKILVNAWWL ANNPAHWKKPEEFRPERFLEEESKVEANGNDFRYLPF GVGRRSCPGIILALPILGITLGRLVQNFELLPPPGQTQL DTTEKGGQFSLHILKHSPIVMKPRT | |
| Cinnamate-4-hydroxylase (C4H) *Fragaria vesca* Accession: XP_004294725.1 | MDLLLLEKTLIGLFIAIVVAIIVSKLRGKKFKLPPGPIPV PVFGNWLQVGDDLNHRNLTDMAKKFGDVFMLRMG QRNLVVVSSPDLAKEVLHTQGVEFGSRTRNVVFDIFT GKGQDMVFTVYGEHWRKMRRIMTVPFFTNKVVQQY RHGWEAEAAAVVEDVKKHPEAATSGMVLRRRLQLM MYNNMYRIMFDRRFESEEDPLFVKLKGLNGERSRLA QSFEYNYGDFIPVLRPFLRGYLKICKEVKEKRIQLFKD YFVDERKKLASTQVTTNEGLKCAIDHILDAQQKGEIN EDNVLYIVENINVAAIETTLWSIEWGIAELVNHPEIQK KLRDELDTVLGHGVQVTEPELHKLPYLQAVVKETLR LRMAIPLLVPHMNLHDAKLGGFDIPAESKILVNAWWL ANNPAHWKKPEEFRPERFLEEESKVEANGNDFRYLPF GVGRRSCPGIILALPILGVTLGRLVQNFEMLPPPGQTQ LDTTEKGGQFSLHILKHSTIVMKPRA | 31 |
| Cinnamate-4-hydroxylase (C4H) *Solanum tuberosum* Accession: ABC69046.1 | MDLLLLEKTLIGLFFAILIAIIVSKLRSKRFKLPPGPIPVP VFGNWLQVGDDLNHRNLTEYAKKFGDVFLLRMGQR NLVVVSSPELAKEVLHTQGVEFGSRTRNVVFDIFTGK GQDMVFTVYGEHWRKMRRIMTVPFFTNKVVQQYRG GWESEAASVVEDVKKNPESATNGIVLRKRLQLMMYN NMFRIMFDRRFESEDDPLFVKLRALNGERSRLAQSFE YNYGDFIPILRPFLRGYLKICKEVKEKRLKLFKDYFVD ERKKLANTKSMDSNALKCAIDHILEAQQKGEINEDNV LYIVENFNVAAIETTLWSIEWGIAELVNHPHIQKKLRD EIDTVLGPGMQVTEPDMPKLPYLQAVIKETLRLRMAI PLLVPHMNLHDAKLAGYDIPAESKILVNAWWLANNP AHWKKPEEFRPERFFEEEKHVEANGNDFRFLPFGVGR RSCPGIILALPILGITLGRLVQNFEMLPPPGQSKLDTSE KGGQFSLHILKHSTIVMKPRSF | 32 |
| 4-coumarate-CoA ligase (4CL) *Daucus carota* Accession: AIT52344.1 | MGDCAAPKQEIIFRSKLPDIYIPKHLPLHSYCFENISKV SDRACLINGATGETFSYAQVELISRRVASGLNKLGIHQ GDTMMILLPNTPEYFFAFLGASYRGAVSTMANPFFTS PEVIKQLKASQAKLIITQACYVEKVKEYAAENNITVVC IDEAPRDCLHFTTLMEADEAEMPEVAIDSDDVVALPY SSGTTGLPKGVMLTHKGLVTSVAQRVDGENPNLYIHS EDVMICILPLFHIYSLNAVLCCGLRAGATILIMQKFDIV PFLELIQKYKVTIGPFVPPIVLAIAKSPVVDNYDLSSVR TVMSGAAPLGKELEDAVRAKFPNAKLGQGYGMTEA GPVLAMCLAFAKEPYEIKSGACGTVVRNAEMKIVDPE THASLPRNQSGEICIRGDQIMKGYLNDPESTKTTIDEE GWLHTGDIGFIDEDDELFIVDRLKEIIKYKGFQVAPAEI EALLLTHPTISDAAVVPMIDEKAGEVPVAFVVRLNGS TTTEEEIKQFVSKQVVFYKRVFRVFFVDAIPKSPSGKIL RKELRARIASGDLPK | 33 |
| 4-coumarate-CoA ligase (4CL) *Striga asiatica* Accession: GER48539.1 | MEPTTKSKDIIFRSKLPDIYIPKHLPLHTYCFENISRFGS RPCLINGSTGEILTYDQVELASRRVGSGLHRLGIRQGD TIMLLLPNSPEFVLAFLGASHIGAVSTMANPFFTPAEV VKQAAASRAKLIVTQACHVDKVRDYAAEHGVKVVC VDGAPPEECLPFSEVASGDEAELPAVKISPDDVVALPY SSGTTGLPKGVMLTHKGLVTSVAQQVDGENPNLYIHS DDVIMCVLPLFHIYSLNSIMLCGLRVGAAILIMQKFEIV PFLELIQRYRVTIGPFVPPIVLAIEKSPVVEKYDLSSVRT VMSGAAPLGRELEDAVRLKFPNAKLGQGYGMTEAGP VLAMCLAFAKEPFEIKSGACGTVVRNAEMKIVDTETG ASLGRNQPGEICIRGDQIMKGYLNDPESTERTIDKEGW LHTGDIGFIDDDDELFIVDRLKEIIKYKGFQVAPAELEA LLLNHPNISDAAVVSMKDEQAGEVPVAYVVKSNGSTI TEDEIKQFVSKQVIFYKRINRVFFIDAIPKSPSGKILRKD LRARLAAGVPN | 34 |
| 4-coumarate-CoA ligase (4CL) *Capsicum annuum* Accession: KAF3620179.1 | MPMENEAKQGDIIFRSKLPDIYIPNHLSLHSYCFENISE FSSRPCLINGANNQIYTYADVELNSRKVAAGLHKQFGI QQKDTIMILLPNSPEFVFAFLGASYLGAISTMANPLFTP AEVVKQVKASNAEIIVTQACHVNKVKDYALENDVKI VCIDSAPEGCVHFSELIQADEHDIPEVQIKPDDVVALP YSSGTTGLPKGVMLTHKGLVTSVAQQVDGENPNLYI HSEDVMLCVLPLFHIYSLNSVLLCGLRVGAAILIMQKF | 35 |

TABLE 11-continued

| Enzyme Sequences: | | |
|---|---|---|
| Enzyme: | Sequence: | SEQ ID: |
| | DIVPFLELIQNYKVTIGPFVPPIVLAIAKSPMVDNYDLS SVRTVMSGAAPLGKELEDTVRAKFPNAKLGQGYGMT EAGPVLAMCLAFAKEPFEIKSGACGTVVRNAEMKIVD PDTGNSLHRNQSGEICIRGDQIMKGYLNDPEATAGTID KEGWLHTGDIGYIDNDDELFIVDRLKELIKYKGFQVA PAELEALLLNHPNISDAAVVPMKDEQAGEVPVAFVVR SNGSTITEDEVKEFISKQVIFYKRIKRVFFVDAVPKSPS GKILRKDLRAKLAAGFPN | |
| 4-coumarate-CoA ligase (4CL) *Camellia sinensis* Accession: ASU87409.1 | MDTKTTQQEIIFRSKLPDIYIPKQLPLHSYCFENISQFSS KPCLINGSTGKVYTYSDVELTSRKVAAGFHNLGIQQR DTIMLLLPNCPEFVFAFLGASYLGAIITMANPFFTPAET IKQAKASNSKLIITQSSYTSKVLDYSSENNVKIICIDSPP DGCLHFSELIQSNETQLPEVEIDSNEVVALPYSSGTTGL PKGVMLTHKGLVTSVAQQVDGENPNLYIHSEDMMM CVLPLFHIYSLNSVLLCGLRVGAAILIMQKFEIGSFLKL IQRYKVTIGPFVPPIVLAIAKSEVVDDYDLSTIRTMMS GAAPLGKELEDAVRAKFPHAKLGQGYGMTEAGPVLA MCLAFAKKPFEIKSGACGTVVRNAEMKIVDPDAGFSL PRNQPGEICIRGDQIMKGYLNDPEATERTIDKQGWLH TGDIGYIDDDDELFIVDRLKELIKYKGFQVAPAELEAL LLNHPTISDAAVVPMKDESAGEVPVAFVVRTNGFEVT ENEIKKYISEQVVFYKINRVYFVDAIPKAPSGKILRK DLRARLAAGIPS | 36 |
| Chaicone synthase (CHS) *Capsicum annuum* Accession: XP_016566084.1 | MVTVEEYRKAQRAEGPATVMAIGTATPSNCVDQSTY PDYYFRITNSEHKTELKEKFKRMCEKSMIKTRYMHLT EEILKENPNMCAYMAPSLDARQDIVVVEVPKLGKEA AQKAIKEWGQPKSKITHLVFCTTSGVDMPGCDYQLA KLLGLRPSVKRLMMYQQGCFAGGTVLRLAKDLAEN NKGARVLVVCSEITAVTFRGPSESHLDSLVGQALFGD GAAAIIMGSDPIPGVERPLFQLVSAAQTLLPDSEGAID GHLREVGLTFHLLKDVPGLISKNIEKSLVEAFQPLGISD WNSLFWIAHPGGPAILDQVELKLGLKPEKLKATREVL SNYGNMSSACVLFILDEMRKASTKEGLGTSGEGLEW GVLFGFGPGLTVETVVLHSVAI | 37 |
| Chalcone synthase (CHS) *Rosa chinensis* Accession: AEC13058.1 | MVTVEEVRKAQRAEGPATVLAIGTATPPNCIDQSTYP DYYFRITKSEHKAELKEKFQRMCDKSMIKKRYMYLT EEILKENPSMCEYMAPSLDARQDMVVVEIPKLGKEAA TKAIKEWGQPKSKITHLVFCTTSGVDMPGADYQLTKL LGLRPSVKRLMMYQQGCFAGGTVLRLAKDLAENNK GARVLVVCSEITAVTFRGPSDTHLDSLVGQALFGDGA AAIIVGSDPLPEVEKPLFELVSAAQTILPDSDGAIDGHL REVGLTFHLLKDVPGLISKNIEKSLNEAFKPLNITDWN SLFWIAHPGGPAILDQVEAKLGLKPEKLEATRHILSEY GNMSSACVLFILDEVRRKSAANGHKTTGEGLEWGVL FGFGPGLTVETVVLHSVAA | 38 |
| Cha:cone synthase (CHS) *Morus alba* var. *multicaulis* Accession: AHL83549.1 | MSMTPSVHEIRKAQRSEGPATVLSIGTATPTNFVPQAD YPDYYFRITNSDHMTDLKDKFKRMCEKSMITKRHMY LTEEILKENPKMCEYMAPSLDARQDIVVVEVPKLGKE AAAKAIKEWGQPKSKITHLIFCTTSGVDMPGADYQLT KLLGLRPSVKRFMMYQQGCFAGGTVLRLAKDLAENN KGARVLVVCSEITAVTFRGPSHTHLDSLVGQALFGDG AAAVILGADPDTSVERPIFELVSAAQTILPDSEGAIDGH LREVGLTFHLLKDVPGLISKNIEKSLVEAFTPIGISDWN SIFWIAHPGGPAILDQVEAKLGLKQEKLSATRHVLSEY GNMSSACVLFILDEVRKKSVEEGKATTGEGLEWGVLF GFGPGLTVETIVLHSLPAV | 39 |
| Chalcone synthase (CHS) *Dendrobium catenatum* Accession: ALE71934.1 | MAPPAMEEIRRAQRAEGPATVLAIGASTPPNALYQAD YPDYYFRITKSEHLTELKEKFKQMCDKSMIRKRYMYL TEEILKENPNICAFMAPSLDARQDIVVTEVPKLAREAS ARAIKEWGQPKSRITHLIFCTTSGVDMPGADYQLTRL LGLRPSVNRIMLYQQGCFAGGTVLRLAKDLAENNAG ARVLVVCSEITAVTFRGPSESHLDSLVGQALFGDGAA AIIVGSDPDLTTERPLFQLVSASQTILPESEGAIDGHLRE MGLTFHLLKDVPGLISKNIQKSLVETFKPLGIHDWNSI FWIAHPGGPAILDQVEIKLGLKEEKLASSRNVLAEYG NMSSACVLFILDEMRRRSAEAGQATTGEGLEWGVLF GFGPGLTVETVVLRSVPIAGAV | 40 |

TABLE 11-continued

| Enzyme Sequences: | | |
|---|---|---|
| Enzyme: | Sequence: | SEQ ID: |
| Chalcone isomerase (CHI) Trifolium pratense Accession: PNX83855.1 | MSAITAIHVENIEFPAVITSPVTGKSYFLGGAGERGLTI EGNFIKFTAIGVYLEDVAVASLATKWKGKSSEELLET LDFYRDIISGPFEKLIRGSKIRELSGPEYSRKVTENCVA HLKSVGTYGDAEVEAMEKFVEAFKPINFPPGASVFYR QSPDGILGVSISIHFFP | 41 |
| Chalcone isomerase (CHI) *Abrus precatorius* Accession: XP_027366189.1 | MAAASLTAVQVENLEFPAVVTSPATGKTYFLGGAGV RGLTIEGNFIKFTGIGVYLEDQAVASLATKWKGKSSEE LVESLDFFRDIISGPFEKLIRGSKIRQLSGPEYSKKVME NCVAHMKSVGTYGDAEAAGIEEFAQAFKPVNFPPGA SVFYRQSPDGVLGLSFSQDATIPEEEAAVIKNKPVSAA VLETMIGEHAVSPDLKRSLAARLPAVLSHGVFKIGN | 42 |
| Chalcone isomerase (CHI) *Arachis duranensis* Accession: XP_015942246.1 | MAAEPSITAIQFENLVFPAVVTPPGSSKSYFLAGAGER GLTIDGKFIKFTGIGVYLEDKAVPSLAGKWKDKSSQQ LLQTLHFYRDIISGPFEKLIRGSKILALSGVEYSRKVME NCVAHMKSVGTYGDAEAEAIQQFAEAFKNVNFKPGA SVFYRQSPLGHLGLSFSQDGNIPEKEAAVIENKPLSSA VLETMIGEHAVSPDLKCSLAARLPAVLQQGIIVTPPQH N | 43 |
| Chalcone isomerase (CHI) *Cephalotus follicularis* Accession: GAV77263.1 | MGPSPSVTELQVENVTFPPSVKPPGSTKTLFLGGAGER GLEIQGKFIKFTAIGVYLEGDAVASLAVKWKGKSKEE LTDSVEFFRDIVTGPFEKFTQVTTILPLTGQQYSEKVSE NCVAFWKSVGIYTDAEAKAIEKFIEVFKEETFPPGSSIL FTQSPNGALTIAFSKDGVIPEVGKAVIENKLLAEGLLE SIIGKHGVSPVAKQCLATRLSELL | 44 |
| Flavanone 3-hydroxylase (F3H) *Abrus precatorius* Accession: XP_027329642.1 | MGSASETVCVTGAAGFIGSWLVMRLIQNGYKVRATV RDPANMKKVKHLLELPNAKTNLSLWKADLAEEGSFD EAIKGCTGVFHVATPMDFESKDPENEVIKPTINGLIDI MKACMKAKTVRRLVFTSSAGTVDVTEHPKPLFDESC WSDVQFCRRVRMTGWMYFVSKTLAEQEAWKFAKEN NIDFISVIPPLVVGPFLVPTMPPSLITALSLITGNESHYAI IKQGQFVHLDDLCLAHIFLFQHPKAQGRYICCSHEATI HDIASLLNQKYPEFNVPTKFKNIPDQLEIIRFSSKKITDL GFKFKYSLEDMFTGAVETCKEKRLLSETAEISGTTQK | 45 |
| Flavanone 3-hydroxylase (F3H) *Camellia sinensis* Accession: AAT66505.1 | MKDSVASATASAPGTVCVTGAAGFIGSWLVMRLLER GYIVRATVRDPANLKKVKHLLDLPKADTNLTLWKAD LNEEGSFDEAIEGCSGVFHVATPMDFESKDPENEVIKP TINGVLSIIRSCTKAKTVKRLVFTSSAGTVNVQEHQQP VFDENNWSDLHFINKKKMTGWMYFVSKTLAEKAAW EAAKENNIDFISIIPTLVGGPFIMPTFPPSLITALSPITRN EGHYSIIKQGQFVHLDDLCESHIFLYERPQAEGRYICSS HDATIHDLAKLMREKWPEYNVPTEFKGIDKDLPVVSF SSKKLIGMGFEFKYSLEDMFRGAIDTCREKGLLPHSFA ENPVNGNKV | 46 |
| Flavanone 3-hydroxylase (F3H) *Nyssa sinensis* Accession: KAA8531902.1 | MVDMKDDDSPATVCVTGAAGFIGSWLIMRLLQQGYI VRATVRDPANMKKVKHLQELEKADKNLTLWKADLT EEGSFDEAIKGCSGVFHVATPMDFESKDPENEVIKPTI NGVLSIVRSCVKAKTVKRLVFTSSAGTVNLQEHQQLV YDENNWSDLDLIYAKKMTGWMYFVSKILAEKAAWE ATKENNIDFISIIPTLVVGPFITPTFPPSLITALSLITGNEA HYSIIKQGQFVHLDDLCEAHIFLYEQPKAEGRYICSSH DATIYDLAKMIREKWPEYNVPTELKGIEKDLQTVSFSS KKLIGMGFEFKYSLEDMYKGAIDTCREKGLLPYSTHE TPANANANANANVKKNQNENTEI | 47 |
| Flavanone 3-hydroxylase (F3H) *Rosa chinensis* Accession: XP_024167119.1 | MASESESVCVTGASGFVGSWLVMRLLDRGYTVRATV RDPANKKKVKHLLDLPKAATHLTLWKADLAEEGSFD EAIKGCTGVFHVATPMDFESKDPENEVIKPTINGVLDI MKACLKAKTVRRLVFTASAGSVNVEETQKPVYDESN WSDVEFCRRVKMTGWMYFASKTLAEQEAWKFAKEN NIDFITIIPTLVIGPFLMPAMPPSLITGLSPLTGNESHYSII KQGQFIHLDDLCQSHIYLYEHPKAEGRYICSSHDATIH EIAKLLREKYPEYNVPTTFKGIEENLPKVHFSSKKLLE TGFEFKYSLEDMFVGAVDACKAKGLLPPPTERVEKQE VDESSVVGVKVTG | 48 |

TABLE 11-continued

| Enzyme Sequences: | | |
|---|---|---|
| Enzyme: | Sequence: | SEQ ID: |
| Flavonoid 3' hydroxylase (F3'H) *Cephalotus follicularis* Accession: GAV84063.1 | MSPLILYSIALAIFLYCLRTLLKRHPHRLPPGPRPWPIIG NLPHMGQMPHHSLAAMARTYGPLMHLRLGFVDVIV AASASVASQLLKTHDANFSSRPHNSGAKYIAYNYQDL VFAPYGPRWRMLRKISSVHLFSGKALDDYRHVRQEE VAVLIRALARAESKQAVNLGQLLNVCTANALGRVML GRRVFGDGSGVSDPMAEEFKSMVVEVMALAGVFNIG DFIPALDWLDLQGVAAKMKNLHKRFDTFLTGLLEEH KKMLVGDGGSEKHKDLLSTLISLKDSADDEGLKLTDT EIKALLLNMFTAGTDTSSSTVEWAIAELIRHPKILAQV LKELDTVVGRDRLVTDLDLPQLTYLQAVIKETFRLHP STPLSLPRVAAESCEIMGYHIPKGSTLLVNVWAIARDP KEWAEPLEFRPERFLPGGEKPNVDIKGNDFEVIPFGAG RRICAGMSLGLRMVQLLTATLVHAFDWDLTSGLMPE DLSMEEAYGLTLQRAEPLMVHPRPRLSPNVY | 49 |
| Flavonoid 3' hydroxylase (F3'H) *Theobroma cacao* Accession: EOY22049.1 | MASFLLYSILSAVFLYFIFATLRKRHRLPLPPGPKPWPII GNLPHMGPVPHHSLAALAKVYGPLMHLRLGFVDVV VAASASVAAQFLKVHDANFSSRPPNSGAKYVAYNYQ DLVFAPYGPRWRMLRKISSVHLFSGKALDDFRHVRQ DEVGVLVRALADAKTKVNLGQLLNVCTVNALGRVM LGKRVFGDGSGKADPEADEFKSMVVELMVLAGVVNI GDFIPALEWLDLQGVQAKMKKLHKRFDRFLSAILEEH KIKARDGSGQHKDLLSTFISLEDADGEGGKLTDTEIKA LLLNMFTAGTDTSSSTVEWAIAELIRHPKILAQVRKEL DSVVGRDRLVSDLDLPNLTYFQAVIKETFRLHPSTPLS LPRMASESCEINGYHIPKGATLLVNVWAIARDPDEWK DPLEFRPERFLPGGERPNADVRGNDFEVIPFGAGRRIC AGMSLGLRMVQLLAATLVHAFDWELADGLMPEKLN MEEAFGLTLQRAAPLMVHPRPRLSPRAY | 50 |
| Flavonoid 3' hydroxylase (F3'H) *Gerbera hybrida* Accession: ABA64468.1 | MTPLTLLIGTCVTGLFLYVLLNRCTRNPNRLPPGPTPW PVVGNLPHLGTIPHHSLAAMAKKYGPLMHLRLGFVD VVVAASASVAAQFLKTHDANFADRPPNSGAKHIAYN YQDLVFAPYGPRWRMLRKICSVHLFSTKALDDFRHV RQEEVAILARALVGAGKSPVKLGQLLNVCTTNALAR VMLGRRVFDSGDAQADEFKDMVVELMVLAGEFNIG DFIPVLDWLDLQGVTKKMKKLHAKFDSFLNTILEEHK TGAGDGVASGKVDLLSTLISLKDDADGEGGKLSDIEI KALLLNLFTAGTDTSSSTIEWAIAELIRNPQLLNQARK EMDTIVGQDRLVTESDLGQLTFLQAIIKETFRLHPSTPL SLPRMALESCEVGGYYIPKGSTLLVNVWAISRDPKIW ADPLEFQPTRFLPGGEKPNTDIKGNDFEVIPFGAGRRIC VGMSLGLRMVQLLTATLIHAFDWELADGLNPKKLNM EEAYGLTLQRAAPLVVHPRPRLAPHVYETTKV | 51 |
| Flavonoid 3' hydroxylase (F3'H) *Phoenix dactylifera* Accession: XP_008791304.2 | MAPLLLLFFTLLLSYLLYYYFFSKERTKGSRAPLPPGP RGWPVLGNLPQLGPKPHHTLHALSRAHGPLFRLRLGS VDVVVAASAAVAAQFLRAHDANFSNRPPNSGAEHIA YNYQDLVFAPYGPGWRARRKLLNVHLFSGKALEDLR PVREGELALLVRALRDRAGANELVDLGRAANKCATN ALARAMVGRRVFQEEEDEKAAEFENMVVELMRLAG VFNVGDFVPGIGWLDLQGVVRRMKELHRRYDGFLDG LIAAHRRAAEGGGGGGKDLLSVLLGLKDEDLDFDGE GAKLTDTDIKALLLNLFTAGTDTTSSTVEWALSELVK HPDILRKAQLELDSVVGGDRLVSESDLPNLPFMQAIIK ETFRLHPSTPLSLPRMAAEECEVAGYCIPKGATLLVNV WAIARDPAVWRDPLEFRPARFLPDGGCEGMDVKGND FGIIPFGAGRRICAGMSLGIRMVQFMTATLAHAFHWD LPEGQMPEKLDMEEAYGLTLQRATPLMVHPVPRLAP TAYQS | 52 |
| Cytochrome P450 reductase (CPR) *Camellia sinensis* Accession: XP_028084858 | MASNSNLIRAIESALGVSFGSELVSDTAIVVVTTSVAVI IGLLFFLLKRSSDRSKESKPVVISKPLLVEEEEEEDEVE AGSGKTKVTMFYGTQTGTAEGFAKSLAKEIKARYEK AIVKVVDLDDYAADDDQYEQKLKKETLVFFMLATYG DGEPTDDAARFYKWFTEENERGAWLQQLTYGVFSLG NRQYEHFNKIGKVVDEQLSKQGAKRLIPVGLGDDDQ CIEDDFAAWRETLWPELDQLLRDEDDANTVSTPYAA AIPEYRVVIHDPLSGRGEAPSFSIDSHLTICEIWSTSREG SNQQISEYFWTSNSLKTMASNSNLIRSIESALGVSFGSE SVSDTAIVVVTTSVAVIIGLLFFLLKRSSDRSKESKPVV ISKPLLVEEEEDEVEAGSGKTKVTLFYGTQTGTAEGFA KSLAEEIKARYEKAIVKVVDLDDYAADDDQYEQKLK KETLVFFMLATYGDGEPTDNAARFYKWFTEENERGA WLQQLTYGVFSLGNRQYEHFNKIGKVVDEQLSKQGA KRLIPVGLGDDDQCIEDDFAAWRETLWPELDQLLRDE | 53 |

TABLE 11-continued

| Enzyme Sequences: | | |
|---|---|---|
| Enzyme: | Sequence: | SEQ ID: |
| | DDANTVSTPYTAAIPEYRVVIHDPTTTSYEDKNLNMA NGNASYDIHHPCRVNVAVQRELHKPESDRSCIHLEFDI SGTGIIYETGDHVGVYADNFDEVVEEAANLLGQPLEL LFSVHADKDDGTSLGGSLPPPFPGPCTLRDALAHYAD LLNPPRKAALSALAAHAVEPSEAERLKFLSSPQGKED YSQWVVASQRSLLEIMAEFPSAKPPLGVFFAAVAPRL QPRYYSISSSPRFVPNRVHVTCALVYGPSPTGRIHKGV CSTWMKNAVPLEKSHDCSSAPIFTRTSNFKLPTDPSIPI IMVGPGTGLAPFRGFLQERLALKEDGVQLGHAMLFFG CRNRRMDFIYEDELNNFVDQGAVSELVVAFSREGPEK EYVQHKLNAKAAQVWGLISQGGYLYVCGDAKGMAR DVHRMLHTIVEQQENVDSRKAEVIVKKLQMEGRYLR DVW | |
| Cytochrome P450 reductase (CPR) *Cephalotus follicularis* Accession: GAV59576.1 | MASNSNLIRAIESALGVSFGSELVSDTAIVVVTTSVAVI IGLLFFLLKRSSDRSKESKPVVISKPLLVEEEEEEDEVE AGSGKTKVTMFYGTQTGTAEGFAKSLAKEIKARYEK AIVKVVDLDDYAADDDQYEQKLKKETLVFFMLATYG DGEPTDDAARFYKWFTEENERGAWLQQLTYGVFSLG NRQYEHFNKIGKVVDEQLSKQGAKRLIPVGLGDDDQ CIEDDFAAWRETLWPELDQLLRDEDDANTVSTPYAA AIPEYRVVIHDPLSGRGEAPSFSIDSHLTICEIWSTSREG SNQQISEYFWTSNSLKTMASNSNLIRSIESALGVSFGSE SVSDTAIVVVTTSVAVIIGLLFFLLKRSSDRSKESKPVV ISKPLLVEEEEDEVEAGSGKTKVTLFYGTQTGTAEGFA KSLAEEIKARYEKAIVKVVDLDDYAADDDQYEQKLK KETLVFFMLATYGDGEPTDNAARFYKWFTEENERGA WLQQLTYGVFSLGNRQYEHFNKIGKVVDEQLSKQGA KRLIPVGLGDDDQCIEDDFAAWRETLWPELDQLLRDE DDANTVSTPYTAAIPEYRVVIHDPTTTSYEDKNLNMA NGNASYDIHHPCRVNVAVQRELHKPESDRSCIHLEFDI SGTGIIYETGDHVGVYADNFDEVVEEAANLLGQPLEL LFSVHADKDDGTSLGGSLPPPFPGPCTLRDALAHYAD LLNPPRKAALSALAAHAVEPSEAERLKFLSSPQGKED YSQWVVASQRSLLEIMAEFPSAKPPLGVFFAAVAPRL QPRYYSISSSPRFVPNRVHVTCALVYGPSPTGRIHKGV CSTWMKNAVPLEKSHDCSSAPIFTRTSNFKLPTDPSIPI IMVGPGTGLAPFRGFLQERLALKEDGVQLGHAMLFFG CRNRRMDFIYEDELNNFVDQGAVSELVVAFSREGPEK EYVQHKLNAKAAQVWGLISQGGYLYVCGDAKGMAR DVHRMLHTIVEQQENVDSRKAEVIVKKLQMEGRYLR DVW | 54 |
| Cytochrome P450 reductase (CPR) *Brassica napus* Accession: XP_013706600.1 | MSSSSSSPFDLMSAIIKGEPVVVSDPANASAYESVAAE LSSMLIENRQFAMIISTSIAVLIGCIVMLLWRRSGGSGS SKRAETLKPLVLKPPREDEVDDGRKKVTIFFGTQTGT AEGFAKALGEEARARYEKTRFKIVDLDDYAADDDEY EEKLKKEDVAFFFLATYGDGEPTDNAARFYKWFTEG DDRGEWLKNLKYGVFGLGNRQYEHFNKVAKVVDDI LVEQGAQRLVHVGLGDDDQCIEDDFTAWREALWPEL DTILREEGDTAVTPYTAAVLEYRVSIHNSADALNEKN LANGNGHAVFDAQHPYRANVAVRRELHTPESDRSCT HLEFDIAGSGLTYETGDHVGVLSDNLNETVEEALRLL DMSPDTYFSLHSDKEDGTPISSSLPPTFPPCSLRTALTR YACLLSSPKKSALLALAAHASDPTEAERLKHLASPAG KDEYSKWVVESQRSLLEVMAEFPSAKPPLGVFFAAV APRLQPRFYSISSSPKIAETRIHVTCALVYEKMPTGRIH KGVCSTWMKSAVPYEKSENCCSAPIFVRQSNFKLPSD SKVPIIMIGPGTGLAPFRGFLQERLALVESGVELGPSVL FFGCRNRRMDFIYEEELQRFLESGALSELSVAFSREGP TKEYVQHKMMDKASDIWNMISQGAYVYVCGDAKG MARDVHRSLHTIAQEQGSMDSTKAESFVKNLQMSGR YLRDVW | 55 |
| Flavonoid 3', 5'-hydroxylase (F3'5'H) *Cephalotus follicularis* Accession: GAV62131 | MALDTFLLRELAAAAVLFLISHYLIHSLLKKSTPPLPPG PKGWPFVGALPLLGTMPHVALAQMAKKYGPVMYLK MGTCGMVVASTPDAARAFLKTLDLNFSNRPPNAGAT HLAYNAQDMVFADYGPRWKLLRKLSNLHMLGGKAL EDWTQVRTVELGHMIQAMCEASRAKEPVVVPEMLTY AMANMIGKVILGHRVFVTQGSESNEFKDMVVELMTS AGYFNIGDFIPSIAWMDLQGIERGMKKLHKRFDALLT KMFEEHMATAHERKGNPDLLDIVMANRDNSEGERLT TTNIKALLLNLFSAGTDTSSSIIEWSLAEMLKNPSILKR AHEEMDQVIGRNRRLEESDIKKLPYLQAICKESFRKHP STPLNLPRVSSQACQVNGYYIPKDTRLSVNIWAIGRDP EVWENPLDFTPERFLSGKNAKIDPRGNDFELIPFGAGR | 56 |

TABLE 11-continued

| Enzyme Sequences: | | |
|---|---|---|
| Enzyme: | Sequence: | SEQ ID: |
| | RICAGTRMGIVLVEYILGTLVHSFDWSLPHGVKLNMD<br>EAFGLALQKAVPLAAIVSPRLAPTAYVV | |
| Flavonoid 3', 5'-<br>hydroxylase<br>(F3'5'H)<br>*Dendrobium*<br>*moniliforme*<br>Accession:<br>AEB96145 | MSIFLITSLLLCLSLHLLLRRRHISRLPLPPGPPNLPIIGA<br>LPFIGPMPHSGLALLARRYGPIMFLKMGIRRVVVASSS<br>TAARTFLKTFDSHFSDRPSGVISKEISYNGQNMVFADY<br>GPKWKLLRKVSSLHLLGSKAMSRWAGVRRDEALSMI<br>QFLKKHSDSEKPVLLPNLLVCAMANVIGRIAMSKRVF<br>HEDGEEAKEFKEMIKELLVGQGASNMEDLVPAIGWL<br>DPMGVRKKMLGLNRRFDRMVSKLLVEHAETAGERQ<br>GNPDLLDLVVASEVKGEDGEGLCEDNIKGFISDLFVA<br>GTDTSAIVIEWAMAEMLKNPSILRRAQEETDRVIGRH<br>RLLDESDIPNLPYLQAICKEALRKHPPTPLSIPHYASEP<br>CEVEGYHIPGETWLLVNIWAIGRDPDVWENPLVFDPE<br>RFLQGEMARIDPMGNDFELIPFGAGRRICAGKLAGMV<br>MVQYYLGTLVHAFDWSLPEGVGELDMEEGPGLVLPK<br>AVPLAVMATPRLPAAAYGLL | 57 |
| Dihydroflavonol 4-<br>reductase (DFR)<br>*Acer palmatum*<br>Accession:<br>AWN08247.1 | MGSEAETVCVTGASGFIGSWLIMRLLERGYTVRATVR<br>DPDNEKKVKHLVELPKAKTHLTLWKADLSDEGSFDE<br>AIHGCTGVFHVATPMDFESKDPENEVIKPTINGVLGIM<br>KACKKAKTVKRLVFTSSAGTVDVEEHKKPVYDENSW<br>SDLDFVQSVKMTGWMYFVSKTLAEKAAWKFAEENSI<br>DFISVIPPLVVGPFLMPSMPPSLITALSPITRNEGHYAII<br>KQGNYVHLDDLCMGHIFLYEHAESKGRYFCSSHSATI<br>LELSKFLRERYPEYDLPTEYKGVDDSLENVVFCSKKIL<br>DLGFQFKYSLEDMFTGAVETCREKGLIPLTNIDKKHV<br>AAKGLIPNNSDEIHVAAAEKTTATA | 58 |
| Dihydroflavonol 4-<br>reductase (DFR)<br>*Abrus precatorius*<br>Accession:<br>XP_027329642.1 | MGSASETVCVTGAAGFIGSWLVMRLIQNGYKVRATV<br>RDPANMKKVKHLLELPNAKTNLSLWKADLAEEGSFD<br>EAIKGCTGVFHVATPMDFESKDPENEVIKPTINGLIDI<br>MKACMKAKTVRRLVFTSSAGTVDVTEHPKPLFDESC<br>WSDVQFCRRVRMTGWMYFVSKTLAEQEAWKFAKEN<br>NIDFISVIPPLVVGPFLVPTMPPSLITALSLITGNESHYAI<br>IKQGQFVHLDDLCLAHIFLFQHPKAQGRYICCSHEATI<br>HDIASLLNQKYPEFNVPTKFKNIPDQLEIIRFSSKKITDL<br>GFKFKYSLEDMFTGAVETCKEKRLLSETAEISGTTQK | 59 |
| Dihydroflavonol 4-<br>reductase (DFR)<br>*Dendrobium*<br>*moniliforme*<br>Accession:<br>AEB96144.1 | MENEKKGPVVVTGASGYVGSWLVMKLLQKGYEVRA<br>TVRDPTNLKKVKPLLDLPRSNELLSIWKADLDGIEGSF<br>DEVIRGSIGVFHVATPMNFQSKDPENEVIQPAINGLLGI<br>LRSCKNAGSVQRVIFTSSAGTVNVEEHQAAAYDETC<br>WSDLDFVNRVKMTGWMYFLSKTLAEKAAWEFVKD<br>NHIHLITIIPTLVVGSFITSEMPPSMITALSLITGNDAHY<br>SILKQIQFVHLDDLCDAHIFLFEHPKANGRYICSSYDST<br>IYGLAEMLKNRYPTYAIPHKFKEIDPDIKCVSFSSKKL<br>MELGFKYKYTMEEMFDDAIKTCREKKLIPLNTEEIVL<br>AAEKFEEVKEQIAVK | 60 |
| Dihydroflavonol 4-<br>reductase (DFR)<br>*Rosa chinensis*<br>Accession:<br>XP_024167119.1 | MASESESVCVTGASGFVGSWLVMRLLDRGYTVRATV<br>RDPANKKKVKHLLDLPKAATHLTLWKADLAEEGSFD<br>EAIKGCTGVFHVATPMDFESKDPENEVIKPTINGVLDI<br>MKACLKAKTVRRLVFTASAGSVNVEETQKPVYDESN<br>WSDVEFCRRVKMTGWMYFASKTLAEQEAWKFAKEN<br>NIDFITIIPTLVIGPFLMPAMPPSLITGLSPLTGNESHYSII<br>KQGQFIHLDDLCQSHIYLYEHPKAEGRYICSSHDATIH<br>EIAKLLREKYPEYNVPTTFKGIEENLPKVHFSSKKLLE<br>TGFEFKYSLEDMFVGAVDACKAKGLLPPPTERVEKQE<br>VDESSVVGVKVTG | 61 |
| Leucoanthocyanidin<br>reductase (LAR)<br>*Camellia sinensis*<br>Accession:<br>XP_028127206.1 | MTVSSPCVGEGQGRVLIIGASGFIGEFIAQASLDSGRTT<br>FLLVRSLDKGAIPSKSKTINSLHDKGAILIHGVIEDQEF<br>VEGILKDHKIDIVISAVGGANILNQLTIVKAIKAVGTIK<br>RFLPSEFGHDVDRANPVEPGLAMYKEKRMVRRLIEES<br>GVPYTYICCNSIASWPYYDNTHPSEVIPPLDRFQIYGD<br>GTVKAYFVDGSDIGKFTMKVVDDIRTLNKSVHFRPSC<br>NFLNMNELSSLWEKKIGYMLPRLTVTEDDLLAAAAE<br>NIIPQSIVASFTHDIFIKGCQVNFSIDGPNEVEVSNLYPD<br>ETFRTMDECFDDFVMKMDRWN | 62 |
| Leucoanthocyanidin<br>reductase (LAR)<br>*Coffea arabica*<br>Accession:<br>XP_027097479.1 | MTRSPSPNGQAEKGSRILIIGATGFIGHFIAQASLASGK<br>STYILSRAAARCPSKARAIKALEDQGAISIHGSVNDQE<br>FMEKTLKEHEIDIVISAVGGGNLLEQVILIRAMKAVGT<br>IKRFLPSEFGHDVDRAEPVEPGLTMYNEKRRVRRLIEE<br>SGVPYTYICCNSIASWPYYDNTHPSEVSPPLDQFQIYG | 63 |

TABLE 11-continued

| Enzyme: | Sequence: | SEQ ID: |
|---|---|---|
| | DGSVKAYFVAGADIGKFTVKATEDVRTLNKIVHFRPS CNFLNINELATLWEKKIGRTLPRVVVSEDDLLAAAEE NIIPQSVVASFTHDIFIKGCQVNFPVDGPNEIEVSSLYP DEPFQTMDECFNEFAGKIEEDKKHVVGTKGKNIAHRL VDVLTAPKLCA | |
| Leucoanthocyanidin reductase (LAR) *Theobroma cacao* Accession: ADD51357.1 | MKSTNMNGSSPNVSEETGRTLVVGSGGFMGRFVTEA SLDSGRPTYILARSSSNSPSKASTIKFLQDRGATVIYGSI TDKEFMEKVLKEHKIEVVISAVGGGSILDQFNLIEAIR NVDTVKRFLPSEFGHDTDRADPVEPGLTMYEQKRQIR RQIEKSGIPYTYICCNSIAAWPYHDNTHPADVLPPLDR FKIYGDGTVKAYFVAGTDIGKFTIMSIEDDRTLNKTVH FQPPSNLLNINEMASLWEEKIGRTLPRVTITEEDLLQM AKEMRIPQSVVAALTHDIFINGCQINFSLDKPTDVEVC SLYPDTPFRTINECFEDFAKKIIDNAKAVSKPAASNNAI FVPTAKPGALPITAICT | 64 |
| Leucoanthocyanidin reductase (LAR) *Fragaria x ananassa* Accession: ABH07785.2 | MTVSPSIASAAKSGRVLIIGATGFIGKFVAEASLDSGLP TYVLVRPGPSRPSKSDTIKSLKDRGAIILHGVMSDKPL MEKLLKEHEIEIVISAVGGATILDQITLVEAITSVGTVK RFLPSEFGHDVDRADPVEPGLTMYLEKRKVRRAIEKS GVPYTYICCNSIASWPYYDNKHPSEVVPPLDQFQIYGD GTVKAYFVDGPDIGKFTMKTVDDIRTMNKNVHFRPSS NLYDINGLASLWEKKIGRTLPKVTITENDLLTMAAEN RIPESIVASFTHDIFIKGCQTNFPIEGPNDVDIGTLYPEE SFRTLDECFNDFLVKVGGKLETDKLAAKNKAAVGVE PMAITATCA | 65 |
| Anthocyanin dioxygenase (ANS) Chenopodium *quinoa* Accession: XP_021735950.1 | MTQNKEPVNQGKSEHDEQRVESLASSGIESIPKEYVRL NEELTSMGNVFEEEKKEEGSQVPTIDIKDIASEDPEVR GKAIQELKRAAMEWGVMHLVNHGISDELIDRVKVAG QTFFELPVEEKEKYANDQASGNVQGYGSKLANSASG RLEWEDYYFHLSYPEDKRDLSIWPETPADYIPAVSEYS KELRYLATKILSALSLALGLEEGRLEKEVGGLEELLLQ FKINYYPKCPQPELALGVEAHTDVSALTFILHNMVPG LQLFYEGKWVTAKCVPNSIIMHIGDTIEILSNGKYKSIL HRGLVNKEKVRISWAVFCEPPKEKIILKPLPDLVSDEE PARYPPRTFAQHVQYKLFRKTQGPQTTITKN | 66 |
| Anthocyanin dioxygenase (ANS) *Iris sanguinea* Accession: QCI56004.1 | MASSKVMPAPARVESLASSGLASIPTEYVRPEWERDD SLGDALEEIKKTEEGPQIPIVDLRGFDSGDEKERLHCM EEVKEAAVEWGVMHIVNHGIAPELIERVRAAGKGFFD LPVEAKERYANNQSEGKIQGYGSKLANNASGQLEWE DYFFHLIFPSDKVDLSIWPKEPADYTEVMMEFAKQLR VVVTKMLSILSLGLGFEEEKLEKKLGGMEELLMQMKI NYYPKCPQPELALGVEAHTDVSSLSFILHNGVPGLQV FHGGRWVNARLVPGSLVVHVGDTLEILSNGRYKSVL HRGLVNKEKVRISWAVFCEPPKEKIVLEPLAELVDKR SPAKYPPRTFAQHIQHKLFKKAQEQLAGGVHIPEAIQN | 67 |
| Anthocyanin dioxygenase (ANS) *Magnolia sprengeri* Accession: AHU88620.1 | MATQVASIPRVEMLASAGIQAIPTEYVRPEAERNSIGD VFEEEKKLEGPQIPVVDLMGLEWENEEVFKKVEEDM KKAASEWGVMHIFNHGISMELMDRVRIAGKAFFDLPI EEKEMYANDQASGKIAGYGSKLANNASGQLEWEDYF FHLIFPEDKRDMSIWPKQPSDYVEATEEFAKQLRGLV TKVLVLLSRGLGVEEDRLEKEFGGMEELLLQMKINYY PKCPQPDLALGVEAHTDVSALTFILHNMVPGLQVFFD DKWVTAKCIPGALVVHIGDSLEILSNGKYRSILHRGLV NKEKVRISWAIFCEPPKEKVVLQPLPELVSEAEPARFT PRTFSQHVRQKLFKKQQDALENLKSE | 68 |
| Anthocyanin dioxygenase (ANS) *Prosopis alba* Accession: XP_028787846.1 | MVSSAAVVATRVERLATSGIKSIPKEYVRPQEELTNIG NVFEEEKKEGPEVPTIDLTEIESEDEVVRARCHETLKK AAQEWGVMNLVNHGIPEELLNQLRKAGETFFSLPIEE KEKYANDQASGKIQGYGSKLANNASGQLEWEDYFFH LVFPEDKCDLSIWPRTPSDYIEVTSEYARQLRGLATKI LGALSLGLGLEKGRLEEEVGGMEELLLQMKINYYPIC PQPELALGVEAHTDVSSLTFLLHNMVPGLQLFYNGQ WITAKCVPNSIFMHIGDTVEILSNGRYKSILHRGLVNK EKVRISWAVFCEPPKEKIILKPLPELVTDDEPARFPPRT FAQHIQHKLFRKCQEGLSK | 69 |
| Anthocyanidin-3-O-glycotransferase (3GT) *Cephalotus* | MPQFTTNEPHVAVLAFPFGTHAAPLITIIHRLAVASPN THFSFLNTSQSNNSIFSSDVYNRQPNLKAHNVWDGVP EGYVFVGKPQESIELFVKAAPETFRKGVEAAVAETGR KVSCLVTDAFFWFAAEIAGELGVPWVPFWTAGPCSLS | 70 |

TABLE 11-continued

Enzyme Sequences:

| Enzyme: | Sequence: | SEQ ID: |
|---|---|---|
| *follicularis* Accession: GAV66155.1 | THVYTDLIRKTIGVGGIEGREDESLEFIPGMSQVVIRDL QEGIVFGNLESVFSDMVHRMGIVLPQAAAIFINSFEEL DLTITNDLKSKFKQFLSIGPLNLASPPPRVPDTNGCLP WLDQQKVASVAYISFGTVMAPSPPELVALAEALEASK IPFIWSLGEKLKVHLPKGFLDKTRTHGIVVPWAPQSDV LENGAVGVFITHCGWNSLLESIAGGVPMICRPFFGDQ RLNGRMVQDVWEIGVTATGGPFTTEGVMGDLDLILS QARGKKMKDNISVLKTLAQTAVGPEGSSAKNYEALL NLVRLSI | |
| Anthocyanidin-3-O-glycotransferase (3GT) *Prunus cerasifera* Accession: AKV89253.1 | MAPQPIDDDHVVYEHHVAALAFPFSTHASPTLALVRR LAAASPNTLFSFFSTSQSNNSLFSNTITNLPRNIKVFDV ADGVPDGYVFAGKPQEDIELFMKAAPHNFTTSLDTCV AHTGKRLTCLITDAFLWFGAHLAHDLGVPWLPLWLS GLNSLSLHVHTDLLRHTIGTQSIAGRENELITKNVNIPG MSKVRIKDLPEGVIFGNLDSVFSRMLHQMGQLLPRAN AVLVNSFEELDITVTNDLKSKFNKLLNVGPFNLAAAA SPPLPEAPTAADDVTGCLSWLDKQKAASSVVYVSFGS VARPPEKELLAMAQALEASGVPFLWSLKDSFKTPLLN ELLIKASNGMVVPWAPQPRVLAHASVGAFVTHCGWN SLLETIAGGVPMICRPFFGDQRVNARLVEDVLEIGVTV EDGVFTKHGLIKYFDQVLSQQRGKKMRDNINTVKLL AQQPVEPKGSSAQNFKLLLDVISGSTKV | 71 |
| Anthocyanidin-3-O-glycotransferase (3GT) *Scutellaria baicalensis* Accession: A0A482AQV3 | MVFQSHIGVLAFPFGTHAAPLLTVVQRLATSSPHTLFS FFNSAVSNSTLFNNGVLDSYDNIRVYHVWDGTPQGQ AFTGSHFEAVGLFLKASPGNFDKVIDEAEVETGLKISC LITDAFLWFGYDLAEKRGVPWLAFWTSAQCALSAHM YTHEILKAVGSNGVGETAEEELIQSLIPGLEMAHLSDL PPEIFFDKNPNPLAITINKMVLKLPKSTAVILNSFEEIDP IITTDLKSKFHHFLNIGPSILSSPTPPPPDDKTGCLAWLD SQTRPKSVVYISFGTVITPPENELAALSEALETCNYPFL WSLNDRAKKSLPTGFLDRTKELGMIVPWAPQPRVLA HRSVGVFVTHCGWNSILESICSGVPLICRPFFGDQKLN SRMVEDSWKIGVRLEGGVLSKTATVEALGRVMMSEE GEIIRENVNEMNEKAK1AVEPKGSSFKNFNKLLEIINAP QSS | 72 |
| Anthocyanidin-3-O-glycotransferase (3GT) *Vitis vinifera* Accession: P51094 | MSQTTTNPHVAVLAFPFSTHAAPLLAVVRRLAAAAPH AVFSFFSTSQSNASIFHDSMHTMQCNIKSYDISDGVPE GYVFAGRPQEDIELFTRAAPESFRQGMVMAVAETGRP VSCLVADAFIWFAADMAAEMGLAWLPFWTAGPNSLS THVYIDEIREKIGVSGIQGREDELLNFIPGMSKVRFRDL QEGIVFGNLNSLFSRMLHRMGQVLPKATAVFINSFEEL DDSLTNDLKSKLKTYLNIGPFNLITPPPVVPNTTGCLQ WLKERKPTSVVYISFGTVTTPPPAEVVALSEALEASRV PFIWSLRDKARVHLPEGFLEKTRGYGMVVPWAPQAE VLAHEAVGAFVTHCGWNSLWESVAGGVPLICRPFFG DQRLNGRMVEDVLEIGVRIEGGVFTKSGLMSCFDQIL SQEKGKKLRENLRALRETADRAVGPKGSSTENFITLV DLVSKPKDV | 73 |
| Acetyl-CoA carboxylase (ACC) *Ustilago maydis* 521 Accession: XP_011390921.1 | MPPPDHKAVSQFIGGNPLETAPASPVADFIRKQGGHS VITKVLICNNGIAAVKEIRSIRKWAYETFGDERAIEFTV MATPEDLKVNADYIRMADQYVEVPGGSNNNNYANV DLIVDVAERAGVHAVWAGWGHASENPRLPESLAASK HKIIFIGPPGSAMRSLGDKISSTIVAQHADVPCMPWSG TGIKETMMSDQGFLTVSDDVYQQACIHTAEEGLEKAE KIGYPVMIKASEGGGGKGIRKCTNGEEFKQLYNAVLG EVPGSPVFVMKLAGQARHLEVQLLADQYGNAISIFGR DCSVQRRHQKIIEEAPVTIAPEDARESMEKAAVRLAK LVGYVSAGTVEWLYSPESGEFAFLELNPRLQVEHPTT EMVSGVNIPAAQLQVAMGIPLYSIRDIRTLYGMDPRG NEVIDFDFSSPESFKTQRKPQPQGHVVACRITAENPDT GFKPGMGALTELNFRSSTSTWGYFSVGTSGALHEYAD SQFGHIFAYGADRSEARKQMVISLKELSIRGDFRTTVE YLIKLLETDAFESNKITTGWLDGLIQDRLTAERPPADL AVICGAAVKAHLLARECEDEYKRILNRGQVPPRDTIK TVFSIDFIYENVKYNFTATRSSVSGWVLYLNGGRTLV QLRPLTDGGLLIGLSGKSHPVYWREEVGMTRLMIDSK TCLIEQENDPTQIRSPSPGKLVRFLVDSGDHVKANQAI AEIEVMKMYLPLVAAEDGVVSFVKTAGVALSPGDIIG ILSLDDPSRVQHAKPFAGQLPDFGMPVIVGNKPHQRY TALVEVLNDILDGYDQSFRMQAVIKELIETLRNPELPY GQASQILSSLGGRIPARLEDVVRNTIEMGHSKNIEFPA ARLRKLTENFLRDSVDPAIRGQVQITIAPLYQLFETYA | 74 |

TABLE 11-continued

| Enzyme Sequences: | | |
|---|---|---|
| Enzyme: | Sequence: | SEQ ID: |
| | GGLKAHEGNVLASFLQKYYEVESQFTGEADVVLELR LQADGDLDKVVALQTSRNGINRKNALLLTLLDKHIKG TSLVSRTSGATMIEALRKLASLQGKSTAPIALKAREVS LDADMPSLADRSAQMQAILRGSVTSSKYGGDDEYHA PSLEVLRELSDSQYSVYDVLHSFFGHREHHVAFAALC TYVVRAYRAYEIVNFDYAVEDFDVEERAVLTWQFQL PRSASSLKERERQVSISDLSMMDNNRRARPIRELRTGA MTSCADVADIPELLPKVLKFFKSSAGASGAPINVLNV AVVDQTDFVDAEVRSQLALYTNACSKEFSAARVRRV TYLLCQPGLYPFFATFRPNEQGIWSEEKAIRNIEPALA YQLELDRVSKNFELTPVPVSSSTIHLYFARGIQNSADT RFFVRSLVRPGRVQGDMAAYLISESDRIVNDILNVIEV ALGQPEYRTADASHIFMSFIYQLDVSLVDVQKAIAGFL ERHGTRFFRLRITGAEIRMILNGPNGEPRPIRAFVTNET GLVVRYETYEETVADDGSVILRGIEPQGKDATLNAQS AHFPYTTKVALQSRRSRAHALQTTFVYDFIDVLGQAV RASWRKVAASKIPGDVIKSAVELVFDEQENLREVKRA PGMNNIGMVAWLVEVLTPEYPAGRKLVVIGNDVTIQ AGSFGPVEDRFFAAASKLARELGVPRLYISANSGARIG LATEALDLFKVKFVGDDPAKGFEYIYLDDESLQAVQA KAPNSVMTKPVQAADGSVHNIITDIIGKPQGGLGVEC LSGSGLIAGETSRAKDQIFTATIITGRSVGIGAYLARLG ERVIQVEGSPLILTGYQALNKLLGREVYTSNLQLGGPQ IMYKNGVSHLTAQDDLDAVRSFVNWISYVPAQRGGP LPIMPTTDSWDRAVTYQPPRGPYDPRWLINGTKAEDG TKLTGLFDEGSFVETLGGWATSVVTGRARLGGIPVGV IAVETRTLERVVPADPANPNSTEQRIMEAGQVWYPNS AYKTAQAIWDFDKEGLPLVILANWRGFSGGQQDMYD EILKQGSKIVDGLSSYKQPVFVHIPPMGELRGGSWVV VDSAINDNGMIEMSADVNSARGGVLEASGLVEIKYRA DKQRATMERLDSVYAKLSKEAAEATDFTAQTTARKA LAEREKQLAPIFTAIATEYADAHDRAGRMLATGVLRS ALPWENARRYFYWRLRRRLTEVAAERTVGEANPTLK HVERLAVLRQFVGAAASDDDKAVAEHLEASADQLLA ASKQLKAQYILAQISTLDPELRAQLAASLK | |
| Acetyl-CoA carboxylase (ACC) *Hesseltinella vesiculosa* Accession: ORX57605.1 | MVDHKSLPGHFLGGNSVDTAPQDPVCEFVKSHQGHT VISKVLIANNGMAAMKEIRSVRKWAYETFGNERAIEF TVMATPEDLKANAEYIRMADNYIEVPGGTNNNNYAN VELIVDVAERTGVHAVWAGWGHASENPRLPEMLAKS KNKCVFIGPPASAMRSLGDKISSTIVAQSADVPTMGW SGDGVSETTTDHNGHVLVNDDVYNSACVKTAEAGLA SAEKIGFPVMIKASEGGGGKGIRKVEDPSTFKQAFAQ VQGEIPGSPIFIMKLAGNARHLEVQLLADQYGNAISLF GRDCSVQRRHQKIIEEAPVTIAKPDIFEQMEKAAVRLG KLVGYVSAGTVEYLYSHHDEKFYFLELNPRLQVEHPT TEMVSGVNLPAAQLQIAMGIPMHRIRDIRVLYGVQPN SASEIDFDLEHPTALQSQRRPMPKGHVIAVRITAENPD AGFKPSGGVMQELNFRSSTNVWGYFSVVSSGAMHEY ADSQFGHIFAYGENRQQARKNMVIALKELSIRGDFRT TVEYIIRLLETPDFTDNTINTGWLDMLISKKLTAERPDT MLAVFCGAVTKAHLASVECWQQYKNSLERGQIPSKE SLKTVFTVDFIYENIRYNFTVTRSAPGIYTLYLNGTKT QVGVRDLSDGGLLISLNGRSHTTYNREEVQATRLMID GKTCLLEKESDPTQLRSPSPGKLVSLLLENGDHIRTGQ AYAEIEVMKMYMPLVASEDGHVQFIKQVGATLEAGD IIGILSLDDPSRVKHALPFTGQVPKYGLPHLTGDKPHQ RFTHLKQTLEYVLQGYDNQGLIQTIVKELSEVLNNPEL PYSELSASMSVLSGRIPGRLEQQLHDLINQAHAQNKG FPAVDIQQAIDTFARDHLTTQAEVNAYKTAVAPIMTIA ASYSNGLKQHEHSVYVDLMEQYYNVEVLFNSNQSRD EEVILALRDQHKDDLEKVINIILSHAKVNIKNNLILMLL DIIYPATSSEALDRCFLPILKHLSEIDSRGTQKVTLKAR EYLILCQLPSLEERQSQMYNILKSSVTESVYGGGTEYR TPSYDAFKDLIDTKFNVFDVLPNFFYHPDSYVSLAALE VYCRRSYHAYKILDVAYNLEHQPYIVAWKFLLQSSA GGGFNNQRIASYSDLTFLLNKTEEEPIRTGAMVALKTL EELEAELPRIMTAFEEEPLPPMLMKQPPPDKTEERMEN ILNISIQGQDMEDDTLRKNMTTLIQAHSDAFRKAALR RITLVVCRDNQTPDYYTFRERNGYEEDETIRHIEPALA YQLELARLSNFDIKPCFIENRQMHVYYAVAKENPSDC RFFIRALVRPGRVKSSMRTADYLISESDRLLTDILDTLE IVSHDYKNSDCNHLFINFIPTFAIEADEVETALKDFVDR HGKRLWKLRVTGAEIRFNIQSKRPDAPVIPLRFTVDNV SGYILKVDVYQEVKTDKNGWILKSVGKIPGAMHMQP LSTPYPTKEWLQPRRYKAHLMGTTYVYDFPELFRQAI | 75 |

TABLE 11-continued

| Enzyme Sequences: | | |
|---|---|---|
| Enzyme: | Sequence: | SEQ ID: |
| | HNLWAQACKADAAVKIPSQVIEAKELVLDDDNQLQA IDRAPGTNTVGMVAWLLTLRTPDYPRGRRVIAIANDI TFKIGSFGVQEDLVFYKASEYARELGVPRVYLSANSG ARIGLADELISRFHVAWKDEDQPGSGFEYLYLLPEEY DALIQQGDAQSVLVQEVQDKGERRFRITDIIGHTDGL GVENLRGSGLIAGATSRAYDDIFTITLVTCRSVGIGAY LVRLGQRTVQNEGQPIILTGAPALNKVLGREVYTSNL QLGGTQIMYKNGVSHLTAENDLEGINKIMQWLSFVPE CRGAPLPMRAGADPIDREIEYLPPKGPSDPRFFLAGKQ ENGKWLSGFFDHGSFVETLSGWARTVVVGRARLGGI PMGVVAVETRTVENIVPADPANADSQEQVVMEAGGV WFPNSAYKTAQAINDFNKGEQLPLMIFANWRGFSGG QRDMYNEVLKYGAQIVDALSNYKQPVFVYVVPNGEL RGGAWVVVDSTINEDMMEMYADTQARGGVLEPEGI VEIKYRRPQLLATMERLDPVYSDLKRRLAALDDSQKE QADELIAQVEAREQALLPVYQQVAIQFADLHDRSGR MEAKGVIRKTLEWRTARHYFYWRVRRRLLEEYAIRK MDESRDQAKTLLQQWFQADTNLDDFDKNDQAVVA WFDAKNLLLDQRIAKLKSEKLKDHVVQLASVDQDAV VEGFSKLMESLSVDQRKEVLHKLATRF | |
| Acetyl-CoA carboxylase (ACC) *Rhodotorula toruloides* NBRC10032 Accession: GEM08739.1 | MASTTPHDSRVVSVSSGKKLYIEVDDGAGKDAPAIVF MHGLGSSTSFWEAPFSRSNLSSRFRLIRYDFDGHGLSP VSLLDAADDGAMIPLVDLVEDLAAVMEWTGVDKVA GIVGHSMSGLVASTFAAKYPQKVEKLVLLGAMRSLN PTVQTNMLKRADTVLESGLSAIVAQVVSAALSDKSKQ DSPLAPAMVRTLVLGTDPLGYAAACRALAGAKDPDY STIKAKTLVVSGESDYLSNKETTEALVNDIPGAKEVQ MDGVGHWHAVEDPAGLAKILDGFFLQGKFSGEAKA VNGSHAVDETPKKPKYDHGRVVKYLGGNSLESAPPS NVADWVRERGGHTVITKILIANNGIAAVKEIRSVRKW AYETFGSERAIEFTVMATPEDLKVNADYIRMADQYVE VPGGTNNNNYANVDVIVDVAERAGVHAVWAGWGH ASENPRLPESLAASKHKIVFIGPPGSAMRSLGDKISSTI VAQHAEVPCMDWSGQGVDQVTQSLEGYVTVADDVY QQACVHDADEGLARASRIGYPVMIKASEGGGGKGIR KVEREQDFKQAFQAVLTEVPGSPVFIMKLAGAARHLE VQVLADQYGNAISLFGRDCSVQRRHQKIIEEAPVTIAK PDTFEQMEKSAVRLAKLVGYVSAGTVEFLYSAADDK FAFLELNPRLQVEHPTTEMVSGVNLPAAQLQVAMGV PLHRIRDIRTLYGKAPNGSSEIDFEFENPESAKTQRKPS PKGHVVAVRITAENPDAGFKPSMGTLQELNFRSSTNV WGYFSVGSAGGLHEFADSQFGHIFAYGSDRSESRKN MVVALKELSIRGDFRTTVEYLIKLLETDAFEQNTITTA WLDSLISARLTAERPDTTLAIICGAVTKAHLASEANIA EYKRILEKGQSPPKELLATVVPLEFVLEDVKYRATASR SSPSSWSIYVNGSNVSVGIRPLADGGLLILLDGRSYTC YAKEEVGALRLSIDSRTVLVAQENDPTQLRSPSPGKL VRYFIESGEHISKGEAYAEIEVMKMIMPLIAAEDGIAQ FIKQPGATLEAGDILGILSLDDPSRVHHAKPFDGQLPA LGLPSIIGTKPHQRFAYLKDVLSNILMGYDNQAIMQSS IKELISVLRNPELPYGEANAVLSTLSGRIPAKLEQTLRQ YIDSAHESGAEFPSAKCRKAIDTTLEQLRPAEAQTVRN FLVAFDDIVYRYRSGLKHHEWSTLAGIFAAYAETEKP FSGKDSDVVLELRDAHRDSLDSVVKIVLSHYKAASKN SLVLALLDVVKDSDSVPLIEQVVSPALKDLADLDSKA TTKVALKAREVLIHIQLPSLDERLGQLEQILKASVTPT VYGEPGHDRTPRGEVLKDVIDSRFTVFDVLPSFFQHQ DQWVSLAALDTYVRRAYRSYNLLNIEHIEADAAEDEP ATVAWSFRMRKAASESEPPTPTTGLTSQRTASYSDLT FLLNNAQSEPIRYGAMFSVRSLDGFRQELGTVLRHFP DSNKGKLQQQPAASSSQEQWNVINVALTVPASAQVD EDALRADFAAHVNAMSAEIDARGMRRLTLLICREGQ YPSYYTVRKQDGTWKELETIRDIEPALAFQLELGRLSN FHLEPCPVENRQVHIYYATAKGNSSDCRFFVRALVRP GRLRGNMKTADYLVSEADRLVTDVLDSLEVASSQRR AADGNHISLNFLYSLRLDFDEVQAALAGFIDRHGKRF WRLRVTGAEIRIVLEDAQGNIQPIRAIIENVSGFVVKYE AYREVTTDKGQVILKSIGPQGALHLQPVNFPYPTKEW LQPKRYKAHVVGTTYVYDFPDLFRQAIRKQWKAVGK TAPAELLVAKELVLDEFGKPQEVARPPGTNNIGMVG WIYTIFTPEYPSGRRVVVIANDITFKIGSFGPEEDRYFY AVTQLARQLGLPRVYLSANSGARLGIAEELVDLFSVA WADSSRPEKGFKYLYLTAEKLGELKNKGEKSVITKRI EDEGETRYQITDIIGLQEGLGVESLKGSGLIAGETSRAY DDIFTITLVTARSVGIGAYLVRLGQRAVQVEGQPIILTG | 76 |

TABLE 11-continued

| Enzyme Sequences: | | |
|---|---|---|
| Enzyme: | Sequence: | SEQ ID: |
| | AGALNKVLGREVYSSNLQLGGTQIMYKNGVSHLTAA NDLEGVLSIVQWLAFVPEHRGAPLPVLPSPVDPWDRSI DYTPIKGAYDPRWFLAGKTDEADGRWLSGFFDKGSF QETLSGWAQTVVVGRARLGGIPMGAIAVETRTIERIIP ADPANPLSNEQKIMEAGQVWYPNSSFKTGQAIFDFNR EGLPLIIFANWRGFSGGQQDMFDEVLKRGSLIVDGLS AYKQPVFVYIVPNGELRGGAWVVLDPSINAEGMMEM YVDETARAGVLEPEGIVEIKLRKDKLLALMDRLDPTY HALRVKSTDASLSPTDAAQAKTELAAREKQLMPIYQQ VALQFADSHDKAGRILSKGCAREALEWSNARRYFYA RLRRRLAEEAAVKRLGEADPTLSRDERLAIVHDAVGQ GVDLNNDLAAAAAFEQGAAAITERVKLARATTVAST LAQLAQDDKEAFAASLQQVLGDKLTAADLARILA | |
| Malonyl-CoA synthase (matB) *Rhodopseudomonas palustris* Accession: WP_011661926.1 | MNANLFSRLFDGLVEADKLAIETLEGERISYGDLVAR SGRMANVLVARGVKPGDRVAAQAEKSVAALVLYLA TVRAGAVYLPLNTAYTLHELDYFIGDAEPKLVVCDPA KREGIAALAQKVGAGVETLDAKGQGSLSEAAAQASV DFATVPREGDDLAAILYTSGTTGRSKGAMLSHDNLAS NSLTLVEFWRFTPDDVLIHALPIYHTHGLFVASNVTLF ARASMIFLPKFDPDAIIQLMSRASVLMGVPTFYTRLLQ SDGLTKEAARHMRLFISGSAPLLADTHREWASRTGHA VLERYGMTETNMNTSNPYDGARVPGAVGPALPGVSL RVVDPETGAELSPGEIGMIEVKGPNVFQGYWRMPEKT KAEFRDDGFFITGDLGKIDADGYVFIVGRGKDLVITGG FNVYPKEVESEIDAISGVVESAVIGVPHADLGEGVTAV VVRDKGASVDEAAVLGALQGQLAKFKMPKRVLFVD DLPRNTMGKVQKNVLREAYAKLYAK | 77 |
| Malonyl-CoA synthase (matB) *Rhizobium* sp. BUS003 Accession: NKF42351.1 | MVNHLFDAIRLSITSPESTFIELEDGKVWTYGAMFNCS ARITHVLVKLGVSPGDRVAVQVEKSAQALMLYLGCL RAGAVYLPLNTAYTPAELEYFLGDATPKLVVVSPCAA EQLEPLARRVGTRLLTLGVNGDGSLMDMASLEPVEF ADIERKADDLAAILYTSGTTGRSKGAMLTHDNLLSNA QTLREHWRFTSADRLIHALPIFHTHGLFVATNVTLLAG GAIYLLSKFDPDQIFALMTRATVMMGVPTFYTRLLQD ERLNKANTRHMRLFISGSAPLLAETHRLFEEYTGHAIL ERYGMTETNMITSNPCDGARVPGTVGYALPGVSVRIT DPVSGEPLAAGEPGMIEVKGPNVFQGYWNMPDKTKE EFRSDGYFTTGDIGVMETDGRISIVGRGKDLIISGGYNI YPKEIENEIDAIEGVVESAVIGVPHPDLGEGVTAIVVG QPKAHLDLTTITNNLQGRLARFKQPKNVIFVDELPRNT MGKVQKNVLRDRYRDLYLK | 78 |
| Malonyl-CoA synthase (matB) *Ochrobactrum* sp. 3-3 Accession: WP_114216069.1 | MANHLFDLVRANATDLTKTFIETETGLKLTYDDLMT GTARYANVLVGLGVKPGDRVAVQVEKSAGAIFLYLA CVRAGAVFLPLNTAYTLTEIEYFLGDAEPALVVCDPA RRDGITEVAKKTGVPAVETLGKGQDGSLFDKAAAAP ETFADVARGPGDLAAILYTSGTTGRSKGAMLSHDNLA SNALTLKDYWRFGADDVLLHALPIFHTHGLFVATNTI LVAGASMLFLPKFDADKVFELMPRATTMMGVPTFYV RLVQDARLTREATKHMRLFISGSAPLLAETHKLFREK TGVSILERYGMTETNMNTSNPYDGDRVAGTVGFPLPG VALRVADPETGAAIPQGEIGVIEVKGPNVFSGYWRMP EKTAAEFRQDGFFITGDLGKIDDQGYVHIVGRGKDLV ISGGYNVYPKEVETEIDGMAGVVESAVIGVPHPDFGE GVTAVVVAEKGASLDEATIIKTLEQRLARYKLPKRVI VVDDLPRNTMGKVQKNLLRDAYKGLYGG | 79 |
| Malonate transporter (matC) *Rhizobiales bacterium* Accession: MBN8942514.1 | MSPELISILVLVVVFVIATTRSVNMGALAFAAAFGVGT LVADLDADGIFAGFPGDLFVVLVGVTYLFAIARANGT TDWLVHAAVRLVRGRVALIPWVMFALTGALTAIGAV SPAAVAIVAPVALSFATRYSISPLLMGTMVVHGAQAG GFSPISIYGSIVNGIVEREKLPGSEIGLFLASLVANLLIA AVLFAVLGGRKLWARGAVTPEGDGAPGKAGTGTTGS GSDTGTGTGTGTGTSAGTGGTAPTAVAVRSDRETGG AEGTGVRLTPARVATLVALVALVVAVLGFDLDAGLT AVTLAVVLSTAWPDDSRRAVGEIAWSTVLLICGVLTY VGVLEEMGTITWAGEGVGGIGVPLLAAVLLCYIGAIV SAFASSVGIMGALIPLAVPFLAQGEIGAVGMVAALAV SATVVDVSPFSTNGALVLAAAPDVDRDRFFRQLMVY GGIVVAAVPALAWLVLVVPGFG | 80 |

TABLE 11-continued

| Enzyme Sequences: | | |
|---|---|---|
| Enzyme: | Sequence: | SEQ ID: |
| Malonate transporter (matC) *Rhizobium leguminosarum* Accession: AAC83457.1 | MGIELLSIGLLIAMFIIATIQPINMGALAFAGAFVLGSMI IGMKTNEIFAGFPSDLFLTLVAVTYLFAIAQINGTIDWL VECAVRLVRGRIGLIPWVMFLVAAIITGFGALGPAAV AILAPVALSFAVQYRIHPVMMGLMVIHGAQAGGFSPI SIYGGITNQIVAKAGLPFAPTSLFLSSFFFNLAIAVLVFF VFGGARVMKHDPASLGPLPELHPEGVSASIRGHGGTP AKPIREHAYGTAADTATTLRLNNERITTLIGLTALGIG ALVFKFNVGLVAMTVAVVLALLSPKTQKAAIDKVSW STVLLIAGIITYVGVMEKAGTVDYVANGISSLGMPLLV ALLLCFTGAIVSAFASSTALLGAIIPLAVPFLLQGHISAI GVVAAIAISTTIVDTSPFSTNGALVVANAPDDSREQVL RQLLIYSALIAIIGPIVAWLVFVVPGLV | 81 |
| Malonate transporter (matC) *Agrobacterium vitis* Accession: WP_180575084.1 | MNIEILSIGLLVAIFIIATIQPINMGVLAFGCTFVLGSLII GMKPADIFAGFPADLFLTLVAVTYLFAIAQINGTIDWL VERSVRMVRGRVGWIPWVMFLVAAIITGFGALGPAA VAILAPVALSFAVQYRIHPVLMGLMVIHGAQAGGFSPI SIYGGITNQIVAKAGLPFAPTSLFLSSFFFNLAIAVLIFFI FGGLSILKQRSSVKGPLPELHPEGISASIKGHGGTPAKP FREHAYGTAADTQSKVRLTTEKVTTLIGLTALGVGAL VFKFNVGLVAITVAVLLALLSPTTQKAAIDKVSWSTV LLISGIITYVGVMEKAGTIDYVAHGISSLGMPLLVALL LCFTGAIVSAFASSTALLGAIIPLAVPFLLQGHISAVGV VAAIAISTTIVDTSPFSTNGALVVANAPDDQRDKVMR QMLIYSALIALIGPVIAWLVFVVPGII | 82 |
| Malonate transporter (matC) *Neorhizobium* sp. Accession: WP_105370917.1 | MSIEILSILLLVAMFVIATIQPINMGALAFACTFVLGSLI IGMKTSDIFAGFPSDLFLTLVAVTYLFAIAQINGTIDWL VECAVRMVRGHVAWIPWVMFVVAAITGFGALGPAA VAILAPVALSFAVQYRIHPVMMGLMVIHGAQAGGFSP ISVYGGITNQIVAKAGLPFAPTSLFLSSFFFNLAIAVLVF FVFGGARIMKQAAGPTGPLPELHPEGVSAAIRGHGGT PAKPIREHAYGTAADTLQTLRLTPEKVFTLIGLTALGI GALVFKFNVGLVAITVAVALALISPKTQKAAVDKVS WSTVLLIAGIITYVGVLEKAGTVNYVANGISSLGMPLL VALLLCFTGAIVSAFASSTALLGAIIPLAVPFLLQGHIS AVGVVAAIAISTTIVDTSPFSTNGALVVANAPDETREQ VLRQLLIYSALIAIIGPVVAWLVFVVPGLV | 83 |
| Malonate CoA-transferase (MdcA) *Moraxella catarrhalis* Accession: WPO64617969.1 | MTTWNQKQQRKAQKLAKACDSGFDKYVPHERIIALL ETVIDRGDRVCLEGNNQKQADFLSKSLSSCNPDIVNG LHIVQSVLALPSHIDVFERGIASKVDFSFAGPQSLRLAQ LVQAQKITIGAIHTYLELYGRYFIDLTPNVALITAHAA DKRGNLYTGANTEDTPAIVEATTFKSGIVIAQVNEIVD ELPRVDIPSDWVDYYTQSPKHNYIEPLFTRDPAQITEIQ ILMAMMAIKGIYAPYKINRLNHGIGFDTAAIELLLPTY AESLGLKGEICTHWALNPHPTLIPAIESGFIHSVHSFGS EVGMENYVKARSDVFFTGADGSMRSNRAFSQTAGLY ACDLFIGSTLQIDLQGNSSTATADRIAGFGGAPNMGSD PHGRRHASYAYMKAGREAVDGSPIKGRKLVVQMVE TYREHMQSVFVNELDAFKLQQKMGADLPPIMIYGDD VTHIVTEEGIANLLLCRTPDEREQAIRGVAGYTPIGLG RDDTMVARLRERKVIQRPEDLGINPMHATRDLLAAKS VKDLVRWSDRLYEPPSRFRNW | 84 |
| Malonate CoA-transferase (MdcA) *Dechloromonas aromatica* Accession: WP_011289741.1 | MNAPQPRQWDSLRQNRARRLERAASLGLAGQNGKEI PVDRIIDLLEAVIQPGDRVCLEGNNQKQADFLSESLAD CDPARINHLSMVQSVLALPSHVDLFERGLATRLDFSFS GPQGARLAKLVQEQRIEIGAIHTYLELFGRYFMDLTPN VALIAAQAADAEGNLYLGPNTEDTPAIVEATAFKGGI VIAQVNERLDKLPRVDVPADWVDFTVLAPKPNYIEPL FTRDPAQITEVQVLMAMMAIKGIYAEYGVTRLNHGIG FDTAAIELLLPTYAADLGLKGKICTHWALNPHPTLIPA IEAGFVESVHCFGSEVGMDDYISARSDIFFTGADGSMR SNRAFSQTAGLYACDMFIGSTLQMDLAGNSSTATLGR ITGFGGAPNMGSDPHGRRHASPAWLKAGREAYGPQA IRGRKLVVQMVETFREHMAPVFVDDLDAWKLQASM GSDLPPIMIYGDDVSHIVTEEGIANLLLCRTPAEREQAI RGVAGFTPVGMARDKGTVENLRDRGIIRRPEDLGIDP RQASRDLLAARSIKDLVRCSGGLYAPPSRFRNW | 85 |
| Malonate CoA-transferase (MdcA) *Pseudomonas cissicola* Accession: | MSRQWDTQADSRRQRLQRAAALAPQGRVVAADDVV ALLEAVIEPGDRVCLEGNNQKQADFLARCLTEVDPAR VHDLHMVQSVLSLAAHLDVFERGIAKRLDFSFSGPQA ARLAGLVSEGRIEIGAIHTYLELFGRYFIDLTPRIALVT AQAADRHGNLYTGPNTEDTPVIVEATAFKGGIVIAQV | 86 |

TABLE 11-continued

| Enzyme Sequences: | | |
|---|---|---|
| Enzyme: | Sequence: | SEQ ID: |
| WP_078590875.1 | NEILDTLPRVDIPADWVDFVTQAPKPNYIEPLFTRDPA QISEIQVLMAMMAIKGIYAEYGVDRLNHGIGFDTAAIE LLLPTYAQSLGLKGKICRHWALNPHPALIPAIESGFVQ SVHSFGSELGMENYIAARPDIFFTGADGSMRSNRALS QTAGLYACDMFIGSTLQIDLQGNSSTATRDRIAGFGG APNMGSDARGRRHASAAWLKAGREAATPGEMPRGR KLVVQMVETFREHMAPAFVDRLDAWELAERANMPL PPVMIYGDDVSHVLTEEGIANLLLCRTPEEREQAIRGV SGYTAVGLGRDKRMVENLRDRGVIKRPDDLGIRPRD ATRDLLAARTVKDLVRWSGGLYDPPKRFRNW | |
| Malonate CoA-transferase (MdcA) *Geobacillus subterraneus* Accession: WP_184319829.1 | MNKIYREKRSWRTRRDRKAKRIEHMKQIAKGKIIPTE KIVEALTALIFPGDRVVIEGNNQKQASFLSKALSQVNP EKVNGLHIIMSSVSRPEHLDLFEKGIARKIDFSYAGPQS LRMSQMLEDGKLVIGEIHTYLELYGRLFIDLTPSVALV AADKADASGNLYTGPNTEETPTLVEATAFRDGIVIAQ VNELADELPRVDIPGSWIDFVVAADHPYELEPLFTRDP RLITEIQILMAMMVIKGIYERHNIQSLNHGIGFNTAAIE LLLPTYGESLGLKGKICKHWALNPHPTLIPAIETGWVE SIHCFGGEVGMEKYIAARPDIFFTGKDGNLRSNRTLSQ VAGQYAVDLFIGSTLQIDRDGNSSTVTNGRLAGFGGA PNMGHDPRGRRHSSPAWLDMITSDHPAAKGRKLVVQ MVETFQKGNRPVFVESLDAIEVGRSARLATTPIMIYGE DVTHIVTEEGIAYLYKASSLEERRQAIAAIAGVTPIGLE RDPRKTEQLRRDGVVAFPEDLGIRRTDAKRSLLAAKSI EELVEWSEGLYEPPARFRSW | 87 |
| Pantothenate kinase (CoaX) *Streptomyces* sp. CLI2509 Accession: WP_095682415.1 | MLLTIDVGNTHTVLGLFDGEEIVEHWRISTDSRRTADE LAVLLQGLMGTHPLLGMELGEGIDGIAICSTVPAVLH ELREVSRRYYGDVPAILVEPGVKTGVPILMDNPKEVG TDRIINAVAAQHLYGGPAIVVDFGTATTFDAVSARGE YTGGVIAPGIEISVEALGLRGAQLRKIELARPRSVIGKS TVEAMQSGILYGFAGQVDGVVQRMACELAPDPADVT VIATGGLAPMVLGEAAVIDHHEPWLTLIGLRLVYERN AGRR | 88 |
| Pantothenate kinase (CoaX) *Streptomyces cinereus* Accession: WP_188874884.1 | MTKLWLDLGNTRLKYWLTDDSGQVLDHAAEQHLQA PAELLKGLTFRLERLNPDFIGVSSVLGQAVNNHVAESL ERLQKPFEFAQVHAKHALMSSDYNPAQLGVDRWLQ MLGIIEPSKKQCVIGCGTAVTIDLVDQGHHLGGYIFPSI YLQRESLFSGTRQISIIDGTFDSIDSGTNTQDAVHHGIM LSIVGAINETIHRYPQFEITMTGGDAHTFEPHLSASVEI RQDLVLAGLQRFFAAKNNTKNQN | 89 |
| Pantothenate kinase (CoaX) *Kitasatospora kifunensis* Accession: WP_184936930.1 | MLLTIDVGNTQTTLGLFDGEEVVDHWRISTDPRRTAD ELAVLMQGLMGRQPGGAGRERVDGLAICSSVPAVLH ELREVTRRYYGDLPAVLVAPGVKTGVHVLMDNPKEV GADRIVNALAANHLYGGPCIVVDFGTATTFDAINERG DYVGGAIAPGIEISVEALGVRGAQLRKIELAKPRNVIG KNTVEGMQSGVLYGFAGQVDGLVTRMAKELSPTDPE DVQVIATGGLAPLVLDEASSIDVHEPWLTLIGLRLVYE RNTAS | 90 |
| glutamyl-tRNA reductase (hemA) *Citrobacter freundii* Accession: NTY05430.1 | MTLLALGINHKTAPVSLRERVTFSPDTLDQALDSLQA LPMVQGGVVLSTCNRTEIYLSVEEQDNLREALIRWLC EYHNLNEEDLRNSLYWHQDNDAVSHLMRVASGLDS LVLGEPQILGQVKKAFADSQKGHQNASALERMFQKS FSVAKRVRTETDIGSSAVSVAFAACTLARQIFESLSTV TVLLVGAGETIELVARHLREHKVKKMIIANRTRERAQ VLADEVGAEVISLSDIDARLQDADIIISSTASPLPIIGKG MVERALKNRRNQPMLLVDIAVPRDVEPEVGKLSNAY LYSVDDLQSIISHNLAQRKAAAVEAETIVEQEASEFMA WLRAQGASDTIREYRSQSEQIRDELTAKALAALQQGG DAQAIMQDLAWKLTNRLIHAPTKSLQQAARDGDSER LNILRDSLGLE | 91 |

TABLE 11-continued

| Enzyme Sequences: | | |
|---|---|---|
| Enzyme: | Sequence: | SEQ ID: |
| glutamyl-tRNA reductase (hemA) *Pseudomonas reactans* Accession: NWA43040.1 | MTLLALGINHKTAPVSLRERVTFSPETIEQALSSLLQQP LVQGGVVLSTCNRTELYLSVEQQENLQEQLVKWLCD YHHLSADEVRKSLYWHQDNAAVSHLMRVASGLDSL VVGEPQILGQVKKAFAESQHGQAVSGELERLFQKSFS VAKRVRTETDIGASAVSVAFAACTLARQIFESLSDVSV LLVGAGETIELVARHLREHKVRHMMIANRTRERAQV LASEVGAEVITLQDIDARLADADIIISSTASPLPIIGKGM VERALKARRNQPMLMVDIAVPRDIEPEVGKLANAYL YSVDDLHSIIQNNMAQRKAAVQAESIVEQESSNFMA WLRSQGAVEIIRDYRSRADLVRAEAEAKALAAIAQGA DVSAVIHELAHKLTNRLIHAPTRSLQQAASDGDVERL QILRDSLGLDQQ | 92 |
| glutamyl-tRNA reductase (hemA) *Gamma-proteobacteria* Accession: WP_193016510.1 | MTLLALGINHKTAPVALREKVSFSPDTMGDALNNLLQ QPAVRGGVVLSTCNRTELYLSMEDKENSHEQLIRWLC QYHQIEPNELQSSIYWHQDNQAVSHLMRVASGLDSL VLGEPQILGQVKKAFADSQNYDSLSSELERLFQKSFSV AKRVRTETQIGANAVSVAFAACTLARQIFESLSSLTILL VGAGETIELVARHLREHQVKKIIIANRTKERAQRLASE VDAEVITLSEIDECLAQADIVISSTASPLPIIGKGMVER ALKKRRNQPMLLVDIAVPRDIEQDVEKLNNVYLYSV DDLEAIIQHNREQRQAAVQAEHIVQQESGQFMDWL RAQGAVGAIREYRDSAETLRAEMTEKAITLIQNGADA EKVIQQLSHQLMNRLIHTPTKSLQQAASDGDIERLNLL RESLGITHN | 93 |
| 5-aminolevulinic acid synthase (ALAS) *Schizophyllum commune* H4-8 Accession: XP_003036856.1 | MGPALDVRGKQLAAGYASVAGQADVEKIHQDQGITI PPNATVEMCPHAKAARDAARIAEDLAAAAASKQQPA KKAGGCPFHAAQAQAQAKPAAAPKETVATADKKGK SPRAAGGFDYEKFYEEELDKKHQDKSYRYFNNINRLA ARFPTAHTAKVTDEVEVWCSNDYLGMGGNPVVLET MHRVLDKYGHGAGGTRNIAGNGALHLSLEQELARLH RKEGALVFTSCYVANDATLSTLGSKMPGCVIFSDRMN HASMIQGIRHSGTKKVIFEHNDLADLEKKLAEYPKETP KIIAFESVYSMCGSIGPIKEICDLAEKYGAITFLDEVHA VGLYGPRGAGVAEHLDYDLHKAAGDSPDAIPGTVMD RVDIITGTLGKSYGAIGGYIAGSARFVDMIRSYAPGFIF TTSLPPATVAGAQASVVYQKEYLGDRQLKQVNVREV KRRFAELDIPVVPGPSHIVPVLVGDAALAKQASDKLL AEHDIYVQAINYPTVARGEERLRITVTQRHTLEQMDH LIGAVDQVFNELNINRVQDWKRLGGRASVGVPGGQD FVEPIWTDEQVGLADGSAPLTLRNGQPNEVSHDAVV AARSRFDWLLGPIPSHIQAKRLGQSLEGTPIAPLAPKQ SSGLKLPVEEMTMGQTIAVAA | 94 |
| 5-aminolevulinic acid synthase (ALAS) *Crassisporium junariophilum* Accession: KAF8165006.1 | MDKIARFKQTCPFLGRTKNSTLRNLSTSSSPRFPSLTAL TERATKCPVMGPALNVRSKEIVAGYASVAANSDVALI HKEKGVFPPPGATVEMCPHASAARAAARMADDLAA AAEKKKGHFTSAAPRDEAAQAAAAGCPFHVKAAAD AAAARKAAAAPAPVKAKEDGGFNYESFYVNELDKK HQDKSYRYFNNINRLAAKFPVAHTSNVKDEVEVWCA NDYLGMGNNPVVLETMHRTLDKYGHGAGGTRNIAG NGAMHLSLEQELATLHRKPAALVFSSCYVANDATLST LGAKLPGCIFFSDTMNHASMIQGMRHSGAKRVLFKH NDLEDLENKLKQYPKDTPKVIAFESVYSMCGSIGPIKE ICDLAEQYGALTFLDEVHAVGLYGPRGAGVAEHLDY DAHVAAGESPHPIKGSVMDRVDIITGTLGKAYGAVGG YIAGSDDFVDMIRSYAPGFIFTTSLPPATVAGARASVV YQKHYVGDRQLKQVNVREVKRRFAELDVPVVPGPSH IVPVLVGDAALAKAASDKLLAEHNIYVQSINYPTVAR GEERLRITVTPRHTLEQMDKLVRAVDKIFAELKINRLA DWKALGGRAGVGLTAGAEEAHVDPMWTEEQLGLLD GTSPRTLRNGEAAVVDAMAVGQARAVFDNLLGPISG KLQSERSVLASSTPAAANPARPAARKVVKMKTGGVP MSEDIPLPPPDVSASA | 95 |
| 5-aminolevulinic acid synthase (ALAS) *Dendrothele bispora* CBS 962.96 Accession: THV05492.1 | MDKLSSLSRFKASCPFLGRTKTSTLRTLCTSSSPRFPSIS ILTERATKCPVMGPALNVRSKEITAGYASVAGSSEVD QIHKQQGVTVPVNATVEMCPHASAARAAARMADDL AAAAAQKKVGSGASSAKAAAAGCPFHKSVAAGASA STASKPSAPIHKASVPGGFDYDNFYNNELEKKHKDKS YRYFNNINRLASKFPVAHTGDVKDEVQVWCSNDYLG MGNNPVVLETMHRTLDKYGHGAGGTRNIAGNGALH LGLEQELAALHRKEAALVFSSCYVANDATLSTLGSKL PGCILFSDKMNHASMIQGMRHSGAKKVIFNHNDLEDL ENKLKQYPKETPKIIAFESVYSMCGSIGPIKEICDLAEK | 96 |

TABLE 11-continued

| Enzyme Sequences: | | |
|---|---|---|
| Enzyme: | Sequence: | SEQ ID: |
| | YGALTFLDEVHAVGLYGPHGAGVAEHLDYNAQKAA GKSPEPIPGSVMDRVDIITGTLGKAYGAVGGYIAGSM DFVDTIRSYAPGFIFTTSLPPATVSGAQASVAYQKEYL GDRQLKQVNVREVKRRFAELDIPVIPGPSHILPVLVGD AALAKAASDKLLTDHDIYVQSINYPTVAVGEERLRIT VTPRHTLEQMDKLVRAVNQVFTELNINRISDWKVAG GRAGVGMGVESVEPIWTDEQLGITDGTTPKTLRDGQR FLVDAQGVTAARGRFDTLLGPMSGSLQANPTLPLVD DELKVPLPTLVAAAA | |
| 5-aminolevulinic acid synthase (ALAS) *Bradyrhizobium japonicum* Accession: A0A0A3YXD2 | MDYAQFFNTALDRLHTERRYRVFADLERIAGRFPHAL WHSPKGKRDVVIWCSNDYLGMGQHPKVVGAMVETA TRVGTGAGGTRNIAGTHHPLVQLEAELADLHGKEASL LFTSGYVSNQTGIATIAKLIPNCLILSDELNHNSMIEGIR QSGCERVVFRHNDLADLEEKLKAAGPNRPKLIACESL YSMDGDVAPLAKICDLAEKYGAMTYVDEVHAVGMY GPRGGGIAERDGVMHRIDILEGTLAKAFGCLGGYIAA NGQIIDAVRSYAPGFIFTTALPPAICSAATAAIRHLKTS NWERERHQDRAARVKAILNAAGLPVMSSDTHIVPLFI GDAEKCKQASDLLLEQHGIYIQPINYPTVAKGTERLRI TPSPYHDDGLIDQLAEALLQVWDRLGLPLKQKSLAAE | 97 |
| Cytochrome b5 *Petunia x hybrida.* Accession: AAD10774.1 | MDKQRVFTLSQVAEHKSKQDCWIIINGRVVDVTKFLE EHPGGEEVLIESAGKDATKEFQDIGHSKAAKNLLFKY QIGYLQGYKASDDSELELNLVTDSIKEPNKAKEMKAY VIKEDPKPKYLTFVEYLLPFLAAAFYLYYRYLTGALQ F | 98 |

TABLE 12

| Glossary of abbreviations | |
|---|---|
| Abbreviation | Full Name |
| 3GT | anthocyanidin-3-O-glycotransferase |
| 4CL | 4-coumarate-CoA ligase |
| ACC | acetyl-CoA carboxylase |
| ACOT | acyl-CoA thioesterase |
| acpP | acyl carrier protein |
| ACS | acetyl-CoA synthase |
| adhE | aldehyde-alcohol dehydrogenase |
| ADP | adenosine diphosphate |
| ALA | 5-aminolevulinic acid |
| ALAS | ALA synthase |
| ANS | anthocyanin dioxygenase |
| aroG | DAHP synthase |
| aroK | shikimate kinase |
| aroL | shikimate kinase |
| ATP | adenosine triphosphate |
| C3G | cyanidin-3-O-glycoside |
| C4H | cinnimate-4-hydroxylase |
| CHI | chalcone isomerase |
| CHS | chalcone synthase |
| CoA | coenzyme A |
| CPR | cytochrome P450 Reductase |
| DAD | diode array detector |
| DAHP | deoxy-d-arabino-heptulosonate-7-phosphate |
| DctPQM | a malonate transporter |
| DFR | dihydroflavonol 4-reductase |
| DHL | dihydrokaempferol |
| DHM | dihydromyricein |
| DHQ | dihydroquercetin |
| DMSO | dimethyl sulfoxide |
| E4P | erythrose-4-phosphate |
| F3'H | flavonoid 3' hydroxylase |
| F3H | flavanone 3-hydroxylase |
| fabB | beta-ketoacyl-ACP synthase I |
| fabD | malonyl-coA-ACP transacylase |
| fabF | beta-ketoacyl-ACP synthase II |
| FadA | 3-ketoacyl-CoA thiolase |
| FadB | fatty acid oxidation complex subunit alpha |
| FadE | acyl-CoA dehydrogenase |
| GltX | glutamyl-tRNA synthetase |

TABLE 12-continued

| Glossary of abbreviations | |
|---|---|
| Abbreviation | Full Name |
| hemA | glutamyl-tRNA reductase |
| hemL | glutamate-1-semialdehyde aminotransferase |
| HPLC | high performance liquid chromatography |
| ldhA | lactate dehydrogenase |
| LAR | leucoanthocyanidin reductase |
| matB | malonyl-CoA synthase |
| matC | malonate transporter |
| mdcA | malonate coA-transferase |
| mdcC | acyl-carrier protein, subunit of mdc |
| mdcD | malonyl-CoA decarboxylase, subunit of mdc |
| mdcE | co-decarboxylase, subunit of mdc |
| pABA | para-aminobenzoic acid |
| PAL | phenylalanine ammonia-lyase |
| PanK | pantothenase kinase |
| Pdh | pyruvate dehydrogenase |
| PEP | phosphoenolpyruvate |
| pHBA | para-hydroxybenzoic acid |
| PHE | phenylalanine |
| pheA | chorismate mutase/prephenate dehydrogenase |
| poxB | pyruvate dehydrogenase |
| ppsA | phosphoenolpyruvate synthase |
| TAL | tyrosine ammonia-lyase |
| TCA | tricarboxylic acid cycle |
| tesA | thioesterase I |
| tesB | thioesterase II |
| tktA | transketolase |
| TRP | tryptophan |
| TYR | tyrosine |
| TyrA | chorismate mutase |
| tyrR | transcriptional regulator |
| ybgC | a thioesterase |
| yciA | a thioesterase |
| ydiB | QUIN/shikamate dehydrogenase |
| ackA-pta | Acetate kinase-phosphate acetyltransferase |

The invention claimed is:

1. An engineered host cell, wherein the engineered host cell comprises one or more genetic modifications to an endogenous gene to increase the production and/or availability of malonyl-CoA in comparison to a wild-type host cell, wherein the engineered host cell expresses acetyl-CoA carboxylase (ACC) having an amino acid sequence at least 85% identical to the polypeptide set forth in SEQ ID NO: 15.

2. The engineered host cell of claim 1, wherein the production and/or availability of malonyl-CoA is increased by transformation of acetyl-CoA to malonyl-CoA.

3. The engineered host cell of claim 1, wherein the engineered host cell comprises one or more genetic modifications to increase expression of acetyl-CoA carboxylase (ACC) in comparison to a wild-type host cell.

4. The engineered host cell of claim 1, wherein the engineered host cell is *E. coli*.

5. The engineered host cell of claim 4, wherein the *E. coli* further comprises genes from fungi.

6. The engineered host cell of claim 3, wherein the acetyl-CoA carboxylase is from a species selected from the group consisting of *Mucor circinelloides, Rhodotorula* toruloides, Lipomyces starkeyi, and *Ustilago maydis*, and orthologs of acetyl-CoA carboxylase having at least 50% amino acid identity to the acetyl-CoA carboxylase of these aforementioned species.

7. The engineered host cell of claim 1, wherein the one or more genetic modification is deletion or attenuation of one or more fatty acid biosynthetic genes resulting in decrease in fatty acid biosynthesis in comparison to a wild-type host cell.

8. The engineered host cell of claim 1, wherein the engineered host cell further comprises-peptides selected from a group consisting of: (i) malonate CoA-transferase having an amino acid sequence at least 80% identical to the polypeptide set forth in SEQ ID NO: 19; (ii) acetyl-CoA synthase (ACS) having an amino acid sequence at least 80% identical to the polypeptide set forth in SEQ ID NO: 16; (iii) malonyl-CoA synthase having an amino acid sequence at least 80% identical SEQ ID NO: 77, SEQ ID NO: 78, or SEQ ID NO: 79; (iv) malonate transporter having an amino acid sequence at least 80% identical to SEQ ID NO: 80, SEQ ID NO: 81, SEQ ID NO: 82, SEQ ID NO: 83, SEQ ID NO: 84, SEQ ID NO: 85, SEQ ID NO: 86, or SEQ ID NO: 87; (v) pantothenate kinase having an amino acid sequence at least 80% identical to SEQ ID NO: 88, SEQ ID NO: 89, or SEQ ID NO: 90; and (vi) any combinations thereof.

9. The engineered host cell of claim 1, wherein the engineered host cell expresses acetyl-CoA carboxylase (ACC) having an amino acid sequence at least 90% identical to the polypeptide set forth in SEQ ID NO: 15.

10. The engineered host cell of claim 1, wherein the engineered host cell expresses acetyl-CoA carboxylase (ACC) having an amino acid sequence at least 95% identical to the polypeptide set forth in SEQ ID NO: 15.

* * * * *

SEQUENCE LISTING

<160> NUMBER OF SEQ ID NOS: 98

<210> SEQ ID NO 1
<211> LENGTH: 510
<212> TYPE: PRT
<213> ORGANISM: Saccharothrix espanaensis

<400> SEQUENCE: 1

```
Met Thr Gln Val Val Glu Arg Gln Ala Asp Arg Leu Ser Ser Arg Glu
1               5                   10                  15

Tyr Leu Ala Arg Val Val Arg Ser Ala Gly Trp Asp Ala Gly Leu Thr
            20                  25                  30

Ser Cys Thr Asp Glu Glu Ile Val Arg Met Gly Ala Ser Ala Arg Thr
        35                  40                  45

Ile Glu Glu Tyr Leu Lys Ser Asp Lys Pro Ile Tyr Gly Leu Thr Gln
    50                  55                  60

Gly Phe Gly Pro Leu Val Leu Phe Asp Ala Asp Ser Glu Leu Glu Gln
65                  70                  75                  80

Gly Gly Ser Leu Ile Ser His Leu Gly Thr Gly Gln Gly Ala Pro Leu
                85                  90                  95

Ala Pro Glu Val Ser Arg Leu Ile Leu Trp Leu Arg Ile Gln Asn Met
            100                 105                 110

Arg Lys Gly Tyr Ser Ala Val Ser Pro Val Phe Trp Gln Lys Leu Ala
        115                 120                 125

Asp Leu Trp Asn Lys Gly Phe Thr Pro Ala Ile Pro Arg His Gly Thr
    130                 135                 140

Val Ser Ala Ser Gly Asp Leu Gln Pro Leu Ala His Ala Ala Leu Ala
145                 150                 155                 160

Phe Thr Gly Val Gly Glu Ala Trp Thr Arg Asp Ala Asp Gly Arg Trp
                165                 170                 175

Ser Thr Val Pro Ala Val Asp Ala Leu Ala Ala Leu Gly Ala Glu Pro
            180                 185                 190

Phe Asp Trp Pro Val Arg Glu Ala Leu Ala Phe Val Asn Gly Thr Gly
        195                 200                 205

Ala Ser Leu Ala Val Ala Val Leu Asn His Arg Ser Ala Leu Arg Leu
    210                 215                 220

Val Arg Ala Cys Ala Val Leu Ser Ala Arg Leu Ala Thr Leu Leu Gly
225                 230                 235                 240

Ala Asn Pro Glu His Tyr Asp Val Gly His Gly Val Ala Arg Gly Gln
                245                 250                 255

Val Gly Gln Leu Thr Ala Ala Glu Trp Ile Arg Gln Gly Leu Pro Arg
            260                 265                 270

Gly Met Val Arg Asp Gly Ser Arg Pro Leu Gln Glu Pro Tyr Ser Leu
        275                 280                 285

Arg Cys Ala Pro Gln Val Leu Gly Ala Val Leu Asp Gln Leu Asp Gly
    290                 295                 300

Ala Gly Asp Val Leu Ala Arg Glu Val Asp Gly Cys Gln Asp Asn Pro
305                 310                 315                 320

Ile Thr Tyr Glu Gly Glu Leu Leu His Gly Gly Asn Phe His Ala Met
                325                 330                 335

Pro Val Gly Phe Ala Ser Asp Gln Ile Gly Leu Ala Met His Met Ala
            340                 345                 350

Ala Tyr Leu Ala Glu Arg Gln Leu Gly Leu Leu Val Ser Pro Val Thr
        355                 360                 365
```

```
Asn Gly Asp Leu Pro Pro Met Leu Thr Pro Arg Ala Gly Arg Gly Ala
    370                 375                 380

Gly Leu Ala Gly Val Gln Ile Ser Ala Thr Ser Phe Val Ser Arg Ile
385                 390                 395                 400

Arg Gln Leu Val Phe Pro Ala Ser Leu Thr Thr Leu Pro Thr Asn Gly
                405                 410                 415

Trp Asn Gln Asp His Val Pro Met Ala Leu Asn Gly Ala Asn Ser Val
            420                 425                 430

Phe Glu Ala Leu Glu Leu Gly Trp Leu Thr Val Gly Ser Leu Ala Val
        435                 440                 445

Gly Val Ala Gln Leu Ala Ala Met Thr Gly His Ala Ala Glu Gly Val
    450                 455                 460

Trp Ala Glu Leu Ala Gly Ile Cys Pro Pro Leu Asp Ala Asp Arg Pro
465                 470                 475                 480

Leu Gly Ala Glu Val Arg Ala Ala Arg Asp Leu Leu Ser Ala His Ala
                485                 490                 495

Asp Gln Leu Leu Val Asp Glu Ala Asp Gly Lys Asp Phe Gly
            500                 505                 510


<210> SEQ ID NO 2
<211> LENGTH: 550
<212> TYPE: PRT
<213> ORGANISM: Brevibacillus laterosporus LMG 15541

<400> SEQUENCE: 2

Met Ser Gln Val Ala Leu Phe Glu Gln Glu Leu Met Leu His Gly Lys
1               5                   10                  15

His Thr Leu Leu Leu Asn Gly Asn Asp Leu Thr Ile Thr Asp Val Ala
            20                  25                  30

Gln Met Ala Lys Gly Thr Phe Glu Ala Phe Thr Phe His Ile Ser Glu
        35                  40                  45

Glu Ala Asn Lys Arg Ile Glu Glu Cys Asn Glu Leu Lys His Glu Ile
    50                  55                  60

Met Asn Gln His Asn Pro Ile Tyr Gly Val Thr Thr Gly Phe Gly Asp
65                  70                  75                  80

Ser Val His Arg Gln Ile Ser Gly Glu Lys Ala Trp Asp Leu Gln Arg
                85                  90                  95

Asn Leu Ile Arg Phe Leu Ser Cys Gly Val Gly Pro Val Ala Asp Glu
            100                 105                 110

Ala Val Ala Arg Ala Thr Met Leu Ile Arg Thr Asn Cys Leu Val Lys
        115                 120                 125

Gly Asn Ser Ala Val Arg Leu Glu Val Ile His Gln Leu Ile Ala Tyr
    130                 135                 140

Met Glu Arg Gly Ile Thr Pro Ile Ile Pro Glu Arg Gly Ser Val Gly
145                 150                 155                 160

Ala Ser Gly Asp Leu Val Pro Leu Ser Tyr Leu Ala Ser Ile Leu Val
                165                 170                 175

Gly Glu Gly Lys Val Leu Tyr Lys Gly Glu Glu Arg Glu Val Ala Glu
            180                 185                 190

Ala Leu Gly Ala Glu Gly Leu Glu Pro Leu Thr Leu Glu Ala Lys Glu
        195                 200                 205

Gly Leu Ala Leu Val Asn Gly Thr Ser Phe Met Ser Ala Phe Ala Cys
    210                 215                 220

Leu Ala Tyr Ala Asp Ala Glu Glu Ile Ala Phe Ile Ala Asp Ile Cys
225                 230                 235                 240
```

```
Thr Ala Met Ala Ser Glu Ala Leu Leu Gly Asn Arg Gly His Phe Tyr
                245                 250                 255

Ser Phe Ile His Glu Gln Lys Pro His Leu Gly Gln Met Ala Ser Ala
            260                 265                 270

Lys Asn Ile Tyr Thr Leu Leu Glu Gly Ser Gln Leu Ser Lys Glu Tyr
        275                 280                 285

Ser Gln Ile Val Gly Asn Asn Glu Lys Leu Asp Ser Lys Ala Tyr Leu
    290                 295                 300

Glu Leu Thr Gln Ser Ile Gln Asp Arg Tyr Ser Ile Arg Cys Ala Pro
305                 310                 315                 320

His Val Thr Gly Val Leu Tyr Asp Thr Leu Asp Trp Val Lys Lys Trp
                325                 330                 335

Leu Glu Val Glu Ile Asn Ser Thr Asn Asp Asn Pro Ile Phe Asp Val
            340                 345                 350

Glu Thr Arg Asp Val Tyr Asn Gly Gly Asn Phe Tyr Gly Gly His Val
        355                 360                 365

Val Gln Ala Met Asp Ser Leu Lys Val Ala Val Ala Asn Ile Ala Asp
    370                 375                 380

Leu Leu Asp Arg Gln Leu Gln Leu Val Val Asp Glu Lys Phe Asn Lys
385                 390                 395                 400

Asp Leu Thr Pro Asn Leu Ile Pro Arg Phe Asn Asn Asp Asn Tyr Glu
                405                 410                 415

Ile Gly Leu His His Gly Phe Lys Gly Met Gln Ile Ala Ser Ser Ala
            420                 425                 430

Leu Thr Ala Glu Ala Leu Lys Met Ser Gly Pro Val Ser Val Phe Ser
        435                 440                 445

Arg Ser Thr Glu Ala His Asn Gln Asp Lys Val Ser Met Gly Thr Ile
    450                 455                 460

Ser Ser Arg Asp Ala Arg Thr Ile Val Glu Leu Thr Gln His Val Ala
465                 470                 475                 480

Ala Ile His Leu Ile Ala Leu Cys Gln Ala Leu Asp Leu Arg Asp Ser
                485                 490                 495

Lys Lys Met Ser Pro Gln Thr Thr Lys Ile Tyr Asn Met Ile Arg Lys
            500                 505                 510

Gln Val Pro Phe Val Glu Arg Asp Arg Ala Leu Asp Gly Asp Ile Glu
        515                 520                 525

Lys Val Val Gln Leu Ile Arg Ser Gly Asn Leu Lys Lys Glu Ile His
    530                 535                 540

Asp Gln Asn Val Asn Asp
545                 550
```

<210> SEQ ID NO 3
<211> LENGTH: 505
<212> TYPE: PRT
<213> ORGANISM: Helianthus annuus L

<400> SEQUENCE: 3

```
Met Asp Leu Leu Leu Ile Glu Lys Thr Leu Leu Ala Leu Phe Ala Ala
1               5                   10                  15

Ile Ile Gly Ala Ile Val Ile Ser Lys Leu Arg Gly Lys Arg Phe Lys
            20                  25                  30

Leu Pro Pro Gly Pro Leu Pro Val Pro Ile Phe Gly Asn Trp Leu Gln
        35                  40                  45

Val Gly Asp Asp Leu Asn His Arg Asn Leu Thr Asp Leu Ala Lys Lys
```

```
    50                  55                  60

Phe Gly Glu Ile Phe Leu Leu Arg Met Gly Gln Arg Asn Leu Val Val
65                  70                  75                  80

Val Ser Ser Pro Asp Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg Tyr Gly Trp Glu Ala Glu Ala Ala Ala Val Val Glu Asp
145                 150                 155                 160

Val Lys Lys Asn Pro Ala Ala Ala Thr Glu Gly Val Val Ile Arg Arg
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Val Lys Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Lys Gly Tyr Leu Lys
225                 230                 235                 240

Leu Cys Lys Glu Val Lys Glu Lys Arg Phe Gln Leu Phe Lys Asp Tyr
                245                 250                 255

Phe Val Asp Glu Arg Lys Lys Leu Glu Ser Thr Lys Ser Val Asp Asn
            260                 265                 270

Asn Gln Leu Lys Cys Ala Ile Asp His Ile Leu Asp Ala Lys Glu Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ala Lys Leu Arg Asn Glu Leu
                325                 330                 335

Asp Thr Lys Leu Gly Pro Gly Val Gln Val Thr Glu Pro Asp Leu His
            340                 345                 350

Lys Leu Pro Tyr Leu Gln Ala Val Ile Lys Glu Thr Leu Arg Leu Arg
        355                 360                 365

Met Ala Ile Pro Leu Leu Val Pro His Met Asn Leu His Asp Ala Lys
    370                 375                 380

Leu Gly Gly Tyr Asp Ile Pro Ala Glu Ser Lys Ile Leu Val Asn Ala
385                 390                 395                 400

Trp Trp Leu Ala Asn Asn Pro Glu Gln Trp Lys Lys Pro Glu Glu Phe
                405                 410                 415

Arg Pro Glu Arg Phe Phe Glu Glu Glu Ser Lys Val Glu Ala Asn Gly
            420                 425                 430

Asn Asp Phe Arg Tyr Leu Pro Phe Gly Val Gly Arg Arg Ser Cys Pro
        435                 440                 445

Gly Ile Ile Leu Ala Leu Pro Ile Leu Gly Ile Thr Ile Gly Arg Leu
    450                 455                 460

Val Gln Asn Phe Glu Leu Leu Pro Pro Pro Gly Gln Ser Lys Val Asp
465                 470                 475                 480
```

```
Thr Thr Glu Lys Gly Gly Gln Phe Ser Leu His Ile Leu Lys His Ser
                485                 490                 495

Thr Ile Val Ala Lys Pro Arg Ala Leu
            500                 505


<210> SEQ ID NO 4
<211> LENGTH: 544
<212> TYPE: PRT
<213> ORGANISM: Petroselinum crispum

<400> SEQUENCE: 4

Met Gly Asp Cys Val Ala Pro Lys Glu Asp Leu Ile Phe Arg Ser Lys
1               5                   10                  15

Leu Pro Asp Ile Tyr Ile Pro Lys His Leu Pro Leu His Thr Tyr Cys
            20                  25                  30

Phe Glu Asn Ile Ser Lys Val Gly Asp Lys Ser Cys Leu Ile Asn Gly
        35                  40                  45

Ala Thr Gly Glu Thr Phe Thr Tyr Ser Gln Val Glu Leu Leu Ser Arg
    50                  55                  60

Lys Val Ala Ser Gly Leu Asn Lys Leu Gly Ile Gln Gln Gly Asp Thr
65                  70                  75                  80

Ile Met Leu Leu Leu Pro Asn Ser Pro Glu Tyr Phe Phe Ala Phe Leu
                85                  90                  95

Gly Ala Ser Tyr Arg Gly Ala Ile Ser Thr Met Ala Asn Pro Phe Phe
            100                 105                 110

Thr Ser Ala Glu Val Ile Lys Gln Leu Lys Ala Ser Gln Ala Lys Leu
        115                 120                 125

Ile Ile Thr Gln Ala Cys Tyr Val Asp Lys Val Lys Asp Tyr Ala Ala
    130                 135                 140

Glu Lys Asn Ile Gln Ile Ile Cys Ile Asp Asp Ala Pro Gln Asp Cys
145                 150                 155                 160

Leu His Phe Ser Lys Leu Met Glu Ala Asp Glu Ser Glu Met Pro Glu
                165                 170                 175

Val Val Ile Asn Ser Asp Asp Val Val Ala Leu Pro Tyr Ser Ser Gly
            180                 185                 190

Thr Thr Gly Leu Pro Lys Gly Val Met Leu Thr His Lys Gly Leu Val
        195                 200                 205

Thr Ser Val Ala Gln Gln Val Asp Gly Asp Asn Pro Asn Leu Tyr Met
    210                 215                 220

His Ser Glu Asp Val Met Ile Cys Ile Leu Pro Leu Phe His Ile Tyr
225                 230                 235                 240

Ser Leu Asn Ala Val Leu Cys Cys Gly Leu Arg Ala Gly Val Thr Ile
                245                 250                 255

Leu Ile Met Gln Lys Phe Asp Ile Val Pro Phe Leu Glu Leu Ile Gln
            260                 265                 270

Lys Tyr Lys Val Thr Ile Gly Pro Phe Val Pro Pro Ile Val Leu Ala
        275                 280                 285

Ile Ala Lys Ser Pro Val Val Asp Lys Tyr Asp Leu Ser Ser Val Arg
    290                 295                 300

Thr Val Met Ser Gly Ala Ala Pro Leu Gly Lys Glu Leu Glu Asp Ala
305                 310                 315                 320

Val Arg Ala Lys Phe Pro Asn Ala Lys Leu Gly Gln Gly Tyr Gly Met
                325                 330                 335

Thr Glu Ala Gly Pro Val Leu Ala Met Cys Leu Ala Phe Ala Lys Glu
```

```
            340                 345                 350

Pro Tyr Glu Ile Lys Ser Gly Ala Cys Gly Thr Val Val Arg Asn Ala
        355                 360                 365

Glu Met Lys Ile Val Asp Pro Glu Thr Asn Ala Ser Leu Pro Arg Asn
    370                 375                 380

Gln Arg Gly Glu Ile Cys Ile Arg Gly Asp Gln Ile Met Lys Gly Tyr
385                 390                 395                 400

Leu Asn Asp Pro Glu Ser Thr Arg Thr Thr Ile Asp Glu Glu Gly Trp
                405                 410                 415

Leu His Thr Gly Asp Ile Gly Phe Ile Asp Asp Asp Asp Glu Leu Phe
            420                 425                 430

Ile Val Asp Arg Leu Lys Glu Ile Ile Lys Tyr Lys Gly Phe Gln Val
        435                 440                 445

Ala Pro Ala Glu Leu Glu Ala Leu Leu Leu Thr His Pro Thr Ile Ser
    450                 455                 460

Asp Ala Ala Val Val Pro Met Ile Asp Glu Lys Ala Gly Glu Val Pro
465                 470                 475                 480

Val Ala Phe Val Val Arg Thr Asn Gly Phe Thr Thr Thr Glu Glu Glu
                485                 490                 495

Ile Lys Gln Phe Val Ser Lys Gln Val Val Phe Tyr Lys Arg Ile Phe
            500                 505                 510

Arg Val Phe Phe Val Asp Ala Ile Pro Lys Ser Pro Ser Gly Lys Ile
        515                 520                 525

Leu Arg Lys Asp Leu Arg Ala Arg Ile Ala Ser Gly Asp Leu Pro Lys
    530                 535                 540


<210> SEQ ID NO 5
<211> LENGTH: 389
<212> TYPE: PRT
<213> ORGANISM: Petunia x hybrida

<400> SEQUENCE: 5

Met Val Thr Val Glu Glu Tyr Arg Lys Ala Gln Arg Ala Glu Gly Pro
1               5                   10                  15

Ala Thr Val Met Ala Ile Gly Thr Ala Thr Pro Thr Asn Cys Val Asp
            20                  25                  30

Gln Ser Thr Tyr Pro Asp Tyr Tyr Phe Arg Ile Thr Asn Ser Glu His
        35                  40                  45

Lys Thr Asp Leu Lys Glu Lys Phe Lys Arg Met Cys Glu Lys Ser Met
    50                  55                  60

Ile Lys Lys Arg Tyr Met His Leu Thr Glu Glu Ile Leu Lys Glu Asn
65                  70                  75                  80

Pro Ser Met Cys Glu Tyr Met Ala Pro Ser Leu Asp Ala Arg Gln Asp
                85                  90                  95

Ile Val Val Val Glu Val Pro Lys Leu Gly Lys Glu Ala Ala Gln Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Cys Asp Tyr Gln Leu
    130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175
```

```
Leu Ala Glu Asn Asn Lys Gly Ala Arg Val Leu Val Val Cys Ser Glu
            180                 185                 190

Ile Thr Ala Val Thr Phe Arg Gly Pro Asn Asp Thr His Leu Asp Ser
        195                 200                 205

Leu Val Gly Gln Ala Leu Phe Gly Asp Gly Ala Gly Ala Ile Ile Ile
    210                 215                 220

Gly Ser Asp Pro Ile Pro Gly Val Glu Arg Pro Leu Phe Glu Leu Val
225                 230                 235                 240

Ser Ala Ala Gln Thr Leu Leu Pro Asp Ser His Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Glu Glu Ala Phe Arg
        275                 280                 285

Pro Leu Ser Ile Ser Asp Trp Asn Ser Leu Phe Trp Ile Ala His Pro
    290                 295                 300

Gly Gly Pro Ala Ile Leu Asp Gln Val Glu Ile Lys Leu Gly Leu Lys
305                 310                 315                 320

Pro Glu Lys Leu Lys Ala Thr Arg Asn Val Leu Ser Asn Tyr Gly Asn
                325                 330                 335

Met Ser Ser Ala Cys Val Leu Phe Ile Leu Asp Glu Met Arg Lys Ala
            340                 345                 350

Ser Ala Lys Glu Gly Leu Gly Thr Thr Gly Glu Gly Leu Glu Trp Gly
        355                 360                 365

Val Leu Phe Gly Phe Gly Pro Gly Leu Thr Val Glu Thr Val Val Leu
    370                 375                 380

His Ser Val Ala Thr
385


<210> SEQ ID NO 6
<211> LENGTH: 222
<212> TYPE: PRT
<213> ORGANISM: Medicago sativa

<400> SEQUENCE: 6

Met Ala Ala Ser Ile Thr Ala Ile Thr Val Glu Asn Leu Glu Tyr Pro
1               5                   10                  15

Ala Val Val Thr Ser Pro Val Thr Gly Lys Ser Tyr Phe Leu Gly Gly
            20                  25                  30

Ala Gly Glu Arg Gly Leu Thr Ile Glu Gly Asn Phe Ile Lys Phe Thr
        35                  40                  45

Ala Ile Gly Val Tyr Leu Glu Asp Ile Ala Val Ala Ser Leu Ala Ala
    50                  55                  60

Lys Trp Lys Gly Lys Ser Ser Glu Glu Leu Leu Glu Thr Leu Asp Phe
65                  70                  75                  80

Tyr Arg Asp Ile Ile Ser Gly Pro Phe Glu Lys Leu Ile Arg Gly Ser
                85                  90                  95

Lys Ile Arg Glu Leu Ser Gly Pro Glu Tyr Ser Arg Lys Val Met Glu
            100                 105                 110

Asn Cys Val Ala His Leu Lys Ser Val Gly Thr Tyr Gly Asp Ala Glu
        115                 120                 125

Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asp Gly Ile Leu
145                 150                 155                 160
```

```
Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Thr Met Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
    210                 215                 220


<210> SEQ ID NO 7
<211> LENGTH: 365
<212> TYPE: PRT
<213> ORGANISM: Rubus occidentalis

<400> SEQUENCE: 7

Met Ala Pro Thr Pro Thr Thr Leu Thr Ala Ile Ala Gly Glu Lys Thr
1               5                   10                  15

Leu Gln Gln Ser Phe Val Arg Asp Glu Asp Glu Arg Pro Lys Val Ala
            20                  25                  30

Tyr Asn Gln Phe Ser Asn Glu Ile Pro Ile Ile Ser Leu Ser Gly Ile
        35                  40                  45

Asp Glu Val Glu Gly Arg Arg Ala Glu Ile Cys Asn Lys Ile Val Glu
    50                  55                  60

Ala Cys Glu Asp Trp Gly Val Phe Gln Ile Val Asp His Gly Val Asp
65                  70                  75                  80

Ala Lys Leu Ile Ser Glu Met Thr Arg Leu Ala Arg Asp Phe Phe Ala
                85                  90                  95

Leu Pro Pro Glu Glu Lys Leu Arg Phe Asp Met Ser Gly Gly Lys Lys
            100                 105                 110

Gly Gly Phe Ile Val Ser Ser His Leu Gln Gly Glu Ala Val Gln Asp
        115                 120                 125

Trp Arg Glu Ile Val Thr Tyr Phe Ser Tyr Pro Val Arg His Arg Asp
    130                 135                 140

Tyr Ser Arg Trp Pro Asp Lys Pro Glu Gly Trp Arg Ala Val Thr Gln
145                 150                 155                 160

Gln Tyr Ser Asp Glu Leu Met Gly Leu Ala Cys Lys Leu Leu Glu Val
                165                 170                 175

Leu Ser Glu Ala Met Gly Leu Glu Lys Glu Ala Leu Thr Lys Ala Cys
            180                 185                 190

Val Asp Met Asp Gln Lys Val Val Val Asn Phe Tyr Pro Lys Cys Pro
        195                 200                 205

Gln Pro Asp Leu Thr Leu Gly Leu Lys Arg His Thr Asp Pro Gly Thr
    210                 215                 220

Ile Thr Leu Leu Leu Gln Asp Gln Val Gly Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Phe Leu Ser Asn Gly Arg Phe
            260                 265                 270

Lys Asn Ala Asp His Gln Ala Val Val Asn Ser Asn His Ser Arg Leu
        275                 280                 285

Ser Ile Ala Thr Phe Gln Asn Pro Ala Gln Glu Ala Ile Val Tyr Pro
    290                 295                 300

Leu Lys Val Arg Glu Gly Glu Lys Pro Ile Leu Glu Glu Pro Ile Thr
```

```
305                 310                 315                 320

Tyr Thr Glu Met Tyr Lys Lys Lys Met Ser Lys Asp Leu Glu Leu Ala
                325                 330                 335

Arg Leu Lys Lys Leu Ala Lys Glu Gln Gln Pro Glu Asp Ser Glu Lys
            340                 345                 350

Ala Lys Leu Glu Val Lys Gln Val Asp Asp Ile Phe Ala
        355                 360                 365


<210> SEQ ID NO 8
<211> LENGTH: 511
<212> TYPE: PRT
<213> ORGANISM: Brassica napus

<400> SEQUENCE: 8

Met Thr Asn Leu Tyr Leu Thr Ile Leu Leu Pro Thr Phe Ile Phe Leu
1               5                   10                  15

Ile Val Leu Val Leu Ser Arg Arg Arg Asn Asn Arg Leu Pro Pro Gly
            20                  25                  30

Pro Asn Pro Trp Pro Ile Ile Gly Asn Leu Pro His Met Gly Pro Lys
        35                  40                  45

Pro His Gln Thr Leu Ala Ala Met Val Thr Thr Tyr Gly Pro Ile Leu
    50                  55                  60

His Leu Arg Leu Gly Phe Ala Asp Val Val Val Ala Ala Ser Lys Ser
65                  70                  75                  80

Val Ala Glu Gln Phe Leu Lys Val His Asp Ala Asn Phe Ala Ser Arg
                85                  90                  95

Pro Pro Asn Ser Gly Ala Lys His Met Ala Tyr Asn Tyr Gln Asp Leu
            100                 105                 110

Val Phe Ala Pro Tyr Gly Gln Arg Trp Arg Met Leu Arg Lys Ile Ser
        115                 120                 125

Ser Val His Leu Phe Ser Ala Lys Ala Leu Glu Asp Phe Lys His Val
    130                 135                 140

Arg Gln Glu Glu Val Gly Thr Leu Met Arg Glu Leu Ala Arg Ala Asn
145                 150                 155                 160

Thr Lys Pro Val Asn Leu Gly Gln Leu Val Asn Met Cys Val Leu Asn
                165                 170                 175

Ala Leu Gly Arg Glu Met Ile Gly Arg Arg Leu Phe Gly Ala Asp Ala
            180                 185                 190

Asp His Lys Ala Glu Glu Phe Arg Ser Met Val Thr Glu Met Met Ala
        195                 200                 205

Leu Ala Gly Val Phe Asn Ile Gly Asp Phe Val Pro Ala Leu Asp Cys
    210                 215                 220

Leu Asp Leu Gln Gly Val Ala Gly Lys Met Lys Arg Leu His Lys Arg
225                 230                 235                 240

Phe Asp Ala Phe Leu Ser Ser Ile Leu Glu Glu His Glu Ala Met Lys
                245                 250                 255

Asn Gly Gln Asp Gln Lys His Thr Asp Met Leu Ser Thr Leu Ile Ser
            260                 265                 270

Leu Lys Gly Thr Asp Phe Asp Gly Glu Gly Gly Thr Leu Thr Asp Thr
        275                 280                 285

Glu Ile Lys Ala Leu Leu Leu Asn Met Phe Thr Ala Gly Thr Asp Thr
    290                 295                 300

Ser Ala Ser Thr Val Asp Trp Ala Ile Ala Glu Leu Ile Arg His Pro
305                 310                 315                 320
```

```
Glu Ile Met Arg Lys Ala Gln Glu Glu Leu Asp Ser Val Val Gly Arg
                325                 330                 335

Gly Arg Pro Ile Asn Glu Ser Asp Leu Ser Gln Leu Pro Tyr Leu Gln
            340                 345                 350

Ala Val Ile Lys Glu Asn Phe Arg Leu His Pro Pro Thr Pro Leu Ser
        355                 360                 365

Leu Pro His Ile Ala Ser Glu Ser Cys Glu Ile Asn Gly Tyr His Ile
    370                 375                 380

Pro Lys Gly Ser Thr Leu Leu Thr Asn Ile Trp Ala Ile Ala Arg Asp
385                 390                 395                 400

Pro Asp Gln Trp Ser Asp Pro Leu Thr Phe Arg Pro Glu Arg Phe Leu
                405                 410                 415

Pro Gly Gly Glu Lys Ala Gly Val Asp Val Lys Gly Asn Asp Phe Glu
            420                 425                 430

Leu Ile Pro Phe Gly Ala Gly Arg Arg Ile Cys Ala Gly Leu Ser Leu
        435                 440                 445

Gly Leu Arg Thr Ile Gln Leu Leu Thr Ala Thr Leu Val His Gly Phe
    450                 455                 460

Glu Trp Glu Leu Ala Gly Gly Val Thr Pro Glu Lys Leu Asn Met Glu
465                 470                 475                 480

Glu Thr Tyr Gly Ile Thr Leu Gln Arg Ala Val Pro Leu Val Val His
                485                 490                 495

Pro Lys Leu Arg Leu Asp Met Ser Ala Tyr Gly Leu Gly Ser Ala
            500                 505                 510


<210> SEQ ID NO 9
<211> LENGTH: 714
<212> TYPE: PRT
<213> ORGANISM: Catharanthus roseus

<400> SEQUENCE: 9

Met Asp Ser Ser Ser Glu Lys Leu Ser Pro Phe Glu Leu Met Ser Ala
1               5                   10                  15

Ile Leu Lys Gly Ala Lys Leu Asp Gly Ser Asn Ser Ser Asp Ser Gly
            20                  25                  30

Val Ala Val Ser Pro Ala Val Met Ala Met Leu Leu Glu Asn Lys Glu
        35                  40                  45

Leu Val Met Ile Leu Thr Thr Ser Val Ala Val Leu Ile Gly Cys Val
    50                  55                  60

Val Val Leu Ile Trp Arg Arg Ser Ser Gly Ser Gly Lys Lys Val Val
65                  70                  75                  80

Glu Pro Pro Lys Leu Ile Val Pro Lys Ser Val Val Glu Pro Glu Glu
                85                  90                  95

Ile Asp Glu Gly Lys Lys Lys Phe Thr Ile Phe Phe Gly Thr Gln Thr
            100                 105                 110

Gly Thr Ala Glu Gly Phe Ala Lys Ala Leu Ala Glu Glu Ala Lys Ala
        115                 120                 125

Arg Tyr Glu Lys Ala Val Ile Lys Val Ile Asp Ile Asp Asp Tyr Ala
    130                 135                 140

Ala Asp Asp Glu Glu Tyr Glu Glu Lys Phe Arg Lys Glu Thr Leu Ala
145                 150                 155                 160

Phe Phe Ile Leu Ala Thr Tyr Gly Asp Gly Glu Pro Thr Asp Asn Ala
                165                 170                 175

Ala Arg Phe Tyr Lys Trp Phe Val Glu Gly Asn Asp Arg Gly Asp Trp
            180                 185                 190
```

```
Leu Lys Asn Leu Gln Tyr Gly Val Phe Gly Leu Gly Asn Arg Gln Tyr
        195                 200                 205

Glu His Phe Asn Lys Ile Ala Lys Val Val Asp Glu Lys Val Ala Glu
    210                 215                 220

Gln Gly Gly Lys Arg Ile Val Pro Leu Val Leu Gly Asp Asp Asp Gln
225                 230                 235                 240

Cys Ile Glu Asp Asp Phe Ala Ala Trp Arg Glu Asn Val Trp Pro Glu
                245                 250                 255

Leu Asp Asn Leu Leu Arg Asp Glu Asp Asp Thr Thr Val Ser Thr Thr
            260                 265                 270

Tyr Thr Ala Ala Ile Pro Glu Tyr Arg Val Val Phe Pro Asp Lys Ser
        275                 280                 285

Asp Ser Leu Ile Ser Glu Ala Asn Gly His Ala Asn Gly Tyr Ala Asn
    290                 295                 300

Gly Asn Thr Val Tyr Asp Ala Gln His Pro Cys Arg Ser Asn Val Ala
305                 310                 315                 320

Val Arg Lys Glu Leu His Thr Pro Ala Ser Asp Arg Ser Cys Thr His
                325                 330                 335

Leu Asp Phe Asp Ile Ala Gly Thr Gly Leu Ser Tyr Gly Thr Gly Asp
            340                 345                 350

His Val Gly Val Tyr Cys Asp Asn Leu Ser Glu Thr Val Glu Glu Ala
        355                 360                 365

Glu Arg Leu Leu Asn Leu Pro Pro Glu Thr Tyr Phe Ser Leu His Ala
    370                 375                 380

Asp Lys Glu Asp Gly Thr Pro Leu Ala Gly Ser Ser Leu Pro Pro Pro
385                 390                 395                 400

Phe Pro Pro Cys Thr Leu Arg Thr Ala Leu Thr Arg Tyr Ala Asp Leu
                405                 410                 415

Leu Asn Thr Pro Lys Lys Ser Ala Leu Leu Ala Leu Ala Ala Tyr Ala
            420                 425                 430

Ser Asp Pro Asn Glu Ala Asp Arg Leu Lys Tyr Leu Ala Ser Pro Ala
        435                 440                 445

Gly Lys Asp Glu Tyr Ala Gln Ser Leu Val Ala Asn Gln Arg Ser Leu
    450                 455                 460

Leu Glu Val Met Ala Glu Phe Pro Ser Ala Lys Pro Pro Leu Gly Val
465                 470                 475                 480

Phe Phe Ala Ala Ile Ala Pro Arg Leu Gln Pro Arg Phe Tyr Ser Ile
                485                 490                 495

Ser Ser Ser Pro Arg Met Ala Pro Ser Arg Ile His Val Thr Cys Ala
            500                 505                 510

Leu Val Tyr Glu Lys Thr Pro Gly Gly Arg Ile His Lys Gly Val Cys
        515                 520                 525

Ser Thr Trp Met Lys Asn Ala Ile Pro Leu Glu Glu Ser Arg Asp Cys
    530                 535                 540

Ser Trp Ala Pro Ile Phe Val Arg Gln Ser Asn Phe Lys Leu Pro Ala
545                 550                 555                 560

Asp Pro Lys Val Pro Val Ile Met Ile Gly Pro Gly Thr Gly Leu Ala
                565                 570                 575

Pro Phe Arg Gly Phe Leu Gln Glu Arg Leu Ala Leu Lys Glu Glu Gly
            580                 585                 590

Ala Glu Leu Gly Thr Ala Val Phe Phe Phe Gly Cys Arg Asn Arg Lys
        595                 600                 605
```

```
Met Asp Tyr Ile Tyr Glu Asp Glu Leu Asn His Phe Leu Glu Ile Gly
    610                 615                 620

Ala Leu Ser Glu Leu Leu Val Ala Phe Ser Arg Glu Gly Pro Thr Lys
625                 630                 635                 640

Gln Tyr Val Gln His Lys Met Ala Glu Lys Ala Ser Asp Ile Trp Arg
                645                 650                 655

Met Ile Ser Asp Gly Ala Tyr Val Tyr Val Cys Gly Asp Ala Lys Gly
            660                 665                 670

Met Ala Arg Asp Val His Arg Thr Leu His Thr Ile Ala Gln Glu Gln
        675                 680                 685

Gly Ser Met Asp Ser Thr Gln Ala Glu Gly Phe Val Lys Asn Leu Gln
    690                 695                 700

Met Thr Gly Arg Tyr Leu Arg Asp Val Trp
705                 710


<210> SEQ ID NO 10
<211> LENGTH: 506
<212> TYPE: PRT
<213> ORGANISM: Delphinium grandiflorum

<400> SEQUENCE: 10

Met Ser Thr Ser Leu Leu Leu Ala Ala Ala Ala Ile Leu Phe Phe Ile
1               5                   10                  15

Thr His Leu Phe Leu Arg Phe Leu Leu Ser Pro Arg Arg Thr Arg Lys
            20                  25                  30

Leu Pro Pro Gly Pro Lys Gly Trp Pro Val Val Gly Ala Leu Pro Met
        35                  40                  45

Leu Gly Asn Met Pro His Ala Ala Leu Ala Asp Leu Ser Arg Arg Tyr
    50                  55                  60

Gly Pro Ile Val Tyr Leu Lys Leu Gly Ser Arg Gly Met Val Val Ala
65                  70                  75                  80

Ser Thr Pro Asp Ser Ala Arg Ala Phe Leu Lys Thr Gln Asp Leu Asn
                85                  90                  95

Phe Ser Asn Arg Pro Thr Asp Ala Gly Ala Thr His Ile Ala Tyr Asn
            100                 105                 110

Ser Gln Asp Met Val Phe Ala Asp Tyr Gly Pro Arg Trp Lys Leu Leu
        115                 120                 125

Arg Lys Leu Ser Ser Leu His Met Leu Gly Gly Lys Ala Val Glu Asp
    130                 135                 140

Trp Ala Val Val Arg Arg Asp Glu Val Gly Tyr Met Val Lys Ala Ile
145                 150                 155                 160

Tyr Glu Ser Ser Cys Ala Gly Glu Ala Val His Val Pro Asp Met Leu
                165                 170                 175

Val Phe Ala Met Ala Asn Met Leu Gly Gln Val Ile Leu Ser Arg Arg
            180                 185                 190

Val Phe Val Thr Lys Gly Val Glu Ser Asn Glu Phe Lys Glu Met Val
        195                 200                 205

Ile Glu Leu Met Thr Ser Ala Gly Leu Phe Asn Val Gly Asp Phe Ile
    210                 215                 220

Pro Ser Ile Ala Trp Met Asp Leu Gln Gly Ile Val Arg Gly Met Lys
225                 230                 235                 240

Arg Leu His Lys Lys Phe Asp Ala Leu Leu Asp Lys Ile Leu Arg Glu
                245                 250                 255

His Thr Ala Thr Arg Arg Glu Arg Lys Glu Lys Pro Asp Leu Val Asp
            260                 265                 270
```

```
Val Leu Met Asp Asn Arg Asp Asn Lys Ser Glu Gln Glu Arg Leu Thr
        275                 280                 285

Asp Thr Asn Ile Lys Ala Leu Leu Leu Asn Leu Phe Ser Ala Gly Thr
    290                 295                 300

Asp Thr Ser Ser Ser Thr Ile Glu Trp Ala Leu Thr Glu Met Ile Lys
305                 310                 315                 320

Asn Pro Ser Ile Phe Gly Arg Ala His Ala Glu Met Asp Gln Val Ile
                325                 330                 335

Gly Arg Asn Arg Arg Leu Glu Glu Ser Asp Ile Pro Lys Leu Pro Tyr
            340                 345                 350

Leu Gln Ala Ile Cys Lys Glu Thr Phe Arg Lys His Pro Ser Thr Pro
        355                 360                 365

Leu Asn Leu Pro Arg Val Ala Ile Glu Pro Cys Glu Val Glu Gly Tyr
    370                 375                 380

His Ile Pro Lys Gly Thr Arg Leu Ser Val Asn Ile Trp Ala Ile Gly
385                 390                 395                 400

Arg Asp Pro Asn Val Trp Glu Asn Pro Leu Glu Phe Asn Pro Asp Arg
                405                 410                 415

Phe Leu Thr Gly Lys Met Ala Lys Ile Asp Pro Arg Gly Asn Asn Phe
            420                 425                 430

Glu Leu Ile Pro Phe Gly Ala Gly Arg Arg Ile Cys Ala Gly Thr Arg
        435                 440                 445

Met Gly Ile Val Leu Val Glu Tyr Ile Leu Gly Ser Leu Val His Ala
    450                 455                 460

Phe Glu Trp Lys Leu Arg Asp Gly Glu Thr Leu Asn Met Glu Glu Thr
465                 470                 475                 480

Phe Gly Ile Ala Leu Gln Lys Ala Val Pro Leu Ala Ala Val Val Thr
                485                 490                 495

Pro Arg Leu Pro Pro Ser Ala Tyr Val Val
            500                 505
```

<210> SEQ ID NO 11
<211> LENGTH: 347
<212> TYPE: PRT
<213> ORGANISM: Anthurium andraeanum

<400> SEQUENCE: 11

```
Met Met His Lys Gly Thr Val Cys Val Thr Gly Ala Ala Gly Phe Val
1               5                   10                  15

Gly Ser Trp Leu Ile Met Arg Leu Leu Glu Gln Gly Tyr Ser Val Lys
            20                  25                  30

Ala Thr Val Arg Asp Pro Ser Asn Met Lys Lys Val Lys His Leu Leu
        35                  40                  45

Asp Leu Pro Gly Ala Ala Asn Arg Leu Thr Leu Trp Lys Ala Asp Leu
    50                  55                  60

Val Asp Glu Gly Ser Phe Asp Glu Pro Ile Gln Gly Cys Thr Gly Val
65                  70                  75                  80

Phe His Val Ala Thr Pro Met Asp Phe Glu Ser Lys Asp Pro Glu Ser
                85                  90                  95

Glu Met Ile Lys Pro Thr Ile Glu Gly Met Leu Asn Val Leu Arg Ser
            100                 105                 110

Cys Ala Arg Ala Ser Ser Thr Val Arg Arg Val Val Phe Thr Ser Ser
        115                 120                 125

Ala Gly Thr Val Ser Ile His Glu Gly Arg Arg His Leu Tyr Asp Glu
```

```
    130                 135                 140

Thr Ser Trp Ser Asp Val Asp Phe Cys Arg Ala Lys Lys Met Thr Gly
145                 150                 155                 160

Trp Met Tyr Phe Val Ser Lys Thr Leu Ala Glu Lys Ala Ala Trp Asp
                165                 170                 175

Phe Ala Glu Lys Asn Asn Ile Asp Phe Ile Ser Ile Ile Pro Thr Leu
            180                 185                 190

Val Asn Gly Pro Phe Val Met Pro Thr Met Pro Pro Ser Met Leu Ser
        195                 200                 205

Ala Leu Ala Leu Ile Thr Arg Asn Glu Pro His Tyr Ser Ile Leu Asn
    210                 215                 220

Pro Val Gln Phe Val His Leu Asp Asp Leu Cys Asn Ala His Ile Phe
225                 230                 235                 240

Leu Phe Glu Cys Pro Asp Ala Lys Gly Arg Tyr Ile Cys Ser Ser His
                245                 250                 255

Asp Val Thr Ile Ala Gly Leu Ala Gln Ile Leu Arg Gln Arg Tyr Pro
            260                 265                 270

Glu Phe Asp Val Pro Thr Glu Phe Gly Glu Met Glu Val Phe Asp Ile
        275                 280                 285

Ile Ser Tyr Ser Ser Lys Lys Leu Thr Asp Leu Gly Phe Glu Phe Lys
    290                 295                 300

Tyr Ser Leu Glu Asp Met Phe Asp Gly Ala Ile Gln Ser Cys Arg Glu
305                 310                 315                 320

Lys Gly Leu Leu Pro Pro Ala Thr Lys Glu Pro Ser Tyr Ala Thr Glu
                325                 330                 335

Gln Leu Ile Ala Thr Gly Gln Asp Asn Gly His
            340                 345


<210> SEQ ID NO 12
<211> LENGTH: 382
<212> TYPE: PRT
<213> ORGANISM: Desmodium uncinatum

<400> SEQUENCE: 12

Met Thr Val Ser Gly Ala Ile Pro Ser Met Thr Lys Asn Arg Thr Leu
1               5                   10                  15

Val Val Gly Gly Thr Gly Phe Ile Gly Gln Phe Ile Thr Lys Ala Ser
            20                  25                  30

Leu Gly Phe Gly Tyr Pro Thr Phe Leu Leu Val Arg Pro Gly Pro Val
        35                  40                  45

Ser Pro Ser Lys Ala Val Ile Ile Lys Thr Phe Gln Asp Lys Gly Ala
    50                  55                  60

Lys Val Ile Tyr Gly Val Ile Asn Asp Lys Glu Cys Met Glu Lys Ile
65                  70                  75                  80

Leu Lys Glu Tyr Glu Ile Asp Val Val Ile Ser Leu Val Gly Gly Ala
                85                  90                  95

Arg Leu Leu Asp Gln Leu Thr Leu Leu Glu Ala Ile Lys Ser Val Lys
            100                 105                 110

Thr Ile Lys Arg Phe Leu Pro Ser Glu Phe Gly His Asp Val Asp Arg
        115                 120                 125

Thr Asp Pro Val Glu Pro Gly Leu Thr Met Tyr Lys Glu Lys Arg Leu
    130                 135                 140

Val Arg Arg Ala Val Glu Glu Tyr Gly Ile Pro Phe Thr Asn Ile Cys
145                 150                 155                 160
```

```
Cys Asn Ser Ile Ala Ser Trp Pro Tyr Tyr Asp Asn Cys His Pro Ser
            165                 170                 175

Gln Val Pro Pro Pro Met Asp Gln Phe Gln Ile Tyr Gly Asp Gly Asn
            180                 185                 190

Thr Lys Ala Tyr Phe Ile Asp Gly Asn Asp Ile Gly Lys Phe Thr Met
        195                 200                 205

Lys Thr Ile Asp Asp Ile Arg Thr Leu Asn Lys Asn Val His Phe Arg
    210                 215                 220

Pro Ser Ser Asn Cys Tyr Ser Ile Asn Glu Leu Ala Ser Leu Trp Glu
225                 230                 235                 240

Lys Lys Ile Gly Arg Thr Leu Pro Arg Phe Thr Val Thr Ala Asp Lys
            245                 250                 255

Leu Leu Ala His Ala Ala Glu Asn Ile Ile Pro Glu Ser Ile Val Ser
            260                 265                 270

Ser Phe Thr His Asp Ile Phe Ile Asn Gly Cys Gln Val Asn Phe Ser
        275                 280                 285

Ile Asp Glu His Ser Asp Val Glu Ile Asp Thr Leu Tyr Pro Asp Glu
    290                 295                 300

Lys Phe Arg Ser Leu Asp Asp Cys Tyr Glu Asp Phe Val Pro Met Val
305                 310                 315                 320

His Asp Lys Ile His Ala Gly Lys Ser Gly Glu Ile Lys Ile Lys Asp
            325                 330                 335

Gly Lys Pro Leu Val Gln Thr Gly Thr Ile Glu Glu Ile Asn Lys Asp
            340                 345                 350

Ile Lys Thr Leu Val Glu Thr Gln Pro Asn Glu Glu Ile Lys Lys Asp
        355                 360                 365

Met Lys Ala Leu Val Glu Ala Val Pro Ile Ser Ala Met Gly
    370                 375                 380


<210> SEQ ID NO 13
<211> LENGTH: 356
<212> TYPE: PRT
<213> ORGANISM: Carica papaya

<400> SEQUENCE: 13

Met Phe Ser Ser Val Ala Val Pro Arg Val Glu Ile Leu Ala Ser Ser
1               5                   10                  15

Gly Ile Glu Ser Ile Pro Lys Glu Tyr Val Arg Pro Gln Glu Glu Leu
            20                  25                  30

Thr Thr Ile Gly Asn Ile Phe Asp Glu Glu Lys Lys Asp Glu Gly Pro
        35                  40                  45

Gln Val Pro Thr Ile Asp Leu Arg Asp Ile Asp Ser Asp Asp Gln Gln
    50                  55                  60

Val Arg Gln Arg Cys Arg Asp Glu Leu Lys Lys Ala Ala Val Asp Trp
65                  70                  75                  80

Gly Val Met His Leu Val Asn His Gly Ile Pro Asp His Leu Ile Asp
                85                  90                  95

Arg Val Lys Lys Ala Gly Gln Ala Phe Phe Glu Leu Pro Val Glu Val
            100                 105                 110

Lys Glu Lys Tyr Ala Asn Asp Gln Ala Ser Gly Asn Ile Gln Gly Tyr
        115                 120                 125

Gly Ser Lys Leu Ala Asn Asn Ala Ser Gly Gln Leu Glu Trp Glu Asp
    130                 135                 140

Tyr Tyr Phe His Leu Ile Phe Pro Glu Glu Lys Arg Asp Leu Ala Ile
145                 150                 155                 160
```

```
Trp Pro Asn Asn Pro Ala Asp Tyr Ile Glu Val Thr Ser Glu Tyr Ala
                165                 170                 175

Arg Gln Leu Arg Arg Leu Val Ser Lys Ile Leu Gly Val Leu Ser Leu
            180                 185                 190

Gly Leu Gly Leu Glu Glu Gly Arg Leu Glu Lys Glu Val Gly Gly Leu
        195                 200                 205

Asp Glu Leu Leu Leu Gln Met Lys Ile Asn Tyr Tyr Pro Thr Cys Pro
    210                 215                 220

Gln Pro Glu Leu Ala Leu Gly Val Glu Ala His Thr Asp Ile Ser Ala
225                 230                 235                 240

Leu Thr Phe Ile Leu His Asn Met Val Pro Gly Leu Gln Leu Phe Tyr
                245                 250                 255

Glu Gly Lys Trp Val Thr Ala Lys Cys Val Pro Asn Ser Ile Val Met
            260                 265                 270

His Val Gly Asp Thr Ile Glu Ile Leu Ser Asn Gly Lys Tyr Lys Ser
        275                 280                 285

Ile Leu His Arg Gly Leu Val Asn Lys Glu Lys Val Arg Ile Ser Trp
    290                 295                 300

Ala Val Phe Cys Glu Pro Pro Lys Glu Lys Ile Ile Leu Lys Pro Leu
305                 310                 315                 320

Pro Glu Thr Val Ser Glu Asn Glu Pro Pro Leu Phe Pro Pro Arg Thr
                325                 330                 335

Phe Ala Gln His Ile Gln His Lys Leu Phe Arg Lys Asn Gln Glu Asn
            340                 345                 350

Leu Glu Ala Lys
        355


<210> SEQ ID NO 14
<211> LENGTH: 456
<212> TYPE: PRT
<213> ORGANISM: Vitis labrusca

<400> SEQUENCE: 14

Met Ser Gln Thr Thr Thr Asn Pro His Val Ala Val Leu Ala Phe Pro
1               5                   10                  15

Phe Ser Thr His Ala Ala Pro Leu Leu Ala Val Val Arg Arg Leu Ala
            20                  25                  30

Val Ala Ala Pro His Ala Val Phe Ser Phe Phe Ser Thr Ser Glu Ser
        35                  40                  45

Asn Ala Ser Ile Phe His Asp Ser Met His Thr Met Gln Cys Asn Ile
    50                  55                  60

Lys Ser Tyr Asp Val Ser Asp Gly Val Pro Glu Gly Tyr Val Phe Thr
65                  70                  75                  80

Gly Arg Pro Gln Glu Gly Ile Asp Leu Phe Met Arg Ala Ala Pro Glu
                85                  90                  95

Ser Phe Arg Gln Gly Met Val Met Ala Val Ala Glu Thr Gly Arg Pro
            100                 105                 110

Val Ser Cys Leu Val Ala Asp Ala Phe Ile Trp Phe Ala Ala Asp Met
        115                 120                 125

Ala Ala Glu Met Gly Val Ala Trp Leu Pro Phe Trp Thr Ala Gly Pro
    130                 135                 140

Asn Ser Leu Ser Thr His Val Tyr Ile Asp Glu Ile Arg Glu Lys Ile
145                 150                 155                 160

Gly Val Ser Gly Ile Gln Gly Arg Glu Asp Glu Leu Leu Asn Phe Ile
```

```
                165                 170                 175

Pro Gly Met Ser Lys Val Arg Phe Arg Asp Leu Gln Glu Gly Ile Val
            180                 185                 190

Phe Gly Asn Leu Asn Ser Leu Phe Ser Arg Leu Leu His Arg Met Gly
        195                 200                 205

Gln Val Leu Pro Lys Ala Thr Ala Val Phe Ile Asn Ser Phe Glu Glu
    210                 215                 220

Leu Asp Asp Ser Leu Thr Asn Asp Leu Lys Ser Lys Leu Lys Thr Tyr
225                 230                 235                 240

Leu Asn Ile Gly Pro Phe Asn Leu Ile Thr Pro Pro Pro Val Val Pro
                245                 250                 255

Asn Thr Thr Gly Cys Leu Gln Trp Leu Lys Glu Arg Lys Pro Thr Ser
            260                 265                 270

Val Val Tyr Ile Ser Phe Gly Thr Val Thr Thr Pro Pro Pro Ala Glu
        275                 280                 285

Leu Val Ala Leu Ala Glu Ala Leu Glu Ala Ser Arg Val Pro Phe Ile
    290                 295                 300

Trp Ser Leu Arg Asp Lys Ala Arg Met His Leu Pro Glu Gly Phe Leu
305                 310                 315                 320

Glu Lys Thr Arg Gly His Gly Met Val Val Pro Trp Ala Pro Gln Ala
                325                 330                 335

Glu Val Leu Ala His Glu Ala Val Gly Ala Phe Val Thr His Cys Gly
            340                 345                 350

Trp Asn Ser Leu Trp Glu Ser Val Ala Gly Gly Val Pro Leu Ile Cys
        355                 360                 365

Arg Pro Phe Phe Gly Asp Gln Arg Leu Asn Gly Arg Met Val Glu Asp
    370                 375                 380

Val Leu Glu Ile Gly Val Arg Ile Glu Gly Gly Val Phe Thr Lys Ser
385                 390                 395                 400

Gly Leu Met Ser Cys Phe Asp Gln Ile Leu Ser Gln Glu Lys Gly Lys
                405                 410                 415

Lys Leu Arg Glu Asn Leu Arg Ala Leu Arg Glu Thr Ala Asp Arg Ala
            420                 425                 430

Val Gly Pro Lys Gly Ser Ser Thr Glu Asn Phe Lys Thr Leu Val Asp
        435                 440                 445

Leu Val Ser Lys Pro Lys Asp Val
    450                 455


<210> SEQ ID NO 15
<211> LENGTH: 2216
<212> TYPE: PRT
<213> ORGANISM: Mucor circinelloides 1006PhL

<400> SEQUENCE: 15

Met Val Glu His Arg Ser Leu Pro Gly His Phe Leu Gly Gly Asn Ser
1               5                   10                  15

Leu Glu Ser Ala Pro Gln Gly Pro Val Lys Asp Phe Val Gln Ala His
            20                  25                  30

Glu Gly His Thr Val Ile Ser Lys Val Leu Ile Ala Asn Asn Gly Met
        35                  40                  45

Ala Ala Met Lys Glu Ile Arg Ser Val Arg Lys Trp Ala Tyr Glu Thr
    50                  55                  60

Phe Gly Asn Glu Arg Ala Ile Glu Phe Thr Val Met Ala Thr Pro Glu
65                  70                  75                  80
```

```
Asp Leu Lys Ala Asn Ala Glu Tyr Ile Arg Met Ala Asp Asn Phe Val
                85                  90                  95

Glu Val Pro Gly Gly Ser Asn Asn Asn Asn Tyr Ala Asn Val Glu Leu
            100                 105                 110

Ile Val Asp Val Ala Glu Arg Thr Ala Val His Ala Val Trp Ala Gly
        115                 120                 125

Trp Gly His Ala Ser Glu Asn Pro Arg Leu Pro Glu Met Leu Ala Lys
    130                 135                 140

Ser Lys His Lys Cys Leu Phe Ile Gly Pro Pro Ala Ser Ala Met Arg
145                 150                 155                 160

Ser Leu Gly Asp Lys Ile Ser Ser Thr Ile Val Ala Gln Ser Ala Gln
                165                 170                 175

Val Pro Thr Met Gly Trp Ser Gly Asp Gly Ile Thr Glu Thr Glu Phe
            180                 185                 190

Asp Ala Ala Gly His Val Ile Val Pro Asp Asn Ala Tyr Asn Glu Ala
        195                 200                 205

Cys Val Lys Thr Ala Glu Gln Gly Leu Lys Ala Ala Glu Lys Ile Gly
    210                 215                 220

Phe Pro Val Met Ile Lys Ala Ser Glu Gly Gly Gly Gly Lys Gly Ile
225                 230                 235                 240

Arg Met Val Lys Asp Gly Ser Asn Phe Ala Gln Leu Phe Ala Gln Val
                245                 250                 255

Gln Gly Glu Ile Pro Gly Ser Pro Ile Phe Ile Met Lys Leu Ala Gly
            260                 265                 270

Asn Ala Arg His Leu Glu Val Gln Leu Leu Ala Asp Gln Tyr Gly Asn
        275                 280                 285

Ala Ile Ser Leu Phe Gly Arg Asp Cys Ser Val Gln Arg Arg His Gln
    290                 295                 300

Lys Ile Ile Glu Glu Ala Pro Val Thr Ile Ala Lys Pro Asp Val Phe
305                 310                 315                 320

Glu Gln Met Glu Lys Ala Ala Val Arg Leu Gly Lys Leu Val Gly Tyr
                325                 330                 335

Val Ser Ala Gly Thr Val Glu Tyr Leu Tyr Ser His His Asp Asp Gln
            340                 345                 350

Phe Tyr Phe Leu Glu Leu Asn Pro Arg Leu Gln Val Glu His Pro Thr
        355                 360                 365

Thr Glu Met Val Ser Gly Val Asn Leu Pro Ala Ala Gln Leu Gln Ile
    370                 375                 380

Ala Met Gly Ile Pro Leu His Arg Ile Arg Asp Ile Arg Val Leu Tyr
385                 390                 395                 400

Gly Val Gln Pro Asn Ser Ala Ser Glu Ile Asp Phe Gly Phe Glu His
                405                 410                 415

Pro Thr Ser Leu Thr Ser His Arg Arg Pro Thr Pro Lys Gly His Val
            420                 425                 430

Ile Ala Cys Arg Ile Thr Ala Glu Asn Pro Asp Ala Gly Phe Lys Pro
        435                 440                 445

Ser Ser Gly Ile Met Gln Glu Leu Asn Phe Arg Ser Ser Thr Asn Val
    450                 455                 460

Trp Gly Tyr Phe Ser Val Val Ser Ala Gly Gly Leu His Glu Tyr Ala
465                 470                 475                 480

Asp Ser Gln Phe Gly His Ile Phe Ala Tyr Gly Glu Asn Arg Gln Gln
                485                 490                 495

Ala Arg Lys Asn Met Val Ile Ala Leu Lys Glu Leu Ser Ile Arg Ala
```

```
            500                 505                 510

Asp Phe Arg Ser Thr Val Glu Tyr Ile Ile Arg Leu Leu Glu Thr Pro
        515                 520                 525

Asp Phe Glu Glu Asn Thr Ile Asn Thr Gly Trp Leu Asp Met Leu Ile
    530                 535                 540

Ser Lys Lys Leu Thr Ala Glu Arg Pro Asp Thr Met Leu Ala Val Phe
545                 550                 555                 560

Cys Gly Ala Val Thr Lys Ala His Met Ala Ser Leu Asp Cys Phe Gln
                565                 570                 575

Gln Tyr Lys Gln Ser Leu Glu Lys Gly Gln Val Pro Ser Lys Gly Ser
            580                 585                 590

Leu Lys Thr Val Phe Thr Val Asp Phe Ile Tyr Glu Glu Val Arg Tyr
        595                 600                 605

Asn Phe Thr Val Thr Gln Ser Ala Pro Gly Ile Tyr Thr Leu Tyr Leu
    610                 615                 620

Asn Gly Thr Lys Thr Gln Val Gly Ile Arg Asp Leu Ser Asp Gly Gly
625                 630                 635                 640

Leu Leu Ile Ser Ile Asp Gly Lys Ser His Thr Thr Tyr Ser Arg Asp
                645                 650                 655

Glu Val Gln Ala Thr Arg Met Met Val Asp Gly Lys Thr Cys Leu Leu
            660                 665                 670

Glu Lys Glu Ser Asp Pro Thr Gln Leu Arg Ser Pro Ser Pro Gly Lys
        675                 680                 685

Leu Val Asn Leu Leu Val Glu Asn Gly Asp His Leu Asn Ala Gly Asp
    690                 695                 700

Ala Tyr Ala Glu Ile Glu Val Met Lys Met Tyr Met Pro Leu Ile Ala
705                 710                 715                 720

Thr Glu Asp Gly His Val Gln Phe Ile Lys Gln Ala Gly Ala Thr Leu
                725                 730                 735

Glu Ala Gly Asp Ile Ile Gly Ile Leu Ser Leu Asp Asp Pro Ser Arg
            740                 745                 750

Val Lys His Ala Leu Pro Phe Asn Gly Thr Val Pro Ala Phe Gly Ala
        755                 760                 765

Pro His Ile Thr Gly Asp Lys Pro Val Gln Arg Phe Asn Ala Thr Lys
    770                 775                 780

Leu Thr Leu Gln His Ile Leu Gln Gly Tyr Asp Asn Gln Ala Leu Val
785                 790                 795                 800

Gln Thr Val Val Lys Asp Phe Ala Asp Ile Leu Asn Asn Pro Asp Leu
                805                 810                 815

Pro Tyr Ser Glu Leu Asn Ser Val Leu Ser Ala Leu Ser Gly Arg Ile
            820                 825                 830

Pro Gln Arg Leu Glu Ala Ser Ile His Lys Leu Ala Asp Glu Ser Lys
        835                 840                 845

Ala Ala Asn Gln Glu Phe Pro Ala Ala Gln Phe Glu Lys Leu Val Glu
    850                 855                 860

Asp Phe Ala Arg Glu His Ile Thr Leu Gln Ser Glu Ala Thr Ala Tyr
865                 870                 875                 880

Lys Asn Ser Val Ala Pro Leu Ser Ser Ile Phe Ala Arg Tyr Arg Asn
                885                 890                 895

Gly Leu Thr Glu His Ala Tyr Ser Asn Tyr Val Glu Leu Met Glu Ala
            900                 905                 910

Tyr Tyr Asp Val Glu Ile Leu Phe Asn Gln Gln Arg Glu Glu Glu Val
        915                 920                 925
```

```
Ile Leu Ser Leu Arg Asp Gln His Lys Asp Asp Leu Asp Lys Val Leu
    930                 935                 940

Ala Val Thr Leu Ser His Ala Lys Val Asn Ile Lys Asn Asn Val Ile
945                 950                 955                 960

Leu Met Leu Leu Asp Leu Ile Asn Pro Val Ser Thr Gly Ser Ala Leu
                965                 970                 975

Asp Lys Tyr Phe Thr Pro Ile Leu Lys Arg Leu Ser Glu Ile Glu Ser
            980                 985                 990

Arg Ala Thr Gln Lys Val Thr Leu  Lys Ala Arg Glu Leu  Leu Ile Leu
        995                 1000                1005

Cys Gln  Leu Pro Ser Tyr Glu  Glu Arg Gln Ala Gln  Met Tyr Gln
    1010                1015                1020

Ile Leu  Lys Asn Ser Val Thr  Glu Ser Val Tyr Gly  Gly Gly Ser
    1025                1030                1035

Glu Tyr  Arg Thr Pro Ser Tyr  Asp Ala Phe Lys Asp  Leu Ile Asp
    1040                1045                1050

Thr Lys  Phe Asn Val Phe Asp  Val Leu Pro His Phe  Phe Tyr His
    1055                1060                1065

Ala Asp  Pro Tyr Ile Ala Leu  Ala Ala Ile Glu Val  Tyr Cys Arg
    1070                1075                1080

Arg Ser  Tyr His Ala Tyr Lys  Ile Leu Asp Val Ala  Tyr Asn Leu
    1085                1090                1095

Glu His  Lys Pro Tyr Val Val  Ala Trp Lys Phe Leu  Leu Gln Thr
    1100                1105                1110

Ala Ala  Asn Gly Ile Asp Ser  Asn Lys Arg Ile Ala  Ser Tyr Ser
    1115                1120                1125

Asp Leu  Thr Phe Leu Leu Asn  Lys Thr Glu Glu Glu  Pro Ile Arg
    1130                1135                1140

Thr Gly  Ala Met Thr Ala Cys  Asn Ser Leu Ala Asp  Leu Gln Ala
    1145                1150                1155

Glu Leu  Pro Arg Ile Leu Thr  Ala Phe Glu Glu Glu  Pro Leu Pro
    1160                1165                1170

Pro Met  Leu Gln Arg Asn Ala  Ala Pro Lys Glu Glu  Arg Met Glu
    1175                1180                1185

Asn Ile  Leu Asn Ile Ala Val  Arg Ala Asp Glu Asp  Met Asp Asp
    1190                1195                1200

Thr Ala  Phe Arg Thr Lys Ile  Cys Glu Met Ile Thr  Ala Asn Ala
    1205                1210                1215

Asp Val  Phe Arg Gln Ala His  Leu Arg Arg Leu Ser  Val Val Val
    1220                1225                1230

Cys Arg  Asp Asn Gln Trp Pro  Asp Tyr Tyr Thr Phe  Arg Glu Arg
    1235                1240                1245

Glu Asn  Tyr Gln Glu Asp Glu  Thr Ile Arg His Ile  Glu Pro Ala
    1250                1255                1260

Met Ala  Tyr Gln Leu Glu Leu  Ala Arg Leu Ser Asn  Phe Asp Ile
    1265                1270                1275

Lys Pro  Cys Phe Ile Glu Asn  Arg Gln Met His Val  Tyr Tyr Ala
    1280                1285                1290

Val Ala  Lys Glu Asn Pro Ser  Asp Cys Arg Phe Phe  Ile Arg Ala
    1295                1300                1305

Leu Val  Arg Pro Gly Arg Val  Lys Ser Ser Met Arg  Thr Ala Asp
    1310                1315                1320
```

```
Tyr Leu  Ile Ser Glu Ser Asp  Arg Leu Leu Thr Asp  Ile Leu Asp
    1325                 1330                 1335

Thr Leu  Glu Ile Val Ser His  Glu Tyr Lys Asn Ser  Asp Cys Asn
    1340                 1345                 1350

His Leu  Phe Ile Asn Phe Ile  Pro Thr Phe Ala Ile  Glu Ala Asp
    1355                 1360                 1365

Asp Val  Glu His Ala Leu Lys  Asp Phe Val Asp Arg  His Gly Lys
    1370                 1375                 1380

Arg Leu  Trp Lys Leu Arg Val  Thr Gly Ala Glu Ile  Arg Phe Asn
    1385                 1390                 1395

Val Gln  Ser Lys Lys Pro Asp  Ala Pro Ile Ile Pro  Met Arg Phe
    1400                 1405                 1410

Thr Val  Asp Asn Val Ser Gly  Phe Ile Leu Lys Val  Glu Val Tyr
    1415                 1420                 1425

Gln Glu  Val Lys Thr Glu Lys  Ser Gly Trp Ile Leu  Lys Ser Val
    1430                 1435                 1440

Asn Lys  Ile Pro Gly Ala Met  His Met Gln Pro Leu  Ser Thr Pro
    1445                 1450                 1455

Tyr Pro  Thr Lys Glu Trp Leu  Gln Pro Arg Arg Tyr  Lys Ala His
    1460                 1465                 1470

Leu Met  Gly Thr Thr Tyr Val  Tyr Asp Phe Pro Glu  Leu Phe Arg
    1475                 1480                 1485

Gln Ser  Val Gln Asn Gln Trp  Thr Gln Ala Ile Lys  Arg Asn Pro
    1490                 1495                 1500

Leu Leu  Lys Gln Pro Ser His  Leu Val Glu Ala Lys  Glu Leu Val
    1505                 1510                 1515

Leu Asp  Glu Asp Asp Val Leu  Gln Glu Ile Asp Arg  Ala Pro Gly
    1520                 1525                 1530

Thr Asn  Thr Val Gly Met Val  Ala Trp Ile Met Thr  Ile Arg Thr
    1535                 1540                 1545

Pro Glu  Tyr Pro Ser Gly Arg  Arg Ile Ile Ala Ile  Ala Asn Asp
    1550                 1555                 1560

Ile Thr  Phe Lys Ile Gly Ser  Phe Gly Val Ala Glu  Asp Gln Val
    1565                 1570                 1575

Phe Tyr  Lys Ala Ser Glu Leu  Ala Arg Ala Leu Gly  Ile Pro Arg
    1580                 1585                 1590

Ile Tyr  Leu Ser Ala Asn Ser  Gly Ala Arg Ile Gly  Leu Ala Asp
    1595                 1600                 1605

Glu Leu  Ile Ser Gln Phe Arg  Ala Ala Trp Lys Asp  Ala Ser Asn
    1610                 1615                 1620

Pro Thr  Ala Gly Phe Lys Tyr  Leu Tyr Leu Thr Pro  Ala Glu Tyr
    1625                 1630                 1635

Asp Val  Leu Ala Gln Gln Gly  Asp Ala Lys Ser Val  Leu Val Glu
    1640                 1645                 1650

Glu Ile  Gln Asp Glu Gly Glu  Thr Arg Leu Arg Ile  Thr Asp Val
    1655                 1660                 1665

Ile Gly  His Thr Asp Gly Leu  Gly Val Glu Asn Leu  Lys Gly Ser
    1670                 1675                 1680

Gly Leu  Ile Ala Gly Ala Thr  Ser Arg Ala Tyr Asp  Asp Ile Phe
    1685                 1690                 1695

Thr Ile  Thr Leu Val Thr Cys  Arg Ser Val Gly Ile  Gly Ala Tyr
    1700                 1705                 1710

Leu Val  Arg Leu Gly Gln Arg  Thr Ile Gln Asn Glu  Gly Gln Pro
```

```
    1715                1720                1725

Ile Ile  Leu Thr Gly Ala Pro  Ala Leu Asn Lys Val  Leu Gly Arg
    1730                1735                1740

Glu Val  Tyr Thr Ser Asn Leu  Gln Leu Gly Gly Thr  Gln Ile Met
    1745                1750                1755

Tyr Lys  Asn Gly Val Ser His  Leu Thr Ala Glu Asn  Asp Leu Glu
    1760                1765                1770

Gly Ile  Ala Lys Ile Val Gln  Trp Leu Ser Phe Val  Pro Asp Val
    1775                1780                1785

Arg Asn  Ala Pro Val Ser Met  Arg Leu Gly Ala Asp  Pro Ile Asp
    1790                1795                1800

Arg Asp  Ile Glu Tyr Thr Pro  Pro Lys Gly Pro Ser  Asp Pro Arg
    1805                1810                1815

Phe Phe  Leu Ala Gly Lys Ser  Glu Asn Gly Lys Trp  Leu Ser Gly
    1820                1825                1830

Phe Phe  Asp Gln Asp Ser Phe  Val Glu Thr Leu Ser  Gly Trp Ala
    1835                1840                1845

Arg Thr  Val Val Val Gly Arg  Ala Arg Leu Gly Gly  Ile Pro Met
    1850                1855                1860

Gly Val  Val Ser Val Glu Thr  Arg Thr Val Glu Asn  Ile Val Pro
    1865                1870                1875

Ala Asp  Pro Ala Asn Ser Asp  Ser Thr Glu Gln Val  Phe Met Glu
    1880                1885                1890

Ala Gly  Gly Val Trp Phe Pro  Asn Ser Ala Tyr Lys  Thr Ala Gln
    1895                1900                1905

Ala Ile  Asn Asp Phe Asn Lys  Gly Glu Gln Leu Pro  Leu Met Ile
    1910                1915                1920

Phe Ala  Asn Trp Arg Gly Phe  Ser Gly Gly Gln Arg  Asp Met Tyr
    1925                1930                1935

Asn Glu  Val Leu Lys Tyr Gly  Ala Gln Ile Val Asp  Ala Leu Ser
    1940                1945                1950

Asn Tyr  Lys Gln Pro Val Phe  Val Tyr Ile Ile Pro  Asn Gly Glu
    1955                1960                1965

Leu Arg  Gly Gly Ala Trp Val  Val Val Asp Pro Thr  Ile Asn Lys
    1970                1975                1980

Asp Met  Met Glu Met Tyr Ala  Asp Asn Asn Ala Arg  Gly Gly Val
    1985                1990                1995

Leu Glu  Pro Glu Gly Ile Val  Glu Ile Lys Tyr Arg  Lys Pro Ala
    2000                2005                2010

Leu Leu  Ala Thr Met Glu Arg  Leu Asp Ala Thr Tyr  Ala Ser Leu
    2015                2020                2025

Lys Lys  Gln Leu Ala Glu Glu  Gly Lys Thr Asp Glu  Glu Lys Ala
    2030                2035                2040

Ala Leu  Lys Val Gln Val Glu  Ala Arg Glu Gln Glu  Leu Leu Pro
    2045                2050                2055

Val Tyr  Gln Gln Ile Ser Ile  Gln Phe Ala Asp Leu  His Asp Arg
    2060                2065                2070

Ala Gly  Arg Met Lys Ala Lys  Gly Val Ile Arg Lys  Ala Leu Asp
    2075                2080                2085

Trp Arg  Arg Ala Arg His Tyr  Phe Tyr Trp Arg Val  Arg Arg Arg
    2090                2095                2100

Leu Cys  Glu Glu Tyr Thr Phe  Arg Lys Ile Val Thr  Ala Thr Ser
    2105                2110                2115
```

```
Ala Ala  Pro Met Pro Arg Glu  Gln Met Leu Asp Leu  Val Lys Gln
    2120                 2125                 2130

Trp Phe  Thr Asn Asp Asn Glu  Thr Val Asn Phe Glu  Asp Ala Asp
    2135                 2140                 2145

Glu Leu  Val Ser Glu Trp Phe  Glu Lys Arg Ala Ser  Val Ile Asp
    2150                 2155                 2160

Gln Arg  Ile Ser Lys Leu Lys  Ser Asp Ala Thr Lys  Glu Gln Ile
    2165                 2170                 2175

Val Ser  Leu Gly Asn Ala Asp  Gln Glu Ala Val Ile  Glu Gly Phe
    2180                 2185                 2190

Ser Gln  Leu Ile Glu Asn Leu  Ser Glu Asp Ala Arg  Ala Glu Ile
    2195                 2200                 2205

Leu Arg  Lys Leu Asn Ser Arg  Phe
    2210                 2215


<210> SEQ ID NO 16
<211> LENGTH: 652
<212> TYPE: PRT
<213> ORGANISM: Salmonella typhimurium

<400> SEQUENCE: 16

Met Ser Gln Thr His Lys His Ala Ile Pro Ala Asn Ile Ala Asp Arg
1               5                   10                  15

Cys Leu Ile Asn Pro Glu Gln Tyr Glu Thr Lys Tyr Lys Gln Ser Ile
            20                  25                  30

Asn Asp Pro Asp Thr Phe Trp Gly Glu Gln Gly Lys Ile Leu Asp Trp
        35                  40                  45

Ile Thr Pro Tyr Gln Lys Val Lys Asn Thr Ser Phe Ala Pro Gly Asn
    50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Thr Ser Gln Ser Lys His Ile Ser Tyr Arg Glu
            100                 105                 110

Leu His Arg Asp Val Cys Arg Phe Ala Asn Thr Leu Leu Asp Leu Gly
        115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Ser Ser Arg Leu Val Ile Thr Ala Asp Glu Gly Val Arg Ala
            180                 185                 190

Gly Arg Ser Ile Pro Leu Lys Lys Asn Val Asp Asp Ala Leu Lys Asn
        195                 200                 205

Pro Asn Val Thr Ser Val Glu His Val Ile Val Leu Lys Arg Thr Gly
    210                 215                 220

Ser Asp Ile Asp Trp Gln Glu Gly Arg Asp Leu Trp Trp Arg Asp Leu
225                 230                 235                 240

Ile Glu Lys Ala Ser Pro Glu His Gln Pro Glu Ala Met Asn Ala Glu
                245                 250                 255

Asp Pro Leu Phe Ile Leu Tyr Thr Ser Gly Ser Thr Gly Lys Pro Lys
```

```
        260                 265                 270

Gly Val Leu His Thr Thr Gly Gly Tyr Leu Val Tyr Ala Ala Thr Thr
    275                 280                 285

Phe Lys Tyr Val Phe Asp Tyr His Pro Gly Asp Ile Tyr Trp Cys Thr
    290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Cys Gln Val Val Asp Lys His Gln Val Asn
            340                 345                 350

Ile Leu Tyr Thr Ala Pro Thr Ala Ile Arg Ala Leu Met Ala Glu Gly
        355                 360                 365

Asp Lys Ala Ile Glu Gly Thr Asp Arg Ser Ser Leu Arg Ile Leu Gly
    370                 375                 380

Ser Val Gly Glu Pro Ile Asn Pro Glu Ala Trp Glu Trp Tyr Trp Lys
385                 390                 395                 400

Lys Ile Gly Lys Glu Lys Cys Pro Val Val Asp Thr Trp Trp Gln Thr
                405                 410                 415

Glu Thr Gly Gly Phe Met Ile Thr Pro Leu Pro Gly Ala Ile Glu Leu
            420                 425                 430

Lys Ala Gly Ser Ala Thr Arg Pro Phe Phe Gly Val Gln Pro Ala Leu
        435                 440                 445

Val Asp Asn Glu Gly His Pro Gln Glu Gly Ala Thr Glu Gly Asn Leu
    450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
    530                 535                 540

Ala Ala Val Val Gly Ile Pro His Ala Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
    610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650
```

<210> SEQ ID NO 17
<211> LENGTH: 485
<212> TYPE: PRT
<213> ORGANISM: Streptomyces coelicolor

<400> SEQUENCE: 17

```
Met Ser Ser Leu Phe Pro Ala Leu Ser Pro Ala Pro Thr Gly Ala Pro
1               5                   10                  15

Ala Asp Arg Pro Ala Leu Arg Phe Gly Glu Arg Ser Leu Thr Tyr Ala
            20                  25                  30

Glu Leu Ala Ala Ala Ala Gly Ala Thr Ala Gly Arg Ile Gly Gly Ala
        35                  40                  45

Gly Arg Val Ala Val Trp Ala Thr Pro Ala Met Glu Thr Gly Val Ala
    50                  55                  60

Val Val Ala Ala Leu Leu Ala Gly Val Ala Ala Val Pro Leu Asn Pro
65                  70                  75                  80

Lys Ser Gly Asp Lys Glu Leu Ala His Ile Leu Ser Asp Ser Ala Pro
                85                  90                  95

Ser Leu Val Leu Ala Pro Pro Asp Ala Glu Leu Pro Pro Ala Leu Gly
            100                 105                 110

Ala Leu Glu Arg Val Asp Val Asp Val Arg Ala Arg Gly Ala Val Pro
        115                 120                 125

Glu Asp Gly Ala Asp Asp Gly Asp Pro Ala Leu Val Val Tyr Thr Ser
    130                 135                 140

Gly Thr Thr Gly Pro Pro Lys Gly Ala Val Ile Pro Arg Arg Ala Leu
145                 150                 155                 160

Ala Thr Thr Leu Asp Ala Leu Ala Asp Ala Trp Gln Trp Thr Gly Glu
                165                 170                 175

Asp Val Leu Val Gln Gly Leu Pro Leu Phe His Val His Gly Leu Val
            180                 185                 190

Leu Gly Ile Leu Gly Pro Leu Arg Arg Gly Gly Ser Val Arg His Leu
        195                 200                 205

Gly Arg Phe Ser Thr Glu Gly Ala Ala Arg Glu Leu Asn Asp Gly Ala
    210                 215                 220

Thr Met Leu Phe Gly Val Pro Thr Met Tyr His Arg Ile Ala Glu Thr
225                 230                 235                 240

Leu Pro Ala Asp Pro Glu Leu Ala Lys Ala Leu Ala Gly Ala Arg Leu
                245                 250                 255

Leu Val Ser Gly Ser Ala Ala Leu Pro Val His Asp His Glu Arg Ile
            260                 265                 270

Ala Ala Ala Thr Gly Arg Arg Val Ile Glu Arg Tyr Gly Met Thr Glu
        275                 280                 285

Thr Leu Met Asn Thr Ser Val Arg Ala Asp Gly Glu Pro Arg Ala Gly
    290                 295                 300

Thr Val Gly Val Pro Leu Pro Gly Val Glu Leu Arg Leu Val Glu Glu
305                 310                 315                 320

Asp Gly Thr Pro Ile Ala Ala Leu Asp Gly Glu Ser Val Gly Glu Ile
                325                 330                 335

Gln Val Arg Gly Pro Asn Leu Phe Thr Glu Tyr Leu Asn Arg Pro Asp
            340                 345                 350

Ala Thr Ala Ala Ala Phe Thr Glu Asp Gly Phe Phe Arg Thr Gly Asp
        355                 360                 365

Met Ala Val Arg Asp Pro Asp Gly Tyr Val Arg Ile Val Gly Arg Lys
    370                 375                 380

Ala Thr Asp Leu Ile Lys Ser Gly Gly Tyr Lys Ile Gly Ala Gly Glu
385                 390                 395                 400

Ile Glu Asn Ala Leu Leu Glu His Pro Glu Val Arg Glu Ala Ala Val
```

```
                405                 410                 415

Thr Gly Glu Pro Asp Pro Asp Leu Gly Glu Arg Ile Val Ala Trp Ile
            420                 425                 430

Val Pro Ala Asp Pro Ala Ala Pro Pro Ala Leu Gly Thr Leu Ala Asp
        435                 440                 445

His Val Ala Ala Arg Leu Ala Pro His Lys Arg Pro Arg Val Val Arg
    450                 455                 460

Tyr Leu Asp Ala Val Pro Arg Asn Asp Met Gly Lys Ile Met Lys Arg
465                 470                 475                 480

Ala Leu Asn Arg Asp
                485


<210> SEQ ID NO 18
<211> LENGTH: 465
<212> TYPE: PRT
<213> ORGANISM: Streptomyces coelicolor

<400> SEQUENCE: 18

Met Ser Pro Glu Leu Ile Ser Ile Leu Val Leu Val Val Val Phe Val
1               5                   10                  15

Ile Ala Thr Thr Arg Ser Val Asn Met Gly Ala Leu Ala Phe Ala Ala
            20                  25                  30

Ala Phe Gly Val Gly Thr Leu Val Ala Asp Leu Asp Ala Asp Gly Ile
        35                  40                  45

Phe Ala Gly Phe Pro Gly Asp Leu Phe Val Val Leu Val Gly Val Thr
    50                  55                  60

Tyr Leu Phe Ala Ile Ala Arg Ala Asn Gly Thr Thr Asp Trp Leu Val
65                  70                  75                  80

His Ala Ala Val Arg Leu Val Arg Gly Arg Val Ala Leu Ile Pro Trp
                85                  90                  95

Val Met Phe Ala Leu Thr Gly Ala Leu Thr Ala Ile Gly Ala Val Ser
            100                 105                 110

Pro Ala Ala Val Ala Ile Val Ala Pro Val Ala Leu Ser Phe Ala Thr
        115                 120                 125

Arg Tyr Ser Ile Ser Pro Leu Leu Met Gly Thr Met Val Val His Gly
    130                 135                 140

Ala Gln Ala Gly Gly Phe Ser Pro Ile Ser Ile Tyr Gly Ser Ile Val
145                 150                 155                 160

Asn Gly Ile Val Glu Arg Glu Lys Leu Pro Gly Ser Glu Ile Gly Leu
                165                 170                 175

Phe Leu Ala Ser Leu Val Ala Asn Leu Leu Ile Ala Ala Val Leu Phe
            180                 185                 190

Ala Val Leu Gly Gly Arg Lys Leu Trp Ala Arg Gly Ala Val Thr Pro
        195                 200                 205

Glu Gly Asp Gly Ala Pro Gly Lys Ala Gly Thr Gly Thr Thr Gly Ser
    210                 215                 220

Gly Ser Asp Thr Gly Thr Gly Thr Gly Thr Gly Thr Gly Thr Ser Ala
225                 230                 235                 240

Gly Thr Gly Gly Thr Ala Pro Thr Ala Val Ala Val Arg Ser Asp Arg
                245                 250                 255

Glu Thr Gly Gly Ala Glu Gly Thr Gly Val Arg Leu Thr Pro Ala Arg
            260                 265                 270

Val Ala Thr Leu Val Ala Leu Val Ala Leu Val Val Ala Val Leu Gly
        275                 280                 285
```

```
Phe Asp Leu Asp Ala Gly Leu Thr Ala Val Thr Leu Ala Val Val Leu
    290                 295                 300

Ser Thr Ala Trp Pro Asp Asp Ser Arg Arg Ala Val Gly Glu Ile Ala
305                 310                 315                 320

Trp Ser Thr Val Leu Leu Ile Cys Gly Val Leu Thr Tyr Val Gly Val
                325                 330                 335

Leu Glu Glu Met Gly Thr Ile Thr Trp Ala Gly Glu Gly Val Gly Gly
            340                 345                 350

Ile Gly Val Pro Leu Leu Ala Ala Val Leu Leu Cys Tyr Ile Gly Ala
        355                 360                 365

Ile Val Ser Ala Phe Ala Ser Ser Val Gly Ile Met Gly Ala Leu Ile
    370                 375                 380

Pro Leu Ala Val Pro Phe Leu Ala Gln Gly Glu Ile Gly Ala Val Gly
385                 390                 395                 400

Met Val Ala Ala Leu Ala Val Ser Ala Thr Val Val Asp Val Ser Pro
                405                 410                 415

Phe Ser Thr Asn Gly Ala Leu Val Leu Ala Ala Ala Pro Asp Val Asp
            420                 425                 430

Arg Asp Arg Phe Phe Arg Gln Leu Met Val Tyr Gly Gly Ile Val Val
        435                 440                 445

Ala Ala Val Pro Ala Leu Ala Trp Leu Val Leu Val Val Pro Gly Phe
    450                 455                 460

Gly
465


<210> SEQ ID NO 19
<211> LENGTH: 548
<212> TYPE: PRT
<213> ORGANISM: Acinetobacter calcoaceticus

<400> SEQUENCE: 19

Met Val Lys Lys Arg Leu Trp Asp Lys Gln Arg Thr Arg Arg Gln Glu
1               5                   10                  15

Lys Leu Asn Leu Ala Gln Gln Lys Gly Phe Ala Lys Gln Val Glu His
            20                  25                  30

Ala Arg Ala Ile Glu Leu Leu Glu Thr Val Ile Ala Ser Gly Asp Arg
        35                  40                  45

Val Cys Leu Glu Gly Asn Asn Gln Lys Gln Ala Asp Phe Leu Ser Lys
    50                  55                  60

Cys Leu Ser Gln Cys Asn Pro Asp Ala Val Asn Asp Leu His Ile Val
65                  70                  75                  80

Gln Ser Val Leu Ala Leu Pro Ser His Ile Asp Val Phe Glu Lys Gly
                85                  90                  95

Ile Ala Ser Lys Val Asp Phe Ser Phe Ala Gly Pro Gln Ser Leu Arg
            100                 105                 110

Leu Ala Gln Leu Val Gln Gln Gln Lys Ile Ser Ile Gly Ser Ile His
        115                 120                 125

Thr Tyr Leu Glu Leu Tyr Gly Arg Tyr Phe Ile Asp Leu Thr Pro Asn
    130                 135                 140

Ile Cys Leu Ile Thr Ala His Ala Ala Asp Arg Glu Gly Asn Leu Tyr
145                 150                 155                 160

Thr Gly Pro Asn Thr Glu Asp Thr Pro Ala Ile Val Glu Ala Thr Ala
                165                 170                 175

Phe Lys Ser Gly Ile Val Ile Ala Gln Val Asn Glu Ile Val Asp Lys
            180                 185                 190
```

```
Leu Pro Arg Val Asp Val Pro Ala Asp Trp Val Asp Phe Tyr Ile Glu
        195                 200                 205

Ser Pro Lys His Asn Tyr Ile Glu Pro Leu Phe Thr Arg Asp Pro Ala
    210                 215                 220

Gln Ile Thr Glu Val Gln Ile Leu Met Ala Met Met Val Ile Lys Gly
225                 230                 235                 240

Ile Tyr Ala Pro Tyr Gln Val Gln Arg Leu Asn His Gly Ile Gly Phe
                245                 250                 255

Asp Thr Ala Ala Ile Glu Leu Leu Leu Pro Thr Tyr Ala Ala Ser Leu
            260                 265                 270

Gly Leu Lys Gly Gln Ile Cys Thr Asn Trp Ala Leu Asn Pro His Pro
        275                 280                 285

Thr Leu Ile Pro Ala Ile Glu Ser Gly Phe Val Asp Ser Val His Ser
    290                 295                 300

Phe Gly Ser Glu Val Gly Met Glu Asp Tyr Ile Lys Glu Arg Pro Asp
305                 310                 315                 320

Val Phe Phe Thr Gly Ser Asp Gly Ser Met Arg Ser Asn Arg Ala Phe
                325                 330                 335

Ser Gln Thr Ala Gly Leu Tyr Ala Cys Asp Ser Phe Ile Gly Ser Thr
            340                 345                 350

Leu Gln Ile Glu Leu Gln Gly Asn Ser Ser Thr Ala Thr Val Asp Arg
        355                 360                 365

Ile Ser Gly Phe Gly Gly Ala Pro Asn Met Gly Ser Asp Pro His Gly
    370                 375                 380

Arg Arg His Ala Ser Tyr Ala Tyr Thr Lys Ala Gly Arg Glu Ala Thr
385                 390                 395                 400

Asp Gly Lys Leu Ile Lys Gly Arg Lys Leu Val Val Gln Thr Val Glu
                405                 410                 415

Thr Tyr Arg Glu His Met His Pro Val Phe Val Glu Glu Leu Asp Ala
            420                 425                 430

Trp Gln Leu Gln Asp Lys Met Asp Ser Glu Leu Pro Pro Ile Met Ile
        435                 440                 445

Tyr Gly Glu Asp Val Thr His Ile Val Thr Glu Glu Gly Ile Ala Asn
    450                 455                 460

Leu Leu Leu Cys Arg Thr Asp Glu Glu Arg Glu Gln Ala Ile Arg Gly
465                 470                 475                 480

Val Ala Gly Tyr Thr Pro Val Gly Leu Lys Arg Asp Ala Ala Lys Val
                485                 490                 495

Glu Glu Leu Arg Gln Arg Gly Ile Ile Gln Arg Pro Glu Asp Leu Gly
            500                 505                 510

Ile Asp Pro Thr Gln Val Ser Arg Asp Leu Leu Ala Ala Lys Ser Val
        515                 520                 525

Lys Asp Leu Val Lys Trp Ser Gly Gly Leu Tyr Ser Pro Pro Ser Arg
    530                 535                 540

Phe Arg Asn Trp
545
```

<210> SEQ ID NO 20
<211> LENGTH: 248
<212> TYPE: PRT
<213> ORGANISM: Pseudomonas aeruginosa

<400> SEQUENCE: 20

```
Met Ile Leu Glu Leu Asp Cys Gly Asn Ser Leu Ile Lys Trp Arg Val
```

```
1               5                   10                  15

Ile Glu Gly Ala Ala Arg Ser Val Ala Gly Gly Leu Ala Glu Ser Asp
            20                  25                  30

Asp Ala Leu Val Glu Gln Leu Thr Ser Gln Gln Ala Leu Pro Val Arg
        35                  40                  45

Ala Cys Arg Leu Val Ser Val Arg Ser Glu Gln Glu Thr Ser Gln Leu
    50                  55                  60

Val Ala Arg Leu Glu Gln Leu Phe Pro Val Ser Ala Leu Val Ala Ser
65                  70                  75                  80

Ser Gly Lys Gln Leu Ala Gly Val Arg Asn Gly Tyr Leu Asp Tyr Gln
                85                  90                  95

Arg Leu Gly Leu Asp Arg Trp Leu Ala Leu Val Ala Ala His His Leu
            100                 105                 110

Ala Lys Lys Ala Cys Leu Val Ile Asp Leu Gly Thr Ala Val Thr Ser
        115                 120                 125

Asp Leu Val Ala Ala Asp Gly Val His Leu Gly Gly Tyr Ile Cys Pro
    130                 135                 140

Gly Met Thr Leu Met Arg Ser Gln Leu Arg Thr His Thr Arg Arg Ile
145                 150                 155                 160

Arg Tyr Asp Asp Ala Glu Ala Arg Arg Ala Leu Ala Ser Leu Gln Pro
                165                 170                 175

Gly Gln Ala Thr Ala Glu Ala Val Glu Arg Gly Cys Leu Leu Met Leu
            180                 185                 190

Arg Gly Phe Val Arg Glu Gln Tyr Ala Met Ala Cys Glu Leu Leu Gly
        195                 200                 205

Pro Asp Cys Glu Ile Phe Leu Thr Gly Gly Asp Ala Glu Leu Val Arg
    210                 215                 220

Asp Glu Leu Ala Gly Ala Arg Ile Met Pro Asp Leu Val Phe Val Gly
225                 230                 235                 240

Leu Ala Leu Ala Cys Pro Ile Glu
                245


<210> SEQ ID NO 21
<211> LENGTH: 420
<212> TYPE: PRT
<213> ORGANISM: Salmonella typhimurium

<400> SEQUENCE: 21

Met Thr Lys Lys Leu Leu Ala Leu Gly Ile Asn His Lys Thr Ala Pro
1               5                   10                  15

Val Ser Leu Arg Glu Arg Val Thr Phe Ser Pro Asp Thr Leu Asp Gln
            20                  25                  30

Ala Leu Asp Ser Leu Leu Ala Gln Pro Met Val Gln Gly Gly Val Val
        35                  40                  45

Leu Ser Thr Cys Asn Arg Thr Glu Leu Tyr Leu Ser Val Glu Glu Gln
    50                  55                  60

Asp Asn Leu Gln Glu Ala Leu Ile Arg Trp Leu Cys Asp Tyr His Asn
65                  70                  75                  80

Leu Asn Glu Asp Asp Leu Arg Asn Ser Leu Tyr Trp His Gln Asp Asn
                85                  90                  95

Asp Ala Val Ser His Leu Met Arg Val Ala Ser Gly Leu Asp Ser Leu
            100                 105                 110

Val Leu Gly Glu Pro Gln Ile Leu Gly Gln Val Lys Lys Ala Phe Ala
        115                 120                 125
```

```
Asp Ser Gln Lys Gly His Leu Asn Ala Ser Ala Leu Arg Arg Met Phe
    130                 135                 140

Gln Lys Ser Phe Ser Val Ala Lys Arg Val Arg Thr Glu Thr Asp Ile
145                 150                 155                 160

Gly Ala Ser Ala Val Ser Val Ala Phe Ala Ala Cys Thr Leu Ala Arg
                165                 170                 175

Gln Ile Phe Glu Ser Leu Ser Thr Val Thr Val Leu Leu Val Gly Ala
            180                 185                 190

Gly Glu Thr Ile Glu Leu Val Ala Arg His Leu Arg Glu His Lys Val
        195                 200                 205

Gln Lys Met Ile Ile Ala Asn Arg Thr Arg Glu Arg Ala Gln Ala Leu
    210                 215                 220

Ala Asp Glu Val Gly Ala Glu Val Ile Ser Leu Ser Asp Ile Asp Ala
225                 230                 235                 240

Arg Leu Gln Asp Ala Asp Ile Ile Ile Ser Ser Thr Ala Ser Pro Leu
                245                 250                 255

Pro Ile Ile Gly Lys Gly Met Val Glu Arg Ala Leu Lys Ser Arg Arg
            260                 265                 270

Asn Gln Pro Met Leu Leu Val Asp Ile Ala Val Pro Arg Asp Val Glu
        275                 280                 285

Pro Glu Val Gly Lys Leu Ala Asn Ala Tyr Leu Tyr Ser Val Asp Asp
    290                 295                 300

Leu Gln Ser Ile Ile Ser His Asn Leu Ala Gln Arg Gln Ala Ala Ala
305                 310                 315                 320

Val Glu Ala Glu Thr Ile Val Glu Gln Glu Ala Ser Glu Phe Met Ala
                325                 330                 335

Trp Leu Arg Ala Gln Gly Ala Ser Glu Thr Ile Arg Glu Tyr Arg Ser
            340                 345                 350

Gln Ser Glu Gln Ile Arg Asp Glu Leu Thr Thr Lys Ala Leu Ser Ala
        355                 360                 365

Leu Gln Gln Gly Gly Asp Ala Gln Ala Ile Leu Gln Asp Leu Ala Trp
    370                 375                 380

Lys Leu Thr Asn Arg Leu Ile His Ala Pro Thr Lys Ser Leu Gln Gln
385                 390                 395                 400

Ala Ala Arg Asp Gly Asp Asp Glu Arg Leu Asn Ile Leu Arg Asp Ser
                405                 410                 415

Leu Gly Leu Glu
            420


<210> SEQ ID NO 22
<211> LENGTH: 401
<212> TYPE: PRT
<213> ORGANISM: Rhodobacter capsulatus

<400> SEQUENCE: 22

Met Asp Tyr Asn Leu Ala Leu Asp Lys Ala Ile Gln Lys Leu His Asp
1               5                   10                  15

Glu Gly Arg Tyr Arg Thr Phe Ile Asp Ile Glu Arg Glu Lys Gly Ala
            20                  25                  30

Phe Pro Lys Ala Gln Trp Asn Arg Pro Asp Gly Gly Lys Gln Asp Ile
        35                  40                  45

Thr Val Trp Cys Gly Asn Asp Tyr Leu Gly Met Gly Gln His Pro Val
    50                  55                  60

Val Leu Ala Ala Met His Glu Ala Leu Glu Ala Val Gly Ala Gly Ser
65                  70                  75                  80
```

```
Gly Gly Thr Arg Asn Ile Ser Gly Thr Thr Ala Tyr His Arg Arg Leu
                85                  90                  95

Glu Ala Glu Ile Ala Asp Leu His Gly Lys Glu Ala Ala Leu Val Phe
            100                 105                 110

Ser Ser Ala Tyr Ile Ala Asn Asp Ala Thr Leu Ser Thr Leu Arg Leu
        115                 120                 125

Leu Phe Pro Gly Leu Ile Ile Tyr Ser Asp Ser Leu Asn His Ala Ser
    130                 135                 140

Met Ile Glu Gly Ile Lys Arg Asn Ala Gly Pro Lys Arg Ile Phe Arg
145                 150                 155                 160

His Asn Asp Val Ala His Leu Arg Glu Leu Ile Ala Ala Asp Asp Pro
                165                 170                 175

Ala Ala Pro Lys Leu Ile Ala Phe Glu Ser Val Tyr Ser Met Asp Gly
            180                 185                 190

Asp Phe Gly Pro Ile Lys Glu Ile Cys Asp Ile Ala Asp Glu Phe Gly
        195                 200                 205

Ala Leu Thr Tyr Ile Asp Glu Val His Ala Val Gly Met Tyr Gly Pro
    210                 215                 220

Arg Gly Ala Gly Val Ala Glu Arg Asp Gly Leu Met His Arg Ile Asp
225                 230                 235                 240

Ile Phe Asn Gly Thr Leu Ala Lys Ala Tyr Gly Val Phe Gly Gly Tyr
                245                 250                 255

Ile Ala Ala Ser Ala Lys Met Val Asp Ala Val Arg Ser Tyr Ala Pro
            260                 265                 270

Gly Phe Ile Phe Ser Thr Ser Leu Pro Pro Ala Ile Ala Ala Gly Ala
        275                 280                 285

Gln Ala Ser Ile Ala Phe Leu Lys Thr Ala Glu Gly Gln Lys Leu Arg
    290                 295                 300

Asp Ala Gln Gln Met His Ala Lys Val Leu Lys Met Arg Leu Lys Ala
305                 310                 315                 320

Leu Gly Met Pro Ile Ile Asp His Gly Ser His Ile Val Pro Val Val
                325                 330                 335

Ile Gly Asp Pro Val His Thr Lys Ala Val Ser Asp Met Leu Leu Ser
            340                 345                 350

Asp Tyr Gly Val Tyr Val Gln Pro Ile Asn Phe Pro Thr Val Pro Arg
        355                 360                 365

Gly Thr Glu Arg Leu Arg Phe Thr Pro Ser Pro Val His Asp Leu Lys
    370                 375                 380

Gln Ile Asp Gly Leu Val His Ala Met Asp Leu Leu Trp Ala Arg Cys
385                 390                 395                 400

Ala


<210> SEQ ID NO 23
<211> LENGTH: 531
<212> TYPE: PRT
<213> ORGANISM: Rhodobacter capsulatus SB 1003

<400> SEQUENCE: 23

Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45
```

```
Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460
```

```
Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530


<210> SEQ ID NO 24
<211> LENGTH: 690
<212> TYPE: PRT
<213> ORGANISM: Trichosporon cutaneum

<400> SEQUENCE: 24

Met Ile Thr Glu Thr Asn Val Ala Lys Pro Ala Ser Thr Lys Val Met
1               5                   10                  15

Asn Gly Asp Ala Ala Lys Ala Ala Pro Val Glu Pro Phe Ala Thr Tyr
            20                  25                  30

Ala His Ser Gln Ala Thr Lys Thr Val Val Ile Asp Gly His Asn Met
        35                  40                  45

Lys Val Gly Asp Val Val Ala Val Ala Arg His Gly Ala Lys Val Glu
    50                  55                  60

Leu Ala Ala Ser Val Ala Gly Pro Val Gln Ala Ser Val Asp Phe Lys
65                  70                  75                  80

Glu Ser Lys Lys His Thr Ser Ile Tyr Gly Val Thr Thr Gly Phe Gly
                85                  90                  95

Gly Ser Ala Asp Thr Arg Thr Ser Asp Thr Glu Ala Leu Gln Ile Ser
            100                 105                 110

Leu Leu Glu His Gln Leu Cys Gly Tyr Leu Pro Thr Asp Pro Thr Tyr
        115                 120                 125

Glu Gly Met Leu Leu Ala Ala Met Pro Ile Pro Ile Val Arg Gly Ala
    130                 135                 140

Met Ala Val Arg Val Asn Ser Cys Val Arg Gly His Ser Gly Val Arg
145                 150                 155                 160

Leu Glu Val Leu Gln Ser Phe Ala Asp Phe Ile Asn Ile Gly Leu Val
                165                 170                 175

Pro Cys Val Pro Leu Arg Gly Thr Ile Ser Ala Ser Gly Asp Leu Ser
            180                 185                 190

Pro Leu Ser Tyr Ile Ala Gly Ala Ile Cys Gly His Pro Asp Val Lys
        195                 200                 205

Val Phe Asp Thr Ala Ala Ser Pro Pro Thr Val Leu Thr Ala Pro Glu
    210                 215                 220

Ala Ile Ala Lys Tyr Lys Leu Lys Thr Val Arg Leu Ala Ser Lys Glu
225                 230                 235                 240

Gly Leu Gly Leu Val Asn Gly Thr Ala Val Ser Ala Ala Ala Gly Ala
                245                 250                 255

Leu Ala Leu Tyr Asp Ala Glu Cys Leu Ala Met Met Ser Gln Thr Asn
            260                 265                 270

Thr Ala Leu Thr Val Glu Ala Leu Asp Gly His Val Gly Ser Phe Ala
        275                 280                 285

Pro Phe Ile Gln Glu Ile Arg Pro His Val Gly Gln Ile Glu Ala Ala
    290                 295                 300
```

```
Lys Asn Ile Arg His Met Leu Ser Asn Ser Lys Leu Ala Val His Glu
305                 310                 315                 320

Glu Pro Glu Leu Leu Ala Asp Gln Asp Ala Gly Ile Leu Arg Gln Asp
                325                 330                 335

Arg Tyr Ala Leu Arg Thr Ser Ala Gln Trp Ile Gly Pro Gln Leu Glu
            340                 345                 350

Met Leu Gly Leu Ala Arg Gln Gln Ile Glu Thr Glu Leu Asn Ser Thr
        355                 360                 365

Thr Asp Asn Pro Leu Ile Asp Val Glu Gly Gly Met Phe His His Gly
    370                 375                 380

Gly Asn Phe Gln Ala Met Ala Val Thr Ser Ala Met Asp Ser Thr Arg
385                 390                 395                 400

Ile Val Leu Gln Asn Leu Gly Lys Leu Ser Phe Ala Gln Val Thr Glu
                405                 410                 415

Leu Ile Asn Cys Glu Met Asn His Gly Leu Pro Ser Asn Leu Ala Gly
            420                 425                 430

Ser Glu Pro Ser Thr Asn Tyr His Cys Lys Gly Leu Asp Ile His Cys
        435                 440                 445

Gly Ala Tyr Cys Ala Glu Leu Gly Phe Leu Ala Asn Pro Met Ser Asn
    450                 455                 460

His Val Gln Ser Thr Glu Met His Asn Gln Ser Val Asn Ser Met Ala
465                 470                 475                 480

Phe Ala Ser Ala Arg Lys Thr Met Glu Ala Asn Glu Val Leu Ser Leu
                485                 490                 495

Leu Leu Gly Ser Gln Met Tyr Cys Ala Thr Gln Ala Leu Asp Leu Arg
            500                 505                 510

Val Met Glu Val Lys Phe Lys Met Ala Ile Val Lys Leu Leu Asn Asp
        515                 520                 525

Thr Leu Thr Lys His Phe Ser Thr Phe Leu Thr Pro Glu Gln Leu Ala
    530                 535                 540

Lys Leu Asn Thr Thr Ala Ala Ile Thr Leu Tyr Lys Arg Leu Asn Gln
545                 550                 555                 560

Thr Pro Ser Trp Asp Ser Ala Pro Arg Phe Glu Asp Ala Ala Lys His
                565                 570                 575

Leu Val Gly Cys Ile Met Asp Ala Leu Met Val Asn Asp Asp Ile Thr
            580                 585                 590

Asp Leu Thr Asn Leu Pro Lys Trp Lys Lys Glu Phe Ala Lys Asp Ala
        595                 600                 605

Gly Asp Leu Tyr Arg Ser Ile Leu Thr Ala Thr Thr Ala Asp Gly Arg
    610                 615                 620

Asn Asp Leu Glu Pro Ala Glu Tyr Leu Gly Gln Thr Arg Ala Val Tyr
625                 630                 635                 640

Glu Ala Ile Arg Ser Asp Leu Gly Val Lys Val Arg Arg Gly Asp Val
                645                 650                 655

Ala Glu Gly Lys Ser Gly Lys Ser Ile Gly Ser Asn Val Ala Arg Ile
            660                 665                 670

Val Glu Ala Met Arg Asp Gly Arg Leu Met Gly Ala Val Ser Lys Met
        675                 680                 685

Phe Phe
    690
```

<210> SEQ ID NO 25
<211> LENGTH: 506

<212> TYPE: PRT
<213> ORGANISM: Flavobacterium johnsoniae

<400> SEQUENCE: 25

```
Met Asn Thr Ile Asn Glu Tyr Leu Ser Leu Glu Glu Phe Glu Ala Ile
1               5                   10                  15

Ile Phe Gly Asn Gln Lys Val Thr Ile Ser Asp Val Val Val Asn Arg
            20                  25                  30

Val Asn Glu Ser Phe Asn Phe Leu Lys Glu Phe Ser Gly Asn Lys Val
        35                  40                  45

Ile Tyr Gly Val Asn Thr Gly Phe Gly Pro Met Ala Gln Tyr Arg Ile
    50                  55                  60

Lys Glu Ser Asp Gln Ile Gln Leu Gln Tyr Asn Leu Ile Arg Ser His
65                  70                  75                  80

Ser Ser Gly Thr Gly Lys Pro Leu Ser Pro Val Cys Ala Lys Ala Ala
                85                  90                  95

Ile Leu Ala Arg Leu Asn Thr Leu Ser Leu Gly Asn Ser Gly Val His
            100                 105                 110

Pro Ser Val Ile Asn Leu Met Ser Glu Leu Ile Asn Lys Asp Ile Thr
        115                 120                 125

Pro Leu Ile Phe Glu His Gly Gly Val Gly Ala Ser Gly Asp Leu Val
    130                 135                 140

Gln Leu Ser His Leu Ala Leu Val Leu Ile Gly Glu Gly Glu Val Phe
145                 150                 155                 160

Tyr Lys Gly Glu Arg Arg Pro Thr Pro Glu Val Phe Glu Ile Glu Gly
                165                 170                 175

Leu Lys Pro Ile Gln Val Glu Ile Arg Glu Gly Leu Ala Leu Ile Asn
            180                 185                 190

Gly Thr Ser Val Met Thr Gly Ile Gly Val Val Asn Val Tyr His Ala
        195                 200                 205

Lys Lys Leu Leu Asp Trp Ser Leu Lys Ser Ser Cys Ala Ile Asn Glu
    210                 215                 220

Leu Val Gln Ala Tyr Asp Asp His Phe Ser Ala Glu Leu Asn Gln Thr
225                 230                 235                 240

Lys Arg His Lys Gly Gln Gln Glu Ile Ala Leu Lys Met Arg Gln Asn
                245                 250                 255

Leu Ser Asp Ser Thr Leu Ile Arg Lys Arg Glu Asp His Leu Tyr Ser
            260                 265                 270

Gly Glu Asn Thr Glu Glu Ile Phe Lys Glu Lys Val Gln Glu Tyr Tyr
        275                 280                 285

Ser Leu Arg Cys Val Pro Gln Ile Leu Gly Pro Val Leu Glu Thr Ile
    290                 295                 300

Asn Asn Val Ala Ser Ile Leu Glu Asp Glu Phe Asn Ser Ala Asn Asp
305                 310                 315                 320

Asn Pro Ile Ile Asp Val Lys Asn Gln His Val Tyr His Gly Gly Asn
                325                 330                 335

Phe His Gly Asp Tyr Ile Ser Leu Glu Met Asp Lys Leu Lys Ile Val
            340                 345                 350

Ile Thr Lys Leu Thr Met Leu Ala Glu Arg Gln Leu Asn Tyr Leu Leu
        355                 360                 365

Asn Ser Lys Ile Asn Glu Leu Leu Pro Pro Phe Val Asn Leu Gly Thr
    370                 375                 380

Leu Gly Phe Asn Phe Gly Met Gln Gly Val Gln Phe Thr Ala Thr Ser
385                 390                 395                 400
```

```
Thr Thr Ala Glu Ser Gln Met Leu Ser Asn Pro Met Tyr Val His Ser
                405                 410                 415

Ile Pro Asn Asn Asn Asp Asn Gln Asp Ile Val Ser Met Gly Thr Asn
            420                 425                 430

Ser Ala Val Ile Thr Ser Lys Val Ile Glu Asn Ala Phe Glu Val Leu
        435                 440                 445

Ala Ile Glu Met Ile Thr Ile Val Gln Ala Ile Asp Tyr Leu Gly Gln
    450                 455                 460

Lys Asp Lys Ile Ser Ser Val Ser Lys Lys Trp Tyr Asp Glu Ile Arg
465                 470                 475                 480

Asn Ile Ile Pro Thr Phe Lys Glu Asp Gln Val Met Tyr Pro Phe Val
                485                 490                 495

Gln Lys Val Lys Asp His Leu Ile Asn Asn
            500                 505


<210> SEQ ID NO 26
<211> LENGTH: 552
<212> TYPE: PRT
<213> ORGANISM: Herpetosiphon aurantiacus DSM 785

<400> SEQUENCE: 26

Met Ser Thr Thr Leu Ile Leu Thr Gly Glu Gly Leu Gly Ile Asp Asp
1               5                   10                  15

Val Val Arg Val Ala Arg His Gln Asp Arg Val Glu Leu Thr Thr Asp
            20                  25                  30

Pro Ala Ile Leu Ala Gln Ile Glu Ala Ser Cys Ala Tyr Ile Asn Gln
        35                  40                  45

Ala Val Lys Glu His Gln Pro Val Tyr Gly Val Thr Thr Gly Phe Gly
    50                  55                  60

Gly Met Ala Asn Val Ile Ile Ser Pro Glu Glu Ala Ala Glu Leu Gln
65                  70                  75                  80

Asn Asn Ala Ile Trp Tyr His Lys Thr Gly Ala Gly Lys Leu Leu Pro
                85                  90                  95

Phe Thr Asp Val Arg Ala Ala Met Leu Leu Arg Ala Asn Ser His Met
            100                 105                 110

Arg Gly Ala Ser Gly Ile Arg Leu Glu Ile Ile Gln Arg Met Val Thr
        115                 120                 125

Phe Leu Asn Ala Asn Val Thr Pro His Val Arg Glu Phe Gly Ser Ile
    130                 135                 140

Gly Ala Ser Gly Asp Leu Val Pro Leu Ile Ser Ile Thr Gly Ala Leu
145                 150                 155                 160

Leu Gly Thr Asp Gln Ala Phe Met Val Asp Phe Asn Gly Glu Thr Leu
                165                 170                 175

Asp Cys Ile Ser Ala Leu Glu Arg Leu Gly Leu Pro Arg Leu Arg Leu
            180                 185                 190

Gln Pro Lys Glu Gly Leu Ala Met Met Asn Gly Thr Ser Val Met Thr
        195                 200                 205

Gly Ile Ala Ala Asn Cys Val His Asp Ala Arg Ile Leu Leu Ala Leu
    210                 215                 220

Ala Leu Glu Ala His Ala Leu Met Ile Gln Gly Leu Gln Gly Thr Asn
225                 230                 235                 240

Gln Ser Phe His Pro Phe Ile His Arg His Lys Pro His Thr Gly Gln
                245                 250                 255

Val Trp Ala Ala Asp His Met Leu Glu Leu Leu Gln Gly Ser Gln Leu
```

```
            260                 265                 270

Ser Arg Asn Glu Leu Asp Gly Ser His Asp Tyr Arg Asp Gly Asp Leu
        275                 280                 285

Ile Gln Asp Arg Tyr Ser Leu Arg Cys Leu Pro Gln Phe Leu Gly Pro
    290                 295                 300

Ile Ile Asp Gly Met Ala Phe Ile Ser His His Leu Arg Val Glu Ile
305                 310                 315                 320

Asn Ser Ala Asn Asp Asn Pro Leu Ile Asp Thr Ala Ser Ala Ala Ser
                325                 330                 335

Tyr His Gly Gly Asn Phe Leu Gly Gln Tyr Ile Gly Val Gly Met Asp
            340                 345                 350

Gln Leu Arg Tyr Tyr Met Gly Leu Met Ala Lys His Leu Asp Val Gln
        355                 360                 365

Ile Ala Leu Leu Val Ser Pro Gln Phe Asn Asn Gly Leu Pro Ala Ser
    370                 375                 380

Leu Val Gly Asn Ile Gln Arg Lys Val Asn Met Gly Leu Lys Gly Leu
385                 390                 395                 400

Gln Leu Thr Ala Asn Ser Ile Met Pro Ile Leu Thr Phe Leu Gly Asn
                405                 410                 415

Ser Leu Ala Asp Arg Phe Pro Thr His Ala Glu Gln Phe Asn Gln Asn
            420                 425                 430

Ile Asn Ser Gln Gly Phe Gly Ser Ala Asn Leu Ala Arg Gln Thr Ile
        435                 440                 445

Gln Thr Leu Gln Gln Tyr Ile Ala Ile Thr Leu Met Phe Gly Val Gln
    450                 455                 460

Ala Val Asp Leu Arg Thr His Lys Leu Ala Gly His Tyr Asn Ala Ala
465                 470                 475                 480

Glu Leu Leu Ser Pro Leu Thr Ala Lys Ile Tyr His Ala Val Arg Ser
                485                 490                 495

Ile Val Lys His Pro Pro Ser Pro Glu Arg Pro Tyr Ile Trp Asn Asp
            500                 505                 510

Asp Glu Gln Val Leu Glu Ala His Ile Ser Ala Leu Ala His Asp Ile
        515                 520                 525

Ala Asn Asp Gly Ser Leu Val Ser Ala Val Glu Gln Thr Leu Ser Gly
    530                 535                 540

Leu Arg Ser Ile Ile Leu Phe Arg
545                 550


<210> SEQ ID NO 27
<211> LENGTH: 714
<212> TYPE: PRT
<213> ORGANISM: Physcomitrella patens

<400> SEQUENCE: 27

Met His Asp Asp Asn Thr Ser Pro Tyr Cys Ile Gly Gln Leu Gly Asn
1               5                   10                  15

Gly Ala Val His Gly Ala Asp Pro Leu Asn Trp Ala Lys Thr Ala Lys
            20                  25                  30

Ala Met Glu Cys Ser His Leu Glu Glu Ile Lys Arg Met Val Asp Thr
        35                  40                  45

Tyr Gln Asn Ala Thr Gln Val Met Ile Glu Gly Ala Thr Leu Thr Val
    50                  55                  60

Pro Gln Val Ala Ala Ile Ala Arg Arg Pro Glu Val His Val Val Leu
65                  70                  75                  80
```

```
Asp Ala Ala Asn Ala Arg Ser Arg Val Asp Glu Ser Ser Asn Trp Val
                85                  90                  95

Leu Asp Arg Ile Met Gly Gly Gly Asp Ile Tyr Gly Val Thr Thr Gly
            100                 105                 110

Phe Gly Ala Thr Ser His Arg Arg Thr Gln Gln Gly Val Glu Leu Gln
        115                 120                 125

Arg Glu Leu Ile Arg Phe Leu Asn Ala Gly Val Leu Ser Lys Gly Asn
    130                 135                 140

Ser Leu Pro Ser Glu Thr Ala Arg Ala Ala Met Leu Val Arg Thr Asn
145                 150                 155                 160

Thr Leu Met Gln Gly Tyr Ser Gly Ile Arg Trp Glu Ile Leu His Ala
                165                 170                 175

Met Glu Lys Leu Leu Asn Ala His Val Thr Pro Lys Leu Pro Leu Arg
            180                 185                 190

Gly Thr Ile Thr Ala Ser Gly Asp Leu Val Pro Leu Ser Tyr Ile Ala
        195                 200                 205

Gly Leu Leu Thr Gly Arg Pro Asn Ser Lys Ala Val Thr Glu Asp Gly
    210                 215                 220

Arg Glu Val Ser Ala Leu Glu Ala Leu Arg Ile Ala Gly Val Glu Lys
225                 230                 235                 240

Pro Phe Glu Leu Ala Pro Lys Glu Gly Leu Ala Leu Val Asn Gly Thr
                245                 250                 255

Ala Val Gly Ser Ala Leu Ala Ser Thr Val Cys Tyr Asp Ala Asn Ile
            260                 265                 270

Met Val Leu Leu Ala Glu Val Leu Ser Ala Leu Phe Cys Glu Val Met
        275                 280                 285

Gln Gly Lys Pro Glu Phe Ala Asp Pro Leu Thr His Lys Leu Lys His
    290                 295                 300

His Pro Gly Gln Met Glu Ala Ala Ala Val Met Glu Trp Val Leu Asp
305                 310                 315                 320

Gly Ser Ser Phe Met Lys Ala Ala Ala Lys Phe Asn Glu Thr Asp Pro
                325                 330                 335

Leu Arg Lys Pro Lys Gln Asp Arg Tyr Ala Leu Arg Thr Ser Pro Gln
            340                 345                 350

Trp Leu Gly Pro Gln Val Glu Val Ile Arg Asn Ala Thr His Ala Ile
        355                 360                 365

Glu Arg Glu Ile Asn Ser Val Asn Asp Asn Pro Ile Ile Asp Ala Ala
    370                 375                 380

Arg Gly Ile Ala Leu His Gly Gly Asn Phe Gln Gly Thr Pro Ile Gly
385                 390                 395                 400

Val Ser Met Asp Asn Met Arg Leu Ser Leu Ala Ala Ile Ala Lys Leu
                405                 410                 415

Met Phe Ala Gln Phe Ser Glu Leu Val Asn Asp Tyr Tyr Asn Asn Gly
            420                 425                 430

Leu Pro Ser Asn Leu Ser Gly Gly Pro Asn Pro Ser Leu Asp Tyr Gly
        435                 440                 445

Met Lys Gly Ala Glu Ile Ala Met Ala Ser Tyr Leu Ser Glu Ile Asn
    450                 455                 460

Tyr Leu Ala Asn Pro Val Thr Thr His Val Gln Ser Ala Glu Gln His
465                 470                 475                 480

Asn Gln Asp Val Asn Ser Leu Gly Leu Val Ser Ala Arg Lys Thr Glu
                485                 490                 495

Glu Ala Met Glu Ile Leu Lys Leu Met Ser Ala Thr Phe Leu Val Gly
```

```
            500                 505                 510

Leu Cys Gln Ala Ile Asp Leu Arg His Val Glu Glu Thr Met Gln Ser
        515                 520                 525

Ala Val Lys Gln Val Val Thr Gln Val Ala Lys Lys Thr Leu Phe Met
    530                 535                 540

Gly Ser Asp Gly Ser Leu Leu Pro Ser Arg Phe Cys Glu Lys Glu Leu
545                 550                 555                 560

Leu Met Val Val Asp Arg Gln Pro Val Phe Ser Tyr Ile Asp Asp Ser
                565                 570                 575

Thr Ser Asp Ser Tyr Pro Leu Met Glu Lys Leu Arg Gly Val Leu Val
            580                 585                 590

Ser Arg Ala Leu Lys Ser Ala Asp Lys Glu Thr Ser Asn Ala Val Phe
        595                 600                 605

Arg Gln Ile Pro Val Phe Glu Ala Glu Leu Lys Leu Gln Leu Ser Arg
    610                 615                 620

Val Val Pro Ala Val Arg Glu Ala Tyr Asp Thr Lys Gly Leu Ser Leu
625                 630                 635                 640

Val Pro Asn Arg Ile Gln Asp Cys Arg Thr Tyr Pro Leu Tyr Lys Leu
                645                 650                 655

Val Arg Gly Asp Leu Lys Thr Gln Leu Leu Ser Gly Gln Arg Thr Val
            660                 665                 670

Ser Pro Gly Gln Glu Ile Glu Lys Val Phe Asn Ala Ile Ser Ala Gly
        675                 680                 685

Gln Leu Val Ala Pro Leu Leu Glu Cys Val Gln Gly Trp Thr Gly Thr
    690                 695                 700

Pro Gly Pro Phe Ser Ala Arg Ala Ser Cys
705                 710


<210> SEQ ID NO 28
<211> LENGTH: 529
<212> TYPE: PRT
<213> ORGANISM: Dictyostelium discoideum AX4

<400> SEQUENCE: 28

Met Ile Glu Thr Asn His Lys Asp Asn Phe Leu Ile Asp Gly Glu Asn
1               5                   10                  15

Lys Asn Leu Glu Ile Asn Asp Ile Ile Ser Ile Ser Lys Gly Glu Lys
            20                  25                  30

Asn Ile Ile Phe Thr Asn Glu Leu Leu Glu Phe Leu Gln Lys Gly Arg
        35                  40                  45

Asp Gln Leu Glu Asn Lys Leu Lys Glu Asn Val Ala Ile Tyr Gly Ile
    50                  55                  60

Asn Thr Gly Phe Gly Gly Asn Gly Asp Leu Ile Ile Pro Phe Asp Lys
65                  70                  75                  80

Leu Asp Tyr His Gln Ser Asn Leu Leu Asp Phe Leu Thr Cys Gly Thr
                85                  90                  95

Gly Asp Phe Phe Asn Asp Gln Tyr Val Arg Gly Ile Gln Phe Ile Ile
            100                 105                 110

Ile Ile Ala Leu Ser Arg Gly Trp Ser Gly Val Arg Pro Met Val Ile
        115                 120                 125

Gln Thr Leu Ala Lys His Leu Asn Lys Gly Ile Ile Pro Gln Val Pro
    130                 135                 140

Met His Gly Ser Val Gly Ala Ser Gly Asp Leu Val Pro Leu Ser Tyr
145                 150                 155                 160
```

-continued

```
Ile Ala Asn Val Leu Cys Gly Lys Gly Met Val Lys Tyr Asn Glu Lys
                165                 170                 175

Leu Met Asn Ala Ser Asp Ala Leu Lys Ile Thr Ser Ile Glu Pro Leu
            180                 185                 190

Val Leu Lys Ser Lys Glu Gly Leu Ala Leu Val Asn Gly Thr Arg Val
        195                 200                 205

Met Ser Ser Val Ser Cys Ile Ser Ile Asn Lys Phe Glu Thr Ile Phe
    210                 215                 220

Lys Ala Ala Ile Gly Ser Ile Ala Leu Ala Val Glu Gly Leu Leu Ala
225                 230                 235                 240

Ser Lys Asp His Tyr Asp Met Arg Ile His Asn Leu Lys Asn His Pro
                245                 250                 255

Gly Gln Ile Leu Ile Ala Gln Ile Leu Asn Lys Tyr Phe Asn Thr Ser
            260                 265                 270

Asp Asn Asn Thr Lys Ser Ser Asn Ile Thr Phe Asn Gln Ser Glu Asn
        275                 280                 285

Val Gln Lys Leu Asp Lys Ser Val Gln Glu Val Tyr Ser Leu Arg Cys
    290                 295                 300

Ala Pro Gln Ile Leu Gly Ile Ile Ser Glu Asn Ile Ser Asn Ala Lys
305                 310                 315                 320

Ile Val Ile Lys Arg Glu Ile Leu Ser Val Asn Asp Asn Pro Leu Ile
                325                 330                 335

Asp Pro Tyr Tyr Gly Asp Val Leu Ser Gly Gly Asn Phe Met Gly Asn
            340                 345                 350

His Ile Ala Arg Ile Met Asp Gly Ile Lys Leu Asp Ile Ser Leu Val
        355                 360                 365

Ala Asn His Leu His Ser Leu Val Ala Leu Met Met His Ser Glu Phe
    370                 375                 380

Ser Lys Gly Leu Pro Asn Ser Leu Ser Pro Asn Pro Gly Ile Tyr Gln
385                 390                 395                 400

Gly Tyr Lys Gly Met Gln Ile Ser Gln Thr Ser Leu Val Val Trp Leu
                405                 410                 415

Arg Gln Glu Ala Ala Pro Ala Cys Ile His Ser Leu Thr Thr Glu Gln
            420                 425                 430

Phe Asn Gln Asp Ile Val Ser Leu Gly Leu His Ser Ala Asn Gly Ala
        435                 440                 445

Ala Ser Met Leu Ile Lys Leu Cys Asp Ile Val Ser Met Thr Leu Ile
    450                 455                 460

Ile Ala Phe Gln Ala Ile Ser Leu Arg Met Lys Ser Ile Glu Asn Phe
465                 470                 475                 480

Lys Leu Pro Asn Lys Val Gln Lys Leu Tyr Ser Ser Ile Ile Lys Ile
                485                 490                 495

Ile Pro Ile Leu Glu Asn Asp Arg Arg Thr Asp Ile Asp Val Arg Glu
            500                 505                 510

Ile Thr Asn Ala Ile Leu Gln Asp Lys Leu Asp Phe Ile Asn Leu Asn
        515                 520                 525

Leu
```

<210> SEQ ID NO 29
<211> LENGTH: 550
<212> TYPE: PRT
<213> ORGANISM: Brevibacillus laterosporus LMG 15441

<400> SEQUENCE: 29

```
Met Ser Gln Val Ala Leu Phe Glu Gln Glu Leu Met Leu His Gly Lys
1               5                   10                  15

His Thr Leu Leu Leu Asn Gly Asn Asp Leu Thr Ile Thr Asp Val Ala
            20                  25                  30

Gln Met Ala Lys Gly Thr Phe Glu Ala Phe Thr Phe His Ile Ser Glu
        35                  40                  45

Glu Ala Asn Lys Arg Ile Glu Glu Cys Asn Glu Leu Lys His Glu Ile
    50                  55                  60

Met Asn Gln His Asn Pro Ile Tyr Gly Val Thr Thr Gly Phe Gly Asp
65                  70                  75                  80

Ser Val His Arg Gln Ile Ser Gly Glu Lys Ala Trp Asp Leu Gln Arg
                85                  90                  95

Asn Leu Ile Arg Phe Leu Ser Cys Gly Val Gly Pro Val Ala Asp Glu
            100                 105                 110

Ala Val Ala Arg Ala Thr Met Leu Ile Arg Thr Asn Cys Leu Val Lys
        115                 120                 125

Gly Asn Ser Ala Val Arg Leu Glu Val Ile His Gln Leu Ile Ala Tyr
    130                 135                 140

Met Glu Arg Gly Ile Thr Pro Ile Ile Pro Glu Arg Gly Ser Val Gly
145                 150                 155                 160

Ala Ser Gly Asp Leu Val Pro Leu Ser Tyr Leu Ala Ser Ile Leu Val
                165                 170                 175

Gly Glu Gly Lys Val Leu Tyr Lys Gly Glu Glu Arg Glu Val Ala Glu
            180                 185                 190

Ala Leu Gly Ala Glu Gly Leu Glu Pro Leu Thr Leu Glu Ala Lys Glu
        195                 200                 205

Gly Leu Ala Leu Val Asn Gly Thr Ser Phe Met Ser Ala Phe Ala Cys
    210                 215                 220

Leu Ala Tyr Ala Asp Ala Glu Glu Ile Ala Phe Ile Ala Asp Ile Cys
225                 230                 235                 240

Thr Ala Met Ala Ser Glu Ala Leu Leu Gly Asn Arg Gly His Phe Tyr
                245                 250                 255

Ser Phe Ile His Glu Gln Lys Pro His Leu Gly Gln Met Ala Ser Ala
            260                 265                 270

Lys Asn Ile Tyr Thr Leu Leu Glu Gly Ser Gln Leu Ser Lys Glu Tyr
        275                 280                 285

Ser Gln Ile Val Gly Asn Asn Glu Lys Leu Asp Ser Lys Ala Tyr Leu
    290                 295                 300

Glu Leu Thr Gln Ser Ile Gln Asp Arg Tyr Ser Ile Arg Cys Ala Pro
305                 310                 315                 320

His Val Thr Gly Val Leu Tyr Asp Thr Leu Asp Trp Val Lys Lys Trp
                325                 330                 335

Leu Glu Val Glu Ile Asn Ser Thr Asn Asp Asn Pro Ile Phe Asp Val
            340                 345                 350

Glu Thr Arg Asp Val Tyr Asn Gly Gly Asn Phe Tyr Gly Gly His Val
        355                 360                 365

Val Gln Ala Met Asp Ser Leu Lys Val Ala Val Ala Asn Ile Ala Asp
    370                 375                 380

Leu Leu Asp Arg Gln Leu Gln Leu Val Val Asp Glu Lys Phe Asn Lys
385                 390                 395                 400

Asp Leu Thr Pro Asn Leu Ile Pro Arg Phe Asn Asn Asp Asn Tyr Glu
                405                 410                 415

Ile Gly Leu His His Gly Phe Lys Gly Met Gln Ile Ala Ser Ser Ala
```

```
            420                 425                 430

Leu Thr Ala Glu Ala Leu Lys Met Ser Gly Pro Val Ser Val Phe Ser
        435                 440                 445

Arg Ser Thr Glu Ala His Asn Gln Asp Lys Val Ser Met Gly Thr Ile
    450                 455                 460

Ser Ser Arg Asp Ala Arg Thr Ile Val Glu Leu Thr Gln His Val Ala
465                 470                 475                 480

Ala Ile His Leu Ile Ala Leu Cys Gln Ala Leu Asp Leu Arg Asp Ser
                485                 490                 495

Lys Lys Met Ser Pro Gln Thr Thr Lys Ile Tyr Asn Met Ile Arg Lys
            500                 505                 510

Gln Val Pro Phe Val Glu Arg Asp Arg Ala Leu Asp Gly Asp Ile Glu
        515                 520                 525

Lys Val Val Gln Leu Ile Arg Ser Gly Asn Leu Lys Lys Glu Ile His
    530                 535                 540

Asp Gln Asn Val Asn Asp
545                 550


<210> SEQ ID NO 30
<211> LENGTH: 504
<212> TYPE: PRT
<213> ORGANISM: Rubus sp. SSL-2007

<400> SEQUENCE: 30

Met Asp Leu Leu Leu Met Glu Lys Thr Leu Leu Gly Leu Phe Val Ala
1               5                   10                  15

Val Val Val Ala Ile Thr Val Ser Lys Leu Arg Gly Lys Lys Phe Lys
            20                  25                  30

Leu Pro Pro Gly Pro Ile Pro Val Pro Val Phe Gly Asn Trp Leu Gln
        35                  40                  45

Val Gly Asp Asp Leu Asn His Arg Asn Leu Thr Glu Met Ala Lys Lys
    50                  55                  60

Phe Gly Glu Val Phe Met Leu Arg Met Gly Gln Arg Asn Leu Val Val
65                  70                  75                  80

Val Ser Ser Pro Asp Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg Tyr Gly Trp Glu Ser Glu Ala Ala Ala Val Val Glu Asp
145                 150                 155                 160

Val Lys Lys His Pro Glu Ala Ala Thr Asn Gly Met Val Leu Arg Arg
                165                 170                 175

Arg Leu Gln Leu Met Met Tyr Asn Asn Met Tyr Arg Ile Met Phe Asp
            180                 185                 190

Arg Arg Phe Glu Ser Glu Asp Asp Pro Leu Phe Val Lys Leu Lys Gly
        195                 200                 205

Leu Asn Gly Glu Arg Ser Arg Leu Ala Gln Ser Phe Glu Tyr Asn Tyr
    210                 215                 220

Gly Asp Phe Ile Pro Val Leu Arg Pro Phe Leu Arg Gly Tyr Leu Lys
225                 230                 235                 240
```

```
Ile Cys Lys Glu Val Lys Glu Lys Arg Ile Gln Leu Phe Lys Asp Tyr
                245                 250                 255

Phe Val Asp Glu Arg Lys Lys Leu Ser Ser Thr Gln Ala Thr Thr Asn
            260                 265                 270

Glu Gly Leu Lys Cys Ala Ile Asp His Ile Leu Asp Ala Gln Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Lys Lys Leu Arg Asp Glu Leu
                325                 330                 335

Asp Thr Val Leu Gly Arg Gly Val Gln Ile Thr Glu Pro Glu Ile Gln
            340                 345                 350

Lys Leu Pro Tyr Leu Gln Ala Val Val Lys Glu Thr Leu Arg Leu Arg
        355                 360                 365

Met Ala Ile Pro Leu Leu Val Pro His Met Asn Leu His Asp Ala Lys
    370                 375                 380

Leu Gly Gly Phe Asp Ile Pro Ala Glu Ser Lys Ile Leu Val Asn Ala
385                 390                 395                 400

Trp Trp Leu Ala Asn Asn Pro Ala His Trp Lys Lys Pro Glu Glu Phe
                405                 410                 415

Arg Pro Glu Arg Phe Leu Glu Glu Glu Ser Lys Val Glu Ala Asn Gly
            420                 425                 430

Asn Asp Phe Arg Tyr Leu Pro Phe Gly Val Gly Arg Arg Ser Cys Pro
        435                 440                 445

Gly Ile Ile Leu Ala Leu Pro Ile Leu Gly Ile Thr Leu Gly Arg Leu
    450                 455                 460

Val Gln Asn Phe Glu Leu Leu Pro Pro Pro Gly Gln Thr Gln Leu Asp
465                 470                 475                 480

Thr Thr Glu Lys Gly Gly Gln Phe Ser Leu His Ile Leu Lys His Ser
                485                 490                 495

Pro Ile Val Met Lys Pro Arg Thr
            500


<210> SEQ ID NO 31
<211> LENGTH: 504
<212> TYPE: PRT
<213> ORGANISM: Fragaria vesca

<400> SEQUENCE: 31

Met Asp Leu Leu Leu Leu Glu Lys Thr Leu Ile Gly Leu Phe Ile Ala
1               5                   10                  15

Ile Val Val Ala Ile Ile Val Ser Lys Leu Arg Gly Lys Lys Phe Lys
            20                  25                  30

Leu Pro Pro Gly Pro Ile Pro Val Pro Val Phe Gly Asn Trp Leu Gln
        35                  40                  45

Val Gly Asp Asp Leu Asn His Arg Asn Leu Thr Asp Met Ala Lys Lys
    50                  55                  60

Phe Gly Asp Val Phe Met Leu Arg Met Gly Gln Arg Asn Leu Val Val
65                  70                  75                  80

Val Ser Ser Pro Asp Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110
```

```
Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg His Gly Trp Glu Ala Glu Ala Ala Ala Val Val Glu Asp
145                 150                 155                 160

Val Lys Lys His Pro Glu Ala Ala Thr Ser Gly Met Val Leu Arg Arg
                165                 170                 175

Arg Leu Gln Leu Met Met Tyr Asn Asn Met Tyr Arg Ile Met Phe Asp
            180                 185                 190

Arg Arg Phe Glu Ser Glu Glu Asp Pro Leu Phe Val Lys Leu Lys Gly
        195                 200                 205

Leu Asn Gly Glu Arg Ser Arg Leu Ala Gln Ser Phe Glu Tyr Asn Tyr
    210                 215                 220

Gly Asp Phe Ile Pro Val Leu Arg Pro Phe Leu Arg Gly Tyr Leu Lys
225                 230                 235                 240

Ile Cys Lys Glu Val Lys Glu Lys Arg Ile Gln Leu Phe Lys Asp Tyr
                245                 250                 255

Phe Val Asp Glu Arg Lys Lys Leu Ala Ser Thr Gln Val Thr Thr Asn
            260                 265                 270

Glu Gly Leu Lys Cys Ala Ile Asp His Ile Leu Asp Ala Gln Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Lys Lys Leu Arg Asp Glu Leu
                325                 330                 335

Asp Thr Val Leu Gly His Gly Val Gln Val Thr Glu Pro Glu Leu His
            340                 345                 350

Lys Leu Pro Tyr Leu Gln Ala Val Val Lys Glu Thr Leu Arg Leu Arg
        355                 360                 365

Met Ala Ile Pro Leu Leu Val Pro His Met Asn Leu His Asp Ala Lys
    370                 375                 380

Leu Gly Gly Phe Asp Ile Pro Ala Glu Ser Lys Ile Leu Val Asn Ala
385                 390                 395                 400

Trp Trp Leu Ala Asn Asn Pro Ala His Trp Lys Lys Pro Glu Glu Phe
                405                 410                 415

Arg Pro Glu Arg Phe Leu Glu Glu Glu Ser Lys Val Glu Ala Asn Gly
            420                 425                 430

Asn Asp Phe Arg Tyr Leu Pro Phe Gly Val Gly Arg Arg Ser Cys Pro
        435                 440                 445

Gly Ile Ile Leu Ala Leu Pro Ile Leu Gly Val Thr Leu Gly Arg Leu
    450                 455                 460

Val Gln Asn Phe Glu Met Leu Pro Pro Pro Gly Gln Thr Gln Leu Asp
465                 470                 475                 480

Thr Thr Glu Lys Gly Gly Gln Phe Ser Leu His Ile Leu Lys His Ser
                485                 490                 495

Thr Ile Val Met Lys Pro Arg Ala
            500
```

<210> SEQ ID NO 32
<211> LENGTH: 505

```
<212> TYPE: PRT
<213> ORGANISM: Solanum tuberosum

<400> SEQUENCE: 32

Met Asp Leu Leu Leu Leu Glu Lys Thr Leu Ile Gly Leu Phe Phe Ala
1               5                   10                  15

Ile Leu Ile Ala Ile Ile Val Ser Lys Leu Arg Ser Lys Arg Phe Lys
            20                  25                  30

Leu Pro Pro Gly Pro Ile Pro Val Pro Val Phe Gly Asn Trp Leu Gln
        35                  40                  45

Val Gly Asp Asp Leu Asn His Arg Asn Leu Thr Glu Tyr Ala Lys Lys
    50                  55                  60

Phe Gly Asp Val Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg Gly Gly Trp Glu Ser Glu Ala Ala Ser Val Val Glu Asp
145                 150                 155                 160

Val Lys Lys Asn Pro Glu Ser Ala Thr Asn Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Val Lys Leu Arg Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Lys Glu Val Lys Glu Lys Arg Leu Lys Leu Phe Lys Asp Tyr
                245                 250                 255

Phe Val Asp Glu Arg Lys Lys Leu Ala Asn Thr Lys Ser Met Asp Ser
            260                 265                 270

Asn Ala Leu Lys Cys Ala Ile Asp His Ile Leu Glu Ala Gln Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro His Ile Gln Lys Lys Leu Arg Asp Glu Ile
                325                 330                 335

Asp Thr Val Leu Gly Pro Gly Met Gln Val Thr Glu Pro Asp Met Pro
            340                 345                 350

Lys Leu Pro Tyr Leu Gln Ala Val Ile Lys Glu Thr Leu Arg Leu Arg
        355                 360                 365

Met Ala Ile Pro Leu Leu Val Pro His Met Asn Leu His Asp Ala Lys
    370                 375                 380

Leu Ala Gly Tyr Asp Ile Pro Ala Glu Ser Lys Ile Leu Val Asn Ala
385                 390                 395                 400
```

```
Trp Trp Leu Ala Asn Asn Pro Ala His Trp Lys Lys Pro Glu Glu Phe
                405                 410                 415

Arg Pro Glu Arg Phe Phe Glu Glu Glu Lys His Val Glu Ala Asn Gly
            420                 425                 430

Asn Asp Phe Arg Phe Leu Pro Phe Gly Val Gly Arg Arg Ser Cys Pro
        435                 440                 445

Gly Ile Ile Leu Ala Leu Pro Ile Leu Gly Ile Thr Leu Gly Arg Leu
    450                 455                 460

Val Gln Asn Phe Glu Met Leu Pro Pro Pro Gly Gln Ser Lys Leu Asp
465                 470                 475                 480

Thr Ser Glu Lys Gly Gly Gln Phe Ser Leu His Ile Leu Lys His Ser
                485                 490                 495

Thr Ile Val Met Lys Pro Arg Ser Phe
            500                 505


<210> SEQ ID NO 33
<211> LENGTH: 544
<212> TYPE: PRT
<213> ORGANISM: Daucus carota

<400> SEQUENCE: 33

Met Gly Asp Cys Ala Ala Pro Lys Gln Glu Ile Ile Phe Arg Ser Lys
1               5                   10                  15

Leu Pro Asp Ile Tyr Ile Pro Lys His Leu Pro Leu His Ser Tyr Cys
            20                  25                  30

Phe Glu Asn Ile Ser Lys Val Ser Asp Arg Ala Cys Leu Ile Asn Gly
        35                  40                  45

Ala Thr Gly Glu Thr Phe Ser Tyr Ala Gln Val Glu Leu Ile Ser Arg
    50                  55                  60

Arg Val Ala Ser Gly Leu Asn Lys Leu Gly Ile His Gln Gly Asp Thr
65                  70                  75                  80

Met Met Ile Leu Leu Pro Asn Thr Pro Glu Tyr Phe Phe Ala Phe Leu
                85                  90                  95

Gly Ala Ser Tyr Arg Gly Ala Val Ser Thr Met Ala Asn Pro Phe Phe
            100                 105                 110

Thr Ser Pro Glu Val Ile Lys Gln Leu Lys Ala Ser Gln Ala Lys Leu
        115                 120                 125

Ile Ile Thr Gln Ala Cys Tyr Val Glu Lys Val Lys Glu Tyr Ala Ala
    130                 135                 140

Glu Asn Asn Ile Thr Val Val Cys Ile Asp Glu Ala Pro Arg Asp Cys
145                 150                 155                 160

Leu His Phe Thr Thr Leu Met Glu Ala Asp Glu Ala Glu Met Pro Glu
                165                 170                 175

Val Ala Ile Asp Ser Asp Asp Val Val Ala Leu Pro Tyr Ser Ser Gly
            180                 185                 190

Thr Thr Gly Leu Pro Lys Gly Val Met Leu Thr His Lys Gly Leu Val
        195                 200                 205

Thr Ser Val Ala Gln Arg Val Asp Gly Glu Asn Pro Asn Leu Tyr Ile
    210                 215                 220

His Ser Glu Asp Val Met Ile Cys Ile Leu Pro Leu Phe His Ile Tyr
225                 230                 235                 240

Ser Leu Asn Ala Val Leu Cys Cys Gly Leu Arg Ala Gly Ala Thr Ile
                245                 250                 255

Leu Ile Met Gln Lys Phe Asp Ile Val Pro Phe Leu Glu Leu Ile Gln
```

```
            260                 265                 270

Lys Tyr Lys Val Thr Ile Gly Pro Phe Val Pro Pro Ile Val Leu Ala
        275                 280                 285

Ile Ala Lys Ser Pro Val Val Asp Asn Tyr Asp Leu Ser Ser Val Arg
    290                 295                 300

Thr Val Met Ser Gly Ala Ala Pro Leu Gly Lys Glu Leu Glu Asp Ala
305                 310                 315                 320

Val Arg Ala Lys Phe Pro Asn Ala Lys Leu Gly Gln Gly Tyr Gly Met
                325                 330                 335

Thr Glu Ala Gly Pro Val Leu Ala Met Cys Leu Ala Phe Ala Lys Glu
            340                 345                 350

Pro Tyr Glu Ile Lys Ser Gly Ala Cys Gly Thr Val Val Arg Asn Ala
        355                 360                 365

Glu Met Lys Ile Val Asp Pro Glu Thr His Ala Ser Leu Pro Arg Asn
    370                 375                 380

Gln Ser Gly Glu Ile Cys Ile Arg Gly Asp Gln Ile Met Lys Gly Tyr
385                 390                 395                 400

Leu Asn Asp Pro Glu Ser Thr Lys Thr Thr Ile Asp Glu Glu Gly Trp
                405                 410                 415

Leu His Thr Gly Asp Ile Gly Phe Ile Asp Glu Asp Asp Glu Leu Phe
            420                 425                 430

Ile Val Asp Arg Leu Lys Glu Ile Ile Lys Tyr Lys Gly Phe Gln Val
        435                 440                 445

Ala Pro Ala Glu Ile Glu Ala Leu Leu Leu Thr His Pro Thr Ile Ser
    450                 455                 460

Asp Ala Ala Val Val Pro Met Ile Asp Glu Lys Ala Gly Glu Val Pro
465                 470                 475                 480

Val Ala Phe Val Val Arg Leu Asn Gly Ser Thr Thr Thr Glu Glu Glu
                485                 490                 495

Ile Lys Gln Phe Val Ser Lys Gln Val Val Phe Tyr Lys Arg Val Phe
            500                 505                 510

Arg Val Phe Phe Val Asp Ala Ile Pro Lys Ser Pro Ser Gly Lys Ile
        515                 520                 525

Leu Arg Lys Glu Leu Arg Ala Arg Ile Ala Ser Gly Asp Leu Pro Lys
    530                 535                 540
```

<210> SEQ ID NO 34
<211> LENGTH: 543
<212> TYPE: PRT
<213> ORGANISM: Striga asiatica

<400> SEQUENCE: 34

```
Met Glu Pro Thr Thr Lys Ser Lys Asp Ile Ile Phe Arg Ser Lys Leu
1               5                   10                  15

Pro Asp Ile Tyr Ile Pro Lys His Leu Pro Leu His Thr Tyr Cys Phe
            20                  25                  30

Glu Asn Ile Ser Arg Phe Gly Ser Arg Pro Cys Leu Ile Asn Gly Ser
        35                  40                  45

Thr Gly Glu Ile Leu Thr Tyr Asp Gln Val Glu Leu Ala Ser Arg Arg
    50                  55                  60

Val Gly Ser Gly Leu His Arg Leu Gly Ile Arg Gln Gly Asp Thr Ile
65                  70                  75                  80

Met Leu Leu Leu Pro Asn Ser Pro Glu Phe Val Leu Ala Phe Leu Gly
                85                  90                  95
```

```
Ala Ser His Ile Gly Ala Val Ser Thr Met Ala Asn Pro Phe Phe Thr
            100                 105                 110

Pro Ala Glu Val Val Lys Gln Ala Ala Ala Ser Arg Ala Lys Leu Ile
        115                 120                 125

Val Thr Gln Ala Cys His Val Asp Lys Val Arg Asp Tyr Ala Ala Glu
    130                 135                 140

His Gly Val Lys Val Val Cys Val Asp Gly Ala Pro Pro Glu Glu Cys
145                 150                 155                 160

Leu Pro Phe Ser Glu Val Ala Ser Gly Asp Glu Ala Glu Leu Pro Ala
                165                 170                 175

Val Lys Ile Ser Pro Asp Asp Val Val Ala Leu Pro Tyr Ser Ser Gly
            180                 185                 190

Thr Thr Gly Leu Pro Lys Gly Val Met Leu Thr His Lys Gly Leu Val
        195                 200                 205

Thr Ser Val Ala Gln Gln Val Asp Gly Glu Asn Pro Asn Leu Tyr Ile
    210                 215                 220

His Ser Asp Asp Val Ile Met Cys Val Leu Pro Leu Phe His Ile Tyr
225                 230                 235                 240

Ser Leu Asn Ser Ile Met Leu Cys Gly Leu Arg Val Gly Ala Ala Ile
                245                 250                 255

Leu Ile Met Gln Lys Phe Glu Ile Val Pro Phe Leu Glu Leu Ile Gln
            260                 265                 270

Arg Tyr Arg Val Thr Ile Gly Pro Phe Val Pro Pro Ile Val Leu Ala
        275                 280                 285

Ile Glu Lys Ser Pro Val Val Glu Lys Tyr Asp Leu Ser Ser Val Arg
    290                 295                 300

Thr Val Met Ser Gly Ala Ala Pro Leu Gly Arg Glu Leu Glu Asp Ala
305                 310                 315                 320

Val Arg Leu Lys Phe Pro Asn Ala Lys Leu Gly Gln Gly Tyr Gly Met
                325                 330                 335

Thr Glu Ala Gly Pro Val Leu Ala Met Cys Leu Ala Phe Ala Lys Glu
            340                 345                 350

Pro Phe Glu Ile Lys Ser Gly Ala Cys Gly Thr Val Val Arg Asn Ala
        355                 360                 365

Glu Met Lys Ile Val Asp Thr Glu Thr Gly Ala Ser Leu Gly Arg Asn
    370                 375                 380

Gln Pro Gly Glu Ile Cys Ile Arg Gly Asp Gln Ile Met Lys Gly Tyr
385                 390                 395                 400

Leu Asn Asp Pro Glu Ser Thr Glu Arg Thr Ile Asp Lys Glu Gly Trp
                405                 410                 415

Leu His Thr Gly Asp Ile Gly Phe Ile Asp Asp Asp Asp Glu Leu Phe
            420                 425                 430

Ile Val Asp Arg Leu Lys Glu Ile Ile Lys Tyr Lys Gly Phe Gln Val
        435                 440                 445

Ala Pro Ala Glu Leu Glu Ala Leu Leu Leu Asn His Pro Asn Ile Ser
    450                 455                 460

Asp Ala Ala Val Val Ser Met Lys Asp Glu Gln Ala Gly Glu Val Pro
465                 470                 475                 480

Val Ala Tyr Val Val Lys Ser Asn Gly Ser Thr Ile Thr Glu Asp Glu
                485                 490                 495

Ile Lys Gln Phe Val Ser Lys Gln Val Ile Phe Tyr Lys Arg Ile Asn
            500                 505                 510

Arg Val Phe Phe Ile Asp Ala Ile Pro Lys Ser Pro Ser Gly Lys Ile
```

```
        515                 520                 525

Leu Arg Lys Asp Leu Arg Ala Arg Leu Ala Ala Gly Val Pro Asn
    530                 535                 540


<210> SEQ ID NO 35
<211> LENGTH: 545
<212> TYPE: PRT
<213> ORGANISM: Capsicum annuum

<400> SEQUENCE: 35

Met Pro Met Glu Asn Glu Ala Lys Gln Gly Asp Ile Ile Phe Arg Ser
1               5                   10                  15

Lys Leu Pro Asp Ile Tyr Ile Pro Asn His Leu Ser Leu His Ser Tyr
            20                  25                  30

Cys Phe Glu Asn Ile Ser Glu Phe Ser Ser Arg Pro Cys Leu Ile Asn
        35                  40                  45

Gly Ala Asn Asn Gln Ile Tyr Thr Tyr Ala Asp Val Glu Leu Asn Ser
    50                  55                  60

Arg Lys Val Ala Ala Gly Leu His Lys Gln Phe Gly Ile Gln Gln Lys
65                  70                  75                  80

Asp Thr Ile Met Ile Leu Leu Pro Asn Ser Pro Glu Phe Val Phe Ala
                85                  90                  95

Phe Leu Gly Ala Ser Tyr Leu Gly Ala Ile Ser Thr Met Ala Asn Pro
            100                 105                 110

Leu Phe Thr Pro Ala Glu Val Val Lys Gln Val Lys Ala Ser Asn Ala
        115                 120                 125

Glu Ile Ile Val Thr Gln Ala Cys His Val Asn Lys Val Lys Asp Tyr
    130                 135                 140

Ala Leu Glu Asn Asp Val Lys Ile Val Cys Ile Asp Ser Ala Pro Glu
145                 150                 155                 160

Gly Cys Val His Phe Ser Glu Leu Ile Gln Ala Asp Glu His Asp Ile
                165                 170                 175

Pro Glu Val Gln Ile Lys Pro Asp Asp Val Val Ala Leu Pro Tyr Ser
            180                 185                 190

Ser Gly Thr Thr Gly Leu Pro Lys Gly Val Met Leu Thr His Lys Gly
        195                 200                 205

Leu Val Thr Ser Val Ala Gln Gln Val Asp Gly Glu Asn Pro Asn Leu
    210                 215                 220

Tyr Ile His Ser Glu Asp Val Met Leu Cys Val Leu Pro Leu Phe His
225                 230                 235                 240

Ile Tyr Ser Leu Asn Ser Val Leu Leu Cys Gly Leu Arg Val Gly Ala
                245                 250                 255

Ala Ile Leu Ile Met Gln Lys Phe Asp Ile Val Pro Phe Leu Glu Leu
            260                 265                 270

Ile Gln Asn Tyr Lys Val Thr Ile Gly Pro Phe Val Pro Pro Ile Val
        275                 280                 285

Leu Ala Ile Ala Lys Ser Pro Met Val Asp Asn Tyr Asp Leu Ser Ser
    290                 295                 300

Val Arg Thr Val Met Ser Gly Ala Ala Pro Leu Gly Lys Glu Leu Glu
305                 310                 315                 320

Asp Thr Val Arg Ala Lys Phe Pro Asn Ala Lys Leu Gly Gln Gly Tyr
                325                 330                 335

Gly Met Thr Glu Ala Gly Pro Val Leu Ala Met Cys Leu Ala Phe Ala
            340                 345                 350
```

```
Lys Glu Pro Phe Glu Ile Lys Ser Gly Ala Cys Gly Thr Val Val Arg
        355                 360                 365

Asn Ala Glu Met Lys Ile Val Asp Pro Asp Thr Gly Asn Ser Leu His
    370                 375                 380

Arg Asn Gln Ser Gly Glu Ile Cys Ile Arg Gly Asp Gln Ile Met Lys
385                 390                 395                 400

Gly Tyr Leu Asn Asp Pro Glu Ala Thr Ala Gly Thr Ile Asp Lys Glu
                405                 410                 415

Gly Trp Leu His Thr Gly Asp Ile Gly Tyr Ile Asp Asn Asp Asp Glu
            420                 425                 430

Leu Phe Ile Val Asp Arg Leu Lys Glu Leu Ile Lys Tyr Lys Gly Phe
        435                 440                 445

Gln Val Ala Pro Ala Glu Leu Glu Ala Leu Leu Leu Asn His Pro Asn
    450                 455                 460

Ile Ser Asp Ala Ala Val Val Pro Met Lys Asp Glu Gln Ala Gly Glu
465                 470                 475                 480

Val Pro Val Ala Phe Val Val Arg Ser Asn Gly Ser Thr Ile Thr Glu
                485                 490                 495

Asp Glu Val Lys Glu Phe Ile Ser Lys Gln Val Ile Phe Tyr Lys Arg
            500                 505                 510

Ile Lys Arg Val Phe Phe Val Asp Ala Val Pro Lys Ser Pro Ser Gly
        515                 520                 525

Lys Ile Leu Arg Lys Asp Leu Arg Ala Lys Leu Ala Ala Gly Phe Pro
    530                 535                 540

Asn
545


<210> SEQ ID NO 36
<211> LENGTH: 542
<212> TYPE: PRT
<213> ORGANISM: Camellia sinensis

<400> SEQUENCE: 36

Met Asp Thr Lys Thr Thr Gln Gln Glu Ile Ile Phe Arg Ser Lys Leu
1               5                   10                  15

Pro Asp Ile Tyr Ile Pro Lys Gln Leu Pro Leu His Ser Tyr Cys Phe
            20                  25                  30

Glu Asn Ile Ser Gln Phe Ser Ser Lys Pro Cys Leu Ile Asn Gly Ser
        35                  40                  45

Thr Gly Lys Val Tyr Thr Tyr Ser Asp Val Glu Leu Thr Ser Arg Lys
    50                  55                  60

Val Ala Ala Gly Phe His Asn Leu Gly Ile Gln Gln Arg Asp Thr Ile
65                  70                  75                  80

Met Leu Leu Leu Pro Asn Cys Pro Glu Phe Val Phe Ala Phe Leu Gly
                85                  90                  95

Ala Ser Tyr Leu Gly Ala Ile Ile Thr Met Ala Asn Pro Phe Phe Thr
            100                 105                 110

Pro Ala Glu Thr Ile Lys Gln Ala Lys Ala Ser Asn Ser Lys Leu Ile
        115                 120                 125

Ile Thr Gln Ser Ser Tyr Thr Ser Lys Val Leu Asp Tyr Ser Ser Glu
    130                 135                 140

Asn Asn Val Lys Ile Ile Cys Ile Asp Ser Pro Pro Asp Gly Cys Leu
145                 150                 155                 160

His Phe Ser Glu Leu Ile Gln Ser Asn Glu Thr Gln Leu Pro Glu Val
                165                 170                 175
```

```
Glu Ile Asp Ser Asn Glu Val Val Ala Leu Pro Tyr Ser Ser Gly Thr
            180                 185                 190

Thr Gly Leu Pro Lys Gly Val Met Leu Thr His Lys Gly Leu Val Thr
        195                 200                 205

Ser Val Ala Gln Gln Val Asp Gly Glu Asn Pro Asn Leu Tyr Ile His
    210                 215                 220

Ser Glu Asp Met Met Met Cys Val Leu Pro Leu Phe His Ile Tyr Ser
225                 230                 235                 240

Leu Asn Ser Val Leu Leu Cys Gly Leu Arg Val Gly Ala Ala Ile Leu
                245                 250                 255

Ile Met Gln Lys Phe Glu Ile Gly Ser Phe Leu Lys Leu Ile Gln Arg
            260                 265                 270

Tyr Lys Val Thr Ile Gly Pro Phe Val Pro Pro Ile Val Leu Ala Ile
        275                 280                 285

Ala Lys Ser Glu Val Val Asp Asp Tyr Asp Leu Ser Thr Ile Arg Thr
    290                 295                 300

Met Met Ser Gly Ala Ala Pro Leu Gly Lys Glu Leu Glu Asp Ala Val
305                 310                 315                 320

Arg Ala Lys Phe Pro His Ala Lys Leu Gly Gln Gly Tyr Gly Met Thr
                325                 330                 335

Glu Ala Gly Pro Val Leu Ala Met Cys Leu Ala Phe Ala Lys Lys Pro
            340                 345                 350

Phe Glu Ile Lys Ser Gly Ala Cys Gly Thr Val Val Arg Asn Ala Glu
        355                 360                 365

Met Lys Ile Val Asp Pro Asp Ala Gly Phe Ser Leu Pro Arg Asn Gln
    370                 375                 380

Pro Gly Glu Ile Cys Ile Arg Gly Asp Gln Ile Met Lys Gly Tyr Leu
385                 390                 395                 400

Asn Asp Pro Glu Ala Thr Glu Arg Thr Ile Asp Lys Gln Gly Trp Leu
                405                 410                 415

His Thr Gly Asp Ile Gly Tyr Ile Asp Asp Asp Asp Glu Leu Phe Ile
            420                 425                 430

Val Asp Arg Leu Lys Glu Leu Ile Lys Tyr Lys Gly Phe Gln Val Ala
        435                 440                 445

Pro Ala Glu Leu Glu Ala Leu Leu Leu Asn His Pro Thr Ile Ser Asp
    450                 455                 460

Ala Ala Val Val Pro Met Lys Asp Glu Ser Ala Gly Glu Val Pro Val
465                 470                 475                 480

Ala Phe Val Val Arg Thr Asn Gly Phe Glu Val Thr Glu Asn Glu Ile
                485                 490                 495

Lys Lys Tyr Ile Ser Glu Gln Val Val Phe Tyr Lys Lys Ile Asn Arg
            500                 505                 510

Val Tyr Phe Val Asp Ala Ile Pro Lys Ala Pro Ser Gly Lys Ile Leu
        515                 520                 525

Arg Lys Asp Leu Arg Ala Arg Leu Ala Ala Gly Ile Pro Ser
    530                 535                 540
```

<210> SEQ ID NO 37
<211> LENGTH: 389
<212> TYPE: PRT
<213> ORGANISM: Capsicum annuum

<400> SEQUENCE: 37

```
Met Val Thr Val Glu Glu Tyr Arg Lys Ala Gln Arg Ala Glu Gly Pro
```

```
1               5                   10                  15

Ala Thr Val Met Ala Ile Gly Thr Ala Thr Pro Ser Asn Cys Val Asp
            20                  25                  30

Gln Ser Thr Tyr Pro Asp Tyr Tyr Phe Arg Ile Thr Asn Ser Glu His
        35                  40                  45

Lys Thr Glu Leu Lys Glu Lys Phe Lys Arg Met Cys Glu Lys Ser Met
    50                  55                  60

Ile Lys Thr Arg Tyr Met His Leu Thr Glu Glu Ile Leu Lys Glu Asn
65                  70                  75                  80

Pro Asn Met Cys Ala Tyr Met Ala Pro Ser Leu Asp Ala Arg Gln Asp
                85                  90                  95

Ile Val Val Val Glu Val Pro Lys Leu Gly Lys Glu Ala Ala Gln Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Cys Asp Tyr Gln Leu
    130                 135                 140

Ala Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Glu Ser His Leu Asp Ser
        195                 200                 205

Leu Val Gly Gln Ala Leu Phe Gly Asp Gly Ala Ala Ala Ile Ile Met
    210                 215                 220

Gly Ser Asp Pro Ile Pro Gly Val Glu Arg Pro Leu Phe Gln Leu Val
225                 230                 235                 240

Ser Ala Ala Gln Thr Leu Leu Pro Asp Ser Glu Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Val Glu Ala Phe Gln
        275                 280                 285

Pro Leu Gly Ile Ser Asp Trp Asn Ser Leu Phe Trp Ile Ala His Pro
    290                 295                 300

Gly Gly Pro Ala Ile Leu Asp Gln Val Glu Leu Lys Leu Gly Leu Lys
305                 310                 315                 320

Pro Glu Lys Leu Lys Ala Thr Arg Glu Val Leu Ser Asn Tyr Gly Asn
                325                 330                 335

Met Ser Ser Ala Cys Val Leu Phe Ile Leu Asp Glu Met Arg Lys Ala
            340                 345                 350

Ser Thr Lys Glu Gly Leu Gly Thr Ser Gly Glu Gly Leu Glu Trp Gly
        355                 360                 365

Val Leu Phe Gly Phe Gly Pro Gly Leu Thr Val Glu Thr Val Val Leu
    370                 375                 380

His Ser Val Ala Ile
385
```

<210> SEQ ID NO 38
<211> LENGTH: 389
<212> TYPE: PRT
<213> ORGANISM: Rosa chinensis

<400> SEQUENCE: 38

```
Met Val Thr Val Glu Glu Val Arg Lys Ala Gln Arg Ala Glu Gly Pro
1               5                   10                  15

Ala Thr Val Leu Ala Ile Gly Thr Ala Thr Pro Pro Asn Cys Ile Asp
            20                  25                  30

Gln Ser Thr Tyr Pro Asp Tyr Tyr Phe Arg Ile Thr Lys Ser Glu His
        35                  40                  45

Lys Ala Glu Leu Lys Glu Lys Phe Gln Arg Met Cys Asp Lys Ser Met
    50                  55                  60

Ile Lys Lys Arg Tyr Met Tyr Leu Thr Glu Glu Ile Leu Lys Glu Asn
65                  70                  75                  80

Pro Ser Met Cys Glu Tyr Met Ala Pro Ser Leu Asp Ala Arg Gln Asp
                85                  90                  95

Met Val Val Val Glu Ile Pro Lys Leu Gly Lys Glu Ala Ala Thr Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Ile Ile Val
    210                 215                 220

Gly Ser Asp Pro Leu Pro Glu Val Glu Lys Pro Leu Phe Glu Leu Val
225                 230                 235                 240

Ser Ala Ala Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Asn Glu Ala Phe Lys
        275                 280                 285

Pro Leu Asn Ile Thr Asp Trp Asn Ser Leu Phe Trp Ile Ala His Pro
    290                 295                 300

Gly Gly Pro Ala Ile Leu Asp Gln Val Glu Ala Lys Leu Gly Leu Lys
305                 310                 315                 320

Pro Glu Lys Leu Glu Ala Thr Arg His Ile Leu Ser Glu Tyr Gly Asn
                325                 330                 335

Met Ser Ser Ala Cys Val Leu Phe Ile Leu Asp Glu Val Arg Arg Lys
            340                 345                 350

Ser Ala Ala Asn Gly His Lys Thr Thr Gly Glu Gly Leu Glu Trp Gly
        355                 360                 365

Val Leu Phe Gly Phe Gly Pro Gly Leu Thr Val Glu Thr Val Val Leu
    370                 375                 380

His Ser Val Ala Ala
385
```

<210> SEQ ID NO 39
<211> LENGTH: 393
<212> TYPE: PRT
<213> ORGANISM: Morus alba var. multicaulis

<400> SEQUENCE: 39

```
Met Ser Met Thr Pro Ser Val His Glu Ile Arg Lys Ala Gln Arg Ser
1               5                   10                  15

Glu Gly Pro Ala Thr Val Leu Ser Ile Gly Thr Ala Thr Pro Thr Asn
            20                  25                  30

Phe Val Pro Gln Ala Asp Tyr Pro Asp Tyr Tyr Phe Arg Ile Thr Asn
        35                  40                  45

Ser Asp His Met Thr Asp Leu Lys Asp Lys Phe Lys Arg Met Cys Glu
    50                  55                  60

Lys Ser Met Ile Thr Lys Arg His Met Tyr Leu Thr Glu Glu Ile Leu
65                  70                  75                  80

Lys Glu Asn Pro Lys Met Cys Glu Tyr Met Ala Pro Ser Leu Asp Ala
                85                  90                  95

Arg Gln Asp Ile Val Val Val Glu Val Pro Lys Leu Gly Lys Glu Ala
            100                 105                 110

Ala Ala Lys Ala Ile Lys Glu Trp Gly Gln Pro Lys Ser Lys Ile Thr
        115                 120                 125

His Leu Ile Phe Cys Thr Thr Ser Gly Val Asp Met Pro Gly Ala Asp
    130                 135                 140

Tyr Gln Leu Thr Lys Leu Leu Gly Leu Arg Pro Ser Val Lys Arg Phe
145                 150                 155                 160

Met Met Tyr Gln Gln Gly Cys Phe Ala Gly Gly Thr Val Leu Arg Leu
                165                 170                 175

Ala Lys Asp Leu Ala Glu Asn Asn Lys Gly Ala Arg Val Leu Val Val
            180                 185                 190

Cys Ser Glu Ile Thr Ala Val Thr Phe Arg Gly Pro Ser His Thr His
        195                 200                 205

Leu Asp Ser Leu Val Gly Gln Ala Leu Phe Gly Asp Gly Ala Ala Ala
    210                 215                 220

Val Ile Leu Gly Ala Asp Pro Asp Thr Ser Val Glu Arg Pro Ile Phe
225                 230                 235                 240

Glu Leu Val Ser Ala Ala Gln Thr Ile Leu Pro Asp Ser Glu Gly Ala
                245                 250                 255

Ile Asp Gly His Leu Arg Glu Val Gly Leu Thr Phe His Leu Leu Lys
            260                 265                 270

Asp Val Pro Gly Leu Ile Ser Lys Asn Ile Glu Lys Ser Leu Val Glu
        275                 280                 285

Ala Phe Thr Pro Ile Gly Ile Ser Asp Trp Asn Ser Ile Phe Trp Ile
    290                 295                 300

Ala His Pro Gly Gly Pro Ala Ile Leu Asp Gln Val Glu Ala Lys Leu
305                 310                 315                 320

Gly Leu Lys Gln Glu Lys Leu Ser Ala Thr Arg His Val Leu Ser Glu
                325                 330                 335

Tyr Gly Asn Met Ser Ser Ala Cys Val Leu Phe Ile Leu Asp Glu Val
            340                 345                 350

Arg Lys Lys Ser Val Glu Glu Gly Lys Ala Thr Thr Gly Glu Gly Leu
        355                 360                 365

Glu Trp Gly Val Leu Phe Gly Phe Gly Pro Gly Leu Thr Val Glu Thr
    370                 375                 380
```

```
Ile Val Leu His Ser Leu Pro Ala Val
385                 390


<210> SEQ ID NO 40
<211> LENGTH: 395
<212> TYPE: PRT
<213> ORGANISM: Dendrobium catenatum

<400> SEQUENCE: 40

Met Ala Pro Pro Ala Met Glu Glu Ile Arg Arg Ala Gln Arg Ala Glu
1               5                   10                  15

Gly Pro Ala Thr Val Leu Ala Ile Gly Ala Ser Thr Pro Pro Asn Ala
            20                  25                  30

Leu Tyr Gln Ala Asp Tyr Pro Asp Tyr Tyr Phe Arg Ile Thr Lys Ser
        35                  40                  45

Glu His Leu Thr Glu Leu Lys Glu Lys Phe Lys Gln Met Cys Asp Lys
    50                  55                  60

Ser Met Ile Arg Lys Arg Tyr Met Tyr Leu Thr Glu Glu Ile Leu Lys
65                  70                  75                  80

Glu Asn Pro Asn Ile Cys Ala Phe Met Ala Pro Ser Leu Asp Ala Arg
                85                  90                  95

Gln Asp Ile Val Val Thr Glu Val Pro Lys Leu Ala Lys Glu Ala Ser
            100                 105                 110

Ala Arg Ala Ile Lys Glu Trp Gly Gln Pro Lys Ser Arg Ile Thr His
        115                 120                 125

Leu Ile Phe Cys Thr Thr Ser Gly Val Asp Met Pro Gly Ala Asp Tyr
    130                 135                 140

Gln Leu Thr Arg Leu Leu Gly Leu Arg Pro Ser Val Asn Arg Ile Met
145                 150                 155                 160

Leu Tyr Gln Gln Gly Cys Phe Ala Gly Gly Thr Val Leu Arg Leu Ala
                165                 170                 175

Lys Asp Leu Ala Glu Asn Asn Ala Gly Ala Arg Val Leu Val Val Cys
            180                 185                 190

Ser Glu Ile Thr Ala Val Thr Phe Arg Gly Pro Ser Glu Ser His Leu
        195                 200                 205

Asp Ser Leu Val Gly Gln Ala Leu Phe Gly Asp Gly Ala Ala Ala Ile
    210                 215                 220

Ile Val Gly Ser Asp Pro Asp Leu Thr Thr Glu Arg Pro Leu Phe Gln
225                 230                 235                 240

Leu Val Ser Ala Ser Gln Thr Ile Leu Pro Glu Ser Glu Gly Ala Ile
                245                 250                 255

Asp Gly His Leu Arg Glu Met Gly Leu Thr Phe His Leu Leu Lys Asp
            260                 265                 270

Val Pro Gly Leu Ile Ser Lys Asn Ile Gln Lys Ser Leu Val Glu Thr
        275                 280                 285

Phe Lys Pro Leu Gly Ile His Asp Trp Asn Ser Ile Phe Trp Ile Ala
    290                 295                 300

His Pro Gly Gly Pro Ala Ile Leu Asp Gln Val Glu Ile Lys Leu Gly
305                 310                 315                 320

Leu Lys Glu Glu Lys Leu Ala Ser Ser Arg Asn Val Leu Ala Glu Tyr
                325                 330                 335

Gly Asn Met Ser Ser Ala Cys Val Leu Phe Ile Leu Asp Glu Met Arg
            340                 345                 350

Arg Arg Ser Ala Glu Ala Gly Gln Ala Thr Thr Gly Glu Gly Leu Glu
        355                 360                 365
```

```
Trp Gly Val Leu Phe Gly Phe Gly Pro Gly Leu Thr Val Glu Thr Val
    370                 375                 380

Val Leu Arg Ser Val Pro Ile Ala Gly Ala Val
385                 390                 395


<210> SEQ ID NO 41
<211> LENGTH: 169
<212> TYPE: PRT
<213> ORGANISM: Trifolium pratense

<400> SEQUENCE: 41

Met Ser Ala Ile Thr Ala Ile His Val Glu Asn Ile Glu Phe Pro Ala
1               5                   10                  15

Val Ile Thr Ser Pro Val Thr Gly Lys Ser Tyr Phe Leu Gly Gly Ala
            20                  25                  30

Gly Glu Arg Gly Leu Thr Ile Glu Gly Asn Phe Ile Lys Phe Thr Ala
        35                  40                  45

Ile Gly Val Tyr Leu Glu Asp Val Ala Val Ala Ser Leu Ala Thr Lys
    50                  55                  60

Trp Lys Gly Lys Ser Ser Glu Glu Leu Leu Glu Thr Leu Asp Phe Tyr
65                  70                  75                  80

Arg Asp Ile Ile Ser Gly Pro Phe Glu Lys Leu Ile Arg Gly Ser Lys
                85                  90                  95

Ile Arg Glu Leu Ser Gly Pro Glu Tyr Ser Arg Lys Val Thr Glu Asn
            100                 105                 110

Cys Val Ala His Leu Lys Ser Val Gly Thr Tyr Gly Asp Ala Glu Val
        115                 120                 125

Glu Ala Met Glu Lys Phe Val Glu Ala Phe Lys Pro Ile Asn Phe Pro
    130                 135                 140

Pro Gly Ala Ser Val Phe Tyr Arg Gln Ser Pro Asp Gly Ile Leu Gly
145                 150                 155                 160

Val Ser Ile Ser Ile His Phe Phe Pro
                165


<210> SEQ ID NO 42
<211> LENGTH: 223
<212> TYPE: PRT
<213> ORGANISM: Abrus precatorius

<400> SEQUENCE: 42

Met Ala Ala Ala Ser Leu Thr Ala Val Gln Val Glu Asn Leu Glu Phe
1               5                   10                  15

Pro Ala Val Val Thr Ser Pro Ala Thr Gly Lys Thr Tyr Phe Leu Gly
            20                  25                  30

Gly Ala Gly Val Arg Gly Leu Thr Ile Glu Gly Asn Phe Ile Lys Phe
        35                  40                  45

Thr Gly Ile Gly Val Tyr Leu Glu Asp Gln Ala Val Ala Ser Leu Ala
    50                  55                  60

Thr Lys Trp Lys Gly Lys Ser Ser Glu Glu Leu Val Glu Ser Leu Asp
65                  70                  75                  80

Phe Phe Arg Asp Ile Ile Ser Gly Pro Phe Glu Lys Leu Ile Arg Gly
                85                  90                  95

Ser Lys Ile Arg Gln Leu Ser Gly Pro Glu Tyr Ser Lys Lys Val Met
            100                 105                 110

Glu Asn Cys Val Ala His Met Lys Ser Val Gly Thr Tyr Gly Asp Ala
        115                 120                 125
```

```
Glu Ala Ala Gly Ile Glu Glu Phe Ala Gln Ala Phe Lys Pro Val Asn
    130                 135                 140

Phe Pro Pro Gly Ala Ser Val Phe Tyr Arg Gln Ser Pro Asp Gly Val
145                 150                 155                 160

Leu Gly Leu Ser Phe Ser Gln Asp Ala Thr Ile Pro Glu Glu Glu Ala
                165                 170                 175

Ala Val Ile Lys Asn Lys Pro Val Ser Ala Ala Val Leu Glu Thr Met
            180                 185                 190

Ile Gly Glu His Ala Val Ser Pro Asp Leu Lys Arg Ser Leu Ala Ala
        195                 200                 205

Arg Leu Pro Ala Val Leu Ser His Gly Val Phe Lys Ile Gly Asn
    210                 215                 220


<210> SEQ ID NO 43
<211> LENGTH: 227
<212> TYPE: PRT
<213> ORGANISM: Arachis duranensis

<400> SEQUENCE: 43

Met Ala Ala Glu Pro Ser Ile Thr Ala Ile Gln Phe Glu Asn Leu Val
1               5                   10                  15

Phe Pro Ala Val Val Thr Pro Pro Gly Ser Ser Lys Ser Tyr Phe Leu
            20                  25                  30

Ala Gly Ala Gly Glu Arg Gly Leu Thr Ile Asp Gly Lys Phe Ile Lys
        35                  40                  45

Phe Thr Gly Ile Gly Val Tyr Leu Glu Asp Lys Ala Val Pro Ser Leu
    50                  55                  60

Ala Gly Lys Trp Lys Asp Lys Ser Ser Gln Gln Leu Leu Gln Thr Leu
65                  70                  75                  80

His Phe Tyr Arg Asp Ile Ile Ser Gly Pro Phe Glu Lys Leu Ile Arg
                85                  90                  95

Gly Ser Lys Ile Leu Ala Leu Ser Gly Val Glu Tyr Ser Arg Lys Val
            100                 105                 110

Met Glu Asn Cys Val Ala His Met Lys Ser Val Gly Thr Tyr Gly Asp
        115                 120                 125

Ala Glu Ala Glu Ala Ile Gln Gln Phe Ala Glu Ala Phe Lys Asn Val
    130                 135                 140

Asn Phe Lys Pro Gly Ala Ser Val Phe Tyr Arg Gln Ser Pro Leu Gly
145                 150                 155                 160

His Leu Gly Leu Ser Phe Ser Gln Asp Gly Asn Ile Pro Glu Lys Glu
                165                 170                 175

Ala Ala Val Ile Glu Asn Lys Pro Leu Ser Ser Ala Val Leu Glu Thr
            180                 185                 190

Met Ile Gly Glu His Ala Val Ser Pro Asp Leu Lys Cys Ser Leu Ala
        195                 200                 205

Ala Arg Leu Pro Ala Val Leu Gln Gln Gly Ile Ile Val Thr Pro Pro
    210                 215                 220

Gln His Asn
225


<210> SEQ ID NO 44
<211> LENGTH: 215
<212> TYPE: PRT
<213> ORGANISM: Cephalotus follicularis

<400> SEQUENCE: 44
```

```
Met Gly Pro Ser Pro Ser Val Thr Glu Leu Gln Val Glu Asn Val Thr
1               5                   10                  15

Phe Pro Pro Ser Val Lys Pro Pro Gly Ser Thr Lys Thr Leu Phe Leu
            20                  25                  30

Gly Gly Ala Gly Glu Arg Gly Leu Glu Ile Gln Gly Lys Phe Ile Lys
        35                  40                  45

Phe Thr Ala Ile Gly Val Tyr Leu Glu Gly Asp Ala Val Ala Ser Leu
    50                  55                  60

Ala Val Lys Trp Lys Gly Lys Ser Lys Glu Glu Leu Thr Asp Ser Val
65                  70                  75                  80

Glu Phe Phe Arg Asp Ile Val Thr Gly Pro Phe Glu Lys Phe Thr Gln
                85                  90                  95

Val Thr Thr Ile Leu Pro Leu Thr Gly Gln Gln Tyr Ser Glu Lys Val
            100                 105                 110

Ser Glu Asn Cys Val Ala Phe Trp Lys Ser Val Gly Ile Tyr Thr Asp
        115                 120                 125

Ala Glu Ala Lys Ala Ile Glu Lys Phe Ile Glu Val Phe Lys Glu Glu
    130                 135                 140

Thr Phe Pro Pro Gly Ser Ser Ile Leu Phe Thr Gln Ser Pro Asn Gly
145                 150                 155                 160

Ala Leu Thr Ile Ala Phe Ser Lys Asp Gly Val Ile Pro Glu Val Gly
                165                 170                 175

Lys Ala Val Ile Glu Asn Lys Leu Leu Ala Glu Gly Leu Leu Glu Ser
            180                 185                 190

Ile Ile Gly Lys His Gly Val Ser Pro Val Ala Lys Gln Cys Leu Ala
        195                 200                 205

Thr Arg Leu Ser Glu Leu Leu
    210                 215
```

<210> SEQ ID NO 45
<211> LENGTH: 337
<212> TYPE: PRT
<213> ORGANISM: Abrus precatorius

<400> SEQUENCE: 45

```
Met Gly Ser Ala Ser Glu Thr Val Cys Val Thr Gly Ala Ala Gly Phe
1               5                   10                  15

Ile Gly Ser Trp Leu Val Met Arg Leu Ile Gln Asn Gly Tyr Lys Val
            20                  25                  30

Arg Ala Thr Val Arg Asp Pro Ala Asn Met Lys Lys Val Lys His Leu
        35                  40                  45

Leu Glu Leu Pro Asn Ala Lys Thr Asn Leu Ser Leu Trp Lys Ala Asp
    50                  55                  60

Leu Ala Glu Glu Gly Ser Phe Asp Glu Ala Ile Lys Gly Cys Thr Gly
65                  70                  75                  80

Val Phe His Val Ala Thr Pro Met Asp Phe Glu Ser Lys Asp Pro Glu
                85                  90                  95

Asn Glu Val Ile Lys Pro Thr Ile Asn Gly Leu Ile Asp Ile Met Lys
            100                 105                 110

Ala Cys Met Lys Ala Lys Thr Val Arg Arg Leu Val Phe Thr Ser Ser
        115                 120                 125

Ala Gly Thr Val Asp Val Thr Glu His Pro Lys Pro Leu Phe Asp Glu
    130                 135                 140

Ser Cys Trp Ser Asp Val Gln Phe Cys Arg Arg Val Arg Met Thr Gly
```

```
145                 150                 155                 160

Trp Met Tyr Phe Val Ser Lys Thr Leu Ala Glu Gln Glu Ala Trp Lys
                165                 170                 175

Phe Ala Lys Glu Asn Asn Ile Asp Phe Ile Ser Val Ile Pro Pro Leu
            180                 185                 190

Val Val Gly Pro Phe Leu Val Pro Thr Met Pro Pro Ser Leu Ile Thr
        195                 200                 205

Ala Leu Ser Leu Ile Thr Gly Asn Glu Ser His Tyr Ala Ile Ile Lys
    210                 215                 220

Gln Gly Gln Phe Val His Leu Asp Asp Leu Cys Leu Ala His Ile Phe
225                 230                 235                 240

Leu Phe Gln His Pro Lys Ala Gln Gly Arg Tyr Ile Cys Cys Ser His
                245                 250                 255

Glu Ala Thr Ile His Asp Ile Ala Ser Leu Leu Asn Gln Lys Tyr Pro
            260                 265                 270

Glu Phe Asn Val Pro Thr Lys Phe Lys Asn Ile Pro Asp Gln Leu Glu
        275                 280                 285

Ile Ile Arg Phe Ser Ser Lys Lys Ile Thr Asp Leu Gly Phe Lys Phe
    290                 295                 300

Lys Tyr Ser Leu Glu Asp Met Phe Thr Gly Ala Val Glu Thr Cys Lys
305                 310                 315                 320

Glu Lys Arg Leu Leu Ser Glu Thr Ala Glu Ile Ser Gly Thr Thr Gln
                325                 330                 335

Lys


<210> SEQ ID NO 46
<211> LENGTH: 347
<212> TYPE: PRT
<213> ORGANISM: Camellia sinensis

<400> SEQUENCE: 46

Met Lys Asp Ser Val Ala Ser Ala Thr Ala Ser Ala Pro Gly Thr Val
1               5                   10                  15

Cys Val Thr Gly Ala Ala Gly Phe Ile Gly Ser Trp Leu Val Met Arg
            20                  25                  30

Leu Leu Glu Arg Gly Tyr Ile Val Arg Ala Thr Val Arg Asp Pro Ala
        35                  40                  45

Asn Leu Lys Lys Val Lys His Leu Leu Asp Leu Pro Lys Ala Asp Thr
    50                  55                  60

Asn Leu Thr Leu Trp Lys Ala Asp Leu Asn Glu Glu Gly Ser Phe Asp
65                  70                  75                  80

Glu Ala Ile Glu Gly Cys Ser Gly Val Phe His Val Ala Thr Pro Met
                85                  90                  95

Asp Phe Glu Ser Lys Asp Pro Glu Asn Glu Val Ile Lys Pro Thr Ile
            100                 105                 110

Asn Gly Val Leu Ser Ile Ile Arg Ser Cys Thr Lys Ala Lys Thr Val
        115                 120                 125

Lys Arg Leu Val Phe Thr Ser Ser Ala Gly Thr Val Asn Val Gln Glu
    130                 135                 140

His Gln Gln Pro Val Phe Asp Glu Asn Asn Trp Ser Asp Leu His Phe
145                 150                 155                 160

Ile Asn Lys Lys Lys Met Thr Gly Trp Met Tyr Phe Val Ser Lys Thr
                165                 170                 175

Leu Ala Glu Lys Ala Ala Trp Glu Ala Ala Lys Glu Asn Asn Ile Asp
```

```
            180                 185                 190

Phe Ile Ser Ile Ile Pro Thr Leu Val Gly Gly Pro Phe Ile Met Pro
        195                 200                 205

Thr Phe Pro Pro Ser Leu Ile Thr Ala Leu Ser Pro Ile Thr Arg Asn
    210                 215                 220

Glu Gly His Tyr Ser Ile Ile Lys Gln Gly Gln Phe Val His Leu Asp
225                 230                 235                 240

Asp Leu Cys Glu Ser His Ile Phe Leu Tyr Glu Arg Pro Gln Ala Glu
                245                 250                 255

Gly Arg Tyr Ile Cys Ser Ser His Asp Ala Thr Ile His Asp Leu Ala
            260                 265                 270

Lys Leu Met Arg Glu Lys Trp Pro Glu Tyr Asn Val Pro Thr Glu Phe
        275                 280                 285

Lys Gly Ile Asp Lys Asp Leu Pro Val Val Ser Phe Ser Ser Lys Lys
    290                 295                 300

Leu Ile Gly Met Gly Phe Glu Phe Lys Tyr Ser Leu Glu Asp Met Phe
305                 310                 315                 320

Arg Gly Ala Ile Asp Thr Cys Arg Glu Lys Gly Leu Leu Pro His Ser
                325                 330                 335

Phe Ala Glu Asn Pro Val Asn Gly Asn Lys Val
            340                 345


<210> SEQ ID NO 47
<211> LENGTH: 359
<212> TYPE: PRT
<213> ORGANISM: Nyssa sinensis

<400> SEQUENCE: 47

Met Val Asp Met Lys Asp Asp Asp Ser Pro Ala Thr Val Cys Val Thr
1               5                   10                  15

Gly Ala Ala Gly Phe Ile Gly Ser Trp Leu Ile Met Arg Leu Leu Gln
            20                  25                  30

Gln Gly Tyr Ile Val Arg Ala Thr Val Arg Asp Pro Ala Asn Met Lys
        35                  40                  45

Lys Val Lys His Leu Gln Glu Leu Glu Lys Ala Asp Lys Asn Leu Thr
    50                  55                  60

Leu Trp Lys Ala Asp Leu Thr Glu Glu Gly Ser Phe Asp Glu Ala Ile
65                  70                  75                  80

Lys Gly Cys Ser Gly Val Phe His Val Ala Thr Pro Met Asp Phe Glu
                85                  90                  95

Ser Lys Asp Pro Glu Asn Glu Val Ile Lys Pro Thr Ile Asn Gly Val
            100                 105                 110

Leu Ser Ile Val Arg Ser Cys Val Lys Ala Lys Thr Val Lys Arg Leu
        115                 120                 125

Val Phe Thr Ser Ser Ala Gly Thr Val Asn Leu Gln Glu His Gln Gln
    130                 135                 140

Leu Val Tyr Asp Glu Asn Asn Trp Ser Asp Leu Asp Leu Ile Tyr Ala
145                 150                 155                 160

Lys Lys Met Thr Gly Trp Met Tyr Phe Val Ser Lys Ile Leu Ala Glu
                165                 170                 175

Lys Ala Ala Trp Glu Ala Thr Lys Glu Asn Asn Ile Asp Phe Ile Ser
            180                 185                 190

Ile Ile Pro Thr Leu Val Val Gly Pro Phe Ile Thr Pro Thr Phe Pro
        195                 200                 205
```

```
Pro Ser Leu Ile Thr Ala Leu Ser Leu Ile Thr Gly Asn Glu Ala His
    210                 215                 220

Tyr Ser Ile Ile Lys Gln Gly Gln Phe Val His Leu Asp Asp Leu Cys
225                 230                 235                 240

Glu Ala His Ile Phe Leu Tyr Glu Gln Pro Lys Ala Glu Gly Arg Tyr
                245                 250                 255

Ile Cys Ser Ser His Asp Ala Thr Ile Tyr Asp Leu Ala Lys Met Ile
            260                 265                 270

Arg Glu Lys Trp Pro Glu Tyr Asn Val Pro Thr Glu Leu Lys Gly Ile
        275                 280                 285

Glu Lys Asp Leu Gln Thr Val Ser Phe Ser Ser Lys Lys Leu Ile Gly
    290                 295                 300

Met Gly Phe Glu Phe Lys Tyr Ser Leu Glu Asp Met Tyr Lys Gly Ala
305                 310                 315                 320

Ile Asp Thr Cys Arg Glu Lys Gly Leu Leu Pro Tyr Ser Thr His Glu
                325                 330                 335

Thr Pro Ala Asn Ala Asn Ala Asn Ala Asn Ala Asn Val Lys Lys Asn
            340                 345                 350

Gln Asn Glu Asn Thr Glu Ile
        355


<210> SEQ ID NO 48
<211> LENGTH: 349
<212> TYPE: PRT
<213> ORGANISM: Rosa chinensis

<400> SEQUENCE: 48

Met Ala Ser Glu Ser Glu Ser Val Cys Val Thr Gly Ala Ser Gly Phe
1               5                   10                  15

Val Gly Ser Trp Leu Val Met Arg Leu Leu Asp Arg Gly Tyr Thr Val
            20                  25                  30

Arg Ala Thr Val Arg Asp Pro Ala Asn Lys Lys Lys Val Lys His Leu
        35                  40                  45

Leu Asp Leu Pro Lys Ala Ala Thr His Leu Thr Leu Trp Lys Ala Asp
    50                  55                  60

Leu Ala Glu Glu Gly Ser Phe Asp Glu Ala Ile Lys Gly Cys Thr Gly
65                  70                  75                  80

Val Phe His Val Ala Thr Pro Met Asp Phe Glu Ser Lys Asp Pro Glu
                85                  90                  95

Asn Glu Val Ile Lys Pro Thr Ile Asn Gly Val Leu Asp Ile Met Lys
            100                 105                 110

Ala Cys Leu Lys Ala Lys Thr Val Arg Arg Leu Val Phe Thr Ala Ser
        115                 120                 125

Ala Gly Ser Val Asn Val Glu Glu Thr Gln Lys Pro Val Tyr Asp Glu
    130                 135                 140

Ser Asn Trp Ser Asp Val Glu Phe Cys Arg Arg Val Lys Met Thr Gly
145                 150                 155                 160

Trp Met Tyr Phe Ala Ser Lys Thr Leu Ala Glu Gln Glu Ala Trp Lys
                165                 170                 175

Phe Ala Lys Glu Asn Asn Ile Asp Phe Ile Thr Ile Ile Pro Thr Leu
            180                 185                 190

Val Ile Gly Pro Phe Leu Met Pro Ala Met Pro Pro Ser Leu Ile Thr
        195                 200                 205

Gly Leu Ser Pro Leu Thr Gly Asn Glu Ser His Tyr Ser Ile Ile Lys
    210                 215                 220
```

```
Gln Gly Gln Phe Ile His Leu Asp Asp Leu Cys Gln Ser His Ile Tyr
225                 230                 235                 240

Leu Tyr Glu His Pro Lys Ala Glu Gly Arg Tyr Ile Cys Ser Ser His
                245                 250                 255

Asp Ala Thr Ile His Glu Ile Ala Lys Leu Leu Arg Glu Lys Tyr Pro
            260                 265                 270

Glu Tyr Asn Val Pro Thr Thr Phe Lys Gly Ile Glu Glu Asn Leu Pro
        275                 280                 285

Lys Val His Phe Ser Ser Lys Lys Leu Leu Glu Thr Gly Phe Glu Phe
    290                 295                 300

Lys Tyr Ser Leu Glu Asp Met Phe Val Gly Ala Val Asp Ala Cys Lys
305                 310                 315                 320

Ala Lys Gly Leu Leu Pro Pro Pro Thr Glu Arg Val Glu Lys Gln Glu
                325                 330                 335

Val Asp Glu Ser Ser Val Val Gly Val Lys Val Thr Gly
            340                 345
```

<210> SEQ ID NO 49
<211> LENGTH: 511
<212> TYPE: PRT
<213> ORGANISM: Cephalotus follicularis

<400> SEQUENCE: 49

```
Met Ser Pro Leu Ile Leu Tyr Ser Ile Ala Leu Ala Ile Phe Leu Tyr
1               5                   10                  15

Cys Leu Arg Thr Leu Leu Lys Arg His Pro His Arg Leu Pro Pro Gly
            20                  25                  30

Pro Arg Pro Trp Pro Ile Ile Gly Asn Leu Pro His Met Gly Gln Met
        35                  40                  45

Pro His His Ser Leu Ala Ala Met Ala Arg Thr Tyr Gly Pro Leu Met
    50                  55                  60

His Leu Arg Leu Gly Phe Val Asp Val Ile Val Ala Ala Ser Ala Ser
65                  70                  75                  80

Val Ala Ser Gln Leu Leu Lys Thr His Asp Ala Asn Phe Ser Ser Arg
                85                  90                  95

Pro His Asn Ser Gly Ala Lys Tyr Ile Ala Tyr Asn Tyr Gln Asp Leu
            100                 105                 110

Val Phe Ala Pro Tyr Gly Pro Arg Trp Arg Met Leu Arg Lys Ile Ser
        115                 120                 125

Ser Val His Leu Phe Ser Gly Lys Ala Leu Asp Asp Tyr Arg His Val
    130                 135                 140

Arg Gln Glu Glu Val Ala Val Leu Ile Arg Ala Leu Ala Arg Ala Glu
145                 150                 155                 160

Ser Lys Gln Ala Val Asn Leu Gly Gln Leu Leu Asn Val Cys Thr Ala
                165                 170                 175

Asn Ala Leu Gly Arg Val Met Leu Gly Arg Arg Val Phe Gly Asp Gly
            180                 185                 190

Ser Gly Val Ser Asp Pro Met Ala Glu Glu Phe Lys Ser Met Val Val
        195                 200                 205

Glu Val Met Ala Leu Ala Gly Val Phe Asn Ile Gly Asp Phe Ile Pro
    210                 215                 220

Ala Leu Asp Trp Leu Asp Leu Gln Gly Val Ala Ala Lys Met Lys Asn
225                 230                 235                 240

Leu His Lys Arg Phe Asp Thr Phe Leu Thr Gly Leu Leu Glu Glu His
```

```
                245                 250                 255

Lys Lys Met Leu Val Gly Asp Gly Gly Ser Glu Lys His Lys Asp Leu
            260                 265                 270

Leu Ser Thr Leu Ile Ser Leu Lys Asp Ser Ala Asp Asp Glu Gly Leu
        275                 280                 285

Lys Leu Thr Asp Thr Glu Ile Lys Ala Leu Leu Leu Asn Met Phe Thr
    290                 295                 300

Ala Gly Thr Asp Thr Ser Ser Ser Thr Val Glu Trp Ala Ile Ala Glu
305                 310                 315                 320

Leu Ile Arg His Pro Lys Ile Leu Ala Gln Val Leu Lys Glu Leu Asp
                325                 330                 335

Thr Val Val Gly Arg Asp Arg Leu Val Thr Asp Leu Asp Leu Pro Gln
            340                 345                 350

Leu Thr Tyr Leu Gln Ala Val Ile Lys Glu Thr Phe Arg Leu His Pro
        355                 360                 365

Ser Thr Pro Leu Ser Leu Pro Arg Val Ala Ala Glu Ser Cys Glu Ile
    370                 375                 380

Met Gly Tyr His Ile Pro Lys Gly Ser Thr Leu Leu Val Asn Val Trp
385                 390                 395                 400

Ala Ile Ala Arg Asp Pro Lys Glu Trp Ala Glu Pro Leu Glu Phe Arg
                405                 410                 415

Pro Glu Arg Phe Leu Pro Gly Gly Glu Lys Pro Asn Val Asp Ile Lys
            420                 425                 430

Gly Asn Asp Phe Glu Val Ile Pro Phe Gly Ala Gly Arg Arg Ile Cys
        435                 440                 445

Ala Gly Met Ser Leu Gly Leu Arg Met Val Gln Leu Leu Thr Ala Thr
    450                 455                 460

Leu Val His Ala Phe Asp Trp Asp Leu Thr Ser Gly Leu Met Pro Glu
465                 470                 475                 480

Asp Leu Ser Met Glu Glu Ala Tyr Gly Leu Thr Leu Gln Arg Ala Glu
                485                 490                 495

Pro Leu Met Val His Pro Arg Pro Arg Leu Ser Pro Asn Val Tyr
            500                 505                 510


<210> SEQ ID NO 50
<211> LENGTH: 507
<212> TYPE: PRT
<213> ORGANISM: Theobroma cacao

<400> SEQUENCE: 50

Met Ala Ser Phe Leu Leu Tyr Ser Ile Leu Ser Ala Val Phe Leu Tyr
1               5                   10                  15

Phe Ile Phe Ala Thr Leu Arg Lys Arg His Arg Leu Pro Leu Pro Pro
            20                  25                  30

Gly Pro Lys Pro Trp Pro Ile Ile Gly Asn Leu Pro His Met Gly Pro
        35                  40                  45

Val Pro His His Ser Leu Ala Ala Leu Ala Lys Val Tyr Gly Pro Leu
    50                  55                  60

Met His Leu Arg Leu Gly Phe Val Asp Val Val Val Ala Ala Ser Ala
65                  70                  75                  80

Ser Val Ala Ala Gln Phe Leu Lys Val His Asp Ala Asn Phe Ser Ser
                85                  90                  95

Arg Pro Pro Asn Ser Gly Ala Lys Tyr Val Ala Tyr Asn Tyr Gln Asp
            100                 105                 110
```

```
Leu Val Phe Ala Pro Tyr Gly Pro Arg Trp Arg Met Leu Arg Lys Ile
        115                 120                 125

Ser Ser Val His Leu Phe Ser Gly Lys Ala Leu Asp Asp Phe Arg His
    130                 135                 140

Val Arg Gln Asp Glu Val Gly Val Leu Val Arg Ala Leu Ala Asp Ala
145                 150                 155                 160

Lys Thr Lys Val Asn Leu Gly Gln Leu Leu Asn Val Cys Thr Val Asn
                165                 170                 175

Ala Leu Gly Arg Val Met Leu Gly Lys Arg Val Phe Gly Asp Gly Ser
            180                 185                 190

Gly Lys Ala Asp Pro Glu Ala Asp Glu Phe Lys Ser Met Val Val Glu
        195                 200                 205

Leu Met Val Leu Ala Gly Val Val Asn Ile Gly Asp Phe Ile Pro Ala
    210                 215                 220

Leu Glu Trp Leu Asp Leu Gln Gly Val Gln Ala Lys Met Lys Lys Leu
225                 230                 235                 240

His Lys Arg Phe Asp Arg Phe Leu Ser Ala Ile Leu Glu Glu His Lys
                245                 250                 255

Ile Lys Ala Arg Asp Gly Ser Gly Gln His Lys Asp Leu Leu Ser Thr
            260                 265                 270

Phe Ile Ser Leu Glu Asp Ala Asp Gly Glu Gly Gly Lys Leu Thr Asp
        275                 280                 285

Thr Glu Ile Lys Ala Leu Leu Leu Asn Met Phe Thr Ala Gly Thr Asp
    290                 295                 300

Thr Ser Ser Ser Thr Val Glu Trp Ala Ile Ala Glu Leu Ile Arg His
305                 310                 315                 320

Pro Lys Ile Leu Ala Gln Val Arg Lys Glu Leu Asp Ser Val Val Gly
                325                 330                 335

Arg Asp Arg Leu Val Ser Asp Leu Asp Leu Pro Asn Leu Thr Tyr Phe
            340                 345                 350

Gln Ala Val Ile Lys Glu Thr Phe Arg Leu His Pro Ser Thr Pro Leu
        355                 360                 365

Ser Leu Pro Arg Met Ala Ser Glu Ser Cys Glu Ile Asn Gly Tyr His
    370                 375                 380

Ile Pro Lys Gly Ala Thr Leu Leu Val Asn Val Trp Ala Ile Ala Arg
385                 390                 395                 400

Asp Pro Asp Glu Trp Lys Asp Pro Leu Glu Phe Arg Pro Glu Arg Phe
                405                 410                 415

Leu Pro Gly Gly Glu Arg Pro Asn Ala Asp Val Arg Gly Asn Asp Phe
            420                 425                 430

Glu Val Ile Pro Phe Gly Ala Gly Arg Arg Ile Cys Ala Gly Met Ser
        435                 440                 445

Leu Gly Leu Arg Met Val Gln Leu Leu Ala Ala Thr Leu Val His Ala
    450                 455                 460

Phe Asp Trp Glu Leu Ala Asp Gly Leu Met Pro Glu Lys Leu Asn Met
465                 470                 475                 480

Glu Glu Ala Phe Gly Leu Thr Leu Gln Arg Ala Ala Pro Leu Met Val
                485                 490                 495

His Pro Arg Pro Arg Leu Ser Pro Arg Ala Tyr
            500                 505
```

<210> SEQ ID NO 51
<211> LENGTH: 512
<212> TYPE: PRT

<213> ORGANISM: Gerbera hybrida

<400> SEQUENCE: 51

```
Met Thr Pro Leu Thr Leu Leu Ile Gly Thr Cys Val Thr Gly Leu Phe
1               5                   10                  15

Leu Tyr Val Leu Leu Asn Arg Cys Thr Arg Asn Pro Asn Arg Leu Pro
            20                  25                  30

Pro Gly Pro Thr Pro Trp Pro Val Val Gly Asn Leu Pro His Leu Gly
        35                  40                  45

Thr Ile Pro His His Ser Leu Ala Ala Met Ala Lys Lys Tyr Gly Pro
    50                  55                  60

Leu Met His Leu Arg Leu Gly Phe Val Asp Val Val Val Ala Ala Ser
65                  70                  75                  80

Ala Ser Val Ala Ala Gln Phe Leu Lys Thr His Asp Ala Asn Phe Ala
                85                  90                  95

Asp Arg Pro Pro Asn Ser Gly Ala Lys His Ile Ala Tyr Asn Tyr Gln
            100                 105                 110

Asp Leu Val Phe Ala Pro Tyr Gly Pro Arg Trp Arg Met Leu Arg Lys
        115                 120                 125

Ile Cys Ser Val His Leu Phe Ser Thr Lys Ala Leu Asp Asp Phe Arg
    130                 135                 140

His Val Arg Gln Glu Glu Val Ala Ile Leu Ala Arg Ala Leu Val Gly
145                 150                 155                 160

Ala Gly Lys Ser Pro Val Lys Leu Gly Gln Leu Leu Asn Val Cys Thr
                165                 170                 175

Thr Asn Ala Leu Ala Arg Val Met Leu Gly Arg Arg Val Phe Asp Ser
            180                 185                 190

Gly Asp Ala Gln Ala Asp Glu Phe Lys Asp Met Val Val Glu Leu Met
        195                 200                 205

Val Leu Ala Gly Glu Phe Asn Ile Gly Asp Phe Ile Pro Val Leu Asp
    210                 215                 220

Trp Leu Asp Leu Gln Gly Val Thr Lys Lys Met Lys Lys Leu His Ala
225                 230                 235                 240

Lys Phe Asp Ser Phe Leu Asn Thr Ile Leu Glu Glu His Lys Thr Gly
                245                 250                 255

Ala Gly Asp Gly Val Ala Ser Gly Lys Val Asp Leu Leu Ser Thr Leu
            260                 265                 270

Ile Ser Leu Lys Asp Asp Ala Asp Gly Glu Gly Gly Lys Leu Ser Asp
        275                 280                 285

Ile Glu Ile Lys Ala Leu Leu Leu Asn Leu Phe Thr Ala Gly Thr Asp
    290                 295                 300

Thr Ser Ser Ser Thr Ile Glu Trp Ala Ile Ala Glu Leu Ile Arg Asn
305                 310                 315                 320

Pro Gln Leu Leu Asn Gln Ala Arg Lys Glu Met Asp Thr Ile Val Gly
                325                 330                 335

Gln Asp Arg Leu Val Thr Glu Ser Asp Leu Gly Gln Leu Thr Phe Leu
            340                 345                 350

Gln Ala Ile Ile Lys Glu Thr Phe Arg Leu His Pro Ser Thr Pro Leu
        355                 360                 365

Ser Leu Pro Arg Met Ala Leu Glu Ser Cys Glu Val Gly Gly Tyr Tyr
    370                 375                 380

Ile Pro Lys Gly Ser Thr Leu Leu Val Asn Val Trp Ala Ile Ser Arg
385                 390                 395                 400
```

```
Asp Pro Lys Ile Trp Ala Asp Pro Leu Glu Phe Gln Pro Thr Arg Phe
                405                 410                 415

Leu Pro Gly Gly Glu Lys Pro Asn Thr Asp Ile Lys Gly Asn Asp Phe
            420                 425                 430

Glu Val Ile Pro Phe Gly Ala Gly Arg Arg Ile Cys Val Gly Met Ser
        435                 440                 445

Leu Gly Leu Arg Met Val Gln Leu Leu Thr Ala Thr Leu Ile His Ala
    450                 455                 460

Phe Asp Trp Glu Leu Ala Asp Gly Leu Asn Pro Lys Lys Leu Asn Met
465                 470                 475                 480

Glu Glu Ala Tyr Gly Leu Thr Leu Gln Arg Ala Ala Pro Leu Val Val
                485                 490                 495

His Pro Arg Pro Arg Leu Ala Pro His Val Tyr Glu Thr Thr Lys Val
            500                 505                 510


<210> SEQ ID NO 52
<211> LENGTH: 517
<212> TYPE: PRT
<213> ORGANISM: Phoenix dactylifera

<400> SEQUENCE: 52

Met Ala Pro Leu Leu Leu Leu Phe Phe Thr Leu Leu Leu Ser Tyr Leu
1               5                   10                  15

Leu Tyr Tyr Tyr Phe Phe Ser Lys Glu Arg Thr Lys Gly Ser Arg Ala
            20                  25                  30

Pro Leu Pro Pro Gly Pro Arg Gly Trp Pro Val Leu Gly Asn Leu Pro
        35                  40                  45

Gln Leu Gly Pro Lys Pro His His Thr Leu His Ala Leu Ser Arg Ala
    50                  55                  60

His Gly Pro Leu Phe Arg Leu Arg Leu Gly Ser Val Asp Val Val Val
65                  70                  75                  80

Ala Ala Ser Ala Ala Val Ala Ala Gln Phe Leu Arg Ala His Asp Ala
                85                  90                  95

Asn Phe Ser Asn Arg Pro Pro Asn Ser Gly Ala Glu His Ile Ala Tyr
            100                 105                 110

Asn Tyr Gln Asp Leu Val Phe Ala Pro Tyr Gly Pro Gly Trp Arg Ala
        115                 120                 125

Arg Arg Lys Leu Leu Asn Val His Leu Phe Ser Gly Lys Ala Leu Glu
    130                 135                 140

Asp Leu Arg Pro Val Arg Glu Gly Glu Leu Ala Leu Leu Val Arg Ala
145                 150                 155                 160

Leu Arg Asp Arg Ala Gly Ala Asn Glu Leu Val Asp Leu Gly Arg Ala
                165                 170                 175

Ala Asn Lys Cys Ala Thr Asn Ala Leu Ala Arg Ala Met Val Gly Arg
            180                 185                 190

Arg Val Phe Gln Glu Glu Glu Asp Glu Lys Ala Ala Glu Phe Glu Asn
        195                 200                 205

Met Val Val Glu Leu Met Arg Leu Ala Gly Val Phe Asn Val Gly Asp
    210                 215                 220

Phe Val Pro Gly Ile Gly Trp Leu Asp Leu Gln Gly Val Val Arg Arg
225                 230                 235                 240

Met Lys Glu Leu His Arg Arg Tyr Asp Gly Phe Leu Asp Gly Leu Ile
                245                 250                 255

Ala Ala His Arg Arg Ala Ala Glu Gly Gly Gly Gly Gly Gly Lys Asp
            260                 265                 270
```

```
Leu Leu Ser Val Leu Leu Gly Leu Lys Asp Glu Asp Leu Asp Phe Asp
        275                 280                 285

Gly Glu Gly Ala Lys Leu Thr Asp Thr Asp Ile Lys Ala Leu Leu Leu
    290                 295                 300

Asn Leu Phe Thr Ala Gly Thr Asp Thr Thr Ser Ser Thr Val Glu Trp
305                 310                 315                 320

Ala Leu Ser Glu Leu Val Lys His Pro Asp Ile Leu Arg Lys Ala Gln
                325                 330                 335

Leu Glu Leu Asp Ser Val Val Gly Gly Asp Arg Leu Val Ser Glu Ser
            340                 345                 350

Asp Leu Pro Asn Leu Pro Phe Met Gln Ala Ile Ile Lys Glu Thr Phe
        355                 360                 365

Arg Leu His Pro Ser Thr Pro Leu Ser Leu Pro Arg Met Ala Ala Glu
    370                 375                 380

Glu Cys Glu Val Ala Gly Tyr Cys Ile Pro Lys Gly Ala Thr Leu Leu
385                 390                 395                 400

Val Asn Val Trp Ala Ile Ala Arg Asp Pro Ala Val Trp Arg Asp Pro
                405                 410                 415

Leu Glu Phe Arg Pro Ala Arg Phe Leu Pro Asp Gly Gly Cys Glu Gly
            420                 425                 430

Met Asp Val Lys Gly Asn Asp Phe Gly Ile Ile Pro Phe Gly Ala Gly
        435                 440                 445

Arg Arg Ile Cys Ala Gly Met Ser Leu Gly Ile Arg Met Val Gln Phe
    450                 455                 460

Met Thr Ala Thr Leu Ala His Ala Phe His Trp Asp Leu Pro Glu Gly
465                 470                 475                 480

Gln Met Pro Glu Lys Leu Asp Met Glu Glu Ala Tyr Gly Leu Thr Leu
                485                 490                 495

Gln Arg Ala Thr Pro Leu Met Val His Pro Val Pro Arg Leu Ala Pro
            500                 505                 510

Thr Ala Tyr Gln Ser
        515


<210> SEQ ID NO 53
<211> LENGTH: 1007
<212> TYPE: PRT
<213> ORGANISM: Camellia sinensis

<400> SEQUENCE: 53

Met Ala Ser Asn Ser Asn Leu Ile Arg Ala Ile Glu Ser Ala Leu Gly
1               5                   10                  15

Val Ser Phe Gly Ser Glu Leu Val Ser Asp Thr Ala Ile Val Val Val
            20                  25                  30

Thr Thr Ser Val Ala Val Ile Ile Gly Leu Leu Phe Phe Leu Leu Lys
        35                  40                  45

Arg Ser Ser Asp Arg Ser Lys Glu Ser Lys Pro Val Val Ile Ser Lys
    50                  55                  60

Pro Leu Leu Val Glu Glu Glu Glu Glu Glu Asp Glu Val Glu Ala Gly
65                  70                  75                  80

Ser Gly Lys Thr Lys Val Thr Met Phe Tyr Gly Thr Gln Thr Gly Thr
                85                  90                  95

Ala Glu Gly Phe Ala Lys Ser Leu Ala Lys Glu Ile Lys Ala Arg Tyr
            100                 105                 110

Glu Lys Ala Ile Val Lys Val Val Asp Leu Asp Asp Tyr Ala Ala Asp
```

```
        115                 120                 125

Asp Asp Gln Tyr Glu Gln Lys Leu Lys Lys Glu Thr Leu Val Phe Phe
    130                 135                 140

Met Leu Ala Thr Tyr Gly Asp Gly Glu Pro Thr Asp Asp Ala Ala Arg
145                 150                 155                 160

Phe Tyr Lys Trp Phe Thr Glu Glu Asn Glu Arg Gly Ala Trp Leu Gln
                165                 170                 175

Gln Leu Thr Tyr Gly Val Phe Ser Leu Gly Asn Arg Gln Tyr Glu His
            180                 185                 190

Phe Asn Lys Ile Gly Lys Val Val Asp Glu Gln Leu Ser Lys Gln Gly
        195                 200                 205

Ala Lys Arg Leu Ile Pro Val Gly Leu Gly Asp Asp Asp Gln Cys Ile
    210                 215                 220

Glu Asp Asp Phe Ala Ala Trp Arg Glu Thr Leu Trp Pro Glu Leu Asp
225                 230                 235                 240

Gln Leu Leu Arg Asp Glu Asp Asp Ala Asn Thr Val Ser Thr Pro Tyr
                245                 250                 255

Ala Ala Ala Ile Pro Glu Tyr Arg Val Val Ile His Asp Pro Leu Ser
            260                 265                 270

Gly Arg Gly Glu Ala Pro Ser Phe Ser Ile Asp Ser His Leu Thr Ile
        275                 280                 285

Cys Glu Ile Trp Ser Thr Ser Arg Glu Gly Ser Asn Gln Gln Ile Ser
    290                 295                 300

Glu Tyr Phe Trp Thr Ser Asn Ser Leu Lys Thr Met Ala Ser Asn Ser
305                 310                 315                 320

Asn Leu Ile Arg Ser Ile Glu Ser Ala Leu Gly Val Ser Phe Gly Ser
                325                 330                 335

Glu Ser Val Ser Asp Thr Ala Ile Val Val Val Thr Thr Ser Val Ala
            340                 345                 350

Val Ile Ile Gly Leu Leu Phe Phe Leu Leu Lys Arg Ser Ser Asp Arg
        355                 360                 365

Ser Lys Glu Ser Lys Pro Val Val Ile Ser Lys Pro Leu Leu Val Glu
    370                 375                 380

Glu Glu Glu Asp Glu Val Glu Ala Gly Ser Gly Lys Thr Lys Val Thr
385                 390                 395                 400

Leu Phe Tyr Gly Thr Gln Thr Gly Thr Ala Glu Gly Phe Ala Lys Ser
                405                 410                 415

Leu Ala Glu Glu Ile Lys Ala Arg Tyr Glu Lys Ala Ile Val Lys Val
            420                 425                 430

Val Asp Leu Asp Asp Tyr Ala Ala Asp Asp Asp Gln Tyr Glu Gln Lys
        435                 440                 445

Leu Lys Lys Glu Thr Leu Val Phe Phe Met Leu Ala Thr Tyr Gly Asp
    450                 455                 460

Gly Glu Pro Thr Asp Asn Ala Ala Arg Phe Tyr Lys Trp Phe Thr Glu
465                 470                 475                 480

Glu Asn Glu Arg Gly Ala Trp Leu Gln Gln Leu Thr Tyr Gly Val Phe
                485                 490                 495

Ser Leu Gly Asn Arg Gln Tyr Glu His Phe Asn Lys Ile Gly Lys Val
            500                 505                 510

Val Asp Glu Gln Leu Ser Lys Gln Gly Ala Lys Arg Leu Ile Pro Val
        515                 520                 525

Gly Leu Gly Asp Asp Asp Gln Cys Ile Glu Asp Asp Phe Ala Ala Trp
    530                 535                 540
```

```
Arg Glu Thr Leu Trp Pro Glu Leu Asp Gln Leu Leu Arg Asp Glu Asp
545                 550                 555                 560

Asp Ala Asn Thr Val Ser Thr Pro Tyr Thr Ala Ala Ile Pro Glu Tyr
                565                 570                 575

Arg Val Val Ile His Asp Pro Thr Thr Thr Ser Tyr Glu Asp Lys Asn
            580                 585                 590

Leu Asn Met Ala Asn Gly Asn Ala Ser Tyr Asp Ile His His Pro Cys
        595                 600                 605

Arg Val Asn Val Ala Val Gln Arg Glu Leu His Lys Pro Glu Ser Asp
    610                 615                 620

Arg Ser Cys Ile His Leu Glu Phe Asp Ile Ser Gly Thr Gly Ile Ile
625                 630                 635                 640

Tyr Glu Thr Gly Asp His Val Gly Val Tyr Ala Asp Asn Phe Asp Glu
                645                 650                 655

Val Val Glu Glu Ala Ala Asn Leu Leu Gly Gln Pro Leu Glu Leu Leu
            660                 665                 670

Phe Ser Val His Ala Asp Lys Asp Asp Gly Thr Ser Leu Gly Gly Ser
        675                 680                 685

Leu Pro Pro Pro Phe Pro Gly Pro Cys Thr Leu Arg Asp Ala Leu Ala
    690                 695                 700

His Tyr Ala Asp Leu Leu Asn Pro Pro Arg Lys Ala Ala Leu Ser Ala
705                 710                 715                 720

Leu Ala Ala His Ala Val Glu Pro Ser Glu Ala Glu Arg Leu Lys Phe
                725                 730                 735

Leu Ser Ser Pro Gln Gly Lys Glu Asp Tyr Ser Gln Trp Val Val Ala
            740                 745                 750

Ser Gln Arg Ser Leu Leu Glu Ile Met Ala Glu Phe Pro Ser Ala Lys
        755                 760                 765

Pro Pro Leu Gly Val Phe Phe Ala Ala Val Ala Pro Arg Leu Gln Pro
    770                 775                 780

Arg Tyr Tyr Ser Ile Ser Ser Ser Pro Arg Phe Val Pro Asn Arg Val
785                 790                 795                 800

His Val Thr Cys Ala Leu Val Tyr Gly Pro Ser Pro Thr Gly Arg Ile
                805                 810                 815

His Lys Gly Val Cys Ser Thr Trp Met Lys Asn Ala Val Pro Leu Glu
            820                 825                 830

Lys Ser His Asp Cys Ser Ser Ala Pro Ile Phe Thr Arg Thr Ser Asn
        835                 840                 845

Phe Lys Leu Pro Thr Asp Pro Ser Ile Pro Ile Ile Met Val Gly Pro
    850                 855                 860

Gly Thr Gly Leu Ala Pro Phe Arg Gly Phe Leu Gln Glu Arg Leu Ala
865                 870                 875                 880

Leu Lys Glu Asp Gly Val Gln Leu Gly His Ala Met Leu Phe Phe Gly
                885                 890                 895

Cys Arg Asn Arg Arg Met Asp Phe Ile Tyr Glu Asp Glu Leu Asn Asn
            900                 905                 910

Phe Val Asp Gln Gly Ala Val Ser Glu Leu Val Val Ala Phe Ser Arg
        915                 920                 925

Glu Gly Pro Glu Lys Glu Tyr Val Gln His Lys Leu Asn Ala Lys Ala
    930                 935                 940

Ala Gln Val Trp Gly Leu Ile Ser Gln Gly Gly Tyr Leu Tyr Val Cys
945                 950                 955                 960
```

```
Gly Asp Ala Lys Gly Met Ala Arg Asp Val His Arg Met Leu His Thr
                965                 970                 975

Ile Val Glu Gln Gln Glu Asn Val Asp Ser Arg Lys Ala Glu Val Ile
            980                 985                 990

Val Lys Lys Leu Gln Met Glu Gly  Arg Tyr Leu Arg Asp  Val Trp
        995                 1000                1005


<210> SEQ ID NO 54
<211> LENGTH: 1007
<212> TYPE: PRT
<213> ORGANISM: Cephalotus follicularis

<400> SEQUENCE: 54

Met Ala Ser Asn Ser Asn Leu Ile Arg Ala Ile Glu Ser Ala Leu Gly
1               5                   10                  15

Val Ser Phe Gly Ser Glu Leu Val Ser Asp Thr Ala Ile Val Val Val
            20                  25                  30

Thr Thr Ser Val Ala Val Ile Ile Gly Leu Leu Phe Phe Leu Leu Lys
        35                  40                  45

Arg Ser Ser Asp Arg Ser Lys Glu Ser Lys Pro Val Val Ile Ser Lys
    50                  55                  60

Pro Leu Leu Val Glu Glu Glu Glu Glu Glu Asp Glu Val Glu Ala Gly
65                  70                  75                  80

Ser Gly Lys Thr Lys Val Thr Met Phe Tyr Gly Thr Gln Thr Gly Thr
                85                  90                  95

Ala Glu Gly Phe Ala Lys Ser Leu Ala Lys Glu Ile Lys Ala Arg Tyr
            100                 105                 110

Glu Lys Ala Ile Val Lys Val Val Asp Leu Asp Asp Tyr Ala Ala Asp
        115                 120                 125

Asp Asp Gln Tyr Glu Gln Lys Leu Lys Lys Glu Thr Leu Val Phe Phe
    130                 135                 140

Met Leu Ala Thr Tyr Gly Asp Gly Glu Pro Thr Asp Asp Ala Ala Arg
145                 150                 155                 160

Phe Tyr Lys Trp Phe Thr Glu Glu Asn Glu Arg Gly Ala Trp Leu Gln
                165                 170                 175

Gln Leu Thr Tyr Gly Val Phe Ser Leu Gly Asn Arg Gln Tyr Glu His
            180                 185                 190

Phe Asn Lys Ile Gly Lys Val Val Asp Glu Gln Leu Ser Lys Gln Gly
        195                 200                 205

Ala Lys Arg Leu Ile Pro Val Gly Leu Gly Asp Asp Asp Gln Cys Ile
    210                 215                 220

Glu Asp Asp Phe Ala Ala Trp Arg Glu Thr Leu Trp Pro Glu Leu Asp
225                 230                 235                 240

Gln Leu Leu Arg Asp Glu Asp Asp Ala Asn Thr Val Ser Thr Pro Tyr
                245                 250                 255

Ala Ala Ala Ile Pro Glu Tyr Arg Val Val Ile His Asp Pro Leu Ser
            260                 265                 270

Gly Arg Gly Glu Ala Pro Ser Phe Ser Ile Asp Ser His Leu Thr Ile
        275                 280                 285

Cys Glu Ile Trp Ser Thr Ser Arg Glu Gly Ser Asn Gln Gln Ile Ser
    290                 295                 300

Glu Tyr Phe Trp Thr Ser Asn Ser Leu Lys Thr Met Ala Ser Asn Ser
305                 310                 315                 320

Asn Leu Ile Arg Ser Ile Glu Ser Ala Leu Gly Val Ser Phe Gly Ser
                325                 330                 335
```

```
Glu Ser Val Ser Asp Thr Ala Ile Val Val Val Thr Thr Ser Val Ala
            340                 345                 350

Val Ile Ile Gly Leu Leu Phe Phe Leu Leu Lys Arg Ser Ser Asp Arg
        355                 360                 365

Ser Lys Glu Ser Lys Pro Val Val Ile Ser Lys Pro Leu Leu Val Glu
    370                 375                 380

Glu Glu Glu Asp Glu Val Glu Ala Gly Ser Gly Lys Thr Lys Val Thr
385                 390                 395                 400

Leu Phe Tyr Gly Thr Gln Thr Gly Thr Ala Glu Gly Phe Ala Lys Ser
                405                 410                 415

Leu Ala Glu Glu Ile Lys Ala Arg Tyr Glu Lys Ala Ile Val Lys Val
            420                 425                 430

Val Asp Leu Asp Asp Tyr Ala Ala Asp Asp Asp Gln Tyr Glu Gln Lys
        435                 440                 445

Leu Lys Lys Glu Thr Leu Val Phe Phe Met Leu Ala Thr Tyr Gly Asp
    450                 455                 460

Gly Glu Pro Thr Asp Asn Ala Ala Arg Phe Tyr Lys Trp Phe Thr Glu
465                 470                 475                 480

Glu Asn Glu Arg Gly Ala Trp Leu Gln Gln Leu Thr Tyr Gly Val Phe
                485                 490                 495

Ser Leu Gly Asn Arg Gln Tyr Glu His Phe Asn Lys Ile Gly Lys Val
            500                 505                 510

Val Asp Glu Gln Leu Ser Lys Gln Gly Ala Lys Arg Leu Ile Pro Val
        515                 520                 525

Gly Leu Gly Asp Asp Asp Gln Cys Ile Glu Asp Asp Phe Ala Ala Trp
    530                 535                 540

Arg Glu Thr Leu Trp Pro Glu Leu Asp Gln Leu Leu Arg Asp Glu Asp
545                 550                 555                 560

Asp Ala Asn Thr Val Ser Thr Pro Tyr Thr Ala Ala Ile Pro Glu Tyr
                565                 570                 575

Arg Val Val Ile His Asp Pro Thr Thr Thr Ser Tyr Glu Asp Lys Asn
            580                 585                 590

Leu Asn Met Ala Asn Gly Asn Ala Ser Tyr Asp Ile His His Pro Cys
        595                 600                 605

Arg Val Asn Val Ala Val Gln Arg Glu Leu His Lys Pro Glu Ser Asp
    610                 615                 620

Arg Ser Cys Ile His Leu Glu Phe Asp Ile Ser Gly Thr Gly Ile Ile
625                 630                 635                 640

Tyr Glu Thr Gly Asp His Val Gly Val Tyr Ala Asp Asn Phe Asp Glu
                645                 650                 655

Val Val Glu Glu Ala Ala Asn Leu Leu Gly Gln Pro Leu Glu Leu Leu
            660                 665                 670

Phe Ser Val His Ala Asp Lys Asp Asp Gly Thr Ser Leu Gly Gly Ser
        675                 680                 685

Leu Pro Pro Pro Phe Pro Gly Pro Cys Thr Leu Arg Asp Ala Leu Ala
    690                 695                 700

His Tyr Ala Asp Leu Leu Asn Pro Pro Arg Lys Ala Ala Leu Ser Ala
705                 710                 715                 720

Leu Ala Ala His Ala Val Glu Pro Ser Glu Ala Glu Arg Leu Lys Phe
                725                 730                 735

Leu Ser Ser Pro Gln Gly Lys Glu Asp Tyr Ser Gln Trp Val Val Ala
            740                 745                 750
```

```
Ser Gln Arg Ser Leu Leu Glu Ile Met Ala Glu Phe Pro Ser Ala Lys
        755                 760                 765

Pro Pro Leu Gly Val Phe Phe Ala Ala Val Ala Pro Arg Leu Gln Pro
    770                 775                 780

Arg Tyr Tyr Ser Ile Ser Ser Ser Pro Arg Phe Val Pro Asn Arg Val
785                 790                 795                 800

His Val Thr Cys Ala Leu Val Tyr Gly Pro Ser Pro Thr Gly Arg Ile
                805                 810                 815

His Lys Gly Val Cys Ser Thr Trp Met Lys Asn Ala Val Pro Leu Glu
            820                 825                 830

Lys Ser His Asp Cys Ser Ser Ala Pro Ile Phe Thr Arg Thr Ser Asn
        835                 840                 845

Phe Lys Leu Pro Thr Asp Pro Ser Ile Pro Ile Ile Met Val Gly Pro
    850                 855                 860

Gly Thr Gly Leu Ala Pro Phe Arg Gly Phe Leu Gln Glu Arg Leu Ala
865                 870                 875                 880

Leu Lys Glu Asp Gly Val Gln Leu Gly His Ala Met Leu Phe Phe Gly
                885                 890                 895

Cys Arg Asn Arg Arg Met Asp Phe Ile Tyr Glu Asp Glu Leu Asn Asn
            900                 905                 910

Phe Val Asp Gln Gly Ala Val Ser Glu Leu Val Val Ala Phe Ser Arg
        915                 920                 925

Glu Gly Pro Glu Lys Glu Tyr Val Gln His Lys Leu Asn Ala Lys Ala
    930                 935                 940

Ala Gln Val Trp Gly Leu Ile Ser Gln Gly Gly Tyr Leu Tyr Val Cys
945                 950                 955                 960

Gly Asp Ala Lys Gly Met Ala Arg Asp Val His Arg Met Leu His Thr
                965                 970                 975

Ile Val Glu Gln Gln Glu Asn Val Asp Ser Arg Lys Ala Glu Val Ile
            980                 985                 990

Val Lys Lys Leu Gln Met Glu Gly  Arg Tyr Leu Arg Asp  Val Trp
        995                 1000                1005


<210> SEQ ID NO 55
<211> LENGTH: 708
<212> TYPE: PRT
<213> ORGANISM: Brassica napus

<400> SEQUENCE: 55

Met Ser Ser Ser Ser Ser Ser Pro Phe Asp Leu Met Ser Ala Ile Ile
1               5                   10                  15

Lys Gly Glu Pro Val Val Val Ser Asp Pro Ala Asn Ala Ser Ala Tyr
            20                  25                  30

Glu Ser Val Ala Ala Glu Leu Ser Ser Met Leu Ile Glu Asn Arg Gln
        35                  40                  45

Phe Ala Met Ile Ile Ser Thr Ser Ile Ala Val Leu Ile Gly Cys Ile
    50                  55                  60

Val Met Leu Leu Trp Arg Arg Ser Gly Gly Ser Gly Ser Ser Lys Arg
65                  70                  75                  80

Ala Glu Thr Leu Lys Pro Leu Val Leu Lys Pro Pro Arg Glu Asp Glu
                85                  90                  95

Val Asp Asp Gly Arg Lys Lys Val Thr Ile Phe Phe Gly Thr Gln Thr
            100                 105                 110

Gly Thr Ala Glu Gly Phe Ala Lys Ala Leu Gly Glu Glu Ala Arg Ala
        115                 120                 125
```

```
Arg Tyr Glu Lys Thr Arg Phe Lys Ile Val Asp Leu Asp Asp Tyr Ala
    130                 135                 140

Ala Asp Asp Asp Glu Tyr Glu Glu Lys Leu Lys Lys Glu Asp Val Ala
145                 150                 155                 160

Phe Phe Phe Leu Ala Thr Tyr Gly Asp Gly Glu Pro Thr Asp Asn Ala
                165                 170                 175

Ala Arg Phe Tyr Lys Trp Phe Thr Glu Gly Asp Asp Arg Gly Glu Trp
            180                 185                 190

Leu Lys Asn Leu Lys Tyr Gly Val Phe Gly Leu Gly Asn Arg Gln Tyr
        195                 200                 205

Glu His Phe Asn Lys Val Ala Lys Val Val Asp Asp Ile Leu Val Glu
    210                 215                 220

Gln Gly Ala Gln Arg Leu Val His Val Gly Leu Gly Asp Asp Asp Gln
225                 230                 235                 240

Cys Ile Glu Asp Asp Phe Thr Ala Trp Arg Glu Ala Leu Trp Pro Glu
                245                 250                 255

Leu Asp Thr Ile Leu Arg Glu Glu Gly Asp Thr Ala Val Thr Pro Tyr
            260                 265                 270

Thr Ala Ala Val Leu Glu Tyr Arg Val Ser Ile His Asn Ser Ala Asp
        275                 280                 285

Ala Leu Asn Glu Lys Asn Leu Ala Asn Gly Asn Gly His Ala Val Phe
    290                 295                 300

Asp Ala Gln His Pro Tyr Arg Ala Asn Val Ala Val Arg Arg Glu Leu
305                 310                 315                 320

His Thr Pro Glu Ser Asp Arg Ser Cys Thr His Leu Glu Phe Asp Ile
                325                 330                 335

Ala Gly Ser Gly Leu Thr Tyr Glu Thr Gly Asp His Val Gly Val Leu
            340                 345                 350

Ser Asp Asn Leu Asn Glu Thr Val Glu Glu Ala Leu Arg Leu Leu Asp
        355                 360                 365

Met Ser Pro Asp Thr Tyr Phe Ser Leu His Ser Asp Lys Glu Asp Gly
    370                 375                 380

Thr Pro Ile Ser Ser Ser Leu Pro Pro Thr Phe Pro Pro Cys Ser Leu
385                 390                 395                 400

Arg Thr Ala Leu Thr Arg Tyr Ala Cys Leu Leu Ser Ser Pro Lys Lys
                405                 410                 415

Ser Ala Leu Leu Ala Leu Ala Ala His Ala Ser Asp Pro Thr Glu Ala
            420                 425                 430

Glu Arg Leu Lys His Leu Ala Ser Pro Ala Gly Lys Asp Glu Tyr Ser
        435                 440                 445

Lys Trp Val Val Glu Ser Gln Arg Ser Leu Leu Glu Val Met Ala Glu
    450                 455                 460

Phe Pro Ser Ala Lys Pro Pro Leu Gly Val Phe Phe Ala Ala Val Ala
465                 470                 475                 480

Pro Arg Leu Gln Pro Arg Phe Tyr Ser Ile Ser Ser Ser Pro Lys Ile
                485                 490                 495

Ala Glu Thr Arg Ile His Val Thr Cys Ala Leu Val Tyr Glu Lys Met
            500                 505                 510

Pro Thr Gly Arg Ile His Lys Gly Val Cys Ser Thr Trp Met Lys Ser
        515                 520                 525

Ala Val Pro Tyr Glu Lys Ser Glu Asn Cys Cys Ser Ala Pro Ile Phe
    530                 535                 540
```

```
Val Arg Gln Ser Asn Phe Lys Leu Pro Ser Asp Ser Lys Val Pro Ile
545                 550                 555                 560

Ile Met Ile Gly Pro Gly Thr Gly Leu Ala Pro Phe Arg Gly Phe Leu
                565                 570                 575

Gln Glu Arg Leu Ala Leu Val Glu Ser Gly Val Glu Leu Gly Pro Ser
            580                 585                 590

Val Leu Phe Phe Gly Cys Arg Asn Arg Arg Met Asp Phe Ile Tyr Glu
        595                 600                 605

Glu Glu Leu Gln Arg Phe Leu Glu Ser Gly Ala Leu Ser Glu Leu Ser
    610                 615                 620

Val Ala Phe Ser Arg Glu Gly Pro Thr Lys Glu Tyr Val Gln His Lys
625                 630                 635                 640

Met Met Asp Lys Ala Ser Asp Ile Trp Asn Met Ile Ser Gln Gly Ala
                645                 650                 655

Tyr Val Tyr Val Cys Gly Asp Ala Lys Gly Met Ala Arg Asp Val His
            660                 665                 670

Arg Ser Leu His Thr Ile Ala Gln Glu Gln Gly Ser Met Asp Ser Thr
        675                 680                 685

Lys Ala Glu Ser Phe Val Lys Asn Leu Gln Met Ser Gly Arg Tyr Leu
    690                 695                 700

Arg Asp Val Trp
705


<210> SEQ ID NO 56
<211> LENGTH: 508
<212> TYPE: PRT
<213> ORGANISM: Cephalotus follicularis

<400> SEQUENCE: 56

Met Ala Leu Asp Thr Phe Leu Leu Arg Glu Leu Ala Ala Ala Ala Val
1               5                   10                  15

Leu Phe Leu Ile Ser His Tyr Leu Ile His Ser Leu Leu Lys Lys Ser
            20                  25                  30

Thr Pro Pro Leu Pro Pro Gly Pro Lys Gly Trp Pro Phe Val Gly Ala
        35                  40                  45

Leu Pro Leu Leu Gly Thr Met Pro His Val Ala Leu Ala Gln Met Ala
    50                  55                  60

Lys Lys Tyr Gly Pro Val Met Tyr Leu Lys Met Gly Thr Cys Gly Met
65                  70                  75                  80

Val Val Ala Ser Thr Pro Asp Ala Ala Arg Ala Phe Leu Lys Thr Leu
                85                  90                  95

Asp Leu Asn Phe Ser Asn Arg Pro Pro Asn Ala Gly Ala Thr His Leu
            100                 105                 110

Ala Tyr Asn Ala Gln Asp Met Val Phe Ala Asp Tyr Gly Pro Arg Trp
        115                 120                 125

Lys Leu Leu Arg Lys Leu Ser Asn Leu His Met Leu Gly Gly Lys Ala
    130                 135                 140

Leu Glu Asp Trp Thr Gln Val Arg Thr Val Glu Leu Gly His Met Ile
145                 150                 155                 160

Gln Ala Met Cys Glu Ala Ser Arg Ala Lys Glu Pro Val Val Val Pro
                165                 170                 175

Glu Met Leu Thr Tyr Ala Met Ala Asn Met Ile Gly Lys Val Ile Leu
            180                 185                 190

Gly His Arg Val Phe Val Thr Gln Gly Ser Glu Ser Asn Glu Phe Lys
        195                 200                 205
```

```
Asp Met Val Val Glu Leu Met Thr Ser Ala Gly Tyr Phe Asn Ile Gly
    210                 215                 220

Asp Phe Ile Pro Ser Ile Ala Trp Met Asp Leu Gln Gly Ile Glu Arg
225                 230                 235                 240

Gly Met Lys Lys Leu His Lys Arg Phe Asp Ala Leu Leu Thr Lys Met
                245                 250                 255

Phe Glu Glu His Met Ala Thr Ala His Glu Arg Lys Gly Asn Pro Asp
            260                 265                 270

Leu Leu Asp Ile Val Met Ala Asn Arg Asp Asn Ser Glu Gly Glu Arg
        275                 280                 285

Leu Thr Thr Thr Asn Ile Lys Ala Leu Leu Leu Asn Leu Phe Ser Ala
    290                 295                 300

Gly Thr Asp Thr Ser Ser Ser Ile Ile Glu Trp Ser Leu Ala Glu Met
305                 310                 315                 320

Leu Lys Asn Pro Ser Ile Leu Lys Arg Ala His Glu Glu Met Asp Gln
                325                 330                 335

Val Ile Gly Arg Asn Arg Arg Leu Glu Glu Ser Asp Ile Lys Lys Leu
            340                 345                 350

Pro Tyr Leu Gln Ala Ile Cys Lys Glu Ser Phe Arg Lys His Pro Ser
        355                 360                 365

Thr Pro Leu Asn Leu Pro Arg Val Ser Ser Gln Ala Cys Gln Val Asn
    370                 375                 380

Gly Tyr Tyr Ile Pro Lys Asp Thr Arg Leu Ser Val Asn Ile Trp Ala
385                 390                 395                 400

Ile Gly Arg Asp Pro Glu Val Trp Glu Asn Pro Leu Asp Phe Thr Pro
                405                 410                 415

Glu Arg Phe Leu Ser Gly Lys Asn Ala Lys Ile Asp Pro Arg Gly Asn
            420                 425                 430

Asp Phe Glu Leu Ile Pro Phe Gly Ala Gly Arg Arg Ile Cys Ala Gly
        435                 440                 445

Thr Arg Met Gly Ile Val Leu Val Glu Tyr Ile Leu Gly Thr Leu Val
    450                 455                 460

His Ser Phe Asp Trp Ser Leu Pro His Gly Val Lys Leu Asn Met Asp
465                 470                 475                 480

Glu Ala Phe Gly Leu Ala Leu Gln Lys Ala Val Pro Leu Ala Ala Ile
                485                 490                 495

Val Ser Pro Arg Leu Ala Pro Thr Ala Tyr Val Val
            500                 505
```

<210> SEQ ID NO 57
<211> LENGTH: 504
<212> TYPE: PRT
<213> ORGANISM: Dendrobium moniliforme

<400> SEQUENCE: 57

```
Met Ser Ile Phe Leu Ile Thr Ser Leu Leu Leu Cys Leu Ser Leu His
1               5                   10                  15

Leu Leu Leu Arg Arg Arg His Ile Ser Arg Leu Pro Leu Pro Pro Gly
            20                  25                  30

Pro Pro Asn Leu Pro Ile Ile Gly Ala Leu Pro Phe Ile Gly Pro Met
        35                  40                  45

Pro His Ser Gly Leu Ala Leu Leu Ala Arg Arg Tyr Gly Pro Ile Met
    50                  55                  60

Phe Leu Lys Met Gly Ile Arg Arg Val Val Val Ala Ser Ser Ser Thr
```

```
65                  70                  75                  80

Ala Ala Arg Thr Phe Leu Lys Thr Phe Asp Ser His Phe Ser Asp Arg
                85                  90                  95

Pro Ser Gly Val Ile Ser Lys Glu Ile Ser Tyr Asn Gly Gln Asn Met
            100                 105                 110

Val Phe Ala Asp Tyr Gly Pro Lys Trp Lys Leu Leu Arg Lys Val Ser
        115                 120                 125

Ser Leu His Leu Leu Gly Ser Lys Ala Met Ser Arg Trp Ala Gly Val
    130                 135                 140

Arg Arg Asp Glu Ala Leu Ser Met Ile Gln Phe Leu Lys Lys His Ser
145                 150                 155                 160

Asp Ser Glu Lys Pro Val Leu Leu Pro Asn Leu Leu Val Cys Ala Met
                165                 170                 175

Ala Asn Val Ile Gly Arg Ile Ala Met Ser Lys Arg Val Phe His Glu
            180                 185                 190

Asp Gly Glu Glu Ala Lys Glu Phe Lys Glu Met Ile Lys Glu Leu Leu
        195                 200                 205

Val Gly Gln Gly Ala Ser Asn Met Glu Asp Leu Val Pro Ala Ile Gly
    210                 215                 220

Trp Leu Asp Pro Met Gly Val Arg Lys Lys Met Leu Gly Leu Asn Arg
225                 230                 235                 240

Arg Phe Asp Arg Met Val Ser Lys Leu Leu Val Glu His Ala Glu Thr
                245                 250                 255

Ala Gly Glu Arg Gln Gly Asn Pro Asp Leu Leu Asp Leu Val Val Ala
            260                 265                 270

Ser Glu Val Lys Gly Glu Asp Gly Glu Gly Leu Cys Glu Asp Asn Ile
        275                 280                 285

Lys Gly Phe Ile Ser Asp Leu Phe Val Ala Gly Thr Asp Thr Ser Ala
    290                 295                 300

Ile Val Ile Glu Trp Ala Met Ala Glu Met Leu Lys Asn Pro Ser Ile
305                 310                 315                 320

Leu Arg Arg Ala Gln Glu Glu Thr Asp Arg Val Ile Gly Arg His Arg
                325                 330                 335

Leu Leu Asp Glu Ser Asp Ile Pro Asn Leu Pro Tyr Leu Gln Ala Ile
            340                 345                 350

Cys Lys Glu Ala Leu Arg Lys His Pro Pro Thr Pro Leu Ser Ile Pro
        355                 360                 365

His Tyr Ala Ser Glu Pro Cys Glu Val Glu Gly Tyr His Ile Pro Gly
    370                 375                 380

Glu Thr Trp Leu Leu Val Asn Ile Trp Ala Ile Gly Arg Asp Pro Asp
385                 390                 395                 400

Val Trp Glu Asn Pro Leu Val Phe Asp Pro Glu Arg Phe Leu Gln Gly
                405                 410                 415

Glu Met Ala Arg Ile Asp Pro Met Gly Asn Asp Phe Glu Leu Ile Pro
            420                 425                 430

Phe Gly Ala Gly Arg Arg Ile Cys Ala Gly Lys Leu Ala Gly Met Val
        435                 440                 445

Met Val Gln Tyr Tyr Leu Gly Thr Leu Val His Ala Phe Asp Trp Ser
    450                 455                 460

Leu Pro Glu Gly Val Gly Glu Leu Asp Met Glu Glu Gly Pro Gly Leu
465                 470                 475                 480

Val Leu Pro Lys Ala Val Pro Leu Ala Val Met Ala Thr Pro Arg Leu
                485                 490                 495
```

```
Pro Ala Ala Ala Tyr Gly Leu Leu
            500


<210> SEQ ID NO 58
<211> LENGTH: 360
<212> TYPE: PRT
<213> ORGANISM: Acer palmatum

<400> SEQUENCE: 58

Met Gly Ser Glu Ala Glu Thr Val Cys Val Thr Gly Ala Ser Gly Phe
1               5                   10                  15

Ile Gly Ser Trp Leu Ile Met Arg Leu Leu Glu Arg Gly Tyr Thr Val
            20                  25                  30

Arg Ala Thr Val Arg Asp Pro Asp Asn Glu Lys Lys Val Lys His Leu
        35                  40                  45

Val Glu Leu Pro Lys Ala Lys Thr His Leu Thr Leu Trp Lys Ala Asp
    50                  55                  60

Leu Ser Asp Glu Gly Ser Phe Asp Glu Ala Ile His Gly Cys Thr Gly
65                  70                  75                  80

Val Phe His Val Ala Thr Pro Met Asp Phe Glu Ser Lys Asp Pro Glu
                85                  90                  95

Asn Glu Val Ile Lys Pro Thr Ile Asn Gly Val Leu Gly Ile Met Lys
            100                 105                 110

Ala Cys Lys Lys Ala Lys Thr Val Lys Arg Leu Val Phe Thr Ser Ser
        115                 120                 125

Ala Gly Thr Val Asp Val Glu Glu His Lys Lys Pro Val Tyr Asp Glu
    130                 135                 140

Asn Ser Trp Ser Asp Leu Asp Phe Val Gln Ser Val Lys Met Thr Gly
145                 150                 155                 160

Trp Met Tyr Phe Val Ser Lys Thr Leu Ala Glu Lys Ala Ala Trp Lys
                165                 170                 175

Phe Ala Glu Glu Asn Ser Ile Asp Phe Ile Ser Val Ile Pro Pro Leu
            180                 185                 190

Val Val Gly Pro Phe Leu Met Pro Ser Met Pro Pro Ser Leu Ile Thr
        195                 200                 205

Ala Leu Ser Pro Ile Thr Arg Asn Glu Gly His Tyr Ala Ile Ile Lys
    210                 215                 220

Gln Gly Asn Tyr Val His Leu Asp Asp Leu Cys Met Gly His Ile Phe
225                 230                 235                 240

Leu Tyr Glu His Ala Glu Ser Lys Gly Arg Tyr Phe Cys Ser Ser His
                245                 250                 255

Ser Ala Thr Ile Leu Glu Leu Ser Lys Phe Leu Arg Glu Arg Tyr Pro
            260                 265                 270

Glu Tyr Asp Leu Pro Thr Glu Tyr Lys Gly Val Asp Asp Ser Leu Glu
        275                 280                 285

Asn Val Val Phe Cys Ser Lys Lys Ile Leu Asp Leu Gly Phe Gln Phe
    290                 295                 300

Lys Tyr Ser Leu Glu Asp Met Phe Thr Gly Ala Val Glu Thr Cys Arg
305                 310                 315                 320

Glu Lys Gly Leu Ile Pro Leu Thr Asn Ile Asp Lys Lys His Val Ala
                325                 330                 335

Ala Lys Gly Leu Ile Pro Asn Asn Ser Asp Glu Ile His Val Ala Ala
            340                 345                 350

Ala Glu Lys Thr Thr Ala Thr Ala
```

355 360

<210> SEQ ID NO 59
<211> LENGTH: 337
<212> TYPE: PRT
<213> ORGANISM: Abrus precatorius

<400> SEQUENCE: 59

Met Gly Ser Ala Ser Glu Thr Val Cys Val Thr Gly Ala Ala Gly Phe
1 5 10 15

Ile Gly Ser Trp Leu Val Met Arg Leu Ile Gln Asn Gly Tyr Lys Val
20 25 30

Arg Ala Thr Val Arg Asp Pro Ala Asn Met Lys Lys Val Lys His Leu
35 40 45

Leu Glu Leu Pro Asn Ala Lys Thr Asn Leu Ser Leu Trp Lys Ala Asp
50 55 60

Leu Ala Glu Glu Gly Ser Phe Asp Glu Ala Ile Lys Gly Cys Thr Gly
65 70 75 80

Val Phe His Val Ala Thr Pro Met Asp Phe Glu Ser Lys Asp Pro Glu
85 90 95

Asn Glu Val Ile Lys Pro Thr Ile Asn Gly Leu Ile Asp Ile Met Lys
100 105 110

Ala Cys Met Lys Ala Lys Thr Val Arg Arg Leu Val Phe Thr Ser Ser
115 120 125

Ala Gly Thr Val Asp Val Thr Glu His Pro Lys Pro Leu Phe Asp Glu
130 135 140

Ser Cys Trp Ser Asp Val Gln Phe Cys Arg Arg Val Arg Met Thr Gly
145 150 155 160

Trp Met Tyr Phe Val Ser Lys Thr Leu Ala Glu Gln Glu Ala Trp Lys
165 170 175

Phe Ala Lys Glu Asn Asn Ile Asp Phe Ile Ser Val Ile Pro Pro Leu
180 185 190

Val Val Gly Pro Phe Leu Val Pro Thr Met Pro Pro Ser Leu Ile Thr
195 200 205

Ala Leu Ser Leu Ile Thr Gly Asn Glu Ser His Tyr Ala Ile Ile Lys
210 215 220

Gln Gly Gln Phe Val His Leu Asp Asp Leu Cys Leu Ala His Ile Phe
225 230 235 240

Leu Phe Gln His Pro Lys Ala Gln Gly Arg Tyr Ile Cys Cys Ser His
245 250 255

Glu Ala Thr Ile His Asp Ile Ala Ser Leu Leu Asn Gln Lys Tyr Pro
260 265 270

Glu Phe Asn Val Pro Thr Lys Phe Lys Asn Ile Pro Asp Gln Leu Glu
275 280 285

Ile Ile Arg Phe Ser Ser Lys Lys Ile Thr Asp Leu Gly Phe Lys Phe
290 295 300

Lys Tyr Ser Leu Glu Asp Met Phe Thr Gly Ala Val Glu Thr Cys Lys
305 310 315 320

Glu Lys Arg Leu Leu Ser Glu Thr Ala Glu Ile Ser Gly Thr Thr Gln
325 330 335

Lys

<210> SEQ ID NO 60
<211> LENGTH: 351
<212> TYPE: PRT

<213> ORGANISM: Dendrobium moniliforme

<400> SEQUENCE: 60

```
Met Glu Asn Glu Lys Lys Gly Pro Val Val Val Thr Gly Ala Ser Gly
1               5                   10                  15

Tyr Val Gly Ser Trp Leu Val Met Lys Leu Leu Gln Lys Gly Tyr Glu
            20                  25                  30

Val Arg Ala Thr Val Arg Asp Pro Thr Asn Leu Lys Lys Val Lys Pro
        35                  40                  45

Leu Leu Asp Leu Pro Arg Ser Asn Glu Leu Leu Ser Ile Trp Lys Ala
    50                  55                  60

Asp Leu Asp Gly Ile Glu Gly Ser Phe Asp Glu Val Ile Arg Gly Ser
65                  70                  75                  80

Ile Gly Val Phe His Val Ala Thr Pro Met Asn Phe Gln Ser Lys Asp
                85                  90                  95

Pro Glu Asn Glu Val Ile Gln Pro Ala Ile Asn Gly Leu Leu Gly Ile
            100                 105                 110

Leu Arg Ser Cys Lys Asn Ala Gly Ser Val Gln Arg Val Ile Phe Thr
        115                 120                 125

Ser Ser Ala Gly Thr Val Asn Val Glu Glu His Gln Ala Ala Ala Tyr
    130                 135                 140

Asp Glu Thr Cys Trp Ser Asp Leu Asp Phe Val Asn Arg Val Lys Met
145                 150                 155                 160

Thr Gly Trp Met Tyr Phe Leu Ser Lys Thr Leu Ala Glu Lys Ala Ala
                165                 170                 175

Trp Glu Phe Val Lys Asp Asn His Ile His Leu Ile Thr Ile Ile Pro
            180                 185                 190

Thr Leu Val Val Gly Ser Phe Ile Thr Ser Glu Met Pro Pro Ser Met
        195                 200                 205

Ile Thr Ala Leu Ser Leu Ile Thr Gly Asn Asp Ala His Tyr Ser Ile
    210                 215                 220

Leu Lys Gln Ile Gln Phe Val His Leu Asp Asp Leu Cys Asp Ala His
225                 230                 235                 240

Ile Phe Leu Phe Glu His Pro Lys Ala Asn Gly Arg Tyr Ile Cys Ser
                245                 250                 255

Ser Tyr Asp Ser Thr Ile Tyr Gly Leu Ala Glu Met Leu Lys Asn Arg
            260                 265                 270

Tyr Pro Thr Tyr Ala Ile Pro His Lys Phe Lys Glu Ile Asp Pro Asp
        275                 280                 285

Ile Lys Cys Val Ser Phe Ser Ser Lys Lys Leu Met Glu Leu Gly Phe
    290                 295                 300

Lys Tyr Lys Tyr Thr Met Glu Glu Met Phe Asp Asp Ala Ile Lys Thr
305                 310                 315                 320

Cys Arg Glu Lys Lys Leu Ile Pro Leu Asn Thr Glu Glu Ile Val Leu
                325                 330                 335

Ala Ala Glu Lys Phe Glu Glu Val Lys Glu Gln Ile Ala Val Lys
            340                 345                 350
```

<210> SEQ ID NO 61
<211> LENGTH: 349
<212> TYPE: PRT
<213> ORGANISM: Rosa chinensis

<400> SEQUENCE: 61

```
Met Ala Ser Glu Ser Glu Ser Val Cys Val Thr Gly Ala Ser Gly Phe
```

```
1               5                   10                  15

Val Gly Ser Trp Leu Val Met Arg Leu Leu Asp Arg Gly Tyr Thr Val
            20                  25                  30

Arg Ala Thr Val Arg Asp Pro Ala Asn Lys Lys Lys Val Lys His Leu
        35                  40                  45

Leu Asp Leu Pro Lys Ala Ala Thr His Leu Thr Leu Trp Lys Ala Asp
    50                  55                  60

Leu Ala Glu Glu Gly Ser Phe Asp Glu Ala Ile Lys Gly Cys Thr Gly
65                  70                  75                  80

Val Phe His Val Ala Thr Pro Met Asp Phe Glu Ser Lys Asp Pro Glu
                85                  90                  95

Asn Glu Val Ile Lys Pro Thr Ile Asn Gly Val Leu Asp Ile Met Lys
            100                 105                 110

Ala Cys Leu Lys Ala Lys Thr Val Arg Arg Leu Val Phe Thr Ala Ser
        115                 120                 125

Ala Gly Ser Val Asn Val Glu Glu Thr Gln Lys Pro Val Tyr Asp Glu
    130                 135                 140

Ser Asn Trp Ser Asp Val Glu Phe Cys Arg Arg Val Lys Met Thr Gly
145                 150                 155                 160

Trp Met Tyr Phe Ala Ser Lys Thr Leu Ala Glu Gln Glu Ala Trp Lys
                165                 170                 175

Phe Ala Lys Glu Asn Asn Ile Asp Phe Ile Thr Ile Ile Pro Thr Leu
            180                 185                 190

Val Ile Gly Pro Phe Leu Met Pro Ala Met Pro Pro Ser Leu Ile Thr
        195                 200                 205

Gly Leu Ser Pro Leu Thr Gly Asn Glu Ser His Tyr Ser Ile Ile Lys
    210                 215                 220

Gln Gly Gln Phe Ile His Leu Asp Asp Leu Cys Gln Ser His Ile Tyr
225                 230                 235                 240

Leu Tyr Glu His Pro Lys Ala Glu Gly Arg Tyr Ile Cys Ser Ser His
                245                 250                 255

Asp Ala Thr Ile His Glu Ile Ala Lys Leu Leu Arg Glu Lys Tyr Pro
            260                 265                 270

Glu Tyr Asn Val Pro Thr Thr Phe Lys Gly Ile Glu Glu Asn Leu Pro
        275                 280                 285

Lys Val His Phe Ser Ser Lys Lys Leu Leu Glu Thr Gly Phe Glu Phe
    290                 295                 300

Lys Tyr Ser Leu Glu Asp Met Phe Val Gly Ala Val Asp Ala Cys Lys
305                 310                 315                 320

Ala Lys Gly Leu Leu Pro Pro Pro Thr Glu Arg Val Glu Lys Gln Glu
                325                 330                 335

Val Asp Glu Ser Ser Val Val Gly Val Lys Val Thr Gly
            340                 345
```

```
<210> SEQ ID NO 62
<211> LENGTH: 326
<212> TYPE: PRT
<213> ORGANISM: Camellia sinensis

<400> SEQUENCE: 62

Met Thr Val Ser Ser Pro Cys Val Gly Glu Gly Gln Gly Arg Val Leu
1               5                   10                  15

Ile Ile Gly Ala Ser Gly Phe Ile Gly Glu Phe Ile Ala Gln Ala Ser
            20                  25                  30
```

```
Leu Asp Ser Gly Arg Thr Thr Phe Leu Leu Val Arg Ser Leu Asp Lys
        35                  40                  45

Gly Ala Ile Pro Ser Lys Ser Lys Thr Ile Asn Ser Leu His Asp Lys
    50                  55                  60

Gly Ala Ile Leu Ile His Gly Val Ile Glu Asp Gln Glu Phe Val Glu
65                  70                  75                  80

Gly Ile Leu Lys Asp His Lys Ile Asp Ile Val Ile Ser Ala Val Gly
                85                  90                  95

Gly Ala Asn Ile Leu Asn Gln Leu Thr Ile Val Lys Ala Ile Lys Ala
            100                 105                 110

Val Gly Thr Ile Lys Arg Phe Leu Pro Ser Glu Phe Gly His Asp Val
        115                 120                 125

Asp Arg Ala Asn Pro Val Glu Pro Gly Leu Ala Met Tyr Lys Glu Lys
    130                 135                 140

Arg Met Val Arg Arg Leu Ile Glu Glu Ser Gly Val Pro Tyr Thr Tyr
145                 150                 155                 160

Ile Cys Cys Asn Ser Ile Ala Ser Trp Pro Tyr Tyr Asp Asn Thr His
                165                 170                 175

Pro Ser Glu Val Ile Pro Pro Leu Asp Arg Phe Gln Ile Tyr Gly Asp
            180                 185                 190

Gly Thr Val Lys Ala Tyr Phe Val Asp Gly Ser Asp Ile Gly Lys Phe
        195                 200                 205

Thr Met Lys Val Val Asp Asp Ile Arg Thr Leu Asn Lys Ser Val His
    210                 215                 220

Phe Arg Pro Ser Cys Asn Phe Leu Asn Met Asn Glu Leu Ser Ser Leu
225                 230                 235                 240

Trp Glu Lys Lys Ile Gly Tyr Met Leu Pro Arg Leu Thr Val Thr Glu
                245                 250                 255

Asp Asp Leu Leu Ala Ala Ala Ala Glu Asn Ile Ile Pro Gln Ser Ile
            260                 265                 270

Val Ala Ser Phe Thr His Asp Ile Phe Ile Lys Gly Cys Gln Val Asn
        275                 280                 285

Phe Ser Ile Asp Gly Pro Asn Glu Val Glu Val Ser Asn Leu Tyr Pro
    290                 295                 300

Asp Glu Thr Phe Arg Thr Met Asp Glu Cys Phe Asp Asp Phe Val Met
305                 310                 315                 320

Lys Met Asp Arg Trp Asn
                325


<210> SEQ ID NO 63
<211> LENGTH: 352
<212> TYPE: PRT
<213> ORGANISM: Coffea arabica

<400> SEQUENCE: 63

Met Thr Arg Ser Pro Ser Pro Asn Gly Gln Ala Glu Lys Gly Ser Arg
1               5                   10                  15

Ile Leu Ile Ile Gly Ala Thr Gly Phe Ile Gly His Phe Ile Ala Gln
            20                  25                  30

Ala Ser Leu Ala Ser Gly Lys Ser Thr Tyr Ile Leu Ser Arg Ala Ala
        35                  40                  45

Ala Arg Cys Pro Ser Lys Ala Arg Ala Ile Lys Ala Leu Glu Asp Gln
    50                  55                  60

Gly Ala Ile Ser Ile His Gly Ser Val Asn Asp Gln Glu Phe Met Glu
65                  70                  75                  80
```

```
Lys Thr Leu Lys Glu His Glu Ile Asp Ile Val Ile Ser Ala Val Gly
                85                  90                  95

Gly Gly Asn Leu Leu Glu Gln Val Ile Leu Ile Arg Ala Met Lys Ala
            100                 105                 110

Val Gly Thr Ile Lys Arg Phe Leu Pro Ser Glu Phe Gly His Asp Val
        115                 120                 125

Asp Arg Ala Glu Pro Val Glu Pro Gly Leu Thr Met Tyr Asn Glu Lys
    130                 135                 140

Arg Arg Val Arg Arg Leu Ile Glu Glu Ser Gly Val Pro Tyr Thr Tyr
145                 150                 155                 160

Ile Cys Cys Asn Ser Ile Ala Ser Trp Pro Tyr Tyr Asp Asn Thr His
                165                 170                 175

Pro Ser Glu Val Ser Pro Pro Leu Asp Gln Phe Gln Ile Tyr Gly Asp
            180                 185                 190

Gly Ser Val Lys Ala Tyr Phe Val Ala Gly Ala Asp Ile Gly Lys Phe
        195                 200                 205

Thr Val Lys Ala Thr Glu Asp Val Arg Thr Leu Asn Lys Ile Val His
    210                 215                 220

Phe Arg Pro Ser Cys Asn Phe Leu Asn Ile Asn Glu Leu Ala Thr Leu
225                 230                 235                 240

Trp Glu Lys Lys Ile Gly Arg Thr Leu Pro Arg Val Val Val Ser Glu
                245                 250                 255

Asp Asp Leu Leu Ala Ala Ala Glu Glu Asn Ile Ile Pro Gln Ser Val
            260                 265                 270

Val Ala Ser Phe Thr His Asp Ile Phe Ile Lys Gly Cys Gln Val Asn
        275                 280                 285

Phe Pro Val Asp Gly Pro Asn Glu Ile Glu Val Ser Ser Leu Tyr Pro
    290                 295                 300

Asp Glu Pro Phe Gln Thr Met Asp Glu Cys Phe Asn Glu Phe Ala Gly
305                 310                 315                 320

Lys Ile Glu Glu Asp Lys Lys His Val Val Gly Thr Lys Gly Lys Asn
                325                 330                 335

Ile Ala His Arg Leu Val Asp Val Leu Thr Ala Pro Lys Leu Cys Ala
            340                 345                 350
```

<210> SEQ ID NO 64
<211> LENGTH: 359
<212> TYPE: PRT
<213> ORGANISM: Theobroma cacao

<400> SEQUENCE: 64

```
Met Lys Ser Thr Asn Met Asn Gly Ser Ser Pro Asn Val Ser Glu Glu
1               5                   10                  15

Thr Gly Arg Thr Leu Val Val Gly Ser Gly Gly Phe Met Gly Arg Phe
            20                  25                  30

Val Thr Glu Ala Ser Leu Asp Ser Gly Arg Pro Thr Tyr Ile Leu Ala
        35                  40                  45

Arg Ser Ser Ser Asn Ser Pro Ser Lys Ala Ser Thr Ile Lys Phe Leu
    50                  55                  60

Gln Asp Arg Gly Ala Thr Val Ile Tyr Gly Ser Ile Thr Asp Lys Glu
65                  70                  75                  80

Phe Met Glu Lys Val Leu Lys Glu His Lys Ile Glu Val Val Ile Ser
                85                  90                  95

Ala Val Gly Gly Gly Ser Ile Leu Asp Gln Phe Asn Leu Ile Glu Ala
```

```
            100                 105                 110

Ile Arg Asn Val Asp Thr Val Lys Arg Phe Leu Pro Ser Glu Phe Gly
        115                 120                 125

His Asp Thr Asp Arg Ala Asp Pro Val Glu Pro Gly Leu Thr Met Tyr
    130                 135                 140

Glu Gln Lys Arg Gln Ile Arg Arg Gln Ile Glu Lys Ser Gly Ile Pro
145                 150                 155                 160

Tyr Thr Tyr Ile Cys Cys Asn Ser Ile Ala Ala Trp Pro Tyr His Asp
                165                 170                 175

Asn Thr His Pro Ala Asp Val Leu Pro Pro Leu Asp Arg Phe Lys Ile
            180                 185                 190

Tyr Gly Asp Gly Thr Val Lys Ala Tyr Phe Val Ala Gly Thr Asp Ile
        195                 200                 205

Gly Lys Phe Thr Ile Met Ser Ile Glu Asp Asp Arg Thr Leu Asn Lys
    210                 215                 220

Thr Val His Phe Gln Pro Pro Ser Asn Leu Leu Asn Ile Asn Glu Met
225                 230                 235                 240

Ala Ser Leu Trp Glu Glu Lys Ile Gly Arg Thr Leu Pro Arg Val Thr
                245                 250                 255

Ile Thr Glu Glu Asp Leu Leu Gln Met Ala Lys Glu Met Arg Ile Pro
            260                 265                 270

Gln Ser Val Val Ala Ala Leu Thr His Asp Ile Phe Ile Asn Gly Cys
        275                 280                 285

Gln Ile Asn Phe Ser Leu Asp Lys Pro Thr Asp Val Glu Val Cys Ser
    290                 295                 300

Leu Tyr Pro Asp Thr Pro Phe Arg Thr Ile Asn Glu Cys Phe Glu Asp
305                 310                 315                 320

Phe Ala Lys Lys Ile Ile Asp Asn Ala Lys Ala Val Ser Lys Pro Ala
                325                 330                 335

Ala Ser Asn Asn Ala Ile Phe Val Pro Thr Ala Lys Pro Gly Ala Leu
            340                 345                 350

Pro Ile Thr Ala Ile Cys Thr
        355
```

<210> SEQ ID NO 65
<211> LENGTH: 350
<212> TYPE: PRT
<213> ORGANISM: Fragaria x ananassa

<400> SEQUENCE: 65

```
Met Thr Val Ser Pro Ser Ile Ala Ser Ala Ala Lys Ser Gly Arg Val
1               5                   10                  15

Leu Ile Ile Gly Ala Thr Gly Phe Ile Gly Lys Phe Val Ala Glu Ala
            20                  25                  30

Ser Leu Asp Ser Gly Leu Pro Thr Tyr Val Leu Val Arg Pro Gly Pro
        35                  40                  45

Ser Arg Pro Ser Lys Ser Asp Thr Ile Lys Ser Leu Lys Asp Arg Gly
    50                  55                  60

Ala Ile Ile Leu His Gly Val Met Ser Asp Lys Pro Leu Met Glu Lys
65                  70                  75                  80

Leu Leu Lys Glu His Glu Ile Glu Ile Val Ile Ser Ala Val Gly Gly
                85                  90                  95

Ala Thr Ile Leu Asp Gln Ile Thr Leu Val Glu Ala Ile Thr Ser Val
            100                 105                 110
```

```
Gly Thr Val Lys Arg Phe Leu Pro Ser Glu Phe Gly His Asp Val Asp
        115                 120                 125

Arg Ala Asp Pro Val Glu Pro Gly Leu Thr Met Tyr Leu Glu Lys Arg
    130                 135                 140

Lys Val Arg Arg Ala Ile Glu Lys Ser Gly Val Pro Tyr Thr Tyr Ile
145                 150                 155                 160

Cys Cys Asn Ser Ile Ala Ser Trp Pro Tyr Tyr Asp Asn Lys His Pro
                165                 170                 175

Ser Glu Val Val Pro Pro Leu Asp Gln Phe Gln Ile Tyr Gly Asp Gly
            180                 185                 190

Thr Val Lys Ala Tyr Phe Val Asp Gly Pro Asp Ile Gly Lys Phe Thr
        195                 200                 205

Met Lys Thr Val Asp Asp Ile Arg Thr Met Asn Lys Asn Val His Phe
    210                 215                 220

Arg Pro Ser Ser Asn Leu Tyr Asp Ile Asn Gly Leu Ala Ser Leu Trp
225                 230                 235                 240

Glu Lys Lys Ile Gly Arg Thr Leu Pro Lys Val Thr Ile Thr Glu Asn
                245                 250                 255

Asp Leu Leu Thr Met Ala Ala Glu Asn Arg Ile Pro Glu Ser Ile Val
            260                 265                 270

Ala Ser Phe Thr His Asp Ile Phe Ile Lys Gly Cys Gln Thr Asn Phe
        275                 280                 285

Pro Ile Glu Gly Pro Asn Asp Val Asp Ile Gly Thr Leu Tyr Pro Glu
    290                 295                 300

Glu Ser Phe Arg Thr Leu Asp Glu Cys Phe Asn Asp Phe Leu Val Lys
305                 310                 315                 320

Val Gly Gly Lys Leu Glu Thr Asp Lys Leu Ala Ala Lys Asn Lys Ala
                325                 330                 335

Ala Val Gly Val Glu Pro Met Ala Ile Thr Ala Thr Cys Ala
            340                 345                 350


<210> SEQ ID NO 66
<211> LENGTH: 369
<212> TYPE: PRT
<213> ORGANISM: Chenopodium quinoa

<400> SEQUENCE: 66

Met Thr Gln Asn Lys Glu Pro Val Asn Gln Gly Lys Ser Glu His Asp
1               5                   10                  15

Glu Gln Arg Val Glu Ser Leu Ala Ser Ser Gly Ile Glu Ser Ile Pro
            20                  25                  30

Lys Glu Tyr Val Arg Leu Asn Glu Glu Leu Thr Ser Met Gly Asn Val
        35                  40                  45

Phe Glu Glu Glu Lys Lys Glu Glu Gly Ser Gln Val Pro Thr Ile Asp
    50                  55                  60

Ile Lys Asp Ile Ala Ser Glu Asp Pro Glu Val Arg Gly Lys Ala Ile
65                  70                  75                  80

Gln Glu Leu Lys Arg Ala Ala Met Glu Trp Gly Val Met His Leu Val
                85                  90                  95

Asn His Gly Ile Ser Asp Glu Leu Ile Asp Arg Val Lys Val Ala Gly
            100                 105                 110

Gln Thr Phe Phe Glu Leu Pro Val Glu Glu Lys Glu Lys Tyr Ala Asn
        115                 120                 125

Asp Gln Ala Ser Gly Asn Val Gln Gly Tyr Gly Ser Lys Leu Ala Asn
    130                 135                 140
```

```
Ser Ala Ser Gly Arg Leu Glu Trp Glu Asp Tyr Tyr Phe His Leu Ser
145                 150                 155                 160

Tyr Pro Glu Asp Lys Arg Asp Leu Ser Ile Trp Pro Glu Thr Pro Ala
                165                 170                 175

Asp Tyr Ile Pro Ala Val Ser Glu Tyr Ser Lys Glu Leu Arg Tyr Leu
            180                 185                 190

Ala Thr Lys Ile Leu Ser Ala Leu Ser Leu Ala Leu Gly Leu Glu Glu
        195                 200                 205

Gly Arg Leu Glu Lys Glu Val Gly Gly Leu Glu Glu Leu Leu Leu Gln
    210                 215                 220

Phe Lys Ile Asn Tyr Tyr Pro Lys Cys Pro Gln Pro Glu Leu Ala Leu
225                 230                 235                 240

Gly Val Glu Ala His Thr Asp Val Ser Ala Leu Thr Phe Ile Leu His
                245                 250                 255

Asn Met Val Pro Gly Leu Gln Leu Phe Tyr Glu Gly Lys Trp Val Thr
            260                 265                 270

Ala Lys Cys Val Pro Asn Ser Ile Ile Met His Ile Gly Asp Thr Ile
        275                 280                 285

Glu Ile Leu Ser Asn Gly Lys Tyr Lys Ser Ile Leu His Arg Gly Leu
    290                 295                 300

Val Asn Lys Glu Lys Val Arg Ile Ser Trp Ala Val Phe Cys Glu Pro
305                 310                 315                 320

Pro Lys Glu Lys Ile Ile Leu Lys Pro Leu Pro Asp Leu Val Ser Asp
                325                 330                 335

Glu Glu Pro Ala Arg Tyr Pro Pro Arg Thr Phe Ala Gln His Val Gln
            340                 345                 350

Tyr Lys Leu Phe Arg Lys Thr Gln Gly Pro Gln Thr Thr Ile Thr Lys
        355                 360                 365

Asn


<210> SEQ ID NO 67
<211> LENGTH: 370
<212> TYPE: PRT
<213> ORGANISM: Iris sanguinea

<400> SEQUENCE: 67

Met Ala Ser Ser Lys Val Met Pro Ala Pro Ala Arg Val Glu Ser Leu
1               5                   10                  15

Ala Ser Ser Gly Leu Ala Ser Ile Pro Thr Glu Tyr Val Arg Pro Glu
            20                  25                  30

Trp Glu Arg Asp Asp Ser Leu Gly Asp Ala Leu Glu Glu Ile Lys Lys
        35                  40                  45

Thr Glu Glu Gly Pro Gln Ile Pro Ile Val Asp Leu Arg Gly Phe Asp
    50                  55                  60

Ser Gly Asp Glu Lys Glu Arg Leu His Cys Met Glu Glu Val Lys Glu
65                  70                  75                  80

Ala Ala Val Glu Trp Gly Val Met His Ile Val Asn His Gly Ile Ala
                85                  90                  95

Pro Glu Leu Ile Glu Arg Val Arg Ala Ala Gly Lys Gly Phe Phe Asp
            100                 105                 110

Leu Pro Val Glu Ala Lys Glu Arg Tyr Ala Asn Asn Gln Ser Glu Gly
        115                 120                 125

Lys Ile Gln Gly Tyr Gly Ser Lys Leu Ala Asn Asn Ala Ser Gly Gln
    130                 135                 140
```

```
Leu Glu Trp Glu Asp Tyr Phe Phe His Leu Ile Phe Pro Ser Asp Lys
145                 150                 155                 160

Val Asp Leu Ser Ile Trp Pro Lys Glu Pro Ala Asp Tyr Thr Glu Val
                165                 170                 175

Met Met Glu Phe Ala Lys Gln Leu Arg Val Val Val Thr Lys Met Leu
            180                 185                 190

Ser Ile Leu Ser Leu Gly Leu Gly Phe Glu Glu Glu Lys Leu Glu Lys
        195                 200                 205

Lys Leu Gly Gly Met Glu Glu Leu Leu Met Gln Met Lys Ile Asn Tyr
    210                 215                 220

Tyr Pro Lys Cys Pro Gln Pro Glu Leu Ala Leu Gly Val Glu Ala His
225                 230                 235                 240

Thr Asp Val Ser Ser Leu Ser Phe Ile Leu His Asn Gly Val Pro Gly
                245                 250                 255

Leu Gln Val Phe His Gly Gly Arg Trp Val Asn Ala Arg Leu Val Pro
            260                 265                 270

Gly Ser Leu Val Val His Val Gly Asp Thr Leu Glu Ile Leu Ser Asn
        275                 280                 285

Gly Arg Tyr Lys Ser Val Leu His Arg Gly Leu Val Asn Lys Glu Lys
    290                 295                 300

Val Arg Ile Ser Trp Ala Val Phe Cys Glu Pro Pro Lys Glu Lys Ile
305                 310                 315                 320

Val Leu Glu Pro Leu Ala Glu Leu Val Asp Lys Arg Ser Pro Ala Lys
                325                 330                 335

Tyr Pro Pro Arg Thr Phe Ala Gln His Ile Gln His Lys Leu Phe Lys
            340                 345                 350

Lys Ala Gln Glu Gln Leu Ala Gly Gly Val His Ile Pro Glu Ala Ile
        355                 360                 365

Gln Asn
    370


<210> SEQ ID NO 68
<211> LENGTH: 360
<212> TYPE: PRT
<213> ORGANISM: Magnolia sprengeri

<400> SEQUENCE: 68

Met Ala Thr Gln Val Ala Ser Ile Pro Arg Val Glu Met Leu Ala Ser
1               5                   10                  15

Ala Gly Ile Gln Ala Ile Pro Thr Glu Tyr Val Arg Pro Glu Ala Glu
            20                  25                  30

Arg Asn Ser Ile Gly Asp Val Phe Glu Glu Glu Lys Lys Leu Glu Gly
        35                  40                  45

Pro Gln Ile Pro Val Val Asp Leu Met Gly Leu Glu Trp Glu Asn Glu
    50                  55                  60

Glu Val Phe Lys Lys Val Glu Glu Asp Met Lys Lys Ala Ala Ser Glu
65                  70                  75                  80

Trp Gly Val Met His Ile Ile Asn His Gly Ile Ser Met Glu Leu Met
                85                  90                  95

Asp Arg Val Arg Ile Ala Gly Lys Ala Phe Phe Asp Leu Pro Ile Glu
            100                 105                 110

Glu Lys Glu Met Tyr Ala Asn Asp Gln Ala Ser Gly Lys Ile Ala Gly
        115                 120                 125

Tyr Gly Ser Lys Leu Ala Asn Asn Ala Ser Gly Gln Leu Glu Trp Glu
```

```
    130                 135                 140

Asp Tyr Phe Phe His Leu Ile Phe Pro Glu Asp Lys Arg Asp Met Ser
145                 150                 155                 160

Ile Trp Pro Lys Gln Pro Ser Asp Tyr Val Glu Ala Thr Glu Glu Phe
                165                 170                 175

Ala Lys Gln Leu Arg Gly Leu Val Thr Lys Val Leu Val Leu Leu Ser
            180                 185                 190

Arg Gly Leu Gly Val Glu Glu Asp Arg Leu Glu Lys Glu Phe Gly Gly
        195                 200                 205

Met Glu Glu Leu Leu Leu Gln Met Lys Ile Asn Tyr Tyr Pro Lys Cys
    210                 215                 220

Pro Gln Pro Asp Leu Ala Leu Gly Val Glu Ala His Thr Asp Val Ser
225                 230                 235                 240

Ala Leu Thr Phe Ile Leu His Asn Met Val Pro Gly Leu Gln Val Phe
                245                 250                 255

Phe Asp Asp Lys Trp Val Thr Ala Lys Cys Ile Pro Gly Ala Leu Val
            260                 265                 270

Val His Ile Gly Asp Ser Leu Glu Ile Leu Ser Asn Gly Lys Tyr Arg
        275                 280                 285

Ser Ile Leu His Arg Gly Leu Val Asn Lys Glu Lys Val Arg Ile Ser
    290                 295                 300

Trp Ala Ile Phe Cys Glu Pro Pro Lys Glu Lys Val Val Leu Gln Pro
305                 310                 315                 320

Leu Pro Glu Leu Val Ser Glu Ala Glu Pro Ala Arg Phe Thr Pro Arg
                325                 330                 335

Thr Phe Ser Gln His Val Arg Gln Lys Leu Phe Lys Lys Gln Gln Asp
            340                 345                 350

Ala Leu Glu Asn Leu Lys Ser Glu
        355                 360


<210> SEQ ID NO 69
<211> LENGTH: 356
<212> TYPE: PRT
<213> ORGANISM: Prosopis alba

<400> SEQUENCE: 69

Met Val Ser Ser Ala Ala Val Val Ala Thr Arg Val Glu Arg Leu Ala
1               5                   10                  15

Thr Ser Gly Ile Lys Ser Ile Pro Lys Glu Tyr Val Arg Pro Gln Glu
            20                  25                  30

Glu Leu Thr Asn Ile Gly Asn Val Phe Glu Glu Glu Lys Lys Glu Gly
        35                  40                  45

Pro Glu Val Pro Thr Ile Asp Leu Thr Glu Ile Glu Ser Glu Asp Glu
    50                  55                  60

Val Val Arg Ala Arg Cys His Glu Thr Leu Lys Lys Ala Ala Gln Glu
65                  70                  75                  80

Trp Gly Val Met Asn Leu Val Asn His Gly Ile Pro Glu Glu Leu Leu
                85                  90                  95

Asn Gln Leu Arg Lys Ala Gly Glu Thr Phe Phe Ser Leu Pro Ile Glu
            100                 105                 110

Glu Lys Glu Lys Tyr Ala Asn Asp Gln Ala Ser Gly Lys Ile Gln Gly
        115                 120                 125

Tyr Gly Ser Lys Leu Ala Asn Asn Ala Ser Gly Gln Leu Glu Trp Glu
    130                 135                 140
```

```
Asp Tyr Phe Phe His Leu Val Phe Pro Glu Asp Lys Cys Asp Leu Ser
145                 150                 155                 160

Ile Trp Pro Arg Thr Pro Ser Asp Tyr Ile Glu Val Thr Ser Glu Tyr
                165                 170                 175

Ala Arg Gln Leu Arg Gly Leu Ala Thr Lys Ile Leu Gly Ala Leu Ser
            180                 185                 190

Leu Gly Leu Gly Leu Glu Lys Gly Arg Leu Glu Glu Glu Val Gly Gly
        195                 200                 205

Met Glu Glu Leu Leu Leu Gln Met Lys Ile Asn Tyr Tyr Pro Ile Cys
    210                 215                 220

Pro Gln Pro Glu Leu Ala Leu Gly Val Glu Ala His Thr Asp Val Ser
225                 230                 235                 240

Ser Leu Thr Phe Leu Leu His Asn Met Val Pro Gly Leu Gln Leu Phe
                245                 250                 255

Tyr Asn Gly Gln Trp Ile Thr Ala Lys Cys Val Pro Asn Ser Ile Phe
            260                 265                 270

Met His Ile Gly Asp Thr Val Glu Ile Leu Ser Asn Gly Arg Tyr Lys
        275                 280                 285

Ser Ile Leu His Arg Gly Leu Val Asn Lys Glu Lys Val Arg Ile Ser
    290                 295                 300

Trp Ala Val Phe Cys Glu Pro Pro Lys Glu Lys Ile Ile Leu Lys Pro
305                 310                 315                 320

Leu Pro Glu Leu Val Thr Asp Asp Glu Pro Ala Arg Phe Pro Pro Arg
                325                 330                 335

Thr Phe Ala Gln His Ile Gln His Lys Leu Phe Arg Lys Cys Gln Glu
            340                 345                 350

Gly Leu Ser Lys
        355


<210> SEQ ID NO 70
<211> LENGTH: 455
<212> TYPE: PRT
<213> ORGANISM: Cephalotus follicularis

<400> SEQUENCE: 70

Met Pro Gln Phe Thr Thr Asn Glu Pro His Val Ala Val Leu Ala Phe
1               5                   10                  15

Pro Phe Gly Thr His Ala Ala Pro Leu Ile Thr Ile Ile His Arg Leu
            20                  25                  30

Ala Val Ala Ser Pro Asn Thr His Phe Ser Phe Leu Asn Thr Ser Gln
        35                  40                  45

Ser Asn Asn Ser Ile Phe Ser Ser Asp Val Tyr Asn Arg Gln Pro Asn
    50                  55                  60

Leu Lys Ala His Asn Val Trp Asp Gly Val Pro Glu Gly Tyr Val Phe
65                  70                  75                  80

Val Gly Lys Pro Gln Glu Ser Ile Glu Leu Phe Val Lys Ala Ala Pro
                85                  90                  95

Glu Thr Phe Arg Lys Gly Val Glu Ala Ala Val Ala Glu Thr Gly Arg
            100                 105                 110

Lys Val Ser Cys Leu Val Thr Asp Ala Phe Phe Trp Phe Ala Ala Glu
        115                 120                 125

Ile Ala Gly Glu Leu Gly Val Pro Trp Val Pro Phe Trp Thr Ala Gly
    130                 135                 140

Pro Cys Ser Leu Ser Thr His Val Tyr Thr Asp Leu Ile Arg Lys Thr
145                 150                 155                 160
```

```
Ile Gly Val Gly Gly Ile Glu Gly Arg Glu Asp Glu Ser Leu Glu Phe
                165                 170                 175

Ile Pro Gly Met Ser Gln Val Val Ile Arg Asp Leu Gln Glu Gly Ile
            180                 185                 190

Val Phe Gly Asn Leu Glu Ser Val Phe Ser Asp Met Val His Arg Met
        195                 200                 205

Gly Ile Val Leu Pro Gln Ala Ala Ala Ile Phe Ile Asn Ser Phe Glu
    210                 215                 220

Glu Leu Asp Leu Thr Ile Thr Asn Asp Leu Lys Ser Lys Phe Lys Gln
225                 230                 235                 240

Phe Leu Ser Ile Gly Pro Leu Asn Leu Ala Ser Pro Pro Pro Arg Val
                245                 250                 255

Pro Asp Thr Asn Gly Cys Leu Pro Trp Leu Asp Gln Gln Lys Val Ala
            260                 265                 270

Ser Val Ala Tyr Ile Ser Phe Gly Thr Val Met Ala Pro Ser Pro Pro
        275                 280                 285

Glu Leu Val Ala Leu Ala Glu Ala Leu Glu Ala Ser Lys Ile Pro Phe
    290                 295                 300

Ile Trp Ser Leu Gly Glu Lys Leu Lys Val His Leu Pro Lys Gly Phe
305                 310                 315                 320

Leu Asp Lys Thr Arg Thr His Gly Ile Val Val Pro Trp Ala Pro Gln
                325                 330                 335

Ser Asp Val Leu Glu Asn Gly Ala Val Gly Val Phe Ile Thr His Cys
            340                 345                 350

Gly Trp Asn Ser Leu Leu Glu Ser Ile Ala Gly Gly Val Pro Met Ile
        355                 360                 365

Cys Arg Pro Phe Phe Gly Asp Gln Arg Leu Asn Gly Arg Met Val Gln
    370                 375                 380

Asp Val Trp Glu Ile Gly Val Thr Ala Thr Gly Gly Pro Phe Thr Thr
385                 390                 395                 400

Glu Gly Val Met Gly Asp Leu Asp Leu Ile Leu Ser Gln Ala Arg Gly
                405                 410                 415

Lys Lys Met Lys Asp Asn Ile Ser Val Leu Lys Thr Leu Ala Gln Thr
            420                 425                 430

Ala Val Gly Pro Glu Gly Ser Ser Ala Lys Asn Tyr Glu Ala Leu Leu
        435                 440                 445

Asn Leu Val Arg Leu Ser Ile
    450                 455


<210> SEQ ID NO 71
<211> LENGTH: 474
<212> TYPE: PRT
<213> ORGANISM: Prunus cerasifera

<400> SEQUENCE: 71

Met Ala Pro Gln Pro Ile Asp Asp Asp His Val Val Tyr Glu His His
1               5                   10                  15

Val Ala Ala Leu Ala Phe Pro Phe Ser Thr His Ala Ser Pro Thr Leu
            20                  25                  30

Ala Leu Val Arg Arg Leu Ala Ala Ala Ser Pro Asn Thr Leu Phe Ser
        35                  40                  45

Phe Phe Ser Thr Ser Gln Ser Asn Asn Ser Leu Phe Ser Asn Thr Ile
    50                  55                  60

Thr Asn Leu Pro Arg Asn Ile Lys Val Phe Asp Val Ala Asp Gly Val
```

```
65                  70                  75                  80

Pro Asp Gly Tyr Val Phe Ala Gly Lys Pro Gln Glu Asp Ile Glu Leu
                85                  90                  95

Phe Met Lys Ala Ala Pro His Asn Phe Thr Thr Ser Leu Asp Thr Cys
            100                 105                 110

Val Ala His Thr Gly Lys Arg Leu Thr Cys Leu Ile Thr Asp Ala Phe
        115                 120                 125

Leu Trp Phe Gly Ala His Leu Ala His Asp Leu Gly Val Pro Trp Leu
    130                 135                 140

Pro Leu Trp Leu Ser Gly Leu Asn Ser Leu Ser Leu His Val His Thr
145                 150                 155                 160

Asp Leu Leu Arg His Thr Ile Gly Thr Gln Ser Ile Ala Gly Arg Glu
                165                 170                 175

Asn Glu Leu Ile Thr Lys Asn Val Asn Ile Pro Gly Met Ser Lys Val
            180                 185                 190

Arg Ile Lys Asp Leu Pro Glu Gly Val Ile Phe Gly Asn Leu Asp Ser
        195                 200                 205

Val Phe Ser Arg Met Leu His Gln Met Gly Gln Leu Leu Pro Arg Ala
    210                 215                 220

Asn Ala Val Leu Val Asn Ser Phe Glu Glu Leu Asp Ile Thr Val Thr
225                 230                 235                 240

Asn Asp Leu Lys Ser Lys Phe Asn Lys Leu Leu Asn Val Gly Pro Phe
                245                 250                 255

Asn Leu Ala Ala Ala Ala Ser Pro Pro Leu Pro Glu Ala Pro Thr Ala
            260                 265                 270

Ala Asp Asp Val Thr Gly Cys Leu Ser Trp Leu Asp Lys Gln Lys Ala
        275                 280                 285

Ala Ser Ser Val Val Tyr Val Ser Phe Gly Ser Val Ala Arg Pro Pro
    290                 295                 300

Glu Lys Glu Leu Leu Ala Met Ala Gln Ala Leu Glu Ala Ser Gly Val
305                 310                 315                 320

Pro Phe Leu Trp Ser Leu Lys Asp Ser Phe Lys Thr Pro Leu Leu Asn
                325                 330                 335

Glu Leu Leu Ile Lys Ala Ser Asn Gly Met Val Val Pro Trp Ala Pro
            340                 345                 350

Gln Pro Arg Val Leu Ala His Ala Ser Val Gly Ala Phe Val Thr His
        355                 360                 365

Cys Gly Trp Asn Ser Leu Leu Glu Thr Ile Ala Gly Gly Val Pro Met
    370                 375                 380

Ile Cys Arg Pro Phe Phe Gly Asp Gln Arg Val Asn Ala Arg Leu Val
385                 390                 395                 400

Glu Asp Val Leu Glu Ile Gly Val Thr Val Glu Asp Gly Val Phe Thr
                405                 410                 415

Lys His Gly Leu Ile Lys Tyr Phe Asp Gln Val Leu Ser Gln Gln Arg
            420                 425                 430

Gly Lys Lys Met Arg Asp Asn Ile Asn Thr Val Lys Leu Leu Ala Gln
        435                 440                 445

Gln Pro Val Glu Pro Lys Gly Ser Ser Ala Gln Asn Phe Lys Leu Leu
    450                 455                 460

Leu Asp Val Ile Ser Gly Ser Thr Lys Val
465                 470
```

<210> SEQ ID NO 72

<211> LENGTH: 457
<212> TYPE: PRT
<213> ORGANISM: Scutellaria baicalensis

<400> SEQUENCE: 72

```
Met Val Phe Gln Ser His Ile Gly Val Leu Ala Phe Pro Phe Gly Thr
1               5                   10                  15

His Ala Ala Pro Leu Leu Thr Val Val Gln Arg Leu Ala Thr Ser Ser
            20                  25                  30

Pro His Thr Leu Phe Ser Phe Phe Asn Ser Ala Val Ser Asn Ser Thr
        35                  40                  45

Leu Phe Asn Asn Gly Val Leu Asp Ser Tyr Asp Asn Ile Arg Val Tyr
    50                  55                  60

His Val Trp Asp Gly Thr Pro Gln Gly Gln Ala Phe Thr Gly Ser His
65                  70                  75                  80

Phe Glu Ala Val Gly Leu Phe Leu Lys Ala Ser Pro Gly Asn Phe Asp
                85                  90                  95

Lys Val Ile Asp Glu Ala Glu Val Glu Thr Gly Leu Lys Ile Ser Cys
            100                 105                 110

Leu Ile Thr Asp Ala Phe Leu Trp Phe Gly Tyr Asp Leu Ala Glu Lys
        115                 120                 125

Arg Gly Val Pro Trp Leu Ala Phe Trp Thr Ser Ala Gln Cys Ala Leu
    130                 135                 140

Ser Ala His Met Tyr Thr His Glu Ile Leu Lys Ala Val Gly Ser Asn
145                 150                 155                 160

Gly Val Gly Glu Thr Ala Glu Glu Glu Leu Ile Gln Ser Leu Ile Pro
                165                 170                 175

Gly Leu Glu Met Ala His Leu Ser Asp Leu Pro Pro Glu Ile Phe Phe
            180                 185                 190

Asp Lys Asn Pro Asn Pro Leu Ala Ile Thr Ile Asn Lys Met Val Leu
        195                 200                 205

Lys Leu Pro Lys Ser Thr Ala Val Ile Leu Asn Ser Phe Glu Glu Ile
    210                 215                 220

Asp Pro Ile Ile Thr Thr Asp Leu Lys Ser Lys Phe His His Phe Leu
225                 230                 235                 240

Asn Ile Gly Pro Ser Ile Leu Ser Ser Pro Thr Pro Pro Pro Pro Asp
                245                 250                 255

Asp Lys Thr Gly Cys Leu Ala Trp Leu Asp Ser Gln Thr Arg Pro Lys
            260                 265                 270

Ser Val Val Tyr Ile Ser Phe Gly Thr Val Ile Thr Pro Pro Glu Asn
        275                 280                 285

Glu Leu Ala Ala Leu Ser Glu Ala Leu Glu Thr Cys Asn Tyr Pro Phe
    290                 295                 300

Leu Trp Ser Leu Asn Asp Arg Ala Lys Lys Ser Leu Pro Thr Gly Phe
305                 310                 315                 320

Leu Asp Arg Thr Lys Glu Leu Gly Met Ile Val Pro Trp Ala Pro Gln
                325                 330                 335

Pro Arg Val Leu Ala His Arg Ser Val Gly Val Phe Val Thr His Cys
            340                 345                 350

Gly Trp Asn Ser Ile Leu Glu Ser Ile Cys Ser Gly Val Pro Leu Ile
        355                 360                 365

Cys Arg Pro Phe Phe Gly Asp Gln Lys Leu Asn Ser Arg Met Val Glu
    370                 375                 380

Asp Ser Trp Lys Ile Gly Val Arg Leu Glu Gly Gly Val Leu Ser Lys
```

```
385                 390                 395                 400

Thr Ala Thr Val Glu Ala Leu Gly Arg Val Met Met Ser Glu Glu Gly
                405                 410                 415

Glu Ile Ile Arg Glu Asn Val Asn Glu Met Asn Glu Lys Ala Lys Ile
            420                 425                 430

Ala Val Glu Pro Lys Gly Ser Ser Phe Lys Asn Phe Asn Lys Leu Leu
        435                 440                 445

Glu Ile Ile Asn Ala Pro Gln Ser Ser
    450                 455


<210> SEQ ID NO 73
<211> LENGTH: 456
<212> TYPE: PRT
<213> ORGANISM: Vitis vinifera

<400> SEQUENCE: 73

Met Ser Gln Thr Thr Thr Asn Pro His Val Ala Val Leu Ala Phe Pro
1               5                   10                  15

Phe Ser Thr His Ala Ala Pro Leu Leu Ala Val Val Arg Arg Leu Ala
            20                  25                  30

Ala Ala Ala Pro His Ala Val Phe Ser Phe Phe Ser Thr Ser Gln Ser
        35                  40                  45

Asn Ala Ser Ile Phe His Asp Ser Met His Thr Met Gln Cys Asn Ile
    50                  55                  60

Lys Ser Tyr Asp Ile Ser Asp Gly Val Pro Glu Gly Tyr Val Phe Ala
65                  70                  75                  80

Gly Arg Pro Gln Glu Asp Ile Glu Leu Phe Thr Arg Ala Ala Pro Glu
                85                  90                  95

Ser Phe Arg Gln Gly Met Val Met Ala Val Ala Glu Thr Gly Arg Pro
            100                 105                 110

Val Ser Cys Leu Val Ala Asp Ala Phe Ile Trp Phe Ala Ala Asp Met
        115                 120                 125

Ala Ala Glu Met Gly Leu Ala Trp Leu Pro Phe Trp Thr Ala Gly Pro
    130                 135                 140

Asn Ser Leu Ser Thr His Val Tyr Ile Asp Glu Ile Arg Glu Lys Ile
145                 150                 155                 160

Gly Val Ser Gly Ile Gln Gly Arg Glu Asp Glu Leu Leu Asn Phe Ile
                165                 170                 175

Pro Gly Met Ser Lys Val Arg Phe Arg Asp Leu Gln Glu Gly Ile Val
            180                 185                 190

Phe Gly Asn Leu Asn Ser Leu Phe Ser Arg Met Leu His Arg Met Gly
        195                 200                 205

Gln Val Leu Pro Lys Ala Thr Ala Val Phe Ile Asn Ser Phe Glu Glu
    210                 215                 220

Leu Asp Asp Ser Leu Thr Asn Asp Leu Lys Ser Lys Leu Lys Thr Tyr
225                 230                 235                 240

Leu Asn Ile Gly Pro Phe Asn Leu Ile Thr Pro Pro Pro Val Val Pro
                245                 250                 255

Asn Thr Thr Gly Cys Leu Gln Trp Leu Lys Glu Arg Lys Pro Thr Ser
            260                 265                 270

Val Val Tyr Ile Ser Phe Gly Thr Val Thr Thr Pro Pro Pro Ala Glu
        275                 280                 285

Val Val Ala Leu Ser Glu Ala Leu Glu Ala Ser Arg Val Pro Phe Ile
    290                 295                 300
```

```
Trp Ser Leu Arg Asp Lys Ala Arg Val His Leu Pro Glu Gly Phe Leu
305                 310                 315                 320

Glu Lys Thr Arg Gly Tyr Gly Met Val Val Pro Trp Ala Pro Gln Ala
                325                 330                 335

Glu Val Leu Ala His Glu Ala Val Gly Ala Phe Val Thr His Cys Gly
            340                 345                 350

Trp Asn Ser Leu Trp Glu Ser Val Ala Gly Gly Val Pro Leu Ile Cys
        355                 360                 365

Arg Pro Phe Phe Gly Asp Gln Arg Leu Asn Gly Arg Met Val Glu Asp
    370                 375                 380

Val Leu Glu Ile Gly Val Arg Ile Glu Gly Gly Val Phe Thr Lys Ser
385                 390                 395                 400

Gly Leu Met Ser Cys Phe Asp Gln Ile Leu Ser Gln Glu Lys Gly Lys
                405                 410                 415

Lys Leu Arg Glu Asn Leu Arg Ala Leu Arg Glu Thr Ala Asp Arg Ala
            420                 425                 430

Val Gly Pro Lys Gly Ser Ser Thr Glu Asn Phe Ile Thr Leu Val Asp
        435                 440                 445

Leu Val Ser Lys Pro Lys Asp Val
    450                 455


<210> SEQ ID NO 74
<211> LENGTH: 2185
<212> TYPE: PRT
<213> ORGANISM: Ustilago maydis 521

<400> SEQUENCE: 74

Met Pro Pro Pro Asp His Lys Ala Val Ser Gln Phe Ile Gly Gly Asn
1               5                   10                  15

Pro Leu Glu Thr Ala Pro Ala Ser Pro Val Ala Asp Phe Ile Arg Lys
            20                  25                  30

Gln Gly Gly His Ser Val Ile Thr Lys Val Leu Ile Cys Asn Asn Gly
        35                  40                  45

Ile Ala Ala Val Lys Glu Ile Arg Ser Ile Arg Lys Trp Ala Tyr Glu
    50                  55                  60

Thr Phe Gly Asp Glu Arg Ala Ile Glu Phe Thr Val Met Ala Thr Pro
65                  70                  75                  80

Glu Asp Leu Lys Val Asn Ala Asp Tyr Ile Arg Met Ala Asp Gln Tyr
                85                  90                  95

Val Glu Val Pro Gly Gly Ser Asn Asn Asn Asn Tyr Ala Asn Val Asp
            100                 105                 110

Leu Ile Val Asp Val Ala Glu Arg Ala Gly Val His Ala Val Trp Ala
        115                 120                 125

Gly Trp Gly His Ala Ser Glu Asn Pro Arg Leu Pro Glu Ser Leu Ala
    130                 135                 140

Ala Ser Lys His Lys Ile Ile Phe Ile Gly Pro Pro Gly Ser Ala Met
145                 150                 155                 160

Arg Ser Leu Gly Asp Lys Ile Ser Ser Thr Ile Val Ala Gln His Ala
                165                 170                 175

Asp Val Pro Cys Met Pro Trp Ser Gly Thr Gly Ile Lys Glu Thr Met
            180                 185                 190

Met Ser Asp Gln Gly Phe Leu Thr Val Ser Asp Asp Val Tyr Gln Gln
        195                 200                 205

Ala Cys Ile His Thr Ala Glu Glu Gly Leu Glu Lys Ala Glu Lys Ile
    210                 215                 220
```

```
Gly Tyr Pro Val Met Ile Lys Ala Ser Glu Gly Gly Gly Gly Lys Gly
225                 230                 235                 240

Ile Arg Lys Cys Thr Asn Gly Glu Glu Phe Lys Gln Leu Tyr Asn Ala
                245                 250                 255

Val Leu Gly Glu Val Pro Gly Ser Pro Val Phe Val Met Lys Leu Ala
            260                 265                 270

Gly Gln Ala Arg His Leu Glu Val Gln Leu Leu Ala Asp Gln Tyr Gly
        275                 280                 285

Asn Ala Ile Ser Ile Phe Gly Arg Asp Cys Ser Val Gln Arg Arg His
    290                 295                 300

Gln Lys Ile Ile Glu Glu Ala Pro Val Thr Ile Ala Pro Glu Asp Ala
305                 310                 315                 320

Arg Glu Ser Met Glu Lys Ala Ala Val Arg Leu Ala Lys Leu Val Gly
                325                 330                 335

Tyr Val Ser Ala Gly Thr Val Glu Trp Leu Tyr Ser Pro Glu Ser Gly
            340                 345                 350

Glu Phe Ala Phe Leu Glu Leu Asn Pro Arg Leu Gln Val Glu His Pro
        355                 360                 365

Thr Thr Glu Met Val Ser Gly Val Asn Ile Pro Ala Ala Gln Leu Gln
    370                 375                 380

Val Ala Met Gly Ile Pro Leu Tyr Ser Ile Arg Asp Ile Arg Thr Leu
385                 390                 395                 400

Tyr Gly Met Asp Pro Arg Gly Asn Glu Val Ile Asp Phe Asp Phe Ser
                405                 410                 415

Ser Pro Glu Ser Phe Lys Thr Gln Arg Lys Pro Gln Pro Gln Gly His
            420                 425                 430

Val Val Ala Cys Arg Ile Thr Ala Glu Asn Pro Asp Thr Gly Phe Lys
        435                 440                 445

Pro Gly Met Gly Ala Leu Thr Glu Leu Asn Phe Arg Ser Ser Thr Ser
    450                 455                 460

Thr Trp Gly Tyr Phe Ser Val Gly Thr Ser Gly Ala Leu His Glu Tyr
465                 470                 475                 480

Ala Asp Ser Gln Phe Gly His Ile Phe Ala Tyr Gly Ala Asp Arg Ser
                485                 490                 495

Glu Ala Arg Lys Gln Met Val Ile Ser Leu Lys Glu Leu Ser Ile Arg
            500                 505                 510

Gly Asp Phe Arg Thr Thr Val Glu Tyr Leu Ile Lys Leu Leu Glu Thr
        515                 520                 525

Asp Ala Phe Glu Ser Asn Lys Ile Thr Thr Gly Trp Leu Asp Gly Leu
    530                 535                 540

Ile Gln Asp Arg Leu Thr Ala Glu Arg Pro Pro Ala Asp Leu Ala Val
545                 550                 555                 560

Ile Cys Gly Ala Ala Val Lys Ala His Leu Leu Ala Arg Glu Cys Glu
                565                 570                 575

Asp Glu Tyr Lys Arg Ile Leu Asn Arg Gly Gln Val Pro Pro Arg Asp
            580                 585                 590

Thr Ile Lys Thr Val Phe Ser Ile Asp Phe Ile Tyr Glu Asn Val Lys
        595                 600                 605

Tyr Asn Phe Thr Ala Thr Arg Ser Ser Val Ser Gly Trp Val Leu Tyr
    610                 615                 620

Leu Asn Gly Gly Arg Thr Leu Val Gln Leu Arg Pro Leu Thr Asp Gly
625                 630                 635                 640
```

```
Gly Leu Leu Ile Gly Leu Ser Gly Lys Ser His Pro Val Tyr Trp Arg
                645                 650                 655

Glu Glu Val Gly Met Thr Arg Leu Met Ile Asp Ser Lys Thr Cys Leu
            660                 665                 670

Ile Glu Gln Glu Asn Asp Pro Thr Gln Ile Arg Ser Pro Ser Pro Gly
        675                 680                 685

Lys Leu Val Arg Phe Leu Val Asp Ser Gly Asp His Val Lys Ala Asn
    690                 695                 700

Gln Ala Ile Ala Glu Ile Glu Val Met Lys Met Tyr Leu Pro Leu Val
705                 710                 715                 720

Ala Ala Glu Asp Gly Val Val Ser Phe Val Lys Thr Ala Gly Val Ala
                725                 730                 735

Leu Ser Pro Gly Asp Ile Ile Gly Ile Leu Ser Leu Asp Asp Pro Ser
            740                 745                 750

Arg Val Gln His Ala Lys Pro Phe Ala Gly Gln Leu Pro Asp Phe Gly
        755                 760                 765

Met Pro Val Ile Val Gly Asn Lys Pro His Gln Arg Tyr Thr Ala Leu
    770                 775                 780

Val Glu Val Leu Asn Asp Ile Leu Asp Gly Tyr Asp Gln Ser Phe Arg
785                 790                 795                 800

Met Gln Ala Val Ile Lys Glu Leu Ile Glu Thr Leu Arg Asn Pro Glu
                805                 810                 815

Leu Pro Tyr Gly Gln Ala Ser Gln Ile Leu Ser Ser Leu Gly Gly Arg
            820                 825                 830

Ile Pro Ala Arg Leu Glu Asp Val Val Arg Asn Thr Ile Glu Met Gly
        835                 840                 845

His Ser Lys Asn Ile Glu Phe Pro Ala Ala Arg Leu Arg Lys Leu Thr
    850                 855                 860

Glu Asn Phe Leu Arg Asp Ser Val Asp Pro Ala Ile Arg Gly Gln Val
865                 870                 875                 880

Gln Ile Thr Ile Ala Pro Leu Tyr Gln Leu Phe Glu Thr Tyr Ala Gly
                885                 890                 895

Gly Leu Lys Ala His Glu Gly Asn Val Leu Ala Ser Phe Leu Gln Lys
            900                 905                 910

Tyr Tyr Glu Val Glu Ser Gln Phe Thr Gly Glu Ala Asp Val Val Leu
        915                 920                 925

Glu Leu Arg Leu Gln Ala Asp Gly Asp Leu Asp Lys Val Val Ala Leu
    930                 935                 940

Gln Thr Ser Arg Asn Gly Ile Asn Arg Lys Asn Ala Leu Leu Leu Thr
945                 950                 955                 960

Leu Leu Asp Lys His Ile Lys Gly Thr Ser Leu Val Ser Arg Thr Ser
                965                 970                 975

Gly Ala Thr Met Ile Glu Ala Leu Arg Lys Leu Ala Ser Leu Gln Gly
            980                 985                 990

Lys Ser Thr Ala Pro Ile Ala Leu  Lys Ala Arg Glu Val  Ser Leu Asp
        995                 1000                1005

Ala Asp  Met Pro Ser Leu Ala  Asp Arg Ser Ala Gln  Met Gln Ala
    1010                1015                1020

Ile Leu  Arg Gly Ser Val Thr  Ser Ser Lys Tyr Gly  Gly Asp Asp
    1025                1030                1035

Glu Tyr  His Ala Pro Ser Leu  Glu Val Leu Arg Glu  Leu Ser Asp
    1040                1045                1050

Ser Gln  Tyr Ser Val Tyr Asp  Val Leu His Ser Phe  Phe Gly His
```

```
    1055                1060                1065

Arg Glu  His His Val Ala Phe  Ala Ala Leu Cys Thr  Tyr Val Val
    1070                1075                1080

Arg Ala  Tyr Arg Ala Tyr Glu  Ile Val Asn Phe Asp  Tyr Ala Val
    1085                1090                1095

Glu Asp  Phe Asp Val Glu Glu  Arg Ala Val Leu Thr  Trp Gln Phe
    1100                1105                1110

Gln Leu  Pro Arg Ser Ala Ser  Ser Leu Lys Glu Arg  Glu Arg Gln
    1115                1120                1125

Val Ser  Ile Ser Asp Leu Ser  Met Met Asp Asn Asn  Arg Arg Ala
    1130                1135                1140

Arg Pro  Ile Arg Glu Leu Arg  Thr Gly Ala Met Thr  Ser Cys Ala
    1145                1150                1155

Asp Val  Ala Asp Ile Pro Glu  Leu Leu Pro Lys Val  Leu Lys Phe
    1160                1165                1170

Phe Lys  Ser Ser Ala Gly Ala  Ser Gly Ala Pro Ile  Asn Val Leu
    1175                1180                1185

Asn Val  Ala Val Val Asp Gln  Thr Asp Phe Val Asp  Ala Glu Val
    1190                1195                1200

Arg Ser  Gln Leu Ala Leu Tyr  Thr Asn Ala Cys Ser  Lys Glu Phe
    1205                1210                1215

Ser Ala  Ala Arg Val Arg Arg  Val Thr Tyr Leu Leu  Cys Gln Pro
    1220                1225                1230

Gly Leu  Tyr Pro Phe Phe Ala  Thr Phe Arg Pro Asn  Glu Gln Gly
    1235                1240                1245

Ile Trp  Ser Glu Glu Lys Ala  Ile Arg Asn Ile Glu  Pro Ala Leu
    1250                1255                1260

Ala Tyr  Gln Leu Glu Leu Asp  Arg Val Ser Lys Asn  Phe Glu Leu
    1265                1270                1275

Thr Pro  Val Pro Val Ser Ser  Ser Thr Ile His Leu  Tyr Phe Ala
    1280                1285                1290

Arg Gly  Ile Gln Asn Ser Ala  Asp Thr Arg Phe Phe  Val Arg Ser
    1295                1300                1305

Leu Val  Arg Pro Gly Arg Val  Gln Gly Asp Met Ala  Ala Tyr Leu
    1310                1315                1320

Ile Ser  Glu Ser Asp Arg Ile  Val Asn Asp Ile Leu  Asn Val Ile
    1325                1330                1335

Glu Val  Ala Leu Gly Gln Pro  Glu Tyr Arg Thr Ala  Asp Ala Ser
    1340                1345                1350

His Ile  Phe Met Ser Phe Ile  Tyr Gln Leu Asp Val  Ser Leu Val
    1355                1360                1365

Asp Val  Gln Lys Ala Ile Ala  Gly Phe Leu Glu Arg  His Gly Thr
    1370                1375                1380

Arg Phe  Phe Arg Leu Arg Ile  Thr Gly Ala Glu Ile  Arg Met Ile
    1385                1390                1395

Leu Asn  Gly Pro Asn Gly Glu  Pro Arg Pro Ile Arg  Ala Phe Val
    1400                1405                1410

Thr Asn  Glu Thr Gly Leu Val  Val Arg Tyr Glu Thr  Tyr Glu Glu
    1415                1420                1425

Thr Val  Ala Asp Asp Gly Ser  Val Ile Leu Arg Gly  Ile Glu Pro
    1430                1435                1440

Gln Gly  Lys Asp Ala Thr Leu  Asn Ala Gln Ser Ala  His Phe Pro
    1445                1450                1455
```

```
Tyr Thr  Thr Lys Val Ala Leu  Gln Ser Arg Arg Ser  Arg Ala His
    1460                 1465                 1470

Ala Leu  Gln Thr Thr Phe Val  Tyr Asp Phe Ile Asp  Val Leu Gly
    1475                 1480                 1485

Gln Ala  Val Arg Ala Ser Trp  Arg Lys Val Ala Ala  Ser Lys Ile
    1490                 1495                 1500

Pro Gly  Asp Val Ile Lys Ser  Ala Val Glu Leu Val  Phe Asp Glu
    1505                 1510                 1515

Gln Glu  Asn Leu Arg Glu Val  Lys Arg Ala Pro Gly  Met Asn Asn
    1520                 1525                 1530

Ile Gly  Met Val Ala Trp Leu  Val Glu Val Leu Thr  Pro Glu Tyr
    1535                 1540                 1545

Pro Ala  Gly Arg Lys Leu Val  Val Ile Gly Asn Asp  Val Thr Ile
    1550                 1555                 1560

Gln Ala  Gly Ser Phe Gly Pro  Val Glu Asp Arg Phe  Phe Ala Ala
    1565                 1570                 1575

Ala Ser  Lys Leu Ala Arg Glu  Leu Gly Val Pro Arg  Leu Tyr Ile
    1580                 1585                 1590

Ser Ala  Asn Ser Gly Ala Arg  Ile Gly Leu Ala Thr  Glu Ala Leu
    1595                 1600                 1605

Asp Leu  Phe Lys Val Lys Phe  Val Gly Asp Asp Pro  Ala Lys Gly
    1610                 1615                 1620

Phe Glu  Tyr Ile Tyr Leu Asp  Asp Glu Ser Leu Gln  Ala Val Gln
    1625                 1630                 1635

Ala Lys  Ala Pro Asn Ser Val  Met Thr Lys Pro Val  Gln Ala Ala
    1640                 1645                 1650

Asp Gly  Ser Val His Asn Ile  Ile Thr Asp Ile Ile  Gly Lys Pro
    1655                 1660                 1665

Gln Gly  Gly Leu Gly Val Glu  Cys Leu Ser Gly Ser  Gly Leu Ile
    1670                 1675                 1680

Ala Gly  Glu Thr Ser Arg Ala  Lys Asp Gln Ile Phe  Thr Ala Thr
    1685                 1690                 1695

Ile Ile  Thr Gly Arg Ser Val  Gly Ile Gly Ala Tyr  Leu Ala Arg
    1700                 1705                 1710

Leu Gly  Glu Arg Val Ile Gln  Val Glu Gly Ser Pro  Leu Ile Leu
    1715                 1720                 1725

Thr Gly  Tyr Gln Ala Leu Asn  Lys Leu Leu Gly Arg  Glu Val Tyr
    1730                 1735                 1740

Thr Ser  Asn Leu Gln Leu Gly  Gly Pro Gln Ile Met  Tyr Lys Asn
    1745                 1750                 1755

Gly Val  Ser His Leu Thr Ala  Gln Asp Asp Leu Asp  Ala Val Arg
    1760                 1765                 1770

Ser Phe  Val Asn Trp Ile Ser  Tyr Val Pro Ala Gln  Arg Gly Gly
    1775                 1780                 1785

Pro Leu  Pro Ile Met Pro Thr  Thr Asp Ser Trp Asp  Arg Ala Val
    1790                 1795                 1800

Thr Tyr  Gln Pro Pro Arg Gly  Pro Tyr Asp Pro Arg  Trp Leu Ile
    1805                 1810                 1815

Asn Gly  Thr Lys Ala Glu Asp  Gly Thr Lys Leu Thr  Gly Leu Phe
    1820                 1825                 1830

Asp Glu  Gly Ser Phe Val Glu  Thr Leu Gly Gly Trp  Ala Thr Ser
    1835                 1840                 1845
```

```
Val Val  Thr Gly Arg Ala Arg  Leu Gly Gly Ile Pro  Val Gly Val
    1850                 1855                 1860

Ile Ala  Val Glu Thr Arg Thr  Leu Glu Arg Val Val  Pro Ala Asp
    1865                 1870                 1875

Pro Ala  Asn Pro Asn Ser Thr  Glu Gln Arg Ile Met  Glu Ala Gly
    1880                 1885                 1890

Gln Val  Trp Tyr Pro Asn Ser  Ala Tyr Lys Thr Ala  Gln Ala Ile
    1895                 1900                 1905

Trp Asp  Phe Asp Lys Glu Gly  Leu Pro Leu Val Ile  Leu Ala Asn
    1910                 1915                 1920

Trp Arg  Gly Phe Ser Gly Gly  Gln Gln Asp Met Tyr  Asp Glu Ile
    1925                 1930                 1935

Leu Lys  Gln Gly Ser Lys Ile  Val Asp Gly Leu Ser  Ser Tyr Lys
    1940                 1945                 1950

Gln Pro  Val Phe Val His Ile  Pro Pro Met Gly Glu  Leu Arg Gly
    1955                 1960                 1965

Gly Ser  Trp Val Val Val Asp  Ser Ala Ile Asn Asp  Asn Gly Met
    1970                 1975                 1980

Ile Glu  Met Ser Ala Asp Val  Asn Ser Ala Arg Gly  Gly Val Leu
    1985                 1990                 1995

Glu Ala  Ser Gly Leu Val Glu  Ile Lys Tyr Arg Ala  Asp Lys Gln
    2000                 2005                 2010

Arg Ala  Thr Met Glu Arg Leu  Asp Ser Val Tyr Ala  Lys Leu Ser
    2015                 2020                 2025

Lys Glu  Ala Ala Glu Ala Thr  Asp Phe Thr Ala Gln  Thr Thr Ala
    2030                 2035                 2040

Arg Lys  Ala Leu Ala Glu Arg  Glu Lys Gln Leu Ala  Pro Ile Phe
    2045                 2050                 2055

Thr Ala  Ile Ala Thr Glu Tyr  Ala Asp Ala His Asp  Arg Ala Gly
    2060                 2065                 2070

Arg Met  Leu Ala Thr Gly Val  Leu Arg Ser Ala Leu  Pro Trp Glu
    2075                 2080                 2085

Asn Ala  Arg Arg Tyr Phe Tyr  Trp Arg Leu Arg Arg  Arg Leu Thr
    2090                 2095                 2100

Glu Val  Ala Ala Glu Arg Thr  Val Gly Glu Ala Asn  Pro Thr Leu
    2105                 2110                 2115

Lys His  Val Glu Arg Leu Ala  Val Leu Arg Gln Phe  Val Gly Ala
    2120                 2125                 2130

Ala Ala  Ser Asp Asp Asp Lys  Ala Val Ala Glu His  Leu Glu Ala
    2135                 2140                 2145

Ser Ala  Asp Gln Leu Leu Ala  Ala Ser Lys Gln Leu  Lys Ala Gln
    2150                 2155                 2160

Tyr Ile  Leu Ala Gln Ile Ser  Thr Leu Asp Pro Glu  Leu Arg Ala
    2165                 2170                 2175

Gln Leu  Ala Ala Ser Leu Lys
    2180                 2185


<210> SEQ ID NO 75
<211> LENGTH: 2213
<212> TYPE: PRT
<213> ORGANISM: Hesseltinella vesiculosa

<400> SEQUENCE: 75

Met Val Asp His Lys Ser Leu Pro Gly His Phe Leu Gly Gly Asn Ser
1               5                   10                  15
```

```
Val Asp Thr Ala Pro Gln Asp Pro Val Cys Glu Phe Val Lys Ser His
            20                  25                  30

Gln Gly His Thr Val Ile Ser Lys Val Leu Ile Ala Asn Asn Gly Met
        35                  40                  45

Ala Ala Met Lys Glu Ile Arg Ser Val Arg Lys Trp Ala Tyr Glu Thr
    50                  55                  60

Phe Gly Asn Glu Arg Ala Ile Glu Phe Thr Val Met Ala Thr Pro Glu
65                  70                  75                  80

Asp Leu Lys Ala Asn Ala Glu Tyr Ile Arg Met Ala Asp Asn Tyr Ile
                85                  90                  95

Glu Val Pro Gly Gly Thr Asn Asn Asn Asn Tyr Ala Asn Val Glu Leu
            100                 105                 110

Ile Val Asp Val Ala Glu Arg Thr Gly Val His Ala Val Trp Ala Gly
        115                 120                 125

Trp Gly His Ala Ser Glu Asn Pro Arg Leu Pro Glu Met Leu Ala Lys
    130                 135                 140

Ser Lys Asn Lys Cys Val Phe Ile Gly Pro Pro Ala Ser Ala Met Arg
145                 150                 155                 160

Ser Leu Gly Asp Lys Ile Ser Ser Thr Ile Val Ala Gln Ser Ala Asp
                165                 170                 175

Val Pro Thr Met Gly Trp Ser Gly Asp Gly Val Ser Glu Thr Thr Thr
            180                 185                 190

Asp His Asn Gly His Val Leu Val Asn Asp Asp Val Tyr Asn Ser Ala
        195                 200                 205

Cys Val Lys Thr Ala Glu Ala Gly Leu Ala Ser Ala Glu Lys Ile Gly
    210                 215                 220

Phe Pro Val Met Ile Lys Ala Ser Glu Gly Gly Gly Gly Lys Gly Ile
225                 230                 235                 240

Arg Lys Val Glu Asp Pro Ser Thr Phe Lys Gln Ala Phe Ala Gln Val
                245                 250                 255

Gln Gly Glu Ile Pro Gly Ser Pro Ile Phe Ile Met Lys Leu Ala Gly
            260                 265                 270

Asn Ala Arg His Leu Glu Val Gln Leu Leu Ala Asp Gln Tyr Gly Asn
        275                 280                 285

Ala Ile Ser Leu Phe Gly Arg Asp Cys Ser Val Gln Arg Arg His Gln
    290                 295                 300

Lys Ile Ile Glu Glu Ala Pro Val Thr Ile Ala Lys Pro Asp Ile Phe
305                 310                 315                 320

Glu Gln Met Glu Lys Ala Ala Val Arg Leu Gly Lys Leu Val Gly Tyr
                325                 330                 335

Val Ser Ala Gly Thr Val Glu Tyr Leu Tyr Ser His His Asp Glu Lys
            340                 345                 350

Phe Tyr Phe Leu Glu Leu Asn Pro Arg Leu Gln Val Glu His Pro Thr
        355                 360                 365

Thr Glu Met Val Ser Gly Val Asn Leu Pro Ala Ala Gln Leu Gln Ile
    370                 375                 380

Ala Met Gly Ile Pro Met His Arg Ile Arg Asp Ile Arg Val Leu Tyr
385                 390                 395                 400

Gly Val Gln Pro Asn Ser Ala Ser Glu Ile Asp Phe Asp Leu Glu His
                405                 410                 415

Pro Thr Ala Leu Gln Ser Gln Arg Arg Pro Met Pro Lys Gly His Val
            420                 425                 430
```

```
Ile Ala Val Arg Ile Thr Ala Glu Asn Pro Asp Ala Gly Phe Lys Pro
        435                 440                 445

Ser Gly Gly Val Met Gln Glu Leu Asn Phe Arg Ser Ser Thr Asn Val
    450                 455                 460

Trp Gly Tyr Phe Ser Val Val Ser Ser Gly Ala Met His Glu Tyr Ala
465                 470                 475                 480

Asp Ser Gln Phe Gly His Ile Phe Ala Tyr Gly Glu Asn Arg Gln Gln
                485                 490                 495

Ala Arg Lys Asn Met Val Ile Ala Leu Lys Glu Leu Ser Ile Arg Gly
            500                 505                 510

Asp Phe Arg Thr Thr Val Glu Tyr Ile Ile Arg Leu Leu Glu Thr Pro
        515                 520                 525

Asp Phe Thr Asp Asn Thr Ile Asn Thr Gly Trp Leu Asp Met Leu Ile
    530                 535                 540

Ser Lys Lys Leu Thr Ala Glu Arg Pro Asp Thr Met Leu Ala Val Phe
545                 550                 555                 560

Cys Gly Ala Val Thr Lys Ala His Leu Ala Ser Val Glu Cys Trp Gln
                565                 570                 575

Gln Tyr Lys Asn Ser Leu Glu Arg Gly Gln Ile Pro Ser Lys Glu Ser
            580                 585                 590

Leu Lys Thr Val Phe Thr Val Asp Phe Ile Tyr Glu Asn Ile Arg Tyr
        595                 600                 605

Asn Phe Thr Val Thr Arg Ser Ala Pro Gly Ile Tyr Thr Leu Tyr Leu
    610                 615                 620

Asn Gly Thr Lys Thr Gln Val Gly Val Arg Asp Leu Ser Asp Gly Gly
625                 630                 635                 640

Leu Leu Ile Ser Leu Asn Gly Arg Ser His Thr Thr Tyr Asn Arg Glu
                645                 650                 655

Glu Val Gln Ala Thr Arg Leu Met Ile Asp Gly Lys Thr Cys Leu Leu
            660                 665                 670

Glu Lys Glu Ser Asp Pro Thr Gln Leu Arg Ser Pro Ser Pro Gly Lys
        675                 680                 685

Leu Val Ser Leu Leu Leu Glu Asn Gly Asp His Ile Arg Thr Gly Gln
    690                 695                 700

Ala Tyr Ala Glu Ile Glu Val Met Lys Met Tyr Met Pro Leu Val Ala
705                 710                 715                 720

Ser Glu Asp Gly His Val Gln Phe Ile Lys Gln Val Gly Ala Thr Leu
                725                 730                 735

Glu Ala Gly Asp Ile Ile Gly Ile Leu Ser Leu Asp Asp Pro Ser Arg
            740                 745                 750

Val Lys His Ala Leu Pro Phe Thr Gly Gln Val Pro Lys Tyr Gly Leu
        755                 760                 765

Pro His Leu Thr Gly Asp Lys Pro His Gln Arg Phe Thr His Leu Lys
    770                 775                 780

Gln Thr Leu Glu Tyr Val Leu Gln Gly Tyr Asp Asn Gln Gly Leu Ile
785                 790                 795                 800

Gln Thr Ile Val Lys Glu Leu Ser Glu Val Leu Asn Asn Pro Glu Leu
                805                 810                 815

Pro Tyr Ser Glu Leu Ser Ala Ser Met Ser Val Leu Ser Gly Arg Ile
            820                 825                 830

Pro Gly Arg Leu Glu Gln Gln Leu His Asp Leu Ile Asn Gln Ala His
        835                 840                 845

Ala Gln Asn Lys Gly Phe Pro Ala Val Asp Ile Gln Gln Ala Ile Asp
```

```
850                 855                 860

Thr Phe Ala Arg Asp His Leu Thr Thr Gln Ala Glu Val Asn Ala Tyr
865                 870                 875                 880

Lys Thr Ala Val Ala Pro Ile Met Thr Ile Ala Ala Ser Tyr Ser Asn
                885                 890                 895

Gly Leu Lys Gln His Glu His Ser Val Tyr Val Asp Leu Met Glu Gln
            900                 905                 910

Tyr Tyr Asn Val Glu Val Leu Phe Asn Ser Asn Gln Ser Arg Asp Glu
        915                 920                 925

Glu Val Ile Leu Ala Leu Arg Asp Gln His Lys Asp Asp Leu Glu Lys
    930                 935                 940

Val Ile Asn Ile Ile Leu Ser His Ala Lys Val Asn Ile Lys Asn Asn
945                 950                 955                 960

Leu Ile Leu Met Leu Leu Asp Ile Ile Tyr Pro Ala Thr Ser Ser Glu
                965                 970                 975

Ala Leu Asp Arg Cys Phe Leu Pro Ile Leu Lys His Leu Ser Glu Ile
            980                 985                 990

Asp Ser Arg Gly Thr Gln Lys Val  Thr Leu Lys Ala Arg  Glu Tyr Leu
        995                 1000                1005

Ile Leu  Cys Gln Leu Pro Ser  Leu Glu Glu Arg Gln  Ser Gln Met
    1010                1015                1020

Tyr Asn  Ile Leu Lys Ser Ser  Val Thr Glu Ser Val  Tyr Gly Gly
    1025                1030                1035

Gly Thr  Glu Tyr Arg Thr Pro  Ser Tyr Asp Ala Phe  Lys Asp Leu
    1040                1045                1050

Ile Asp  Thr Lys Phe Asn Val  Phe Asp Val Leu Pro  Asn Phe Phe
    1055                1060                1065

Tyr His  Pro Asp Ser Tyr Val  Ser Leu Ala Ala Leu  Glu Val Tyr
    1070                1075                1080

Cys Arg  Arg Ser Tyr His Ala  Tyr Lys Ile Leu Asp  Val Ala Tyr
    1085                1090                1095

Asn Leu  Glu His Gln Pro Tyr  Ile Val Ala Trp Lys  Phe Leu Leu
    1100                1105                1110

Gln Ser  Ser Ala Gly Gly Gly  Phe Asn Asn Gln Arg  Ile Ala Ser
    1115                1120                1125

Tyr Ser  Asp Leu Thr Phe Leu  Leu Asn Lys Thr Glu  Glu Glu Pro
    1130                1135                1140

Ile Arg  Thr Gly Ala Met Val  Ala Leu Lys Thr Leu  Glu Glu Leu
    1145                1150                1155

Glu Ala  Glu Leu Pro Arg Ile  Met Thr Ala Phe Glu  Glu Glu Pro
    1160                1165                1170

Leu Pro  Pro Met Leu Met Lys  Gln Pro Pro Pro Asp  Lys Thr Glu
    1175                1180                1185

Glu Arg  Met Glu Asn Ile Leu  Asn Ile Ser Ile Gln  Gly Gln Asp
    1190                1195                1200

Met Glu  Asp Asp Thr Leu Arg  Lys Asn Met Thr Thr  Leu Ile Gln
    1205                1210                1215

Ala His  Ser Asp Ala Phe Arg  Lys Ala Ala Leu Arg  Arg Ile Thr
    1220                1225                1230

Leu Val  Val Cys Arg Asp Asn  Gln Thr Pro Asp Tyr  Tyr Thr Phe
    1235                1240                1245

Arg Glu  Arg Asn Gly Tyr Glu  Glu Asp Glu Thr Ile  Arg His Ile
    1250                1255                1260
```

```
Glu Pro  Ala Leu Ala Tyr Gln  Leu Glu Leu Ala Arg  Leu Ser Asn
    1265                 1270                 1275

Phe Asp  Ile Lys Pro Cys Phe  Ile Glu Asn Arg Gln  Met His Val
    1280                 1285                 1290

Tyr Tyr  Ala Val Ala Lys Glu  Asn Pro Ser Asp Cys  Arg Phe Phe
    1295                 1300                 1305

Ile Arg  Ala Leu Val Arg Pro  Gly Arg Val Lys Ser  Ser Met Arg
    1310                 1315                 1320

Thr Ala  Asp Tyr Leu Ile Ser  Glu Ser Asp Arg Leu  Leu Thr Asp
    1325                 1330                 1335

Ile Leu  Asp Thr Leu Glu Ile  Val Ser His Asp Tyr  Lys Asn Ser
    1340                 1345                 1350

Asp Cys  Asn His Leu Phe Ile  Asn Phe Ile Pro Thr  Phe Ala Ile
    1355                 1360                 1365

Glu Ala  Asp Glu Val Glu Thr  Ala Leu Lys Asp Phe  Val Asp Arg
    1370                 1375                 1380

His Gly  Lys Arg Leu Trp Lys  Leu Arg Val Thr Gly  Ala Glu Ile
    1385                 1390                 1395

Arg Phe  Asn Ile Gln Ser Lys  Arg Pro Asp Ala Pro  Val Ile Pro
    1400                 1405                 1410

Leu Arg  Phe Thr Val Asp Asn  Val Ser Gly Tyr Ile  Leu Lys Val
    1415                 1420                 1425

Asp Val  Tyr Gln Glu Val Lys  Thr Asp Lys Asn Gly  Trp Ile Leu
    1430                 1435                 1440

Lys Ser  Val Gly Lys Ile Pro  Gly Ala Met His Met  Gln Pro Leu
    1445                 1450                 1455

Ser Thr  Pro Tyr Pro Thr Lys  Glu Trp Leu Gln Pro  Arg Arg Tyr
    1460                 1465                 1470

Lys Ala  His Leu Met Gly Thr  Thr Tyr Val Tyr Asp  Phe Pro Glu
    1475                 1480                 1485

Leu Phe  Arg Gln Ala Ile His  Asn Leu Trp Ala Gln  Ala Cys Lys
    1490                 1495                 1500

Ala Asp  Ala Ala Val Lys Ile  Pro Ser Gln Val Ile  Glu Ala Lys
    1505                 1510                 1515

Glu Leu  Val Leu Asp Asp Asp  Asn Gln Leu Gln Ala  Ile Asp Arg
    1520                 1525                 1530

Ala Pro  Gly Thr Asn Thr Val  Gly Met Val Ala Trp  Leu Leu Thr
    1535                 1540                 1545

Leu Arg  Thr Pro Asp Tyr Pro  Arg Gly Arg Arg Val  Ile Ala Ile
    1550                 1555                 1560

Ala Asn  Asp Ile Thr Phe Lys  Ile Gly Ser Phe Gly  Val Gln Glu
    1565                 1570                 1575

Asp Leu  Val Phe Tyr Lys Ala  Ser Glu Tyr Ala Arg  Glu Leu Gly
    1580                 1585                 1590

Val Pro  Arg Val Tyr Leu Ser  Ala Asn Ser Gly Ala  Arg Ile Gly
    1595                 1600                 1605

Leu Ala  Asp Glu Leu Ile Ser  Arg Phe His Val Ala  Trp Lys Asp
    1610                 1615                 1620

Glu Asp  Gln Pro Gly Ser Gly  Phe Glu Tyr Leu Tyr  Leu Leu Pro
    1625                 1630                 1635

Glu Glu  Tyr Asp Ala Leu Ile  Gln Gln Gly Asp Ala  Gln Ser Val
    1640                 1645                 1650
```

```
Leu Val  Gln Glu Val Gln Asp  Lys Gly Glu Arg Arg  Phe Arg Ile
    1655                 1660                 1665

Thr Asp  Ile Ile Gly His Thr  Asp Gly Leu Gly Val  Glu Asn Leu
    1670                 1675                 1680

Arg Gly  Ser Gly Leu Ile Ala  Gly Ala Thr Ser Arg  Ala Tyr Asp
    1685                 1690                 1695

Asp Ile  Phe Thr Ile Thr Leu  Val Thr Cys Arg Ser  Val Gly Ile
    1700                 1705                 1710

Gly Ala  Tyr Leu Val Arg Leu  Gly Gln Arg Thr Val  Gln Asn Glu
    1715                 1720                 1725

Gly Gln  Pro Ile Ile Leu Thr  Gly Ala Pro Ala Leu  Asn Lys Val
    1730                 1735                 1740

Leu Gly  Arg Glu Val Tyr Thr  Ser Asn Leu Gln Leu  Gly Gly Thr
    1745                 1750                 1755

Gln Ile  Met Tyr Lys Asn Gly  Val Ser His Leu Thr  Ala Glu Asn
    1760                 1765                 1770

Asp Leu  Glu Gly Ile Asn Lys  Ile Met Gln Trp Leu  Ser Phe Val
    1775                 1780                 1785

Pro Glu  Cys Arg Gly Ala Pro  Leu Pro Met Arg Ala  Gly Ala Asp
    1790                 1795                 1800

Pro Ile  Asp Arg Glu Ile Glu  Tyr Leu Pro Pro Lys  Gly Pro Ser
    1805                 1810                 1815

Asp Pro  Arg Phe Phe Leu Ala  Gly Lys Gln Glu Asn  Gly Lys Trp
    1820                 1825                 1830

Leu Ser  Gly Phe Phe Asp His  Gly Ser Phe Val Glu  Thr Leu Ser
    1835                 1840                 1845

Gly Trp  Ala Arg Thr Val Val  Val Gly Arg Ala Arg  Leu Gly Gly
    1850                 1855                 1860

Ile Pro  Met Gly Val Val Ala  Val Glu Thr Arg Thr  Val Glu Asn
    1865                 1870                 1875

Ile Val  Pro Ala Asp Pro Ala  Asn Ala Asp Ser Gln  Glu Gln Val
    1880                 1885                 1890

Val Met  Glu Ala Gly Gly Val  Trp Phe Pro Asn Ser  Ala Tyr Lys
    1895                 1900                 1905

Thr Ala  Gln Ala Ile Asn Asp  Phe Asn Lys Gly Glu  Gln Leu Pro
    1910                 1915                 1920

Leu Met  Ile Phe Ala Asn Trp  Arg Gly Phe Ser Gly  Gly Gln Arg
    1925                 1930                 1935

Asp Met  Tyr Asn Glu Val Leu  Lys Tyr Gly Ala Gln  Ile Val Asp
    1940                 1945                 1950

Ala Leu  Ser Asn Tyr Lys Gln  Pro Val Phe Val Tyr  Val Val Pro
    1955                 1960                 1965

Asn Gly  Glu Leu Arg Gly Gly  Ala Trp Val Val Val  Asp Ser Thr
    1970                 1975                 1980

Ile Asn  Glu Asp Met Met Glu  Met Tyr Ala Asp Thr  Gln Ala Arg
    1985                 1990                 1995

Gly Gly  Val Leu Glu Pro Glu  Gly Ile Val Glu Ile  Lys Tyr Arg
    2000                 2005                 2010

Arg Pro  Gln Leu Leu Ala Thr  Met Glu Arg Leu Asp  Pro Val Tyr
    2015                 2020                 2025

Ser Asp  Leu Lys Arg Arg Leu  Ala Ala Leu Asp Asp  Ser Gln Lys
    2030                 2035                 2040

Glu Gln  Ala Asp Glu Leu Ile  Ala Gln Val Glu Ala  Arg Glu Gln
```

```
    2045                2050                2055

Ala Leu  Leu Pro Val Tyr Gln  Gln Val Ala Ile Gln  Phe Ala Asp
    2060                2065                2070

Leu His  Asp Arg Ser Gly Arg  Met Glu Ala Lys Gly  Val Ile Arg
    2075                2080                2085

Lys Thr  Leu Glu Trp Arg Thr  Ala Arg His Tyr Phe  Tyr Trp Arg
    2090                2095                2100

Val Arg  Arg Arg Leu Leu Glu  Glu Tyr Ala Ile Arg  Lys Met Asp
    2105                2110                2115

Glu Ser  Arg Asp Gln Ala Lys  Thr Leu Leu Gln Gln  Trp Phe Gln
    2120                2125                2130

Ala Asp  Thr Asn Leu Asp Asp  Phe Asp Lys Asn Asp  Gln Ala Val
    2135                2140                2145

Val Ala  Trp Phe Asp Ala Lys  Asn Leu Leu Leu Asp  Gln Arg Ile
    2150                2155                2160

Ala Lys  Leu Lys Ser Glu Lys  Leu Lys Asp His Val  Val Gln Leu
    2165                2170                2175

Ala Ser  Val Asp Gln Asp Ala  Val Val Glu Gly Phe  Ser Lys Leu
    2180                2185                2190

Met Glu  Ser Leu Ser Val Asp  Gln Arg Lys Glu Val  Leu His Lys
    2195                2200                2205

Leu Ala  Thr Arg Phe
    2210


<210> SEQ ID NO 76
<211> LENGTH: 2515
<212> TYPE: PRT
<213> ORGANISM: Rhodotorula toruloides NBRC10032

<400> SEQUENCE: 76

Met Ala Ser Thr Thr Pro His Asp Ser Arg Val Val Ser Val Ser Ser
1               5                   10                  15

Gly Lys Lys Leu Tyr Ile Glu Val Asp Asp Gly Ala Gly Lys Asp Ala
            20                  25                  30

Pro Ala Ile Val Phe Met His Gly Leu Gly Ser Ser Thr Ser Phe Trp
        35                  40                  45

Glu Ala Pro Phe Ser Arg Ser Asn Leu Ser Ser Arg Phe Arg Leu Ile
    50                  55                  60

Arg Tyr Asp Phe Asp Gly His Gly Leu Ser Pro Val Ser Leu Leu Asp
65                  70                  75                  80

Ala Ala Asp Asp Gly Ala Met Ile Pro Leu Val Asp Leu Val Glu Asp
                85                  90                  95

Leu Ala Ala Val Met Glu Trp Thr Gly Val Asp Lys Val Ala Gly Ile
            100                 105                 110

Val Gly His Ser Met Ser Gly Leu Val Ala Ser Thr Phe Ala Ala Lys
        115                 120                 125

Tyr Pro Gln Lys Val Glu Lys Leu Val Leu Leu Gly Ala Met Arg Ser
    130                 135                 140

Leu Asn Pro Thr Val Gln Thr Asn Met Leu Lys Arg Ala Asp Thr Val
145                 150                 155                 160

Leu Glu Ser Gly Leu Ser Ala Ile Val Ala Gln Val Val Ser Ala Ala
                165                 170                 175

Leu Ser Asp Lys Ser Lys Gln Asp Ser Pro Leu Ala Pro Ala Met Val
            180                 185                 190
```

```
Arg Thr Leu Val Leu Gly Thr Asp Pro Leu Gly Tyr Ala Ala Ala Cys
        195                 200                 205

Arg Ala Leu Ala Gly Ala Lys Asp Pro Asp Tyr Ser Thr Ile Lys Ala
    210                 215                 220

Lys Thr Leu Val Val Ser Gly Glu Ser Asp Tyr Leu Ser Asn Lys Glu
225                 230                 235                 240

Thr Thr Glu Ala Leu Val Asn Asp Ile Pro Gly Ala Lys Glu Val Gln
                245                 250                 255

Met Asp Gly Val Gly His Trp His Ala Val Glu Asp Pro Ala Gly Leu
            260                 265                 270

Ala Lys Ile Leu Asp Gly Phe Phe Leu Gln Gly Lys Phe Ser Gly Glu
        275                 280                 285

Ala Lys Ala Val Asn Gly Ser His Ala Val Asp Glu Thr Pro Lys Lys
    290                 295                 300

Pro Lys Tyr Asp His Gly Arg Val Val Lys Tyr Leu Gly Gly Asn Ser
305                 310                 315                 320

Leu Glu Ser Ala Pro Pro Ser Asn Val Ala Asp Trp Val Arg Glu Arg
                325                 330                 335

Gly Gly His Thr Val Ile Thr Lys Ile Leu Ile Ala Asn Asn Gly Ile
            340                 345                 350

Ala Ala Val Lys Glu Ile Arg Ser Val Arg Lys Trp Ala Tyr Glu Thr
        355                 360                 365

Phe Gly Ser Glu Arg Ala Ile Glu Phe Thr Val Met Ala Thr Pro Glu
    370                 375                 380

Asp Leu Lys Val Asn Ala Asp Tyr Ile Arg Met Ala Asp Gln Tyr Val
385                 390                 395                 400

Glu Val Pro Gly Gly Thr Asn Asn Asn Asn Tyr Ala Asn Val Asp Val
                405                 410                 415

Ile Val Asp Val Ala Glu Arg Ala Gly Val His Ala Val Trp Ala Gly
            420                 425                 430

Trp Gly His Ala Ser Glu Asn Pro Arg Leu Pro Glu Ser Leu Ala Ala
        435                 440                 445

Ser Lys His Lys Ile Val Phe Ile Gly Pro Pro Gly Ser Ala Met Arg
    450                 455                 460

Ser Leu Gly Asp Lys Ile Ser Ser Thr Ile Val Ala Gln His Ala Glu
465                 470                 475                 480

Val Pro Cys Met Asp Trp Ser Gly Gln Gly Val Asp Gln Val Thr Gln
                485                 490                 495

Ser Leu Glu Gly Tyr Val Thr Val Ala Asp Asp Val Tyr Gln Gln Ala
            500                 505                 510

Cys Val His Asp Ala Asp Glu Gly Leu Ala Arg Ala Ser Arg Ile Gly
        515                 520                 525

Tyr Pro Val Met Ile Lys Ala Ser Glu Gly Gly Gly Gly Lys Gly Ile
    530                 535                 540

Arg Lys Val Glu Arg Glu Gln Asp Phe Lys Gln Ala Phe Gln Ala Val
545                 550                 555                 560

Leu Thr Glu Val Pro Gly Ser Pro Val Phe Ile Met Lys Leu Ala Gly
                565                 570                 575

Ala Ala Arg His Leu Glu Val Gln Val Leu Ala Asp Gln Tyr Gly Asn
            580                 585                 590

Ala Ile Ser Leu Phe Gly Arg Asp Cys Ser Val Gln Arg Arg His Gln
        595                 600                 605

Lys Ile Ile Glu Glu Ala Pro Val Thr Ile Ala Lys Pro Asp Thr Phe
```

```
    610                 615                 620

Glu Gln Met Glu Lys Ser Ala Val Arg Leu Ala Lys Leu Val Gly Tyr
625                 630                 635                 640

Val Ser Ala Gly Thr Val Glu Phe Leu Tyr Ser Ala Ala Asp Asp Lys
                645                 650                 655

Phe Ala Phe Leu Glu Leu Asn Pro Arg Leu Gln Val Glu His Pro Thr
            660                 665                 670

Thr Glu Met Val Ser Gly Val Asn Leu Pro Ala Ala Gln Leu Gln Val
        675                 680                 685

Ala Met Gly Val Pro Leu His Arg Ile Arg Asp Ile Arg Thr Leu Tyr
    690                 695                 700

Gly Lys Ala Pro Asn Gly Ser Ser Glu Ile Asp Phe Glu Phe Glu Asn
705                 710                 715                 720

Pro Glu Ser Ala Lys Thr Gln Arg Lys Pro Ser Pro Lys Gly His Val
                725                 730                 735

Val Ala Val Arg Ile Thr Ala Glu Asn Pro Asp Ala Gly Phe Lys Pro
            740                 745                 750

Ser Met Gly Thr Leu Gln Glu Leu Asn Phe Arg Ser Ser Thr Asn Val
        755                 760                 765

Trp Gly Tyr Phe Ser Val Gly Ser Ala Gly Gly Leu His Glu Phe Ala
    770                 775                 780

Asp Ser Gln Phe Gly His Ile Phe Ala Tyr Gly Ser Asp Arg Ser Glu
785                 790                 795                 800

Ser Arg Lys Asn Met Val Val Ala Leu Lys Glu Leu Ser Ile Arg Gly
                805                 810                 815

Asp Phe Arg Thr Thr Val Glu Tyr Leu Ile Lys Leu Leu Glu Thr Asp
            820                 825                 830

Ala Phe Glu Gln Asn Thr Ile Thr Thr Ala Trp Leu Asp Ser Leu Ile
        835                 840                 845

Ser Ala Arg Leu Thr Ala Glu Arg Pro Asp Thr Thr Leu Ala Ile Ile
    850                 855                 860

Cys Gly Ala Val Thr Lys Ala His Leu Ala Ser Glu Ala Asn Ile Ala
865                 870                 875                 880

Glu Tyr Lys Arg Ile Leu Glu Lys Gly Gln Ser Pro Pro Lys Glu Leu
                885                 890                 895

Leu Ala Thr Val Val Pro Leu Glu Phe Val Leu Glu Asp Val Lys Tyr
            900                 905                 910

Arg Ala Thr Ala Ser Arg Ser Ser Pro Ser Ser Trp Ser Ile Tyr Val
        915                 920                 925

Asn Gly Ser Asn Val Ser Val Gly Ile Arg Pro Leu Ala Asp Gly Gly
    930                 935                 940

Leu Leu Ile Leu Leu Asp Gly Arg Ser Tyr Thr Cys Tyr Ala Lys Glu
945                 950                 955                 960

Glu Val Gly Ala Leu Arg Leu Ser Ile Asp Ser Arg Thr Val Leu Val
                965                 970                 975

Ala Gln Glu Asn Asp Pro Thr Gln Leu Arg Ser Pro Ser Pro Gly Lys
            980                 985                 990

Leu Val Arg Tyr Phe Ile Glu Ser  Gly Glu His Ile Ser  Lys Gly Glu
        995                 1000                1005

Ala Tyr  Ala Glu Ile Glu Val  Met Lys Met Ile Met  Pro Leu Ile
    1010                1015                1020

Ala Ala  Glu Asp Gly Ile Ala  Gln Phe Ile Lys Gln  Pro Gly Ala
    1025                1030                1035
```

```
Thr Leu  Glu Ala Gly Asp Ile  Leu Gly Ile Leu Ser  Leu Asp Asp
    1040                 1045                 1050

Pro Ser  Arg Val His His Ala  Lys Pro Phe Asp Gly  Gln Leu Pro
    1055                 1060                 1065

Ala Leu  Gly Leu Pro Ser Ile  Ile Gly Thr Lys Pro  His Gln Arg
    1070                 1075                 1080

Phe Ala  Tyr Leu Lys Asp Val  Leu Ser Asn Ile Leu  Met Gly Tyr
    1085                 1090                 1095

Asp Asn  Gln Ala Ile Met Gln  Ser Ser Ile Lys Glu  Leu Ile Ser
    1100                 1105                 1110

Val Leu  Arg Asn Pro Glu Leu  Pro Tyr Gly Glu Ala  Asn Ala Val
    1115                 1120                 1125

Leu Ser  Thr Leu Ser Gly Arg  Ile Pro Ala Lys Leu  Glu Gln Thr
    1130                 1135                 1140

Leu Arg  Gln Tyr Ile Asp Ser  Ala His Glu Ser Gly  Ala Glu Phe
    1145                 1150                 1155

Pro Ser  Ala Lys Cys Arg Lys  Ala Ile Asp Thr Thr  Leu Glu Gln
    1160                 1165                 1170

Leu Arg  Pro Ala Glu Ala Gln  Thr Val Arg Asn Phe  Leu Val Ala
    1175                 1180                 1185

Phe Asp  Asp Ile Val Tyr Arg  Tyr Arg Ser Gly Leu  Lys His His
    1190                 1195                 1200

Glu Trp  Ser Thr Leu Ala Gly  Ile Phe Ala Ala Tyr  Ala Glu Thr
    1205                 1210                 1215

Glu Lys  Pro Phe Ser Gly Lys  Asp Ser Asp Val Val  Leu Glu Leu
    1220                 1225                 1230

Arg Asp  Ala His Arg Asp Ser  Leu Asp Ser Val Val  Lys Ile Val
    1235                 1240                 1245

Leu Ser  His Tyr Lys Ala Ala  Ser Lys Asn Ser Leu  Val Leu Ala
    1250                 1255                 1260

Leu Leu  Asp Val Val Lys Asp  Ser Asp Ser Val Pro  Leu Ile Glu
    1265                 1270                 1275

Gln Val  Val Ser Pro Ala Leu  Lys Asp Leu Ala Asp  Leu Asp Ser
    1280                 1285                 1290

Lys Ala  Thr Thr Lys Val Ala  Leu Lys Ala Arg Glu  Val Leu Ile
    1295                 1300                 1305

His Ile  Gln Leu Pro Ser Leu  Asp Glu Arg Leu Gly  Gln Leu Glu
    1310                 1315                 1320

Gln Ile  Leu Lys Ala Ser Val  Thr Pro Thr Val Tyr  Gly Glu Pro
    1325                 1330                 1335

Gly His  Asp Arg Thr Pro Arg  Gly Glu Val Leu Lys  Asp Val Ile
    1340                 1345                 1350

Asp Ser  Arg Phe Thr Val Phe  Asp Val Leu Pro Ser  Phe Phe Gln
    1355                 1360                 1365

His Gln  Asp Gln Trp Val Ser  Leu Ala Ala Leu Asp  Thr Tyr Val
    1370                 1375                 1380

Arg Arg  Ala Tyr Arg Ser Tyr  Asn Leu Leu Asn Ile  Glu His Ile
    1385                 1390                 1395

Glu Ala  Asp Ala Ala Glu Asp  Glu Pro Ala Thr Val  Ala Trp Ser
    1400                 1405                 1410

Phe Arg  Met Arg Lys Ala Ala  Ser Glu Ser Glu Pro  Pro Thr Pro
    1415                 1420                 1425
```

-continued

```
Thr Thr  Gly Leu Thr Ser Gln  Arg Thr Ala Ser Tyr  Ser Asp Leu
    1430                 1435                 1440

Thr Phe  Leu Leu Asn Asn Ala  Gln Ser Glu Pro Ile  Arg Tyr Gly
    1445                 1450                 1455

Ala Met  Phe Ser Val Arg Ser  Leu Asp Gly Phe Arg  Gln Glu Leu
    1460                 1465                 1470

Gly Thr  Val Leu Arg His Phe  Pro Asp Ser Asn Lys  Gly Lys Leu
    1475                 1480                 1485

Gln Gln  Gln Pro Ala Ala Ser  Ser Ser Gln Glu Gln  Trp Asn Val
    1490                 1495                 1500

Ile Asn  Val Ala Leu Thr Val  Pro Ala Ser Ala Gln  Val Asp Glu
    1505                 1510                 1515

Asp Ala  Leu Arg Ala Asp Phe  Ala Ala His Val Asn  Ala Met Ser
    1520                 1525                 1530

Ala Glu  Ile Asp Ala Arg Gly  Met Arg Arg Leu Thr  Leu Leu Ile
    1535                 1540                 1545

Cys Arg  Glu Gly Gln Tyr Pro  Ser Tyr Tyr Thr Val  Arg Lys Gln
    1550                 1555                 1560

Asp Gly  Thr Trp Lys Glu Leu  Glu Thr Ile Arg Asp  Ile Glu Pro
    1565                 1570                 1575

Ala Leu  Ala Phe Gln Leu Glu  Leu Gly Arg Leu Ser  Asn Phe His
    1580                 1585                 1590

Leu Glu  Pro Cys Pro Val Glu  Asn Arg Gln Val His  Ile Tyr Tyr
    1595                 1600                 1605

Ala Thr  Ala Lys Gly Asn Ser  Ser Asp Cys Arg Phe  Phe Val Arg
    1610                 1615                 1620

Ala Leu  Val Arg Pro Gly Arg  Leu Arg Gly Asn Met  Lys Thr Ala
    1625                 1630                 1635

Asp Tyr  Leu Val Ser Glu Ala  Asp Arg Leu Val Thr  Asp Val Leu
    1640                 1645                 1650

Asp Ser  Leu Glu Val Ala Ser  Ser Gln Arg Arg Ala  Ala Asp Gly
    1655                 1660                 1665

Asn His  Ile Ser Leu Asn Phe  Leu Tyr Ser Leu Arg  Leu Asp Phe
    1670                 1675                 1680

Asp Glu  Val Gln Ala Ala Leu  Ala Gly Phe Ile Asp  Arg His Gly
    1685                 1690                 1695

Lys Arg  Phe Trp Arg Leu Arg  Val Thr Gly Ala Glu  Ile Arg Ile
    1700                 1705                 1710

Val Leu  Glu Asp Ala Gln Gly  Asn Ile Gln Pro Ile  Arg Ala Ile
    1715                 1720                 1725

Ile Glu  Asn Val Ser Gly Phe  Val Val Lys Tyr Glu  Ala Tyr Arg
    1730                 1735                 1740

Glu Val  Thr Thr Asp Lys Gly  Gln Val Ile Leu Lys  Ser Ile Gly
    1745                 1750                 1755

Pro Gln  Gly Ala Leu His Leu  Gln Pro Val Asn Phe  Pro Tyr Pro
    1760                 1765                 1770

Thr Lys  Glu Trp Leu Gln Pro  Lys Arg Tyr Lys Ala  His Val Val
    1775                 1780                 1785

Gly Thr  Thr Tyr Val Tyr Asp  Phe Pro Asp Leu Phe  Arg Gln Ala
    1790                 1795                 1800

Ile Arg  Lys Gln Trp Lys Ala  Val Gly Lys Thr Ala  Pro Ala Glu
    1805                 1810                 1815

Leu Leu  Val Ala Lys Glu Leu  Val Leu Asp Glu Phe  Gly Lys Pro
```

```
    1820                1825                1830

Gln Glu  Val Ala Arg Pro Pro  Gly Thr Asn Asn Ile  Gly Met Val
    1835                1840                1845

Gly Trp  Ile Tyr Thr Ile Phe  Thr Pro Glu Tyr Pro  Ser Gly Arg
    1850                1855                1860

Arg Val  Val Val Ile Ala Asn  Asp Ile Thr Phe Lys  Ile Gly Ser
    1865                1870                1875

Phe Gly  Pro Glu Glu Asp Arg  Tyr Phe Tyr Ala Val  Thr Gln Leu
    1880                1885                1890

Ala Arg  Gln Leu Gly Leu Pro  Arg Val Tyr Leu Ser  Ala Asn Ser
    1895                1900                1905

Gly Ala  Arg Leu Gly Ile Ala  Glu Glu Leu Val Asp  Leu Phe Ser
    1910                1915                1920

Val Ala  Trp Ala Asp Ser Ser  Arg Pro Glu Lys Gly  Phe Lys Tyr
    1925                1930                1935

Leu Tyr  Leu Thr Ala Glu Lys  Leu Gly Glu Leu Lys  Asn Lys Gly
    1940                1945                1950

Glu Lys  Ser Val Ile Thr Lys  Arg Ile Glu Asp Glu  Gly Glu Thr
    1955                1960                1965

Arg Tyr  Gln Ile Thr Asp Ile  Ile Gly Leu Gln Glu  Gly Leu Gly
    1970                1975                1980

Val Glu  Ser Leu Lys Gly Ser  Gly Leu Ile Ala Gly  Glu Thr Ser
    1985                1990                1995

Arg Ala  Tyr Asp Asp Ile Phe  Thr Ile Thr Leu Val  Thr Ala Arg
    2000                2005                2010

Ser Val  Gly Ile Gly Ala Tyr  Leu Val Arg Leu Gly  Gln Arg Ala
    2015                2020                2025

Val Gln  Val Glu Gly Gln Pro  Ile Ile Leu Thr Gly  Ala Gly Ala
    2030                2035                2040

Leu Asn  Lys Val Leu Gly Arg  Glu Val Tyr Ser Ser  Asn Leu Gln
    2045                2050                2055

Leu Gly  Gly Thr Gln Ile Met  Tyr Lys Asn Gly Val  Ser His Leu
    2060                2065                2070

Thr Ala  Ala Asn Asp Leu Glu  Gly Val Leu Ser Ile  Val Gln Trp
    2075                2080                2085

Leu Ala  Phe Val Pro Glu His  Arg Gly Ala Pro Leu  Pro Val Leu
    2090                2095                2100

Pro Ser  Pro Val Asp Pro Trp  Asp Arg Ser Ile Asp  Tyr Thr Pro
    2105                2110                2115

Ile Lys  Gly Ala Tyr Asp Pro  Arg Trp Phe Leu Ala  Gly Lys Thr
    2120                2125                2130

Asp Glu  Ala Asp Gly Arg Trp  Leu Ser Gly Phe Phe  Asp Lys Gly
    2135                2140                2145

Ser Phe  Gln Glu Thr Leu Ser  Gly Trp Ala Gln Thr  Val Val Val
    2150                2155                2160

Gly Arg  Ala Arg Leu Gly Gly  Ile Pro Met Gly Ala  Ile Ala Val
    2165                2170                2175

Glu Thr  Arg Thr Ile Glu Arg  Ile Ile Pro Ala Asp  Pro Ala Asn
    2180                2185                2190

Pro Leu  Ser Asn Glu Gln Lys  Ile Met Glu Ala Gly  Gln Val Trp
    2195                2200                2205

Tyr Pro  Asn Ser Ser Phe Lys  Thr Gly Gln Ala Ile  Phe Asp Phe
    2210                2215                2220
```

```
Asn Arg  Glu Gly Leu Pro Leu  Ile Ile Phe Ala Asn  Trp Arg Gly
    2225                 2230                 2235

Phe Ser  Gly Gly Gln Gln Asp  Met Phe Asp Glu Val  Leu Lys Arg
    2240                 2245                 2250

Gly Ser  Leu Ile Val Asp Gly  Leu Ser Ala Tyr Lys  Gln Pro Val
    2255                 2260                 2265

Phe Val  Tyr Ile Val Pro Asn  Gly Glu Leu Arg Gly  Gly Ala Trp
    2270                 2275                 2280

Val Val  Leu Asp Pro Ser Ile  Asn Ala Glu Gly Met  Met Glu Met
    2285                 2290                 2295

Tyr Val  Asp Glu Thr Ala Arg  Ala Gly Val Leu Glu  Pro Glu Gly
    2300                 2305                 2310

Ile Val  Glu Ile Lys Leu Arg  Lys Asp Lys Leu Leu  Ala Leu Met
    2315                 2320                 2325

Asp Arg  Leu Asp Pro Thr Tyr  His Ala Leu Arg Val  Lys Ser Thr
    2330                 2335                 2340

Asp Ala  Ser Leu Ser Pro Thr  Asp Ala Ala Gln Ala  Lys Thr Glu
    2345                 2350                 2355

Leu Ala  Ala Arg Glu Lys Gln  Leu Met Pro Ile Tyr  Gln Gln Val
    2360                 2365                 2370

Ala Leu  Gln Phe Ala Asp Ser  His Asp Lys Ala Gly  Arg Ile Leu
    2375                 2380                 2385

Ser Lys  Gly Cys Ala Arg Glu  Ala Leu Glu Trp Ser  Asn Ala Arg
    2390                 2395                 2400

Arg Tyr  Phe Tyr Ala Arg Leu  Arg Arg Arg Leu Ala  Glu Glu Ala
    2405                 2410                 2415

Ala Val  Lys Arg Leu Gly Glu  Ala Asp Pro Thr Leu  Ser Arg Asp
    2420                 2425                 2430

Glu Arg  Leu Ala Ile Val His  Asp Ala Val Gly Gln  Gly Val Asp
    2435                 2440                 2445

Leu Asn  Asn Asp Leu Ala Ala  Ala Ala Ala Phe Glu  Gln Gly Ala
    2450                 2455                 2460

Ala Ala  Ile Thr Glu Arg Val  Lys Leu Ala Arg Ala  Thr Thr Val
    2465                 2470                 2475

Ala Ser  Thr Leu Ala Gln Leu  Ala Gln Asp Asp Lys  Glu Ala Phe
    2480                 2485                 2490

Ala Ala  Ser Leu Gln Gln Val  Leu Gly Asp Lys Leu  Thr Ala Ala
    2495                 2500                 2505

Asp Leu  Ala Arg Ile Leu Ala
    2510                 2515
```

<210> SEQ ID NO 77
<211> LENGTH: 504
<212> TYPE: PRT
<213> ORGANISM: Rhodopseudomonas palustris

<400> SEQUENCE: 77

```
Met Asn Ala Asn Leu Phe Ser Arg Leu Phe Asp Gly Leu Val Glu Ala
1               5                   10                  15

Asp Lys Leu Ala Ile Glu Thr Leu Glu Gly Glu Arg Ile Ser Tyr Gly
            20                  25                  30

Asp Leu Val Ala Arg Ser Gly Arg Met Ala Asn Val Leu Val Ala Arg
        35                  40                  45

Gly Val Lys Pro Gly Asp Arg Val Ala Ala Gln Ala Glu Lys Ser Val
```

-continued

```
    50                  55                  60

Ala Ala Leu Val Leu Tyr Leu Ala Thr Val Arg Ala Gly Ala Val Tyr
65                  70                  75                  80

Leu Pro Leu Asn Thr Ala Tyr Thr Leu His Glu Leu Asp Tyr Phe Ile
                85                  90                  95

Gly Asp Ala Glu Pro Lys Leu Val Val Cys Asp Pro Ala Lys Arg Glu
            100                 105                 110

Gly Ile Ala Ala Leu Ala Gln Lys Val Gly Ala Gly Val Glu Thr Leu
        115                 120                 125

Asp Ala Lys Gly Gln Gly Ser Leu Ser Glu Ala Ala Ala Gln Ala Ser
    130                 135                 140

Val Asp Phe Ala Thr Val Pro Arg Glu Gly Asp Asp Leu Ala Ala Ile
145                 150                 155                 160

Leu Tyr Thr Ser Gly Thr Thr Gly Arg Ser Lys Gly Ala Met Leu Ser
                165                 170                 175

His Asp Asn Leu Ala Ser Asn Ser Leu Thr Leu Val Glu Phe Trp Arg
            180                 185                 190

Phe Thr Pro Asp Asp Val Leu Ile His Ala Leu Pro Ile Tyr His Thr
        195                 200                 205

His Gly Leu Phe Val Ala Ser Asn Val Thr Leu Phe Ala Arg Ala Ser
    210                 215                 220

Met Ile Phe Leu Pro Lys Phe Asp Pro Asp Ala Ile Ile Gln Leu Met
225                 230                 235                 240

Ser Arg Ala Ser Val Leu Met Gly Val Pro Thr Phe Tyr Thr Arg Leu
                245                 250                 255

Leu Gln Ser Asp Gly Leu Thr Lys Glu Ala Ala Arg His Met Arg Leu
            260                 265                 270

Phe Ile Ser Gly Ser Ala Pro Leu Leu Ala Asp Thr His Arg Glu Trp
        275                 280                 285

Ala Ser Arg Thr Gly His Ala Val Leu Glu Arg Tyr Gly Met Thr Glu
    290                 295                 300

Thr Asn Met Asn Thr Ser Asn Pro Tyr Asp Gly Ala Arg Val Pro Gly
305                 310                 315                 320

Ala Val Gly Pro Ala Leu Pro Gly Val Ser Leu Arg Val Val Asp Pro
                325                 330                 335

Glu Thr Gly Ala Glu Leu Ser Pro Gly Glu Ile Gly Met Ile Glu Val
            340                 345                 350

Lys Gly Pro Asn Val Phe Gln Gly Tyr Trp Arg Met Pro Glu Lys Thr
        355                 360                 365

Lys Ala Glu Phe Arg Asp Asp Gly Phe Phe Ile Thr Gly Asp Leu Gly
    370                 375                 380

Lys Ile Asp Ala Asp Gly Tyr Val Phe Ile Val Gly Arg Gly Lys Asp
385                 390                 395                 400

Leu Val Ile Thr Gly Gly Phe Asn Val Tyr Pro Lys Glu Val Glu Ser
                405                 410                 415

Glu Ile Asp Ala Ile Ser Gly Val Val Glu Ser Ala Val Ile Gly Val
            420                 425                 430

Pro His Ala Asp Leu Gly Glu Gly Val Thr Ala Val Val Val Arg Asp
        435                 440                 445

Lys Gly Ala Ser Val Asp Glu Ala Ala Val Leu Gly Ala Leu Gln Gly
    450                 455                 460

Gln Leu Ala Lys Phe Lys Met Pro Lys Arg Val Leu Phe Val Asp Asp
465                 470                 475                 480
```

```
Leu Pro Arg Asn Thr Met Gly Lys Val Gln Lys Asn Val Leu Arg Glu
                485                 490                 495

Ala Tyr Ala Lys Leu Tyr Ala Lys
            500


<210> SEQ ID NO 78
<211> LENGTH: 504
<212> TYPE: PRT
<213> ORGANISM: Rhizobium  sp. BUS003

<400> SEQUENCE: 78

Met Val Asn His Leu Phe Asp Ala Ile Arg Leu Ser Ile Thr Ser Pro
1               5                   10                  15

Glu Ser Thr Phe Ile Glu Leu Glu Asp Gly Lys Val Trp Thr Tyr Gly
            20                  25                  30

Ala Met Phe Asn Cys Ser Ala Arg Ile Thr His Val Leu Val Lys Leu
        35                  40                  45

Gly Val Ser Pro Gly Asp Arg Val Ala Val Gln Val Glu Lys Ser Ala
    50                  55                  60

Gln Ala Leu Met Leu Tyr Leu Gly Cys Leu Arg Ala Gly Ala Val Tyr
65                  70                  75                  80

Leu Pro Leu Asn Thr Ala Tyr Thr Pro Ala Glu Leu Glu Tyr Phe Leu
                85                  90                  95

Gly Asp Ala Thr Pro Lys Leu Val Val Val Ser Pro Cys Ala Ala Glu
            100                 105                 110

Gln Leu Glu Pro Leu Ala Arg Arg Val Gly Thr Arg Leu Leu Thr Leu
        115                 120                 125

Gly Val Asn Gly Asp Gly Ser Leu Met Asp Met Ala Ser Leu Glu Pro
    130                 135                 140

Val Glu Phe Ala Asp Ile Glu Arg Lys Ala Asp Asp Leu Ala Ala Ile
145                 150                 155                 160

Leu Tyr Thr Ser Gly Thr Thr Gly Arg Ser Lys Gly Ala Met Leu Thr
                165                 170                 175

His Asp Asn Leu Leu Ser Asn Ala Gln Thr Leu Arg Glu His Trp Arg
            180                 185                 190

Phe Thr Ser Ala Asp Arg Leu Ile His Ala Leu Pro Ile Phe His Thr
        195                 200                 205

His Gly Leu Phe Val Ala Thr Asn Val Thr Leu Leu Ala Gly Gly Ala
    210                 215                 220

Ile Tyr Leu Leu Ser Lys Phe Asp Pro Asp Gln Ile Phe Ala Leu Met
225                 230                 235                 240

Thr Arg Ala Thr Val Met Met Gly Val Pro Thr Phe Tyr Thr Arg Leu
                245                 250                 255

Leu Gln Asp Glu Arg Leu Asn Lys Ala Asn Thr Arg His Met Arg Leu
            260                 265                 270

Phe Ile Ser Gly Ser Ala Pro Leu Leu Ala Glu Thr His Arg Leu Phe
        275                 280                 285

Glu Glu Tyr Thr Gly His Ala Ile Leu Glu Arg Tyr Gly Met Thr Glu
    290                 295                 300

Thr Asn Met Ile Thr Ser Asn Pro Cys Asp Gly Ala Arg Val Pro Gly
305                 310                 315                 320

Thr Val Gly Tyr Ala Leu Pro Gly Val Ser Val Arg Ile Thr Asp Pro
                325                 330                 335

Val Ser Gly Glu Pro Leu Ala Ala Gly Glu Pro Gly Met Ile Glu Val
```

```
            340                 345                 350

Lys Gly Pro Asn Val Phe Gln Gly Tyr Trp Asn Met Pro Asp Lys Thr
        355                 360                 365

Lys Glu Glu Phe Arg Ser Asp Gly Tyr Phe Thr Thr Gly Asp Ile Gly
    370                 375                 380

Val Met Glu Thr Asp Gly Arg Ile Ser Ile Val Gly Arg Gly Lys Asp
385                 390                 395                 400

Leu Ile Ile Ser Gly Gly Tyr Asn Ile Tyr Pro Lys Glu Ile Glu Asn
                405                 410                 415

Glu Ile Asp Ala Ile Glu Gly Val Val Glu Ser Ala Val Ile Gly Val
            420                 425                 430

Pro His Pro Asp Leu Gly Glu Gly Val Thr Ala Ile Val Val Gly Gln
        435                 440                 445

Pro Lys Ala His Leu Asp Leu Thr Thr Ile Thr Asn Asn Leu Gln Gly
    450                 455                 460

Arg Leu Ala Arg Phe Lys Gln Pro Lys Asn Val Ile Phe Val Asp Glu
465                 470                 475                 480

Leu Pro Arg Asn Thr Met Gly Lys Val Gln Lys Asn Val Leu Arg Asp
                485                 490                 495

Arg Tyr Arg Asp Leu Tyr Leu Lys
            500


<210> SEQ ID NO 79
<211> LENGTH: 505
<212> TYPE: PRT
<213> ORGANISM: Ochrobactrum sp. 3-3

<400> SEQUENCE: 79

Met Ala Asn His Leu Phe Asp Leu Val Arg Ala Asn Ala Thr Asp Leu
1               5                   10                  15

Thr Lys Thr Phe Ile Glu Thr Glu Thr Gly Leu Lys Leu Thr Tyr Asp
            20                  25                  30

Asp Leu Met Thr Gly Thr Ala Arg Tyr Ala Asn Val Leu Val Gly Leu
        35                  40                  45

Gly Val Lys Pro Gly Asp Arg Val Ala Val Gln Val Glu Lys Ser Ala
    50                  55                  60

Gly Ala Ile Phe Leu Tyr Leu Ala Cys Val Arg Ala Gly Ala Val Phe
65                  70                  75                  80

Leu Pro Leu Asn Thr Ala Tyr Thr Leu Thr Glu Ile Glu Tyr Phe Leu
                85                  90                  95

Gly Asp Ala Glu Pro Ala Leu Val Val Cys Asp Pro Ala Arg Arg Asp
            100                 105                 110

Gly Ile Thr Glu Val Ala Lys Lys Thr Gly Val Pro Ala Val Glu Thr
        115                 120                 125

Leu Gly Lys Gly Gln Asp Gly Ser Leu Phe Asp Lys Ala Ala Ala Ala
    130                 135                 140

Pro Glu Thr Phe Ala Asp Val Ala Arg Gly Pro Gly Asp Leu Ala Ala
145                 150                 155                 160

Ile Leu Tyr Thr Ser Gly Thr Thr Gly Arg Ser Lys Gly Ala Met Leu
                165                 170                 175

Ser His Asp Asn Leu Ala Ser Asn Ala Leu Thr Leu Lys Asp Tyr Trp
            180                 185                 190

Arg Phe Gly Ala Asp Asp Val Leu Leu His Ala Leu Pro Ile Phe His
        195                 200                 205
```

```
Thr His Gly Leu Phe Val Ala Thr Asn Thr Ile Leu Val Ala Gly Ala
    210                 215                 220

Ser Met Leu Phe Leu Pro Lys Phe Asp Ala Asp Lys Val Phe Glu Leu
225                 230                 235                 240

Met Pro Arg Ala Thr Thr Met Met Gly Val Pro Thr Phe Tyr Val Arg
                245                 250                 255

Leu Val Gln Asp Ala Arg Leu Thr Arg Glu Ala Thr Lys His Met Arg
            260                 265                 270

Leu Phe Ile Ser Gly Ser Ala Pro Leu Leu Ala Glu Thr His Lys Leu
        275                 280                 285

Phe Arg Glu Lys Thr Gly Val Ser Ile Leu Glu Arg Tyr Gly Met Thr
    290                 295                 300

Glu Thr Asn Met Asn Thr Ser Asn Pro Tyr Asp Gly Asp Arg Val Ala
305                 310                 315                 320

Gly Thr Val Gly Phe Pro Leu Pro Gly Val Ala Leu Arg Val Ala Asp
                325                 330                 335

Pro Glu Thr Gly Ala Ala Ile Pro Gln Gly Glu Ile Gly Val Ile Glu
            340                 345                 350

Val Lys Gly Pro Asn Val Phe Ser Gly Tyr Trp Arg Met Pro Glu Lys
        355                 360                 365

Thr Ala Ala Glu Phe Arg Gln Asp Gly Phe Phe Ile Thr Gly Asp Leu
    370                 375                 380

Gly Lys Ile Asp Asp Gln Gly Tyr Val His Ile Val Gly Arg Gly Lys
385                 390                 395                 400

Asp Leu Val Ile Ser Gly Gly Tyr Asn Val Tyr Pro Lys Glu Val Glu
                405                 410                 415

Thr Glu Ile Asp Gly Met Ala Gly Val Val Glu Ser Ala Val Ile Gly
            420                 425                 430

Val Pro His Pro Asp Phe Gly Glu Gly Val Thr Ala Val Val Val Ala
        435                 440                 445

Glu Lys Gly Ala Ser Leu Asp Glu Ala Thr Ile Ile Lys Thr Leu Glu
    450                 455                 460

Gln Arg Leu Ala Arg Tyr Lys Leu Pro Lys Arg Val Ile Val Val Asp
465                 470                 475                 480

Asp Leu Pro Arg Asn Thr Met Gly Lys Val Gln Lys Asn Leu Leu Arg
                485                 490                 495

Asp Ala Tyr Lys Gly Leu Tyr Gly Gly
            500                 505


<210> SEQ ID NO 80
<211> LENGTH: 465
<212> TYPE: PRT
<213> ORGANISM: Rhizobiales bacterium

<400> SEQUENCE: 80

Met Ser Pro Glu Leu Ile Ser Ile Leu Val Leu Val Val Val Phe Val
1               5                   10                  15

Ile Ala Thr Thr Arg Ser Val Asn Met Gly Ala Leu Ala Phe Ala Ala
            20                  25                  30

Ala Phe Gly Val Gly Thr Leu Val Ala Asp Leu Asp Ala Asp Gly Ile
        35                  40                  45

Phe Ala Gly Phe Pro Gly Asp Leu Phe Val Val Leu Val Gly Val Thr
    50                  55                  60

Tyr Leu Phe Ala Ile Ala Arg Ala Asn Gly Thr Thr Asp Trp Leu Val
65                  70                  75                  80
```

```
His Ala Ala Val Arg Leu Val Arg Gly Arg Val Ala Leu Ile Pro Trp
                85                  90                  95

Val Met Phe Ala Leu Thr Gly Ala Leu Thr Ala Ile Gly Ala Val Ser
            100                 105                 110

Pro Ala Ala Val Ala Ile Val Ala Pro Val Ala Leu Ser Phe Ala Thr
        115                 120                 125

Arg Tyr Ser Ile Ser Pro Leu Leu Met Gly Thr Met Val Val His Gly
    130                 135                 140

Ala Gln Ala Gly Gly Phe Ser Pro Ile Ser Ile Tyr Gly Ser Ile Val
145                 150                 155                 160

Asn Gly Ile Val Glu Arg Glu Lys Leu Pro Gly Ser Glu Ile Gly Leu
                165                 170                 175

Phe Leu Ala Ser Leu Val Ala Asn Leu Leu Ile Ala Ala Val Leu Phe
            180                 185                 190

Ala Val Leu Gly Gly Arg Lys Leu Trp Ala Arg Gly Ala Val Thr Pro
        195                 200                 205

Glu Gly Asp Gly Ala Pro Gly Lys Ala Gly Thr Gly Thr Thr Gly Ser
    210                 215                 220

Gly Ser Asp Thr Gly Thr Gly Thr Gly Thr Gly Thr Gly Thr Ser Ala
225                 230                 235                 240

Gly Thr Gly Gly Thr Ala Pro Thr Ala Val Ala Val Arg Ser Asp Arg
                245                 250                 255

Glu Thr Gly Gly Ala Glu Gly Thr Gly Val Arg Leu Thr Pro Ala Arg
            260                 265                 270

Val Ala Thr Leu Val Ala Leu Val Ala Leu Val Val Ala Val Leu Gly
        275                 280                 285

Phe Asp Leu Asp Ala Gly Leu Thr Ala Val Thr Leu Ala Val Val Leu
    290                 295                 300

Ser Thr Ala Trp Pro Asp Asp Ser Arg Arg Ala Val Gly Glu Ile Ala
305                 310                 315                 320

Trp Ser Thr Val Leu Leu Ile Cys Gly Val Leu Thr Tyr Val Gly Val
                325                 330                 335

Leu Glu Glu Met Gly Thr Ile Thr Trp Ala Gly Glu Gly Val Gly Gly
            340                 345                 350

Ile Gly Val Pro Leu Leu Ala Ala Val Leu Leu Cys Tyr Ile Gly Ala
        355                 360                 365

Ile Val Ser Ala Phe Ala Ser Ser Val Gly Ile Met Gly Ala Leu Ile
    370                 375                 380

Pro Leu Ala Val Pro Phe Leu Ala Gln Gly Glu Ile Gly Ala Val Gly
385                 390                 395                 400

Met Val Ala Ala Leu Ala Val Ser Ala Thr Val Val Asp Val Ser Pro
                405                 410                 415

Phe Ser Thr Asn Gly Ala Leu Val Leu Ala Ala Ala Pro Asp Val Asp
            420                 425                 430

Arg Asp Arg Phe Phe Arg Gln Leu Met Val Tyr Gly Gly Ile Val Val
        435                 440                 445

Ala Ala Val Pro Ala Leu Ala Trp Leu Val Leu Val Val Pro Gly Phe
    450                 455                 460

Gly
465
```

<210> SEQ ID NO 81
<211> LENGTH: 448

```
<212> TYPE: PRT
<213> ORGANISM: Rhizobium leguminosarum

<400> SEQUENCE: 81

Met Gly Ile Glu Leu Leu Ser Ile Gly Leu Leu Ile Ala Met Phe Ile
1               5                   10                  15

Ile Ala Thr Ile Gln Pro Ile Asn Met Gly Ala Leu Ala Phe Ala Gly
            20                  25                  30

Ala Phe Val Leu Gly Ser Met Ile Ile Gly Met Lys Thr Asn Glu Ile
        35                  40                  45

Phe Ala Gly Phe Pro Ser Asp Leu Phe Leu Thr Leu Val Ala Val Thr
    50                  55                  60

Tyr Leu Phe Ala Ile Ala Gln Ile Asn Gly Thr Ile Asp Trp Leu Val
65                  70                  75                  80

Glu Cys Ala Val Arg Leu Val Arg Gly Arg Ile Gly Leu Ile Pro Trp
                85                  90                  95

Val Met Phe Leu Val Ala Ala Ile Ile Thr Gly Phe Gly Ala Leu Gly
            100                 105                 110

Pro Ala Ala Val Ala Ile Leu Ala Pro Val Ala Leu Ser Phe Ala Val
        115                 120                 125

Gln Tyr Arg Ile His Pro Val Met Met Gly Leu Met Val Ile His Gly
    130                 135                 140

Ala Gln Ala Gly Gly Phe Ser Pro Ile Ser Ile Tyr Gly Gly Ile Thr
145                 150                 155                 160

Asn Gln Ile Val Ala Lys Ala Gly Leu Pro Phe Ala Pro Thr Ser Leu
                165                 170                 175

Phe Leu Ser Ser Phe Phe Phe Asn Leu Ala Ile Ala Val Leu Val Phe
            180                 185                 190

Phe Val Phe Gly Gly Ala Arg Val Met Lys His Asp Pro Ala Ser Leu
        195                 200                 205

Gly Pro Leu Pro Glu Leu His Pro Glu Gly Val Ser Ala Ser Ile Arg
    210                 215                 220

Gly His Gly Gly Thr Pro Ala Lys Pro Ile Arg Glu His Ala Tyr Gly
225                 230                 235                 240

Thr Ala Ala Asp Thr Ala Thr Thr Leu Arg Leu Asn Asn Glu Arg Ile
                245                 250                 255

Thr Thr Leu Ile Gly Leu Thr Ala Leu Gly Ile Gly Ala Leu Val Phe
            260                 265                 270

Lys Phe Asn Val Gly Leu Val Ala Met Thr Val Ala Val Val Leu Ala
        275                 280                 285

Leu Leu Ser Pro Lys Thr Gln Lys Ala Ala Ile Asp Lys Val Ser Trp
    290                 295                 300

Ser Thr Val Leu Leu Ile Ala Gly Ile Ile Thr Tyr Val Gly Val Met
305                 310                 315                 320

Glu Lys Ala Gly Thr Val Asp Tyr Val Ala Asn Gly Ile Ser Ser Leu
                325                 330                 335

Gly Met Pro Leu Leu Val Ala Leu Leu Leu Cys Phe Thr Gly Ala Ile
            340                 345                 350

Val Ser Ala Phe Ala Ser Ser Thr Ala Leu Leu Gly Ala Ile Ile Pro
        355                 360                 365

Leu Ala Val Pro Phe Leu Leu Gln Gly His Ile Ser Ala Ile Gly Val
    370                 375                 380

Val Ala Ala Ile Ala Ile Ser Thr Thr Ile Val Asp Thr Ser Pro Phe
385                 390                 395                 400
```

```
Ser Thr Asn Gly Ala Leu Val Val Ala Asn Ala Pro Asp Asp Ser Arg
                405                 410                 415

Glu Gln Val Leu Arg Gln Leu Leu Ile Tyr Ser Ala Leu Ile Ala Ile
            420                 425                 430

Ile Gly Pro Ile Val Ala Trp Leu Val Phe Val Val Pro Gly Leu Val
        435                 440                 445


<210> SEQ ID NO 82
<211> LENGTH: 448
<212> TYPE: PRT
<213> ORGANISM: Agrobacterium vitis

<400> SEQUENCE: 82

Met Asn Ile Glu Ile Leu Ser Ile Gly Leu Leu Val Ala Ile Phe Ile
1               5                   10                  15

Ile Ala Thr Ile Gln Pro Ile Asn Met Gly Val Leu Ala Phe Gly Cys
            20                  25                  30

Thr Phe Val Leu Gly Ser Leu Ile Ile Gly Met Lys Pro Ala Asp Ile
        35                  40                  45

Phe Ala Gly Phe Pro Ala Asp Leu Phe Leu Thr Leu Val Ala Val Thr
    50                  55                  60

Tyr Leu Phe Ala Ile Ala Gln Ile Asn Gly Thr Ile Asp Trp Leu Val
65                  70                  75                  80

Glu Arg Ser Val Arg Met Val Arg Gly Arg Val Gly Trp Ile Pro Trp
                85                  90                  95

Val Met Phe Leu Val Ala Ala Ile Ile Thr Gly Phe Gly Ala Leu Gly
            100                 105                 110

Pro Ala Ala Val Ala Ile Leu Ala Pro Val Ala Leu Ser Phe Ala Val
        115                 120                 125

Gln Tyr Arg Ile His Pro Val Leu Met Gly Leu Met Val Ile His Gly
    130                 135                 140

Ala Gln Ala Gly Gly Phe Ser Pro Ile Ser Ile Tyr Gly Gly Ile Thr
145                 150                 155                 160

Asn Gln Ile Val Ala Lys Ala Gly Leu Pro Phe Ala Pro Thr Ser Leu
                165                 170                 175

Phe Leu Ser Ser Phe Phe Phe Asn Leu Ala Ile Ala Val Leu Ile Phe
            180                 185                 190

Phe Ile Phe Gly Gly Leu Ser Ile Leu Lys Gln Arg Ser Ser Val Lys
        195                 200                 205

Gly Pro Leu Pro Glu Leu His Pro Glu Gly Ile Ser Ala Ser Ile Lys
    210                 215                 220

Gly His Gly Gly Thr Pro Ala Lys Pro Phe Arg Glu His Ala Tyr Gly
225                 230                 235                 240

Thr Ala Ala Asp Thr Gln Ser Lys Val Arg Leu Thr Thr Glu Lys Val
                245                 250                 255

Thr Thr Leu Ile Gly Leu Thr Ala Leu Gly Val Gly Ala Leu Val Phe
            260                 265                 270

Lys Phe Asn Val Gly Leu Val Ala Ile Thr Val Ala Val Leu Leu Ala
        275                 280                 285

Leu Leu Ser Pro Thr Thr Gln Lys Ala Ala Ile Asp Lys Val Ser Trp
    290                 295                 300

Ser Thr Val Leu Leu Ile Ser Gly Ile Ile Thr Tyr Val Gly Val Met
305                 310                 315                 320

Glu Lys Ala Gly Thr Ile Asp Tyr Val Ala His Gly Ile Ser Ser Leu
```

```
                325                 330                 335

Gly Met Pro Leu Leu Val Ala Leu Leu Leu Cys Phe Thr Gly Ala Ile
            340                 345                 350

Val Ser Ala Phe Ala Ser Ser Thr Ala Leu Leu Gly Ala Ile Ile Pro
        355                 360                 365

Leu Ala Val Pro Phe Leu Leu Gln Gly His Ile Ser Ala Val Gly Val
    370                 375                 380

Val Ala Ala Ile Ala Ile Ser Thr Thr Ile Val Asp Thr Ser Pro Phe
385                 390                 395                 400

Ser Thr Asn Gly Ala Leu Val Val Ala Asn Ala Pro Asp Asp Gln Arg
                405                 410                 415

Asp Lys Val Met Arg Gln Met Leu Ile Tyr Ser Ala Leu Ile Ala Leu
            420                 425                 430

Ile Gly Pro Val Ile Ala Trp Leu Val Phe Val Val Pro Gly Ile Ile
        435                 440                 445


<210> SEQ ID NO 83
<211> LENGTH: 448
<212> TYPE: PRT
<213> ORGANISM: Neorhizobium sp.

<400> SEQUENCE: 83

Met Ser Ile Glu Ile Leu Ser Ile Leu Leu Leu Val Ala Met Phe Val
1               5                   10                  15

Ile Ala Thr Ile Gln Pro Ile Asn Met Gly Ala Leu Ala Phe Ala Cys
            20                  25                  30

Thr Phe Val Leu Gly Ser Leu Ile Ile Gly Met Lys Thr Ser Asp Ile
        35                  40                  45

Phe Ala Gly Phe Pro Ser Asp Leu Phe Leu Thr Leu Val Ala Val Thr
    50                  55                  60

Tyr Leu Phe Ala Ile Ala Gln Ile Asn Gly Thr Ile Asp Trp Leu Val
65                  70                  75                  80

Glu Cys Ala Val Arg Met Val Arg Gly His Val Ala Trp Ile Pro Trp
                85                  90                  95

Val Met Phe Val Val Ala Ala Ile Ile Thr Gly Phe Gly Ala Leu Gly
            100                 105                 110

Pro Ala Ala Val Ala Ile Leu Ala Pro Val Ala Leu Ser Phe Ala Val
        115                 120                 125

Gln Tyr Arg Ile His Pro Val Met Met Gly Leu Met Val Ile His Gly
    130                 135                 140

Ala Gln Ala Gly Gly Phe Ser Pro Ile Ser Val Tyr Gly Gly Ile Thr
145                 150                 155                 160

Asn Gln Ile Val Ala Lys Ala Gly Leu Pro Phe Ala Pro Thr Ser Leu
                165                 170                 175

Phe Leu Ser Ser Phe Phe Phe Asn Leu Ala Ile Ala Val Leu Val Phe
            180                 185                 190

Phe Val Phe Gly Gly Ala Arg Ile Met Lys Gln Ala Ala Gly Pro Thr
        195                 200                 205

Gly Pro Leu Pro Glu Leu His Pro Glu Gly Val Ser Ala Ala Ile Arg
    210                 215                 220

Gly His Gly Gly Thr Pro Ala Lys Pro Ile Arg Glu His Ala Tyr Gly
225                 230                 235                 240

Thr Ala Ala Asp Thr Leu Gln Thr Leu Arg Leu Thr Pro Glu Lys Val
                245                 250                 255
```

```
Phe Thr Leu Ile Gly Leu Thr Ala Leu Gly Ile Gly Ala Leu Val Phe
            260                 265                 270

Lys Phe Asn Val Gly Leu Val Ala Ile Thr Val Ala Val Ala Leu Ala
        275                 280                 285

Leu Ile Ser Pro Lys Thr Gln Lys Ala Ala Val Asp Lys Val Ser Trp
    290                 295                 300

Ser Thr Val Leu Leu Ile Ala Gly Ile Ile Thr Tyr Val Gly Val Leu
305                 310                 315                 320

Glu Lys Ala Gly Thr Val Asn Tyr Val Ala Asn Gly Ile Ser Ser Leu
                325                 330                 335

Gly Met Pro Leu Leu Val Ala Leu Leu Leu Cys Phe Thr Gly Ala Ile
            340                 345                 350

Val Ser Ala Phe Ala Ser Ser Thr Ala Leu Leu Gly Ala Ile Ile Pro
        355                 360                 365

Leu Ala Val Pro Phe Leu Leu Gln Gly His Ile Ser Ala Val Gly Val
    370                 375                 380

Val Ala Ala Ile Ala Ile Ser Thr Thr Ile Val Asp Thr Ser Pro Phe
385                 390                 395                 400

Ser Thr Asn Gly Ala Leu Val Val Ala Asn Ala Pro Asp Glu Thr Arg
                405                 410                 415

Glu Gln Val Leu Arg Gln Leu Leu Ile Tyr Ser Ala Leu Ile Ala Ile
            420                 425                 430

Ile Gly Pro Val Val Ala Trp Leu Val Phe Val Val Pro Gly Leu Val
        435                 440                 445
```

<210> SEQ ID NO 84
<211> LENGTH: 545
<212> TYPE: PRT
<213> ORGANISM: Moraxella catarrhalis

<400> SEQUENCE: 84

```
Met Thr Thr Trp Asn Gln Lys Gln Gln Arg Lys Ala Gln Lys Leu Ala
1               5                   10                  15

Lys Ala Cys Asp Ser Gly Phe Asp Lys Tyr Val Pro His Glu Arg Ile
            20                  25                  30

Ile Ala Leu Leu Glu Thr Val Ile Asp Arg Gly Asp Arg Val Cys Leu
        35                  40                  45

Glu Gly Asn Asn Gln Lys Gln Ala Asp Phe Leu Ser Lys Ser Leu Ser
    50                  55                  60

Ser Cys Asn Pro Asp Ile Val Asn Gly Leu His Ile Val Gln Ser Val
65                  70                  75                  80

Leu Ala Leu Pro Ser His Ile Asp Val Phe Glu Arg Gly Ile Ala Ser
                85                  90                  95

Lys Val Asp Phe Ser Phe Ala Gly Pro Gln Ser Leu Arg Leu Ala Gln
            100                 105                 110

Leu Val Gln Ala Gln Lys Ile Thr Ile Gly Ala Ile His Thr Tyr Leu
        115                 120                 125

Glu Leu Tyr Gly Arg Tyr Phe Ile Asp Leu Thr Pro Asn Val Ala Leu
    130                 135                 140

Ile Thr Ala His Ala Ala Asp Lys Arg Gly Asn Leu Tyr Thr Gly Ala
145                 150                 155                 160

Asn Thr Glu Asp Thr Pro Ala Ile Val Glu Ala Thr Thr Phe Lys Ser
                165                 170                 175

Gly Ile Val Ile Ala Gln Val Asn Glu Ile Val Asp Glu Leu Pro Arg
            180                 185                 190
```

Val Asp Ile Pro Ser Asp Trp Val Asp Tyr Tyr Thr Gln Ser Pro Lys
195 200 205

His Asn Tyr Ile Glu Pro Leu Phe Thr Arg Asp Pro Ala Gln Ile Thr
210 215 220

Glu Ile Gln Ile Leu Met Ala Met Met Ala Ile Lys Gly Ile Tyr Ala
225 230 235 240

Pro Tyr Lys Ile Asn Arg Leu Asn His Gly Ile Gly Phe Asp Thr Ala
245 250 255

Ala Ile Glu Leu Leu Leu Pro Thr Tyr Ala Glu Ser Leu Gly Leu Lys
260 265 270

Gly Glu Ile Cys Thr His Trp Ala Leu Asn Pro His Pro Thr Leu Ile
275 280 285

Pro Ala Ile Glu Ser Gly Phe Ile His Ser Val His Ser Phe Gly Ser
290 295 300

Glu Val Gly Met Glu Asn Tyr Val Lys Ala Arg Ser Asp Val Phe Phe
305 310 315 320

Thr Gly Ala Asp Gly Ser Met Arg Ser Asn Arg Ala Phe Ser Gln Thr
325 330 335

Ala Gly Leu Tyr Ala Cys Asp Leu Phe Ile Gly Ser Thr Leu Gln Ile
340 345 350

Asp Leu Gln Gly Asn Ser Ser Thr Ala Thr Ala Asp Arg Ile Ala Gly
355 360 365

Phe Gly Gly Ala Pro Asn Met Gly Ser Asp Pro His Gly Arg Arg His
370 375 380

Ala Ser Tyr Ala Tyr Met Lys Ala Gly Arg Glu Ala Val Asp Gly Ser
385 390 395 400

Pro Ile Lys Gly Arg Lys Leu Val Val Gln Met Val Glu Thr Tyr Arg
405 410 415

Glu His Met Gln Ser Val Phe Val Asn Glu Leu Asp Ala Phe Lys Leu
420 425 430

Gln Gln Lys Met Gly Ala Asp Leu Pro Pro Ile Met Ile Tyr Gly Asp
435 440 445

Asp Val Thr His Ile Val Thr Glu Glu Gly Ile Ala Asn Leu Leu Leu
450 455 460

Cys Arg Thr Pro Asp Glu Arg Glu Gln Ala Ile Arg Gly Val Ala Gly
465 470 475 480

Tyr Thr Pro Ile Gly Leu Gly Arg Asp Asp Thr Met Val Ala Arg Leu
485 490 495

Arg Glu Arg Lys Val Ile Gln Arg Pro Glu Asp Leu Gly Ile Asn Pro
500 505 510

Met His Ala Thr Arg Asp Leu Leu Ala Ala Lys Ser Val Lys Asp Leu
515 520 525

Val Arg Trp Ser Asp Arg Leu Tyr Glu Pro Pro Ser Arg Phe Arg Asn
530 535 540

Trp
545

<210> SEQ ID NO 85
<211> LENGTH: 554
<212> TYPE: PRT
<213> ORGANISM: Dechloromonas aromatica

<400> SEQUENCE: 85

Met Asn Ala Pro Gln Pro Arg Gln Trp Asp Ser Leu Arg Gln Asn Arg

-continued

```
1               5                   10                  15

Ala Arg Arg Leu Glu Arg Ala Ala Ser Leu Gly Leu Ala Gly Gln Asn
            20                  25                  30

Gly Lys Glu Ile Pro Val Asp Arg Ile Ile Asp Leu Leu Glu Ala Val
        35                  40                  45

Ile Gln Pro Gly Asp Arg Val Cys Leu Glu Gly Asn Asn Gln Lys Gln
    50                  55                  60

Ala Asp Phe Leu Ser Glu Ser Leu Ala Asp Cys Asp Pro Ala Arg Ile
65                  70                  75                  80

Asn His Leu Ser Met Val Gln Ser Val Leu Ala Leu Pro Ser His Val
                85                  90                  95

Asp Leu Phe Glu Arg Gly Leu Ala Thr Arg Leu Asp Phe Ser Phe Ser
            100                 105                 110

Gly Pro Gln Gly Ala Arg Leu Ala Lys Leu Val Gln Glu Gln Arg Ile
        115                 120                 125

Glu Ile Gly Ala Ile His Thr Tyr Leu Glu Leu Phe Gly Arg Tyr Phe
    130                 135                 140

Met Asp Leu Thr Pro Asn Val Ala Leu Ile Ala Ala Gln Ala Ala Asp
145                 150                 155                 160

Ala Glu Gly Asn Leu Tyr Leu Gly Pro Asn Thr Glu Asp Thr Pro Ala
                165                 170                 175

Ile Val Glu Ala Thr Ala Phe Lys Gly Gly Ile Val Ile Ala Gln Val
            180                 185                 190

Asn Glu Arg Leu Asp Lys Leu Pro Arg Val Asp Val Pro Ala Asp Trp
        195                 200                 205

Val Asp Phe Thr Val Leu Ala Pro Lys Pro Asn Tyr Ile Glu Pro Leu
    210                 215                 220

Phe Thr Arg Asp Pro Ala Gln Ile Thr Glu Val Gln Val Leu Met Ala
225                 230                 235                 240

Met Met Ala Ile Lys Gly Ile Tyr Ala Glu Tyr Gly Val Thr Arg Leu
                245                 250                 255

Asn His Gly Ile Gly Phe Asp Thr Ala Ala Ile Glu Leu Leu Leu Pro
            260                 265                 270

Thr Tyr Ala Ala Asp Leu Gly Leu Lys Gly Lys Ile Cys Thr His Trp
        275                 280                 285

Ala Leu Asn Pro His Pro Thr Leu Ile Pro Ala Ile Glu Ala Gly Phe
    290                 295                 300

Val Glu Ser Val His Cys Phe Gly Ser Glu Val Gly Met Asp Asp Tyr
305                 310                 315                 320

Ile Ser Ala Arg Ser Asp Ile Phe Phe Thr Gly Ala Asp Gly Ser Met
                325                 330                 335

Arg Ser Asn Arg Ala Phe Ser Gln Thr Ala Gly Leu Tyr Ala Cys Asp
            340                 345                 350

Met Phe Ile Gly Ser Thr Leu Gln Met Asp Leu Ala Gly Asn Ser Ser
        355                 360                 365

Thr Ala Thr Leu Gly Arg Ile Thr Gly Phe Gly Gly Ala Pro Asn Met
    370                 375                 380

Gly Ser Asp Pro His Gly Arg Arg His Ala Ser Pro Ala Trp Leu Lys
385                 390                 395                 400

Ala Gly Arg Glu Ala Tyr Gly Pro Gln Ala Ile Arg Gly Arg Lys Leu
                405                 410                 415

Val Val Gln Met Val Glu Thr Phe Arg Glu His Met Ala Pro Val Phe
            420                 425                 430
```

```
Val Asp Asp Leu Asp Ala Trp Lys Leu Gln Ala Ser Met Gly Ser Asp
        435                 440                 445

Leu Pro Pro Ile Met Ile Tyr Gly Asp Asp Val Ser His Ile Val Thr
    450                 455                 460

Glu Glu Gly Ile Ala Asn Leu Leu Leu Cys Arg Thr Pro Ala Glu Arg
465                 470                 475                 480

Glu Gln Ala Ile Arg Gly Val Ala Gly Phe Thr Pro Val Gly Met Ala
                485                 490                 495

Arg Asp Lys Gly Thr Val Glu Asn Leu Arg Asp Arg Gly Ile Ile Arg
            500                 505                 510

Arg Pro Glu Asp Leu Gly Ile Asp Pro Arg Gln Ala Ser Arg Asp Leu
        515                 520                 525

Leu Ala Ala Arg Ser Ile Lys Asp Leu Val Arg Cys Ser Gly Gly Leu
    530                 535                 540

Tyr Ala Pro Pro Ser Arg Phe Arg Asn Trp
545                 550


<210> SEQ ID NO 86
<211> LENGTH: 548
<212> TYPE: PRT
<213> ORGANISM: Pseudomonas cissicola

<400> SEQUENCE: 86

Met Ser Arg Gln Trp Asp Thr Gln Ala Asp Ser Arg Arg Gln Arg Leu
1               5                   10                  15

Gln Arg Ala Ala Ala Leu Ala Pro Gln Gly Arg Val Val Ala Ala Asp
            20                  25                  30

Asp Val Val Ala Leu Leu Glu Ala Val Ile Glu Pro Gly Asp Arg Val
        35                  40                  45

Cys Leu Glu Gly Asn Asn Gln Lys Gln Ala Asp Phe Leu Ala Arg Cys
    50                  55                  60

Leu Thr Glu Val Asp Pro Ala Arg Val His Asp Leu His Met Val Gln
65                  70                  75                  80

Ser Val Leu Ser Leu Ala Ala His Leu Asp Val Phe Glu Arg Gly Ile
                85                  90                  95

Ala Lys Arg Leu Asp Phe Ser Phe Ser Gly Pro Gln Ala Ala Arg Leu
            100                 105                 110

Ala Gly Leu Val Ser Glu Gly Arg Ile Glu Ile Gly Ala Ile His Thr
        115                 120                 125

Tyr Leu Glu Leu Phe Gly Arg Tyr Phe Ile Asp Leu Thr Pro Arg Ile
    130                 135                 140

Ala Leu Val Thr Ala Gln Ala Ala Asp Arg His Gly Asn Leu Tyr Thr
145                 150                 155                 160

Gly Pro Asn Thr Glu Asp Thr Pro Val Ile Val Glu Ala Thr Ala Phe
                165                 170                 175

Lys Gly Gly Ile Val Ile Ala Gln Val Asn Glu Ile Leu Asp Thr Leu
            180                 185                 190

Pro Arg Val Asp Ile Pro Ala Asp Trp Val Asp Phe Val Thr Gln Ala
        195                 200                 205

Pro Lys Pro Asn Tyr Ile Glu Pro Leu Phe Thr Arg Asp Pro Ala Gln
    210                 215                 220

Ile Ser Glu Ile Gln Val Leu Met Ala Met Met Ala Ile Lys Gly Ile
225                 230                 235                 240

Tyr Ala Glu Tyr Gly Val Asp Arg Leu Asn His Gly Ile Gly Phe Asp
```

```
                245                 250                 255

Thr Ala Ala Ile Glu Leu Leu Leu Pro Thr Tyr Ala Gln Ser Leu Gly
            260                 265                 270

Leu Lys Gly Lys Ile Cys Arg His Trp Ala Leu Asn Pro His Pro Ala
        275                 280                 285

Leu Ile Pro Ala Ile Glu Ser Gly Phe Val Gln Ser Val His Ser Phe
    290                 295                 300

Gly Ser Glu Leu Gly Met Glu Asn Tyr Ile Ala Ala Arg Pro Asp Ile
305                 310                 315                 320

Phe Phe Thr Gly Ala Asp Gly Ser Met Arg Ser Asn Arg Ala Leu Ser
                325                 330                 335

Gln Thr Ala Gly Leu Tyr Ala Cys Asp Met Phe Ile Gly Ser Thr Leu
            340                 345                 350

Gln Ile Asp Leu Gln Gly Asn Ser Ser Thr Ala Thr Arg Asp Arg Ile
        355                 360                 365

Ala Gly Phe Gly Gly Ala Pro Asn Met Gly Ser Asp Ala Arg Gly Arg
    370                 375                 380

Arg His Ala Ser Ala Ala Trp Leu Lys Ala Gly Arg Glu Ala Ala Thr
385                 390                 395                 400

Pro Gly Glu Met Pro Arg Gly Arg Lys Leu Val Val Gln Met Val Glu
                405                 410                 415

Thr Phe Arg Glu His Met Ala Pro Ala Phe Val Asp Arg Leu Asp Ala
            420                 425                 430

Trp Glu Leu Ala Glu Arg Ala Asn Met Pro Leu Pro Pro Val Met Ile
        435                 440                 445

Tyr Gly Asp Asp Val Ser His Val Leu Thr Glu Glu Gly Ile Ala Asn
    450                 455                 460

Leu Leu Leu Cys Arg Thr Pro Glu Glu Arg Glu Gln Ala Ile Arg Gly
465                 470                 475                 480

Val Ser Gly Tyr Thr Ala Val Gly Leu Gly Arg Asp Lys Arg Met Val
                485                 490                 495

Glu Asn Leu Arg Asp Arg Gly Val Ile Lys Arg Pro Asp Asp Leu Gly
            500                 505                 510

Ile Arg Pro Arg Asp Ala Thr Arg Asp Leu Leu Ala Ala Arg Thr Val
        515                 520                 525

Lys Asp Leu Val Arg Trp Ser Gly Gly Leu Tyr Asp Pro Pro Lys Arg
    530                 535                 540

Phe Arg Asn Trp
545
```

<210> SEQ ID NO 87
<211> LENGTH: 550
<212> TYPE: PRT
<213> ORGANISM: Geobacillus subterraneus

<400> SEQUENCE: 87

```
Met Asn Lys Ile Tyr Arg Glu Lys Arg Ser Trp Arg Thr Arg Arg Asp
1               5                   10                  15

Arg Lys Ala Lys Arg Ile Glu His Met Lys Gln Ile Ala Lys Gly Lys
            20                  25                  30

Ile Ile Pro Thr Glu Lys Ile Val Glu Ala Leu Thr Ala Leu Ile Phe
        35                  40                  45

Pro Gly Asp Arg Val Val Ile Glu Gly Asn Asn Gln Lys Gln Ala Ser
    50                  55                  60
```

```
Phe Leu Ser Lys Ala Leu Ser Gln Val Asn Pro Glu Lys Val Asn Gly
65                  70                  75                  80

Leu His Ile Ile Met Ser Ser Val Ser Arg Pro Glu His Leu Asp Leu
                85                  90                  95

Phe Glu Lys Gly Ile Ala Arg Lys Ile Asp Phe Ser Tyr Ala Gly Pro
            100                 105                 110

Gln Ser Leu Arg Met Ser Gln Met Leu Glu Asp Gly Lys Leu Val Ile
        115                 120                 125

Gly Glu Ile His Thr Tyr Leu Glu Leu Tyr Gly Arg Leu Phe Ile Asp
    130                 135                 140

Leu Thr Pro Ser Val Ala Leu Val Ala Ala Asp Lys Ala Asp Ala Ser
145                 150                 155                 160

Gly Asn Leu Tyr Thr Gly Pro Asn Thr Glu Glu Thr Pro Thr Leu Val
                165                 170                 175

Glu Ala Thr Ala Phe Arg Asp Gly Ile Val Ile Ala Gln Val Asn Glu
            180                 185                 190

Leu Ala Asp Glu Leu Pro Arg Val Asp Ile Pro Gly Ser Trp Ile Asp
        195                 200                 205

Phe Val Val Ala Ala Asp His Pro Tyr Glu Leu Glu Pro Leu Phe Thr
    210                 215                 220

Arg Asp Pro Arg Leu Ile Thr Glu Ile Gln Ile Leu Met Ala Met Met
225                 230                 235                 240

Val Ile Lys Gly Ile Tyr Glu Arg His Asn Ile Gln Ser Leu Asn His
                245                 250                 255

Gly Ile Gly Phe Asn Thr Ala Ala Ile Glu Leu Leu Leu Pro Thr Tyr
            260                 265                 270

Gly Glu Ser Leu Gly Leu Lys Gly Lys Ile Cys Lys His Trp Ala Leu
        275                 280                 285

Asn Pro His Pro Thr Leu Ile Pro Ala Ile Glu Thr Gly Trp Val Glu
    290                 295                 300

Ser Ile His Cys Phe Gly Gly Glu Val Gly Met Glu Lys Tyr Ile Ala
305                 310                 315                 320

Ala Arg Pro Asp Ile Phe Phe Thr Gly Lys Asp Gly Asn Leu Arg Ser
                325                 330                 335

Asn Arg Thr Leu Ser Gln Val Ala Gly Gln Tyr Ala Val Asp Leu Phe
            340                 345                 350

Ile Gly Ser Thr Leu Gln Ile Asp Arg Asp Gly Asn Ser Ser Thr Val
        355                 360                 365

Thr Asn Gly Arg Leu Ala Gly Phe Gly Gly Ala Pro Asn Met Gly His
    370                 375                 380

Asp Pro Arg Gly Arg Arg His Ser Ser Pro Ala Trp Leu Asp Met Ile
385                 390                 395                 400

Thr Ser Asp His Pro Ala Ala Lys Gly Arg Lys Leu Val Val Gln Met
                405                 410                 415

Val Glu Thr Phe Gln Lys Gly Asn Arg Pro Val Phe Val Glu Ser Leu
            420                 425                 430

Asp Ala Ile Glu Val Gly Arg Ser Ala Arg Leu Ala Thr Thr Pro Ile
        435                 440                 445

Met Ile Tyr Gly Glu Asp Val Thr His Ile Val Thr Glu Glu Gly Ile
    450                 455                 460

Ala Tyr Leu Tyr Lys Ala Ser Ser Leu Glu Glu Arg Arg Gln Ala Ile
465                 470                 475                 480

Ala Ala Ile Ala Gly Val Thr Pro Ile Gly Leu Glu Arg Asp Pro Arg
```

```
                485                 490                 495

Lys Thr Glu Gln Leu Arg Arg Asp Gly Val Val Ala Phe Pro Glu Asp
            500                 505                 510

Leu Gly Ile Arg Arg Thr Asp Ala Lys Arg Ser Leu Leu Ala Ala Lys
        515                 520                 525

Ser Ile Glu Glu Leu Val Glu Trp Ser Glu Gly Leu Tyr Glu Pro Pro
    530                 535                 540

Ala Arg Phe Arg Ser Trp
545                 550


<210> SEQ ID NO 88
<211> LENGTH: 265
<212> TYPE: PRT
<213> ORGANISM: Streptomyces sp. CLI2509

<400> SEQUENCE: 88

Met Leu Leu Thr Ile Asp Val Gly Asn Thr His Thr Val Leu Gly Leu
1               5                   10                  15

Phe Asp Gly Glu Glu Ile Val Glu His Trp Arg Ile Ser Thr Asp Ser
            20                  25                  30

Arg Arg Thr Ala Asp Glu Leu Ala Val Leu Leu Gln Gly Leu Met Gly
        35                  40                  45

Thr His Pro Leu Leu Gly Met Glu Leu Gly Glu Gly Ile Asp Gly Ile
    50                  55                  60

Ala Ile Cys Ser Thr Val Pro Ala Val Leu His Glu Leu Arg Glu Val
65                  70                  75                  80

Ser Arg Arg Tyr Tyr Gly Asp Val Pro Ala Ile Leu Val Glu Pro Gly
                85                  90                  95

Val Lys Thr Gly Val Pro Ile Leu Met Asp Asn Pro Lys Glu Val Gly
            100                 105                 110

Thr Asp Arg Ile Ile Asn Ala Val Ala Ala Gln His Leu Tyr Gly Gly
        115                 120                 125

Pro Ala Ile Val Val Asp Phe Gly Thr Ala Thr Thr Phe Asp Ala Val
    130                 135                 140

Ser Ala Arg Gly Glu Tyr Thr Gly Gly Val Ile Ala Pro Gly Ile Glu
145                 150                 155                 160

Ile Ser Val Glu Ala Leu Gly Leu Arg Gly Ala Gln Leu Arg Lys Ile
                165                 170                 175

Glu Leu Ala Arg Pro Arg Ser Val Ile Gly Lys Ser Thr Val Glu Ala
            180                 185                 190

Met Gln Ser Gly Ile Leu Tyr Gly Phe Ala Gly Gln Val Asp Gly Val
        195                 200                 205

Val Gln Arg Met Ala Cys Glu Leu Ala Pro Asp Pro Ala Asp Val Thr
    210                 215                 220

Val Ile Ala Thr Gly Gly Leu Ala Pro Met Val Leu Gly Glu Ala Ala
225                 230                 235                 240

Val Ile Asp His His Glu Pro Trp Leu Thr Leu Ile Gly Leu Arg Leu
                245                 250                 255

Val Tyr Glu Arg Asn Ala Gly Arg Arg
            260                 265


<210> SEQ ID NO 89
<211> LENGTH: 248
<212> TYPE: PRT
<213> ORGANISM: Streptomyces cinereus
```

<400> SEQUENCE: 89

```
Met Thr Lys Leu Trp Leu Asp Leu Gly Asn Thr Arg Leu Lys Tyr Trp
1               5                   10                  15

Leu Thr Asp Asp Ser Gly Gln Val Leu Asp His Ala Ala Glu Gln His
            20                  25                  30

Leu Gln Ala Pro Ala Glu Leu Leu Lys Gly Leu Thr Phe Arg Leu Glu
        35                  40                  45

Arg Leu Asn Pro Asp Phe Ile Gly Val Ser Ser Val Leu Gly Gln Ala
    50                  55                  60

Val Asn Asn His Val Ala Glu Ser Leu Glu Arg Leu Gln Lys Pro Phe
65                  70                  75                  80

Glu Phe Ala Gln Val His Ala Lys His Ala Leu Met Ser Ser Asp Tyr
                85                  90                  95

Asn Pro Ala Gln Leu Gly Val Asp Arg Trp Leu Gln Met Leu Gly Ile
            100                 105                 110

Ile Glu Pro Ser Lys Lys Gln Cys Val Ile Gly Cys Gly Thr Ala Val
        115                 120                 125

Thr Ile Asp Leu Val Asp Gln Gly His His Leu Gly Gly Tyr Ile Phe
    130                 135                 140

Pro Ser Ile Tyr Leu Gln Arg Glu Ser Leu Phe Ser Gly Thr Arg Gln
145                 150                 155                 160

Ile Ser Ile Ile Asp Gly Thr Phe Asp Ser Ile Asp Ser Gly Thr Asn
                165                 170                 175

Thr Gln Asp Ala Val His His Gly Ile Met Leu Ser Ile Val Gly Ala
            180                 185                 190

Ile Asn Glu Thr Ile His Arg Tyr Pro Gln Phe Glu Ile Thr Met Thr
        195                 200                 205

Gly Gly Asp Ala His Thr Phe Glu Pro His Leu Ser Ala Ser Val Glu
    210                 215                 220

Ile Arg Gln Asp Leu Val Leu Ala Gly Leu Gln Arg Phe Phe Ala Ala
225                 230                 235                 240

Lys Asn Asn Thr Lys Asn Gln Asn
                245
```

<210> SEQ ID NO 90
<211> LENGTH: 263
<212> TYPE: PRT
<213> ORGANISM: Kitasatospora kifunensis

<400> SEQUENCE: 90

```
Met Leu Leu Thr Ile Asp Val Gly Asn Thr Gln Thr Thr Leu Gly Leu
1               5                   10                  15

Phe Asp Gly Glu Glu Val Val Asp His Trp Arg Ile Ser Thr Asp Pro
            20                  25                  30

Arg Arg Thr Ala Asp Glu Leu Ala Val Leu Met Gln Gly Leu Met Gly
        35                  40                  45

Arg Gln Pro Gly Gly Ala Gly Arg Glu Arg Val Asp Gly Leu Ala Ile
    50                  55                  60

Cys Ser Ser Val Pro Ala Val Leu His Glu Leu Arg Glu Val Thr Arg
65                  70                  75                  80

Arg Tyr Tyr Gly Asp Leu Pro Ala Val Leu Val Ala Pro Gly Val Lys
                85                  90                  95

Thr Gly Val His Val Leu Met Asp Asn Pro Lys Glu Val Gly Ala Asp
            100                 105                 110
```

```
Arg Ile Val Asn Ala Leu Ala Ala Asn His Leu Tyr Gly Gly Pro Cys
        115                 120                 125

Ile Val Val Asp Phe Gly Thr Ala Thr Thr Phe Asp Ala Ile Asn Glu
    130                 135                 140

Arg Gly Asp Tyr Val Gly Gly Ala Ile Ala Pro Gly Ile Glu Ile Ser
145                 150                 155                 160

Val Glu Ala Leu Gly Val Arg Gly Ala Gln Leu Arg Lys Ile Glu Leu
                165                 170                 175

Ala Lys Pro Arg Asn Val Ile Gly Lys Asn Thr Val Glu Gly Met Gln
            180                 185                 190

Ser Gly Val Leu Tyr Gly Phe Ala Gly Gln Val Asp Gly Leu Val Thr
        195                 200                 205

Arg Met Ala Lys Glu Leu Ser Pro Thr Asp Pro Glu Asp Val Gln Val
    210                 215                 220

Ile Ala Thr Gly Gly Leu Ala Pro Leu Val Leu Asp Glu Ala Ser Ser
225                 230                 235                 240

Ile Asp Val His Glu Pro Trp Leu Thr Leu Ile Gly Leu Arg Leu Val
                245                 250                 255

Tyr Glu Arg Asn Thr Ala Ser
            260


<210> SEQ ID NO 91
<211> LENGTH: 418
<212> TYPE: PRT
<213> ORGANISM: Citrobacter freundii

<400> SEQUENCE: 91

Met Thr Leu Leu Ala Leu Gly Ile Asn His Lys Thr Ala Pro Val Ser
1               5                   10                  15

Leu Arg Glu Arg Val Thr Phe Ser Pro Asp Thr Leu Asp Gln Ala Leu
            20                  25                  30

Asp Ser Leu Gln Ala Leu Pro Met Val Gln Gly Gly Val Val Leu Ser
        35                  40                  45

Thr Cys Asn Arg Thr Glu Ile Tyr Leu Ser Val Glu Glu Gln Asp Asn
    50                  55                  60

Leu Arg Glu Ala Leu Ile Arg Trp Leu Cys Glu Tyr His Asn Leu Asn
65                  70                  75                  80

Glu Glu Asp Leu Arg Asn Ser Leu Tyr Trp His Gln Asp Asn Asp Ala
                85                  90                  95

Val Ser His Leu Met Arg Val Ala Ser Gly Leu Asp Ser Leu Val Leu
            100                 105                 110

Gly Glu Pro Gln Ile Leu Gly Gln Val Lys Lys Ala Phe Ala Asp Ser
        115                 120                 125

Gln Lys Gly His Gln Asn Ala Ser Ala Leu Glu Arg Met Phe Gln Lys
    130                 135                 140

Ser Phe Ser Val Ala Lys Arg Val Arg Thr Glu Thr Asp Ile Gly Ser
145                 150                 155                 160

Ser Ala Val Ser Val Ala Phe Ala Ala Cys Thr Leu Ala Arg Gln Ile
                165                 170                 175

Phe Glu Ser Leu Ser Thr Val Thr Val Leu Leu Val Gly Ala Gly Glu
            180                 185                 190

Thr Ile Glu Leu Val Ala Arg His Leu Arg Glu His Lys Val Lys Lys
        195                 200                 205

Met Ile Ile Ala Asn Arg Thr Arg Glu Arg Ala Gln Val Leu Ala Asp
    210                 215                 220
```

```
Glu Val Gly Ala Glu Val Ile Ser Leu Ser Asp Ile Asp Ala Arg Leu
225                 230                 235                 240

Gln Asp Ala Asp Ile Ile Ile Ser Ser Thr Ala Ser Pro Leu Pro Ile
                245                 250                 255

Ile Gly Lys Gly Met Val Glu Arg Ala Leu Lys Asn Arg Arg Asn Gln
            260                 265                 270

Pro Met Leu Leu Val Asp Ile Ala Val Pro Arg Asp Val Glu Pro Glu
        275                 280                 285

Val Gly Lys Leu Ser Asn Ala Tyr Leu Tyr Ser Val Asp Asp Leu Gln
    290                 295                 300

Ser Ile Ile Ser His Asn Leu Ala Gln Arg Lys Ala Ala Ala Val Glu
305                 310                 315                 320

Ala Glu Thr Ile Val Glu Gln Glu Ala Ser Glu Phe Met Ala Trp Leu
                325                 330                 335

Arg Ala Gln Gly Ala Ser Asp Thr Ile Arg Glu Tyr Arg Ser Gln Ser
            340                 345                 350

Glu Gln Ile Arg Asp Glu Leu Thr Ala Lys Ala Leu Ala Ala Leu Gln
        355                 360                 365

Gln Gly Gly Asp Ala Gln Ala Ile Met Gln Asp Leu Ala Trp Lys Leu
    370                 375                 380

Thr Asn Arg Leu Ile His Ala Pro Thr Lys Ser Leu Gln Gln Ala Ala
385                 390                 395                 400

Arg Asp Gly Asp Ser Glu Arg Leu Asn Ile Leu Arg Asp Ser Leu Gly
                405                 410                 415

Leu Glu


<210> SEQ ID NO 92
<211> LENGTH: 420
<212> TYPE: PRT
<213> ORGANISM: Pseudomonas reactans

<400> SEQUENCE: 92

Met Thr Leu Leu Ala Leu Gly Ile Asn His Lys Thr Ala Pro Val Ser
1               5                   10                  15

Leu Arg Glu Arg Val Thr Phe Ser Pro Glu Thr Ile Glu Gln Ala Leu
            20                  25                  30

Ser Ser Leu Leu Gln Gln Pro Leu Val Gln Gly Gly Val Val Leu Ser
        35                  40                  45

Thr Cys Asn Arg Thr Glu Leu Tyr Leu Ser Val Glu Gln Gln Glu Asn
    50                  55                  60

Leu Gln Glu Gln Leu Val Lys Trp Leu Cys Asp Tyr His His Leu Ser
65                  70                  75                  80

Ala Asp Glu Val Arg Lys Ser Leu Tyr Trp His Gln Asp Asn Ala Ala
                85                  90                  95

Val Ser His Leu Met Arg Val Ala Ser Gly Leu Asp Ser Leu Val Val
            100                 105                 110

Gly Glu Pro Gln Ile Leu Gly Gln Val Lys Lys Ala Phe Ala Glu Ser
        115                 120                 125

Gln His Gly Gln Ala Val Ser Gly Glu Leu Glu Arg Leu Phe Gln Lys
    130                 135                 140

Ser Phe Ser Val Ala Lys Arg Val Arg Thr Glu Thr Asp Ile Gly Ala
145                 150                 155                 160

Ser Ala Val Ser Val Ala Phe Ala Ala Cys Thr Leu Ala Arg Gln Ile
                165                 170                 175
```

```
Phe Glu Ser Leu Ser Asp Val Ser Val Leu Leu Val Gly Ala Gly Glu
            180                 185                 190

Thr Ile Glu Leu Val Ala Arg His Leu Arg Glu His Lys Val Arg His
        195                 200                 205

Met Met Ile Ala Asn Arg Thr Arg Glu Arg Ala Gln Val Leu Ala Ser
    210                 215                 220

Glu Val Gly Ala Glu Val Ile Thr Leu Gln Asp Ile Asp Ala Arg Leu
225                 230                 235                 240

Ala Asp Ala Asp Ile Ile Ile Ser Ser Thr Ala Ser Pro Leu Pro Ile
                245                 250                 255

Ile Gly Lys Gly Met Val Glu Arg Ala Leu Lys Ala Arg Arg Asn Gln
            260                 265                 270

Pro Met Leu Met Val Asp Ile Ala Val Pro Arg Asp Ile Glu Pro Glu
        275                 280                 285

Val Gly Lys Leu Ala Asn Ala Tyr Leu Tyr Ser Val Asp Asp Leu His
    290                 295                 300

Ser Ile Ile Gln Asn Asn Met Ala Gln Arg Lys Ala Ala Ala Val Gln
305                 310                 315                 320

Ala Glu Ser Ile Val Glu Gln Glu Ser Ser Asn Phe Met Ala Trp Leu
                325                 330                 335

Arg Ser Gln Gly Ala Val Glu Ile Ile Arg Asp Tyr Arg Ser Arg Ala
            340                 345                 350

Asp Leu Val Arg Ala Glu Ala Glu Ala Lys Ala Leu Ala Ala Ile Ala
        355                 360                 365

Gln Gly Ala Asp Val Ser Ala Val Ile His Glu Leu Ala His Lys Leu
    370                 375                 380

Thr Asn Arg Leu Ile His Ala Pro Thr Arg Ser Leu Gln Gln Ala Ala
385                 390                 395                 400

Ser Asp Gly Asp Val Glu Arg Leu Gln Ile Leu Arg Asp Ser Leu Gly
                405                 410                 415

Leu Asp Gln Gln
            420


<210> SEQ ID NO 93
<211> LENGTH: 420
<212> TYPE: PRT
<213> ORGANISM: Gammaproteobacteria

<400> SEQUENCE: 93

Met Thr Leu Leu Ala Leu Gly Ile Asn His Lys Thr Ala Pro Val Ala
1               5                   10                  15

Leu Arg Glu Lys Val Ser Phe Ser Pro Asp Thr Met Gly Asp Ala Leu
            20                  25                  30

Asn Asn Leu Leu Gln Gln Pro Ala Val Arg Gly Gly Val Val Leu Ser
        35                  40                  45

Thr Cys Asn Arg Thr Glu Leu Tyr Leu Ser Met Glu Asp Lys Glu Asn
    50                  55                  60

Ser His Glu Gln Leu Ile Arg Trp Leu Cys Gln Tyr His Gln Ile Glu
65                  70                  75                  80

Pro Asn Glu Leu Gln Ser Ser Ile Tyr Trp His Gln Asp Asn Gln Ala
                85                  90                  95

Val Ser His Leu Met Arg Val Ala Ser Gly Leu Asp Ser Leu Val Leu
            100                 105                 110

Gly Glu Pro Gln Ile Leu Gly Gln Val Lys Lys Ala Phe Ala Asp Ser
```

```
        115                 120                 125

Gln Asn Tyr Asp Ser Leu Ser Ser Glu Leu Glu Arg Leu Phe Gln Lys
    130                 135                 140

Ser Phe Ser Val Ala Lys Arg Val Arg Thr Glu Thr Gln Ile Gly Ala
145                 150                 155                 160

Asn Ala Val Ser Val Ala Phe Ala Ala Cys Thr Leu Ala Arg Gln Ile
                165                 170                 175

Phe Glu Ser Leu Ser Ser Leu Thr Ile Leu Leu Val Gly Ala Gly Glu
            180                 185                 190

Thr Ile Glu Leu Val Ala Arg His Leu Arg Glu His Gln Val Lys Lys
        195                 200                 205

Ile Ile Ile Ala Asn Arg Thr Lys Glu Arg Ala Gln Arg Leu Ala Ser
    210                 215                 220

Glu Val Asp Ala Glu Val Ile Thr Leu Ser Glu Ile Asp Glu Cys Leu
225                 230                 235                 240

Ala Gln Ala Asp Ile Val Ile Ser Ser Thr Ala Ser Pro Leu Pro Ile
                245                 250                 255

Ile Gly Lys Gly Met Val Glu Arg Ala Leu Lys Lys Arg Arg Asn Gln
            260                 265                 270

Pro Met Leu Leu Val Asp Ile Ala Val Pro Arg Asp Ile Glu Gln Asp
        275                 280                 285

Val Glu Lys Leu Asn Asn Val Tyr Leu Tyr Ser Val Asp Asp Leu Glu
    290                 295                 300

Ala Ile Ile Gln His Asn Arg Glu Gln Arg Gln Ala Ala Ala Val Gln
305                 310                 315                 320

Ala Glu His Ile Val Gln Gln Glu Ser Gly Gln Phe Met Asp Trp Leu
                325                 330                 335

Arg Ala Gln Gly Ala Val Gly Ala Ile Arg Glu Tyr Arg Asp Ser Ala
            340                 345                 350

Glu Thr Leu Arg Ala Glu Met Thr Glu Lys Ala Ile Thr Leu Ile Gln
        355                 360                 365

Asn Gly Ala Asp Ala Glu Lys Val Ile Gln Gln Leu Ser His Gln Leu
    370                 375                 380

Met Asn Arg Leu Ile His Thr Pro Thr Lys Ser Leu Gln Gln Ala Ala
385                 390                 395                 400

Ser Asp Gly Asp Ile Glu Arg Leu Asn Leu Leu Arg Glu Ser Leu Gly
                405                 410                 415

Ile Thr His Asn
            420


<210> SEQ ID NO 94
<211> LENGTH: 645
<212> TYPE: PRT
<213> ORGANISM: Schizophyllum commune H4-8

<400> SEQUENCE: 94

Met Gly Pro Ala Leu Asp Val Arg Gly Lys Gln Leu Ala Ala Gly Tyr
1               5                   10                  15

Ala Ser Val Ala Gly Gln Ala Asp Val Glu Lys Ile His Gln Asp Gln
            20                  25                  30

Gly Ile Thr Ile Pro Pro Asn Ala Thr Val Glu Met Cys Pro His Ala
        35                  40                  45

Lys Ala Ala Arg Asp Ala Ala Arg Ile Ala Glu Asp Leu Ala Ala Ala
    50                  55                  60
```

```
Ala Ala Ser Lys Gln Gln Pro Ala Lys Lys Ala Gly Gly Cys Pro Phe
65                  70                  75                  80

His Ala Ala Gln Ala Gln Ala Gln Ala Lys Pro Ala Ala Ala Pro Lys
                85                  90                  95

Glu Thr Val Ala Thr Ala Asp Lys Lys Gly Lys Ser Pro Arg Ala Ala
            100                 105                 110

Gly Gly Phe Asp Tyr Glu Lys Phe Tyr Glu Glu Glu Leu Asp Lys Lys
        115                 120                 125

His Gln Asp Lys Ser Tyr Arg Tyr Phe Asn Asn Ile Asn Arg Leu Ala
    130                 135                 140

Ala Arg Phe Pro Thr Ala His Thr Ala Lys Val Thr Asp Glu Val Glu
145                 150                 155                 160

Val Trp Cys Ser Asn Asp Tyr Leu Gly Met Gly Gly Asn Pro Val Val
                165                 170                 175

Leu Glu Thr Met His Arg Val Leu Asp Lys Tyr Gly His Gly Ala Gly
            180                 185                 190

Gly Thr Arg Asn Ile Ala Gly Asn Gly Ala Leu His Leu Ser Leu Glu
        195                 200                 205

Gln Glu Leu Ala Arg Leu His Arg Lys Glu Gly Ala Leu Val Phe Thr
    210                 215                 220

Ser Cys Tyr Val Ala Asn Asp Ala Thr Leu Ser Thr Leu Gly Ser Lys
225                 230                 235                 240

Met Pro Gly Cys Val Ile Phe Ser Asp Arg Met Asn His Ala Ser Met
                245                 250                 255

Ile Gln Gly Ile Arg His Ser Gly Thr Lys Lys Val Ile Phe Glu His
            260                 265                 270

Asn Asp Leu Ala Asp Leu Glu Lys Lys Leu Ala Glu Tyr Pro Lys Glu
        275                 280                 285

Thr Pro Lys Ile Ile Ala Phe Glu Ser Val Tyr Ser Met Cys Gly Ser
    290                 295                 300

Ile Gly Pro Ile Lys Glu Ile Cys Asp Leu Ala Glu Lys Tyr Gly Ala
305                 310                 315                 320

Ile Thr Phe Leu Asp Glu Val His Ala Val Gly Leu Tyr Gly Pro Arg
                325                 330                 335

Gly Ala Gly Val Ala Glu His Leu Asp Tyr Asp Leu His Lys Ala Ala
            340                 345                 350

Gly Asp Ser Pro Asp Ala Ile Pro Gly Thr Val Met Asp Arg Val Asp
        355                 360                 365

Ile Ile Thr Gly Thr Leu Gly Lys Ser Tyr Gly Ala Ile Gly Gly Tyr
    370                 375                 380

Ile Ala Gly Ser Ala Arg Phe Val Asp Met Ile Arg Ser Tyr Ala Pro
385                 390                 395                 400

Gly Phe Ile Phe Thr Thr Ser Leu Pro Pro Ala Thr Val Ala Gly Ala
                405                 410                 415

Gln Ala Ser Val Val Tyr Gln Lys Glu Tyr Leu Gly Asp Arg Gln Leu
            420                 425                 430

Lys Gln Val Asn Val Arg Glu Val Lys Arg Arg Phe Ala Glu Leu Asp
        435                 440                 445

Ile Pro Val Val Pro Gly Pro Ser His Ile Val Pro Val Leu Val Gly
    450                 455                 460

Asp Ala Ala Leu Ala Lys Gln Ala Ser Asp Lys Leu Leu Ala Glu His
465                 470                 475                 480

Asp Ile Tyr Val Gln Ala Ile Asn Tyr Pro Thr Val Ala Arg Gly Glu
```

```
                485                 490                 495

Glu Arg Leu Arg Ile Thr Val Thr Gln Arg His Thr Leu Glu Gln Met
            500                 505                 510

Asp His Leu Ile Gly Ala Val Asp Gln Val Phe Asn Glu Leu Asn Ile
        515                 520                 525

Asn Arg Val Gln Asp Trp Lys Arg Leu Gly Gly Arg Ala Ser Val Gly
    530                 535                 540

Val Pro Gly Gly Gln Asp Phe Val Glu Pro Ile Trp Thr Asp Glu Gln
545                 550                 555                 560

Val Gly Leu Ala Asp Gly Ser Ala Pro Leu Thr Leu Arg Asn Gly Gln
                565                 570                 575

Pro Asn Glu Val Ser His Asp Ala Val Val Ala Ala Arg Ser Arg Phe
            580                 585                 590

Asp Trp Leu Leu Gly Pro Ile Pro Ser His Ile Gln Ala Lys Arg Leu
        595                 600                 605

Gly Gln Ser Leu Glu Gly Thr Pro Ile Ala Pro Leu Ala Pro Lys Gln
    610                 615                 620

Ser Ser Gly Leu Lys Leu Pro Val Glu Glu Met Thr Met Gly Gln Thr
625                 630                 635                 640

Ile Ala Val Ala Ala
                645


<210> SEQ ID NO 95
<211> LENGTH: 708
<212> TYPE: PRT
<213> ORGANISM: Crassisporium funariophilum

<400> SEQUENCE: 95

Met Asp Lys Ile Ala Arg Phe Lys Gln Thr Cys Pro Phe Leu Gly Arg
1               5                   10                  15

Thr Lys Asn Ser Thr Leu Arg Asn Leu Ser Thr Ser Ser Ser Pro Arg
            20                  25                  30

Phe Pro Ser Leu Thr Ala Leu Thr Glu Arg Ala Thr Lys Cys Pro Val
        35                  40                  45

Met Gly Pro Ala Leu Asn Val Arg Ser Lys Glu Ile Val Ala Gly Tyr
    50                  55                  60

Ala Ser Val Ala Ala Asn Ser Asp Val Ala Leu Ile His Lys Glu Lys
65                  70                  75                  80

Gly Val Phe Pro Pro Pro Gly Ala Thr Val Glu Met Cys Pro His Ala
                85                  90                  95

Ser Ala Ala Arg Ala Ala Ala Arg Met Ala Asp Asp Leu Ala Ala Ala
            100                 105                 110

Ala Glu Lys Lys Lys Gly His Phe Thr Ser Ala Ala Pro Arg Asp Glu
        115                 120                 125

Ala Ala Gln Ala Ala Ala Ala Gly Cys Pro Phe His Val Lys Ala Ala
    130                 135                 140

Ala Asp Ala Ala Ala Ala Arg Lys Ala Ala Ala Ala Pro Ala Pro Val
145                 150                 155                 160

Lys Ala Lys Glu Asp Gly Gly Phe Asn Tyr Glu Ser Phe Tyr Val Asn
                165                 170                 175

Glu Leu Asp Lys Lys His Gln Asp Lys Ser Tyr Arg Tyr Phe Asn Asn
            180                 185                 190

Ile Asn Arg Leu Ala Ala Lys Phe Pro Val Ala His Thr Ser Asn Val
        195                 200                 205
```

```
Lys Asp Glu Val Glu Val Trp Cys Ala Asn Asp Tyr Leu Gly Met Gly
    210                 215                 220

Asn Asn Pro Val Val Leu Glu Thr Met His Arg Thr Leu Asp Lys Tyr
225                 230                 235                 240

Gly His Gly Ala Gly Gly Thr Arg Asn Ile Ala Gly Asn Gly Ala Met
                245                 250                 255

His Leu Ser Leu Glu Gln Glu Leu Ala Thr Leu His Arg Lys Pro Ala
            260                 265                 270

Ala Leu Val Phe Ser Ser Cys Tyr Val Ala Asn Asp Ala Thr Leu Ser
        275                 280                 285

Thr Leu Gly Ala Lys Leu Pro Gly Cys Ile Phe Phe Ser Asp Thr Met
    290                 295                 300

Asn His Ala Ser Met Ile Gln Gly Met Arg His Ser Gly Ala Lys Arg
305                 310                 315                 320

Val Leu Phe Lys His Asn Asp Leu Glu Asp Leu Glu Asn Lys Leu Lys
                325                 330                 335

Gln Tyr Pro Lys Asp Thr Pro Lys Val Ile Ala Phe Glu Ser Val Tyr
            340                 345                 350

Ser Met Cys Gly Ser Ile Gly Pro Ile Lys Glu Ile Cys Asp Leu Ala
        355                 360                 365

Glu Gln Tyr Gly Ala Leu Thr Phe Leu Asp Glu Val His Ala Val Gly
    370                 375                 380

Leu Tyr Gly Pro Arg Gly Ala Gly Val Ala Glu His Leu Asp Tyr Asp
385                 390                 395                 400

Ala His Val Ala Ala Gly Glu Ser Pro His Pro Ile Lys Gly Ser Val
                405                 410                 415

Met Asp Arg Val Asp Ile Ile Thr Gly Thr Leu Gly Lys Ala Tyr Gly
            420                 425                 430

Ala Val Gly Gly Tyr Ile Ala Gly Ser Asp Asp Phe Val Asp Met Ile
        435                 440                 445

Arg Ser Tyr Ala Pro Gly Phe Ile Phe Thr Thr Ser Leu Pro Pro Ala
    450                 455                 460

Thr Val Ala Gly Ala Arg Ala Ser Val Val Tyr Gln Lys His Tyr Val
465                 470                 475                 480

Gly Asp Arg Gln Leu Lys Gln Val Asn Val Arg Glu Val Lys Arg Arg
                485                 490                 495

Phe Ala Glu Leu Asp Val Pro Val Val Pro Gly Pro Ser His Ile Val
            500                 505                 510

Pro Val Leu Val Gly Asp Ala Ala Leu Ala Lys Ala Ala Ser Asp Lys
        515                 520                 525

Leu Leu Ala Glu His Asn Ile Tyr Val Gln Ser Ile Asn Tyr Pro Thr
    530                 535                 540

Val Ala Arg Gly Glu Glu Arg Leu Arg Ile Thr Val Thr Pro Arg His
545                 550                 555                 560

Thr Leu Glu Gln Met Asp Lys Leu Val Arg Ala Val Asp Lys Ile Phe
                565                 570                 575

Ala Glu Leu Lys Ile Asn Arg Leu Ala Asp Trp Lys Ala Leu Gly Gly
            580                 585                 590

Arg Ala Gly Val Gly Leu Thr Ala Gly Ala Glu Glu Ala His Val Asp
        595                 600                 605

Pro Met Trp Thr Glu Glu Gln Leu Gly Leu Leu Asp Gly Thr Ser Pro
    610                 615                 620

Arg Thr Leu Arg Asn Gly Glu Ala Ala Val Val Asp Ala Met Ala Val
```

```
625                 630                 635                 640

Gly Gln Ala Arg Ala Val Phe Asp Asn Leu Leu Gly Pro Ile Ser Gly
                645                 650                 655

Lys Leu Gln Ser Glu Arg Ser Val Leu Ala Ser Ser Thr Pro Ala Ala
            660                 665                 670

Ala Asn Pro Ala Arg Pro Ala Ala Arg Lys Val Val Lys Met Lys Thr
        675                 680                 685

Gly Gly Val Pro Met Ser Glu Asp Ile Pro Leu Pro Pro Pro Asp Val
    690                 695                 700

Ser Ala Ser Ala
705


<210> SEQ ID NO 96
<211> LENGTH: 677
<212> TYPE: PRT
<213> ORGANISM: Dendrothele bispora CBS 962.96

<400> SEQUENCE: 96

Met Asp Lys Leu Ser Ser Leu Ser Arg Phe Lys Ala Ser Cys Pro Phe
1               5                   10                  15

Leu Gly Arg Thr Lys Thr Ser Thr Leu Arg Thr Leu Cys Thr Ser Ser
            20                  25                  30

Ser Pro Arg Phe Pro Ser Ile Ser Ile Leu Thr Glu Arg Ala Thr Lys
        35                  40                  45

Cys Pro Val Met Gly Pro Ala Leu Asn Val Arg Ser Lys Glu Ile Thr
    50                  55                  60

Ala Gly Tyr Ala Ser Val Ala Gly Ser Ser Glu Val Asp Gln Ile His
65                  70                  75                  80

Lys Gln Gln Gly Val Thr Val Pro Val Asn Ala Thr Val Glu Met Cys
                85                  90                  95

Pro His Ala Ser Ala Ala Arg Ala Ala Ala Arg Met Ala Asp Asp Leu
            100                 105                 110

Ala Ala Ala Ala Ala Gln Lys Lys Val Gly Ser Gly Ala Ser Ser Ala
        115                 120                 125

Lys Ala Ala Ala Ala Gly Cys Pro Phe His Lys Ser Val Ala Ala Gly
    130                 135                 140

Ala Ser Ala Ser Thr Ala Ser Lys Pro Ser Ala Pro Ile His Lys Ala
145                 150                 155                 160

Ser Val Pro Gly Gly Phe Asp Tyr Asp Asn Phe Tyr Asn Asn Glu Leu
                165                 170                 175

Glu Lys Lys His Lys Asp Lys Ser Tyr Arg Tyr Phe Asn Asn Ile Asn
            180                 185                 190

Arg Leu Ala Ser Lys Phe Pro Val Ala His Thr Gly Asp Val Lys Asp
        195                 200                 205

Glu Val Gln Val Trp Cys Ser Asn Asp Tyr Leu Gly Met Gly Asn Asn
    210                 215                 220

Pro Val Val Leu Glu Thr Met His Arg Thr Leu Asp Lys Tyr Gly His
225                 230                 235                 240

Gly Ala Gly Gly Thr Arg Asn Ile Ala Gly Asn Gly Ala Leu His Leu
                245                 250                 255

Gly Leu Glu Gln Glu Leu Ala Ala Leu His Arg Lys Glu Ala Ala Leu
            260                 265                 270

Val Phe Ser Ser Cys Tyr Val Ala Asn Asp Ala Thr Leu Ser Thr Leu
        275                 280                 285
```

```
Gly Ser Lys Leu Pro Gly Cys Ile Leu Phe Ser Asp Lys Met Asn His
    290                 295                 300

Ala Ser Met Ile Gln Gly Met Arg His Ser Gly Ala Lys Lys Val Ile
305                 310                 315                 320

Phe Asn His Asn Asp Leu Glu Asp Leu Glu Asn Lys Leu Lys Gln Tyr
                325                 330                 335

Pro Lys Glu Thr Pro Lys Ile Ile Ala Phe Glu Ser Val Tyr Ser Met
            340                 345                 350

Cys Gly Ser Ile Gly Pro Ile Lys Glu Ile Cys Asp Leu Ala Glu Lys
        355                 360                 365

Tyr Gly Ala Leu Thr Phe Leu Asp Glu Val His Ala Val Gly Leu Tyr
    370                 375                 380

Gly Pro His Gly Ala Gly Val Ala Glu His Leu Asp Tyr Asn Ala Gln
385                 390                 395                 400

Lys Ala Ala Gly Lys Ser Pro Glu Pro Ile Pro Gly Ser Val Met Asp
                405                 410                 415

Arg Val Asp Ile Ile Thr Gly Thr Leu Gly Lys Ala Tyr Gly Ala Val
            420                 425                 430

Gly Gly Tyr Ile Ala Gly Ser Met Asp Phe Val Asp Thr Ile Arg Ser
        435                 440                 445

Tyr Ala Pro Gly Phe Ile Phe Thr Thr Ser Leu Pro Pro Ala Thr Val
    450                 455                 460

Ser Gly Ala Gln Ala Ser Val Ala Tyr Gln Lys Glu Tyr Leu Gly Asp
465                 470                 475                 480

Arg Gln Leu Lys Gln Val Asn Val Arg Glu Val Lys Arg Arg Phe Ala
                485                 490                 495

Glu Leu Asp Ile Pro Val Ile Pro Gly Pro Ser His Ile Leu Pro Val
            500                 505                 510

Leu Val Gly Asp Ala Ala Leu Ala Lys Ala Ala Ser Asp Lys Leu Leu
        515                 520                 525

Thr Asp His Asp Ile Tyr Val Gln Ser Ile Asn Tyr Pro Thr Val Ala
    530                 535                 540

Val Gly Glu Glu Arg Leu Arg Ile Thr Val Thr Pro Arg His Thr Leu
545                 550                 555                 560

Glu Gln Met Asp Lys Leu Val Arg Ala Val Asn Gln Val Phe Thr Glu
                565                 570                 575

Leu Asn Ile Asn Arg Ile Ser Asp Trp Lys Val Ala Gly Gly Arg Ala
            580                 585                 590

Gly Val Gly Met Gly Val Glu Ser Val Glu Pro Ile Trp Thr Asp Glu
        595                 600                 605

Gln Leu Gly Ile Thr Asp Gly Thr Thr Pro Lys Thr Leu Arg Asp Gly
    610                 615                 620

Gln Arg Phe Leu Val Asp Ala Gln Gly Val Thr Ala Ala Arg Gly Arg
625                 630                 635                 640

Phe Asp Thr Leu Leu Gly Pro Met Ser Gly Ser Leu Gln Ala Asn Pro
                645                 650                 655

Thr Leu Pro Leu Val Asp Asp Glu Leu Lys Val Pro Leu Pro Thr Leu
            660                 665                 670

Val Ala Ala Ala Ala
        675
```

<210> SEQ ID NO 97
<211> LENGTH: 409
<212> TYPE: PRT

<213> ORGANISM: Bradyrhizobium japonicum

<400> SEQUENCE: 97

```
Met Asp Tyr Ala Gln Phe Phe Asn Thr Ala Leu Asp Arg Leu His Thr
1               5                   10                  15

Glu Arg Arg Tyr Arg Val Phe Ala Asp Leu Glu Arg Ile Ala Gly Arg
            20                  25                  30

Phe Pro His Ala Leu Trp His Ser Pro Lys Gly Lys Arg Asp Val Val
        35                  40                  45

Ile Trp Cys Ser Asn Asp Tyr Leu Gly Met Gly Gln His Pro Lys Val
    50                  55                  60

Val Gly Ala Met Val Glu Thr Ala Thr Arg Val Gly Thr Gly Ala Gly
65                  70                  75                  80

Gly Thr Arg Asn Ile Ala Gly Thr His His Pro Leu Val Gln Leu Glu
                85                  90                  95

Ala Glu Leu Ala Asp Leu His Gly Lys Glu Ala Ser Leu Leu Phe Thr
            100                 105                 110

Ser Gly Tyr Val Ser Asn Gln Thr Gly Ile Ala Thr Ile Ala Lys Leu
        115                 120                 125

Ile Pro Asn Cys Leu Ile Leu Ser Asp Glu Leu Asn His Asn Ser Met
    130                 135                 140

Ile Glu Gly Ile Arg Gln Ser Gly Cys Glu Arg Val Val Phe Arg His
145                 150                 155                 160

Asn Asp Leu Ala Asp Leu Glu Glu Lys Leu Lys Ala Ala Gly Pro Asn
                165                 170                 175

Arg Pro Lys Leu Ile Ala Cys Glu Ser Leu Tyr Ser Met Asp Gly Asp
            180                 185                 190

Val Ala Pro Leu Ala Lys Ile Cys Asp Leu Ala Glu Lys Tyr Gly Ala
        195                 200                 205

Met Thr Tyr Val Asp Glu Val His Ala Val Gly Met Tyr Gly Pro Arg
    210                 215                 220

Gly Gly Gly Ile Ala Glu Arg Asp Gly Val Met His Arg Ile Asp Ile
225                 230                 235                 240

Leu Glu Gly Thr Leu Ala Lys Ala Phe Gly Cys Leu Gly Gly Tyr Ile
                245                 250                 255

Ala Ala Asn Gly Gln Ile Ile Asp Ala Val Arg Ser Tyr Ala Pro Gly
            260                 265                 270

Phe Ile Phe Thr Thr Ala Leu Pro Pro Ala Ile Cys Ser Ala Ala Thr
        275                 280                 285

Ala Ala Ile Arg His Leu Lys Thr Ser Asn Trp Glu Arg Glu Arg His
    290                 295                 300

Gln Asp Arg Ala Ala Arg Val Lys Ala Ile Leu Asn Ala Ala Gly Leu
305                 310                 315                 320

Pro Val Met Ser Ser Asp Thr His Ile Val Pro Leu Phe Ile Gly Asp
                325                 330                 335

Ala Glu Lys Cys Lys Gln Ala Ser Asp Leu Leu Leu Glu Gln His Gly
            340                 345                 350

Ile Tyr Ile Gln Pro Ile Asn Tyr Pro Thr Val Ala Lys Gly Thr Glu
        355                 360                 365

Arg Leu Arg Ile Thr Pro Ser Pro Tyr His Asp Asp Gly Leu Ile Asp
    370                 375                 380

Gln Leu Ala Glu Ala Leu Leu Gln Val Trp Asp Arg Leu Gly Leu Pro
385                 390                 395                 400
```

-continued

```
Leu Lys Gln Lys Ser Leu Ala Ala Glu
                405


<210> SEQ ID NO 98
<211> LENGTH: 149
<212> TYPE: PRT
<213> ORGANISM: Petunia x hybrida

<400> SEQUENCE: 98

Met Asp Lys Gln Arg Val Phe Thr Leu Ser Gln Val Ala Glu His Lys
1               5                   10                  15

Ser Lys Gln Asp Cys Trp Ile Ile Ile Asn Gly Arg Val Val Asp Val
            20                  25                  30

Thr Lys Phe Leu Glu Glu His Pro Gly Gly Glu Glu Val Leu Ile Glu
        35                  40                  45

Ser Ala Gly Lys Asp Ala Thr Lys Glu Phe Gln Asp Ile Gly His Ser
    50                  55                  60

Lys Ala Ala Lys Asn Leu Leu Phe Lys Tyr Gln Ile Gly Tyr Leu Gln
65                  70                  75                  80

Gly Tyr Lys Ala Ser Asp Asp Ser Glu Leu Glu Leu Asn Leu Val Thr
                85                  90                  95

Asp Ser Ile Lys Glu Pro Asn Lys Ala Lys Glu Met Lys Ala Tyr Val
            100                 105                 110

Ile Lys Glu Asp Pro Lys Pro Lys Tyr Leu Thr Phe Val Glu Tyr Leu
        115                 120                 125

Leu Pro Phe Leu Ala Ala Ala Phe Tyr Leu Tyr Tyr Arg Tyr Leu Thr
    130                 135                 140

Gly Ala Leu Gln Phe
145
```